US009422356B2

(12) United States Patent
Lee et al.

(10) Patent No.: US 9,422,356 B2
(45) Date of Patent: Aug. 23, 2016

(54) ARTIFICIAL SIGNAL PEPTIDE FOR EXPRESSING AN INSOLUBLE PROTEIN AS A SOLUBLE ACTIVE FORM

(71) Applicant: Republic of Korea (Republic of National Fisheries Research and Devlopment Institute), Busan (KR)

(72) Inventors: Sang Jun Lee, Busan (KR); Young Ok Kim, Busan (KR); Bo Hye Nam, Busan (KR); Hee Jeong Kong, Busan (KR); Kyung Kil Kim, Busan (KR)

(73) Assignee: Republic of Korea (Republic of National Fisheries Research and Development Institute), Busan (KR)

( * ) Notice: Subject to any disclaimer, the term of this patent is extended or adjusted under 35 U.S.C. 154(b) by 0 days.

(21) Appl. No.: 14/309,764

(22) Filed: Jun. 19, 2014

(65) Prior Publication Data

US 2014/0377801 A1   Dec. 25, 2014

Related U.S. Application Data

(63) Continuation-in-part of application No. 12/745,187, filed as application No. PCT/KR2008/002173 on Apr. 17, 2008, now abandoned, said application No. 12/745,187 is a continuation-in-part of application No. 12/162,118, filed as application No. PCT/KR2007/000515 on Jan. 30, 2007, now abandoned, said application No. 12/162,118 is a continuation-in-part of application No. 13/643,137, filed as application No. PCT/KR2011/001465 on Mar. 3, 2011, now abandoned.

(30) Foreign Application Priority Data

| Jan. 31, 2006 | (KR) | ........................ 10-2006-0009418 |
| Mar. 9, 2006 | (KR) | ........................ 10-2006-0022389 |
| Nov. 28, 2007 | (KR) | ........................ 10-2007-0121977 |
| Apr. 16, 2008 | (KR) | ........................ 10-2008-0035162 |
| May 11, 2010 | (KR) | ........................ 10-2010-0043855 |

(51) Int. Cl.
  *C07K 14/575*   (2006.01)
  *C07K 7/06*   (2006.01)

(52) U.S. Cl.
  CPC ................ *C07K 14/575* (2013.01); *C07K 7/06* (2013.01); *C07K 2319/00* (2013.01); *C07K 2319/035* (2013.01)

(58) Field of Classification Search
  None
  See application file for complete search history.

(56) References Cited

U.S. PATENT DOCUMENTS

| 6,291,662 B1 | 9/2001 | Bandyopadhyay et al. |
| 2008/0112926 A1* | 5/2008 | Kungl ................ C07K 14/5421 424/85.2 |
| 2013/0084602 A1 | 4/2013 | Lee et al. |

FOREIGN PATENT DOCUMENTS

| CN | 1388131 A | 1/2003 |
| CN | 1641025 A | 11/2004 |
| KR | 10-2007-0079025 | 8/2007 |
| KR | 10-2007-0121977 | 11/2007 |
| KR | 10-2009-0055457 | 6/2009 |
| WO | WO 2007/089093 | 8/2007 |
| WO | WO 2009/069862 | 6/2009 |

OTHER PUBLICATIONS

Ohtani et al.; Molecular Cloning of a Novel Human Collectin from Liver (CL-L1); The Journal of Biological Chemistry; vol. 274, No. 19, pp. 13681-13689, published May 7, 1999.*
Abdullah et al., "Removal of Poly-Histidine Fusion Tags From Recombinant Proteins Purified by Expanded Bed Adsorption," *Biotechnology and Bioengineering*, vol. 92, No. 4, pp. 501-513, 2005.
Ahn et al., "Enhanced secretion of *Bacillus stearothermophilus* L1 lipase in *Saccharomyces cerevisiae* by translational fusion to cellulose-binding domain," *Applied Microbiol. Biotechnol.*, vol. 64, pp. 833-839, 2004.
Andersson et al., "A 30-residue-long "export initiation domain" adjacent to the signal sequence is critical for protein translocation across the inner membrane of *Escherichia coli*," *PNAS*, U.S.A., vol. 88, pp. 9751-9754, 1991.
Baneyx, "Recombinant protein expression in *Escherichia coli*," *Current Opinion in Biotechnology*, vol. 10, pp. 411-421, 1999.
Bendtsen et al., "Improved Prediction of Signal Peptides: SignalP 3.0," *Journal of Molecular Biology*, vol. 340, No. 4, pp. 783-795, 2004.

(Continued)

*Primary Examiner* — Antonio Galisteo Gonzalez
(74) *Attorney, Agent, or Firm* — Klarquist Sparkman, LLP

(57) ABSTRACT

The present invention relates to expression vectors and methods for enhancing soluble expression and secretion of an insoluble heterologous protein, particularly a bulky folded active heterologous protein which has one or more transmembrane-like domains or intramolecular disulfide bonds by linking a leader peptide with acidic or basic pI and high hydrophilicity thereto; by substituting one or more amino acids within N-terminal of the heterologous protein with ones having acidic or neutral pI and high hydrophilicity; or reducing elevating $\Delta G_{RNA}$ value of a polynucleotide encoding the leader peptide having basic pI value and high hydrophilicity. The expression vector and the method may be used to produce of heterologous protein and to transduce of therapeutic proteins in a patient by preventing formation of insoluble inclusion body and by enhancing secretional efficiency of the heterologous protein into the periplasm or outside cell.

6 Claims, 19 Drawing Sheets

(56) References Cited

OTHER PUBLICATIONS

Berks, "A common export pathway for proteins binding complex redox cofactors?," *Molecular Microbiology*, vol. 22, No. 3, pp. 393-404, 1996.
Blachly-Dyson and Stevens, "Yeast Carboxypeptidase Y Can Be Translocated and Glycosylated without its Amino-terminal Signal Sequence," *Journal of Cell Biology*, vol. 104, pp. 1183-1191, 1987.
Brasseur et al., "Orientation into the lipid bilayer of an asymmetric amphipathic helical peptide located at the N-terminus of viral fusion proteins," *Biochimica et Biophysica Acta*, vol. 1029, pp. 267-273, 1990.
Campion et al., "Amino-Terminal Charge Affects the Periplasmic Accumulation of Recombinant Heregulin/EGF Hybrids Exported Using the *Escherichia coli* Alkaline Phosphatase Signal Sequence," *Protein Expression and Purification*, vol. 10, No. 3, pp. 331-339, 1997.
Cheng et al., "DOMpro: Protein Domain Prediction Using Profiles, Secondary Structure, Relative Solvent Accessibility, and Recursive Neural Networks," *Data Mining and Knowledge Discovery*, vol. 13, pp. 1-10, 2006.
Collier et al., "*Escherichia coli* signal peptides direct inefficient secretion of an outer membrane protein (OmpA) and periplasmic proteins (maltose-binding protein, ribose-binding protein, and alkaline phosphatase) in Bacillus subtilis," *Journal of Bacteriology*, vol. 176, No. 10, pp. 3013-3020, 1994.
Dietz and Bahr, "Peptide-enhanced cellular internalization of proteins in neuroscience," *Brain Research Bulletin*, vol. 68, pp. 103-114, 2005.
Dodt et al., "Expression, secretion and processing of hirudin in *E. coli* using the alkaline phosphatase signal sequence," *FEBS*, vol. 202, No. 2, pp. 373-377, 1986.
Duffaud and Inouye, "Signal Peptidases Recognize a Structural Feature at the Cleavage Site of Secretory Proteins," *Journal of Biological Chemistry*, vol. 263, No. 21, pp. 10224-10228, 1988.
Duffaud et al., "Expression and Secretion of Foreign Proteins in *Escherichia coli*," *Meth. Enzymol.*, vol. 153, pp. 492-507, 1987.
Filpula et al., "Structural and Functional Repetition in a Marine Mussel Adhesive Protein," *Biotechnol. Prog.*, vol. 6, pp. 171-177, 1990.
Fisher et al., "Exploration of twin-arginine translocation for expression and purification of correctly folded proteins in *Escherichia coli*," *Microb. Biotechnol.*, vol. 1, pp. 403-415, 2008.
Ghrayeb et al., "Secretion cloning vectors in *Escherichia coli*," *EMBO Journal*, vol. 3, No. 10, pp. 2437-2442, 1984.
Goldstein et al., "Enhancement of Protein Translocation across the Membrane by Specific Mutation in the Hydrophobic Region of the Signal Peptide," *Journal of Bacteriology*, vol. 172, No. 3, pp. 1225-1231, 1990.
Humphreys et al., "High-Level Periplasmic Expression in *Escherichia coli* Using a Eukaryotic Signal Peptide: Importance of Codon Usage at the 5' End of the Coding Sequence," *Protein Expression and Purification*, vol. 20, pp. 252-264, 2000.
Itoh et al., "Artificial insertion of peptides between signal peptide and mature protein: effect on secretion and processing of hybrid thermostable α-amylases in *Bacillus subtilis* and *Escherichia coli* cells," *Journal of General Microbiology*, vol. 136, pp. 1551-1558, 1990.

Izard and Kendall, "Signal peptides: exquisitely designed transport promoters," *Molecular Microbiology*, vol. 13, No. 5, pp. 765-773, 1994.
Jeong and Lee, "Secretory Production of Human Granulocyte Colony-Stimulating Factor in *Escherichia coli*," *Protein Expression and Purification*, vol. 23, pp. 311-318, 2001.
Jobling et al., "Construction and Characterization of Versatile Cloning Vectors for Efficient Delivery of Native Foreign Proteins to the Periplasm of *Escherichia coli*," *Plasmid*, vol. 38, pp. 158-173, 1997.
Kim et al., "Molecular Cloning and Expression Analysis of Two Hepcidin Genes from Olive Flounder *Paralichthys olivaceus*," *Biosci. Biotechnol. Biochem.*, vol. 69, No. 7, pp. 1411-1414, 2005.
Kohl et al., "Engineered gene for *Escherichia coli* alkaline phosphatase for the construction of translational fusions," *Nucleic Acids Research*, vol. 18, No. 4, p. 1069, 1990.
Lammertyn and Anne, "Modifications of *Streptomyces* signal peptides and their effects on protein production and secretion," *FEMS Microbiology Letters*, vol. 160, pp. 1-10, 1998.
Lee et al., "Secretory Production of Therapeutic Proteins in *Escherichia coli*," *Methods in Molecular Biology*, vol. 308, pp. 31-41, 2005.
Lee et al., "Soluble Expression of Recombinant Olive Flounder Hepcidin I Using a Novel Secretion Enhancer," *Molecules and Cells*, vol. 26, pp. 140-145, 2008.
Lehnhardt et al., "Modulation of the Effects of Mutations in the Basic Region of the OmpA Signal Peptide by the Mature Portion of the Protein," *Journal of Biological Chemistry*, vol. 263, No. 21, pp. 10300-10303, 1988.
Morioka-Fujimoto et al., "Modified Enterotoxin Signal Sequences Increase Secretion Level of the Recombinant Human Epidermal Growth Factor in *Escherichia coli*," *Journal of Biological Chemistry*, vol. 266, No. 3, pp. 1728-1732, 1991.
Oka et al., "Efficacies of Different Secretion Vectors for Secretion of Human Epidermal Growth Factor by *Escherichia coli*," *Agric. Biol. Chem.*, vol. 51, No. 4, pp. 1099-1104, 1987.
Prehn et al., "Structure and biosynthesis of the signal-sequence receptor," *Eur. J. Biochem.*, vol. 188, pp. 439-445, 1990.
Robinson, "The twin-Arginine Translocation System: A Novel Means of Transporting Folded Proteins in Chloroplasts and Bacteria," *Biol. Chem.*, vol. 381, pp. 89-93, 2000.
Schwarze et al., "In Vivo Protein Transduction: Delivery of a Biologically Active Protein into the Mouse," *Science*, vol. 285, pp. 1569-1572, 1999.
Stark and Boyd, "The killer toxin of *Kluyveromyces lactis*: characterization of the toxin subunits and identification of the genes which encode them," *EMBO Journal*, vol. 5, No. 8, pp. 1995-2002, 1986.
Suciu and Inouye, "The 19-residue pro-peptide of staphylococcal nuclease has a profound secretion-enhancing ability in *Escherichia coli*," *Molecular Microbiology*, vol. 21, No. 1, pp. 181-195, 1996.
Triplett et al., "Functional Signal Peptides Bind a Soluble N-terminal Fragment of SecA and Inhibit Its ATPase Activity," *Journal of Biological Chemistry*, vol. 276, No. 22, pp. 19648-19655, 2001.
Zhang et al., "Alteration in the IL-2 signal peptide affects secretion of protein in vitro and in vivo," *Journal of Gene Medicine*, vol. 7, No. 3, pp. 354-365, 2005.
Zhao et al., "Effects of additional sequences directly downstream from the AUG on the expression of GFP gene," *Biochem. Biophys. Acta.*, vol. 1630(2-3), pp. 84-95, 2003.

* cited by examiner

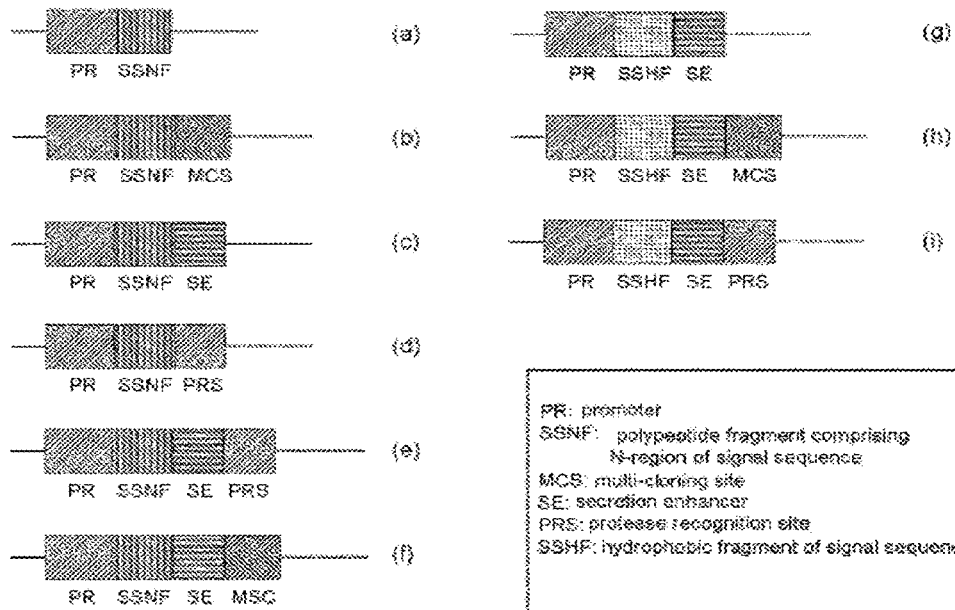

10 kDa ➡

10 kDa ➡

10 kDa ➡

M    1    2    3    4    5

10 kDa ➡

M    1    2    3    4    5

10 kDa ➡

M    1    2    3    4    5    6

10 kDa ➡

M    1    2    3    4    5    6 a) ofHepcidin1 b) OmpASP$_{1-10}$-Xa-ofHepcidin1 c) OmpASP$_{1-10}$-LysArg-Xa-ofHepcidin1 d) OmpASP$_{1-10}$-6XArg-Xa-ofHepcidin1

FIG. 10B
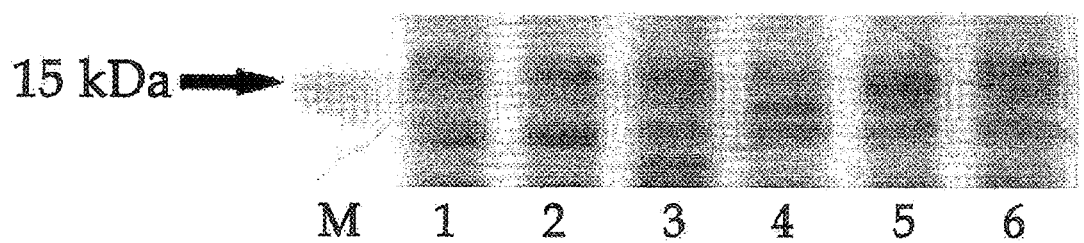
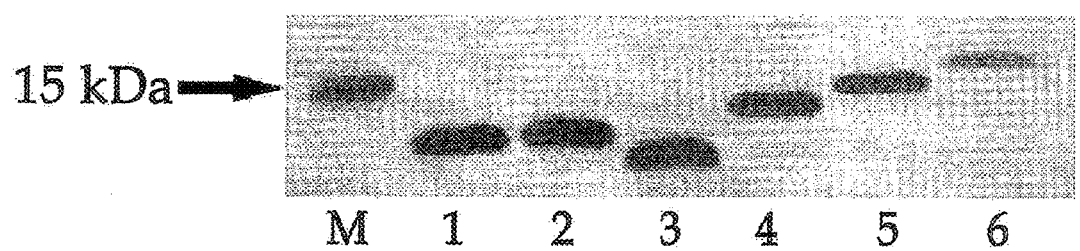
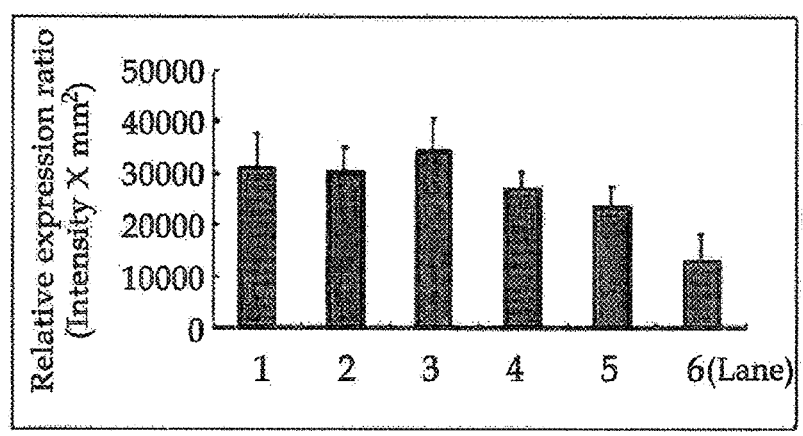

FIG. 13A
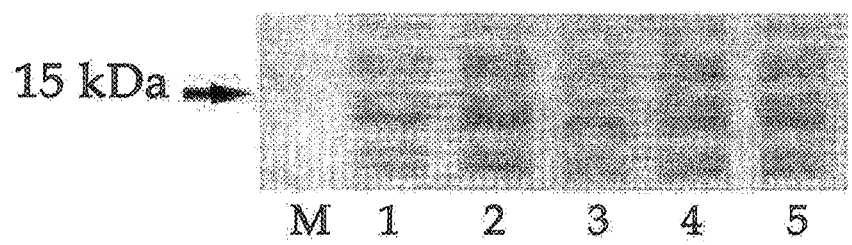
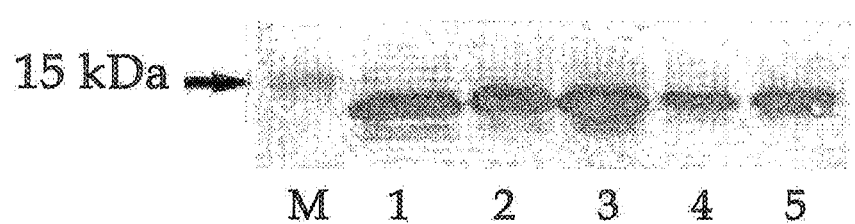
FIG. 13B
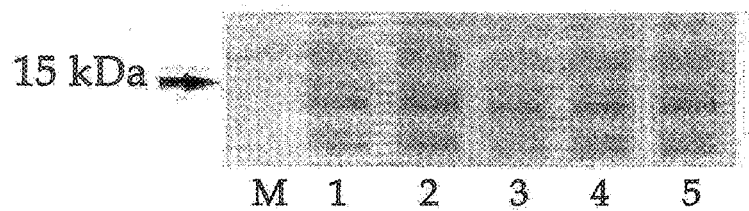
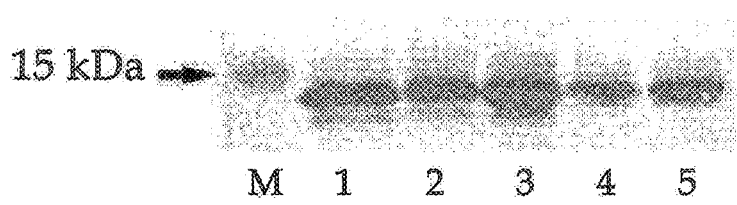

FIG. 17A
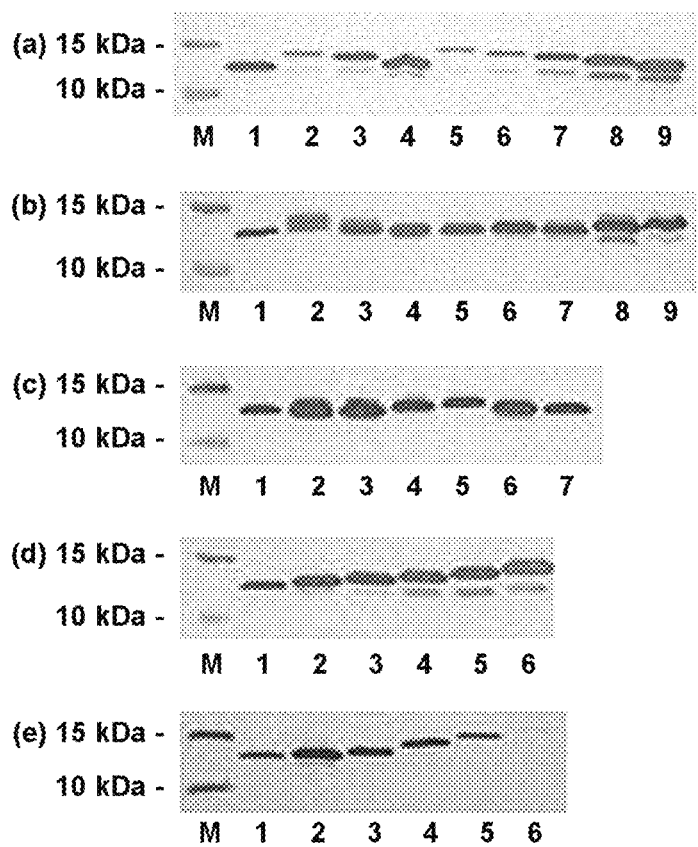
FIG. 17B
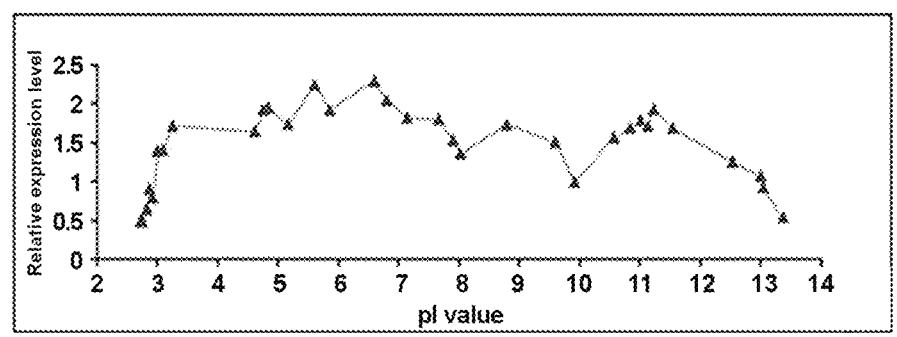
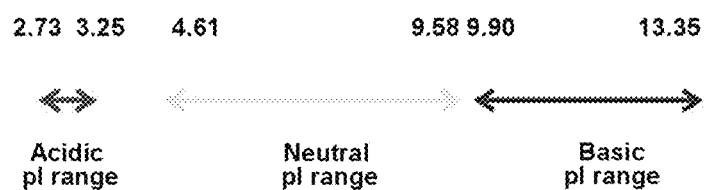

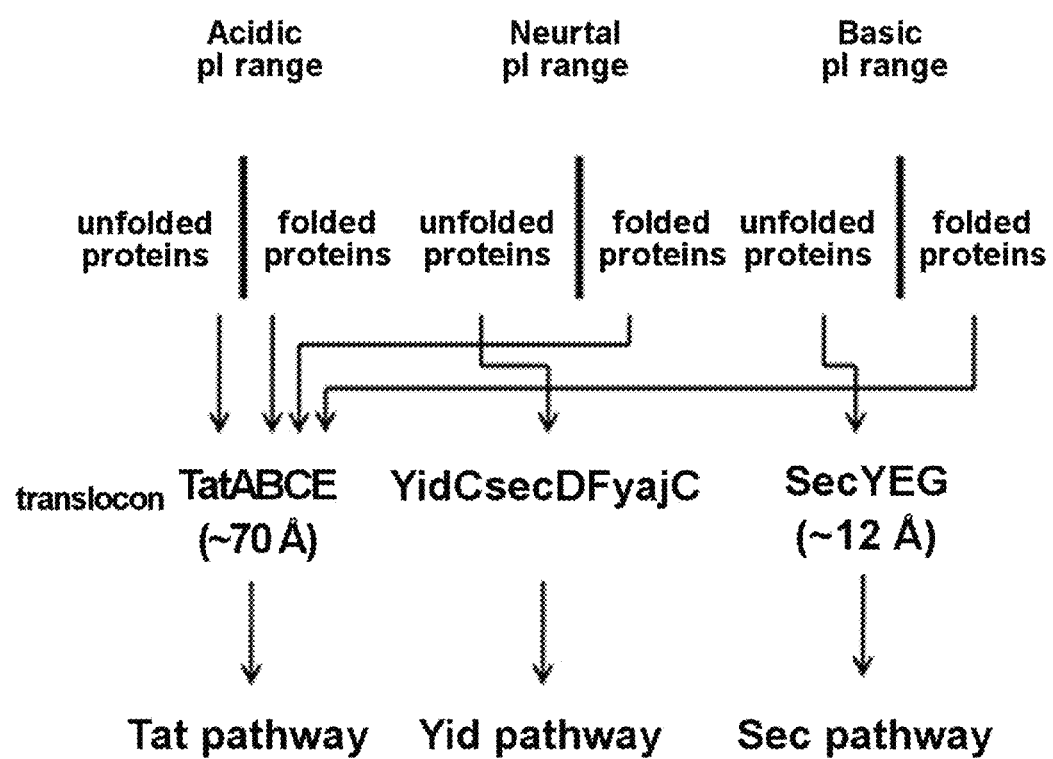

30 kDa -

M  1  2  3  4  5

30 kDa -

M  1  2  3  4  5 though these problems are exemplified thus the
ARTIFICIAL SIGNAL PEPTIDE FOR EXPRESSING AN INSOLUBLE PROTEIN AS A SOLUBLE ACTIVE FORM This application is a Continuation-in-Part application of co-pending U.S. application Ser. No. 12/162,118, filed Jul. 24, 2008; U.S. application Ser. No. 12/745,187, filed May 27, 2010; and U.S. application Ser. No. 13/643,137, filed Oct. 24, 2012. U.S. application Ser. No. 12/162,118 is the U.S. §371 National Stage of International Application No. PCT/KR2007/000515, filed Jan. 30, 2007, which was published in English under PCT Article 21(2), which in turn claims priority to Korean Application No. 10-2006-0009418, filed Jan. 31, 2006, and Korean Application No. 10-2006-0022389, filed Mar. 9, 2006. U.S. application Ser. No. 12/745,187 is the U.S. National Stage of International Application No. PCT/KR2008/002173, filed Apr. 17, 2008, which was published in English under PCT Article 21(2), which in turn claims the benefit of Korean Patent Application No. 10-2007-0121977, filed Nov. 28, 2007 and Korean Patent Application No. 10-2008-0035162, filed Apr. 16, 2008. U.S. application Ser. No. 13/643,137 is the U.S. National Stage of International Application No. PCT/KR2011/001465, filed Mar. 3, 2011, which was published in English under PCT Article 21(2), which in turn claims the benefit of Korean Patent Application No. 2010-0043855, filed May 11, 2010. All of the referenced patent documents are incorporated herein by reference in their entirety.

TECHNICAL FIELD

The present invention relates to expression vectors and methods for enhancing the soluble expression of heterologous proteins in cytosol and the secretion thereof.

BACKGROUND ARTS

The key point of current biotechnology is the production of heterologous proteins and particularly the production of soluble proteins in native form easily. The production of soluble proteins is important for the synthesis and the recovery of active proteins, the crystallization for functional researches, and the industrialization thereof. Until now many researches related to the production of recombinant heterologous proteins using *E. coli*. The reason why *E. coli* is used is that it has many benefits such as easy manipulation, its rapid growth rate, safe expression, low cost and relative convenience of scale-up.

However *E. coli* has no post-translation chaperons and post-translational processing, thus recombinant heterologous proteins expressed in *E. coli* are not folded properly or are formed as insoluble inclusion bodies (Baneyx, *Curr. Opin. Biotechnol.*, 10: 411-421, 1999).

In order to solve these problems, researches on the structure and the function of signal sequences based on the fact that signal sequences make proteins be secreted into the periplasm and vectors for expressing soluble heterologous proteins have been developed using various signal sequences from the researches (Ghrayeb et al., *EMBO J.* 3: 2437-2442, 1984; Kohl et al., *Nucleic Acids Res.*, 18: 1069, 1990; Morika-Fujimoto et al., *J. Biol. Chem.*, 266: 1728-1732, 1991).

DISCLOSURES

Technical Problem

However, previous expression vectors did not express insoluble proteins such as hepcidin, defensin and GFP (green fluorescent protein) well in soluble form.

Thus, the present invention is designed in order to solve many problems including these problems. The purpose of the present invention is to provide an artificial signal peptide for enhancing soluble expression and secretion of insoluble proteins.

The other purpose of the present invention is to provide a method for enhancing soluble expression and secretion of insoluble proteins using the artificial signal peptide.

However these technical problems are exemplified thus the scope of the present invention is not limited thereto.

Technical Solution

According to an aspect of the present invention, an artificial signal peptide consisting of an amino acid sequence of $M(X)_{5-8}$, wherein X is hydrophilic charged amino acid is provided.

The hydrophilic charged amino acid may be a basic amino acid or an acidic amino acid. The basic amino acid may be lysine or arginine. The acidic amino acid may be glutamic acid or aspartic acid.

The artificial signal peptide may be selected from a group consisting of:

|  |  |
|---|---|
| MRRRRRRR; | (SEQ ID NO: 115) |
| MKKKKKKK; | (SEQ ID NO: 116) |
| MKKKKKK; | (SEQ ID NO: 224) |
| MEEEEEE; and | (SEQ ID NO: 223) |
| MDDDDDD. | (SEQ ID NO: 222) |

According to another aspect of the present invention, a method for enhancing soluble expression of insoluble protein comprising providing a recombinant gene construct consisting of a promoter and a nucleotide encoding the artificial signal peptide and a heterologous protein fused thereto and there is no intervention amino acid sequence between the artificial signal sequence and the heterologous protein, transforming a host cell with the recombinant gene construct, culturing transformed host cell.

The heterologous protein may be an insoluble protein.

The host may be gram-negative bacteria and the gram-negative bacteria may be *E. coli*.

The present invention provides an expression vector containing a gene construct composed of polynucleotide encoding a modified signal sequence consisting of a polypeptide fragment containing an N-region of the signal sequence or a hydrophobic fragment containing the N-region and central characteristic hydrophobic region of the signal sequence and/or a hydrophilic enhancing sequence linked to the N-region fragment and/or the hydrophobic fragment of the signal sequence as a secretional enhancer.

The present invention also provides a recombinant expression vector for the production of a fusion protein containing the modified signal sequence and a heterologous gene.

The present invention further provides a transformant prepared by transforming a host cell with the above expression vector or the recombinant expression vector.

The present invention also provides a method for improving the secretional efficiency of a recombinant protein by using the above transformant.

The present invention also provides a method for producing a recombinant fusion protein.

The present invention also provides a recombinant fusion protein produced by the method of the above.

The present invention also provides a method for producing a heterologous protein.

The present invention also provides a pharmaceutical use of the recombinant fusion protein.

The descriptions of the terms used in the present invention are provided hereinafter.

"Heterologous protein" or "target heterologous protein" indicates the protein that is targeted to be mass-produced by those in the art, precisely every protein that is able to be expressed in a transformant by a recombinant expression vector containing a polynucleotide encoding the target protein.

"Fusion protein" indicates the protein with the addition of another protein or another amino acid sequence in the N-terminal or the C-terminal of the native heterologous protein.

"Signal sequence" indicates the sequence that is involved in efficient directing of a heterologous protein expressed in a virus, a prokaryotic cell or a eukaryotic cell to the periplasm or outside of cells by helping the protein to pass through the cytoplasmic membrane. The signal sequence is composed of the positively charged N-region, the central characteristic hydrophobic region and the C-region with a cleavage site. A signal sequence fragment used in the present invention indicates a part of either one of up to the positively charged N-region, up to the central characteristic hydrophobic region and up to the C-region with a cleavage site or a whole signal sequence.

"Polypeptide" herein indicates the multimer molecule in which at least two amino acids are linked by peptide bond and a protein is also considered as one of the polypeptide.

"Polypeptide fragment" indicates the polypeptide sequence which is in a minimum length or longer with keeping the polypeptide function. If not mentioned otherwise, the polypeptide fragment herein does not include a full-length polypeptide. For example, 'the polypeptide fragment containing an N-region of the signal sequence' of the invention indicates a shortened signal sequence functioning as a signal sequence but not a whole signal sequence.

"Polynucleotide" indicates the multimer molecule in which at least two nucleic acids are linked by phosphodiester bond and both DNA and RNA are included.

"Artificial signal peptide" indicates a non-occurring signal peptide in nature and one is manufactured by genetic recombination.

"Secretional enhancer" indicates the hydrophilic polypeptide composed of hydrophilic amino acids increasing hydrophilicity of the signal sequence.

"N-region" indicates the strong base sequence located at the N-terminal which is well-preserved in general signal sequences and composed of 3-10 amino acids, depending on a signal sequence.

"Central specific hydrophobic region" indicates the region next to an N-region in the general signal sequence structure which is highly hydrophobic by comprising multiple hydrophobic amino acids.

"Modified signal sequence" indicates not a whole signal sequence but the N-region thereof or the polypeptide in which a secretional enhancer is linked to an N-region or a truncated hydrophobic signal peptide comprising an N-region and central specific hydrophobic region or the polypeptide with the addition of a recognition site of a protease in addition to the above.

"Signal sequence fragment" or "truncated signal sequence" indicates the part of a signal sequence. If not mentioned otherwise herein, this fragment indicates the fragment excluding the C-terminal region from the signal sequence.

The present invention is described in more detail hereinafter.

The present inventors constructed pET-22b(+)[omp-ASP( )-7×mefp1*] clone by PCR using the template presented in FIG. 2 by the fusion of the 5'-end of 7×mefp1 encoding a heterologous protein with the coding sequence of a region from OmpASP$_{1-3}$, the part of a signal sequence OmpA inducing secretion in *E. coli*, to the whole coding sequence of OmpASP$_{1-23}$ (see Table 1). The constructed vector clone was transformed into *E. coli* BL21(DE3) and the expression of a target protein was induced for 3 hours using IPTG. As a result, the clones constructed above all expressed soluble recombinant Mefp1 in *E. coli* (see Table 1 and FIG. 3)

A signal sequence has the arrangement of a positively charged N-region starting from Met, a central characteristic hydrophobic region and a C-region ending with a cleavage site. The signal sequence regulates folding of a precursor protein and plays a key role in protein secretion (Izard et al., Biochemistry 34:9904-9912, 1995; Wickner et al., Annu. Rev. Biochem. 60:101-124, 1991).

As of today, pI value, hydrophobicity, molecular weight and stability of a whole protein have been known as critical factors affecting the expression of a recombinant protein in soluble form. The present inventors prepared modified signal sequences and investigated pI values from the whole and a part of a signal sequence OmpASP, which is from OmpASP$_{1-3}$, to the whole OmpASP$_{1-23}$. As a result, pI values of them were all 10.55, regardless of the lengths of them (Table 2). All clones were treated with IPTG for 3 hours to induce the expression of a soluble target protein and the result showed that they all produced soluble Mefp1, regardless of the length of OmpASP (see FIG. 3). The above result indicates that not hydrophobicity but high pI value acts as a directional signal for the expression of soluble Mefp1 not only in a part of OmpASP but also in the whole OmpASP. This result also indicates that the positively charged N-region alone can express nascent polypeptide chains in soluble form, which was the astonishing founding first made by the present inventors. The N-region of a signal sequence happens to contain glutamic acid or aspartic acid instead of a positively charged basic amino acid, and in this case, pI value might be up to 4. Even so, the N-region can be used as a directional signal sequence. The preferable pI value of the modified signal sequence is at least 8 and more preferably at least 9 and most preferably at least 10.

In the present invention, *E. coli* originated OmpA signal sequence was used, but signal sequences having a OmpA signal sequence-like structure such as CT-B (cholera toxin subunit B) signal sequence, LT-B (*E. coli* heat-labile enterotoxin B subunit) signal sequence, BAP (bacterial alkaline phosphatase) signal sequence (Izard and Kendall, Mol. Microbiol. 13:765-773, 1994), Yeast carboxypeptidase Y signal sequence (Blachly-Dyson and Stevens, J. Cell. Biol. 104: 1183-1191, 1987), *Kluyveromyces lactis* killer toxin gamma subunit signal sequence (Stark and Boyd., EMBO J. 5(8): 1995-2002, 1986), bovine growth hormone signal sequence (Lewin, B. (Ed), GENES V, p 290. Oxford University Press, 1994), influenza neuraminidase signal-anchor (Lewin, B. (Ed), GENES V, p 297. Oxford University Press, 1994), Translocon-associated protein subunit alpha (TPAP-α) (Prehn et al., Eur. J. Biochem. 188(2): 439-445, 1990) signal sequence and Twin-arginine translocation (Tat) signal sequence (Robisnon, Biol. Chem. 381(2): 89-93, 2000) can also be used. In addition, any other virus, prokaryote and eukaryotic signal sequences and leader sequences having a similar structure to that of the above can be used. All of the above sequences have high hydrophobicity.

To produce a recombinant fusion protein, the C-terminal of the modified signal sequence region having a protease recognition site provides a site for the fusion of a heterologous protein. Once a recombinant protein is expressed, it is treated with a protease, leading to the recovery of a native form of the heterologous protein. Based on the above results, the present inventors designed to fuse the recognition site of factor Xa protease, for cutting the C-terminal end of the recognition, to OmpASP$_{1-8}$ and constructed pET-22b(+) (ompASP$_{1-8}$-Xa-7×mefp1*) clone by PCR using 7×mefp1 as a template (FIG. 2) and the expression of the clone in E. coli was investigated (Table 1). As a result, the clone produced a soluble protein. It was further confirmed that the modified signal sequence used as a directional signal sequence was eliminated by treating with the protease factor Xa and the native form of Mefp1 was obtained (see FIG. 4).

The recognition site of factor Xa protease used in the present invention has preferably the sequence of Ile-Glu-Gly-Arg.

The recognition site of factor Xa protease used in the present invention has preferably the sequence of Ile-Glu-Gly-Arg (SEQ ID NO: 273).

The recognition site of protease of the invention is preferably selected from a group consisting of factor Xa protease, enterokinase (Asp-Asp-Asp-Asp-Lys, SEQ ID NO: 274) genenase I (His-Tyr) and furin (Arg-X-X-Arg, SEQ ID NO: 275).

The present inventors investigated the functions of the native form of protein recovered from the expressed recombinant. Adhesive property of the recombinant Mefp1 was tested. As a result, the recombinant Mefp1 had excellent adhesive property, compared with the control BSA (see FIG. 5). Therefore, the production method of a recombinant protein of the present invention was confirmed to be effective in production of a heterologous protein in soluble native form without damaging the functions thereof.

To investigate the effect of the modified signal sequence in any other regions than OmpASP fragment on soluble Mefp1 expression, the present inventors selected a SmaI site for cloning blunt-end DNA fragments conveniently, designed the signal sequence as OmpASP$_{1-8}$-SmaI-Xa, and constructed pET-22b(+)(ompASP$_{1-8}$-SmaI-Xa-7×mefp1*) clone with PCR (see Table 1). A clone with the insertion of an amino acid having a high pI and hydrophilicity such as Arg or Lys in the SmaI site was also constructed. The clone containing the amino acid having a high pI and hydrophilicity was also confirmed to express a recombinant Mefp1 and in fact the secretion thereof was somewhat increased.

In another experimental embodiment, olive flounder Hepcidin I was not expressed as a soluble fusion protein by OmpASP$_{tr}$ (see Table 3).

To screen a secretional enhancer, the present inventors designed the signal sequence region as OmpASP$_{1-10}$-( )-Xa and inserted up to 6 homologous sequences of the selected amino acids affecting pI value and hydrophobicity/hydrophilicity, which are 6×Arg, 6×Lys, 6×Glu, 6×Asp, 6×Tyr, 6×Phe, 6×Trp, into the ( ) site (see Table 4). PCR was performed using olive flounder Hepcidin I gene (Kim et al., Biosci. Biotechnol. Biochem. 69:1411-1414, 2005) as a template to construct pET-22b(+)[ompASP$_{1-10}$-( )-Xa-ofhepcidinI**] clone (see Table 3). The clones were tested in E. coli. Those clones having 6×Arg and 6×Lys with high pI and hydrophilicity expressed soluble olive flounder Hepcidin I very strongly, while other clones inserted with other amino acids expressed soluble olive flounder Hepcidin I very weakly (see FIG. 6). The above results suggest that the expression of soluble olive flounder Hepcidin I is associated with high pI values and hydrophilic amino acids Arg and Lys, and therefore proved that Arg and Lys inserted into the C-terminal of a signal sequence acted as a secretional enhancer (see Table 4).

The present inventors further investigated the effect of the modified signal sequence region with the various length of OmpASP fragment in the N-terminal and the various form of -( )-Xa in the C-terminal on hydrophilicity. First, the N-terminal signal sequence OmpASP is prepared in various lengths, which were attached to the C-terminal -6×Arg-Xa, followed by PCR to construct pET-22b(+)[ompASP(-6×Arg-Xa-ofhepcidinI**] (see Table 3). The clones were tested in E. coli. As a result, as the length of the OmpASP sequence decreased, hydrophilicity was increased by the Hopp & Woods scale (Example 6) and the yield of the soluble target protein was increased (see FIG. 7). The Hopp & Woods scale hydropathy profile also revealed that the OmpASP$_{1-6}$-6×Arg-Xa attached with the shortest N-region sequence of OmpASP$_{1-6}$ exhibited only a hydrophilic curve. When the signal sequence longer than OmpASP$_{1-8}$ attached to the -6×Arg-Xa, the resultant signal sequence exhibited a hydrophobic curve in the N-terminal and a hydrophilic curve in the C-terminal, which was resemble with the general transmembrane-like domain. From the above results it was confirmed that the addition of an amino acid with a strong hydrophilicity to the C-terminal of a hydrophobic fragment composed of a basic N-region and central characteristic hydrophobic region results in a transmembrane-like domain structure and when the hydrophilicity in the C-terminal of the signal sequence region is larger than that of transmembrane domain or transmembrane-like domain or amphipathic domain of nascent target polypeptide chains, the nascent target polypeptide chains are able to be expressed in soluble form. This founding was first made by the present inventors, which is astonishing result. Based on the method of the invention, those proteins generally not expressed in soluble form such as membrane proteins can now be expressed in soluble form, which can further contribute to improvement of membrane permeability of various proteins applicable as a biological agent with the increase of drug delivery. In relation to drug delivery, the conventional protein drugs have a common disadvantage of not passing through blood-brain barrier. But, according to the method of the invention, this disadvantage can be overcome, indicating the realization of effective drug delivery. That is, a therapeutic protein (for example, anti-beta-amyloid antibody) for various brain diseases can be directly injected through the blood vessel instead of injecting directly into the cerebral ventricle.

The present inventors set the length of a signal sequence as OmpASP$_{1-10}$ in the N-terminal, attached 2~10 hydrophilic amino acids to the C-terminal of the -( )-Xa region, and followed by PCR to construct the general clone of pET-22b(+)[ompASP$_{1-10}$-( )-Xa-ofhepcidinI**] (see Table 3). The constructed clones were expressed in E. coli. As the amount of hydrophilic amino acids attached to the C-terminal of the signal sequence region (the modified signal sequence), the Hopp & Woods scale hydrophilicity was increased (Example 6), which was paralleled with the increased yield of a soluble target protein (see FIG. 8). According to the Hopp & Woods scale hydropathy profile, every signal sequence expressing a soluble form of a protein exhibited a hydrophobic curve in the N-terminal region and a hydrophilic curve in the C-terminal region, indicating a transmembrane-like domain structure was formed.

So, the modified signal sequence increases hydrophilicity and thereby enables the expression of a target protein in soluble form in the above two cases, suggesting that the Hopp & Woods scale hydrophilicity might be used as indexes for soluble expression of a target protein. pI value of OmpASP fragment originated from the N-region of a signal sequence is closely involved in a directional signal and hydrophilicity level of the -( )-Xa in the C-terminal is important to determine the role of a secretional enhancer. If the length of the N-terminal region is set as OmpASP$_{1-10}$ and the C-terminal region is modified, every signal sequence expressing a soluble protein will exhibit a hydrophobic curve in the N-terminal region and a hydrophilic curve in the C-terminal region, which is a transmembrane domain-like hyperbolic curve. So, the hydropathy profile according to the Hopp & Woods scale can be used as a secondary index.

The hydropathy profile of olive flounder Hepcidin I (without  region) and a signal sequence by Hopp & Woods scale thereof were simulated by using a computer program (see FIGS. 9A-D). The control olive flounder Hepcidin I molecule had an amphipathic domain (FIG. 9A), while the hypothetical signal sequence-olive flounder Hepcidin I fusion protein included two transmembrane-like domains; one in the signal sequence and the other in olive flounder Hepcidin I region (FIGS. 9B, 9C and 9D). The recombinant olive flounder Hepcidin I expressed strongly in soluble form contained a transmembrane-like domain having a higher hydrophilicity in the signal sequence than the amphipathic domain of Hepcidin I (FIG. 9D). The clone pET-22b(+)[ompASP$_{1-10}$-6×Arg-Xa-ofhepcidinI] corresponding to the fusion protein of FIG. 9D was expressed in soluble form (see FIG. 8 lane 4). Therefore, it was confirmed that a signal sequence having a transmembrane-like domain with a higher hydrophilicity than the general transmembrane-like domain of the target molecules is required to express such molecules having one or more of transmembrane domain, transmembrane-like domain or amphipathic domain in soluble form to overcome the barrier. To predict the expression of a soluble target protein, the Hopp & Woods scale hydrophobicity/hydrophilicity and hydropathy profiles can be used as indexes.

Therefore, the method of the present invention can be effectively used for the production of a soluble heterologous protein with a native N-terminal form.

DESCRIPTION OF DRAWINGS

The application of the preferred embodiments of the present invention is best understood with reference to the accompanying drawings, wherein:

FIG. 1 is a schematic diagram illustrating various exemplary embodiments on the expression vector of the invention.

FIG. 2 is a diagram illustrating the sequence of the cloned mefp1 clone, pBluescriptIISK(+)-La-7×mefp1-Ra:
  La (left-adaptor): underlined BamHI/EcoRI/SmaI region;
  Linker: linker DNA (TACAAA);
  Ala Lys Pro Ser Tyr Pro Pro Thr Tyr Lys (SEQ ID NO: 1): a basic unit of Mefp1; and
  Ra (right adaptor): underlined Arg/HindIII/SalI/XhoI region.

FIG. 3A, SDS-PAGE;
FIG. 3B, Western blotting;
  Right upper arrow: recombinant Mefp1;
  Right lower arrow: Mefp1 with OmpA signal sequence (OmpASP) cleavage (matured form with OmpASP1-21 cleavage by OmpA signal peptidase);
  Lane 1: OmpASP$_{1-3}$-7×Mefp1*;
  Lane 2: OmpASP$_{1-5}$-7×Mefp1*;
  Lane 3: OmpASP$_{1-7}$-7×Mefp1*;
  Lane 4: OmpASP$_{1-9}$-7×Mefp1*;
  Lane 5: OmpASP$_{1-11}$-7×Mefp1*;
  Lane 6: OmpASP$_{1-13}$-7×Mefp1*;
  Lane 7: OmpASP$_{1-15}$-7×Mefp1*;
  Lane 8: OmpASP$_{1-21}$-7×Mefp1* (half of OmpASP$_{1-21}$ was cleaved by OmpA signal peptidase but the other half was not since OmpA signal sequence was attached to Mefp1 sequence as some of the sequence was absent); and
  Lane 9: OmpASP$_{1-23}$-7×Mefp1* (OmpASP1-21 was completely cleaved by OmpA signal peptidase because OmpA signal sequence was fully preserved).

FIG. 4A, SDS-PAGE;
FIG. 4B, Western blotting;
  Right upper arrow: recombinant Mefp1(OmpASP$_{1-8}$-Xa-7×Mefp1*);
  Right lower arrow: native form Mefp1(7×Mefp1*);
  Lane 1: non-induced whole cells for 3 h;
  Lane 2: expression-induced whole cells for 3 h;
  Lane 3: expression-induced soluble supernatant fraction for 3 h; and
  Lane 4: Mefp1 with a native N-terminal region produced by treating the three-hour expression-induced soluble supernatant fraction with factor Xa protease.

FIG. 6A, SDS-PAGE;
FIG. 6B, Western blotting;
  Arrow: recombinant of Hepcidin I;
  M: marker;
  Lane 1: control;
  Lane 2: 6×Arg (SEQ ID NO: 282);
  Lane 3: 6×Lys (SEQ ID NO: 283);
  Lane 4: 6×Glu (SEQ ID NO: 284);
  Lane 5: 6×Asp (SEQ ID NO: 285);
  Lane 6: 6×Tyr (SEQ ID NO: 286); and
  Lane 7: 6×Trp (SEQ ID NO: 287).

FIG. 7A, SDS-PAGE;
FIG. 7B, Western blotting;
  Arrow: recombinant of Hepcidin I;
  M: marker;
  Lane 1: pET22b(+)[ompASP($_{1-6}$)-6×Arg-Xa-ofhepcidinI**];
  Lane 2: pET22b(+)[ompASP($_{1-8}$)-6×Arg-xa-ofhepcidinI**];
  Lane 3: pET22b(+)[ompASP($_{1-10}$)-6×Arg-Xa-ofhepcidinI**];

Lane 4: pET22b(+)[ompASP$_{(1-12)}$-6×Arg-Xa-ofhepcidinI**]; and

Lane 5: pET22b(+)[ompASP$_{(1-14)}$-6×Arg-Xa-ofhepcidinI**].

Figure 8A:
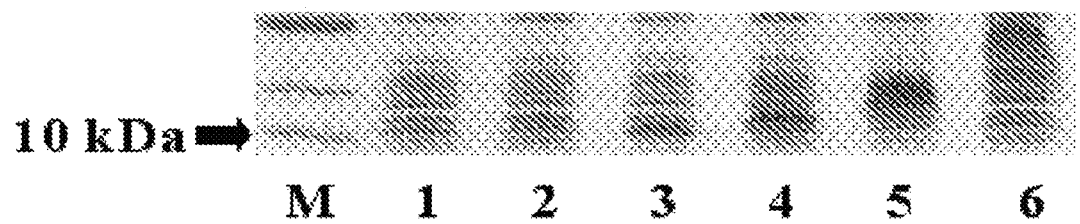
Figure 8B:
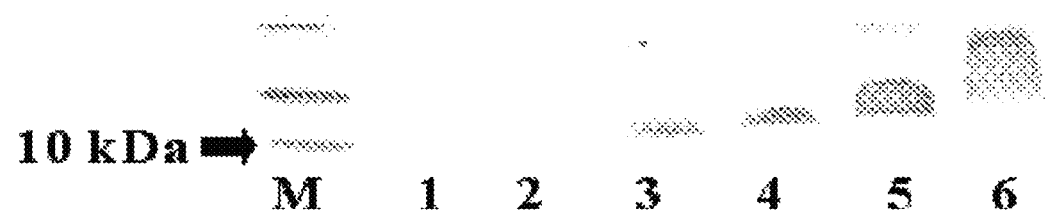

FIGS. 8A and 8B are images illustrating the effect of high pI value and hydrophilic amino acids in a signal sequence on the expression of Hepcidin I. The soluble supernatant fraction was induced with IPTG for 3 hours. Western blotting was performed as described in FIG. 3:

FIG. 8A, SDS-PAGE;
FIG. 8B, Western blotting;
Arrow: recombinant of Hepcidin I;
M: marker;
Lane 1: control; pET22b(+)[ompASP$_{1-10}$-Xa-ofhepcidinI**];
Lane 2: pET22b(+)[ompASP$_{1-10}$-(LysArg)-Xa-ofhepcidinI**];
Lane 3: pET22b(+)[ompASP$_{1-10}$-(4×Arg)-Xa-ofhepcidinI**];
Lane 4: pET22b(+)[ompASP$_{1-10}$-(6×Arg)-Xa-ofhepcidinI**];
Lane 5: pET22b(+)[ompASP$_{1-10}$-(8×Arg)-Xa-ofhepcidinI**]; and
Lane 6: pET22b(+)[ompASP$_{1-10}$-(10×Arg)-Xa-ofhepcidinI**].

Figure 9A:
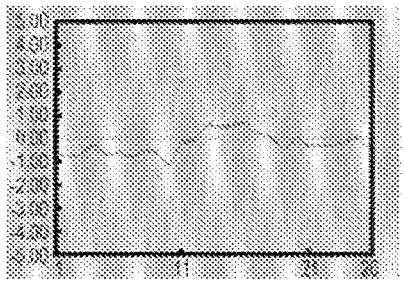
Figure 9B:
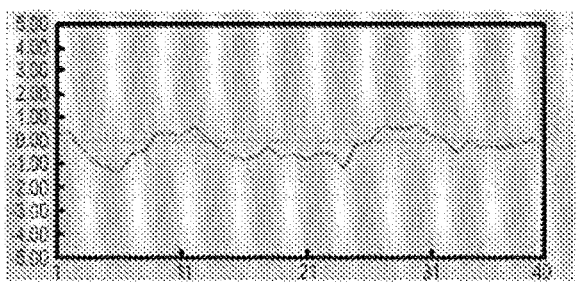
Figure 9C:
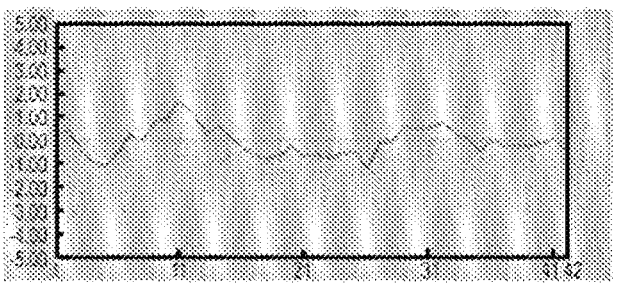
Figure 9D:
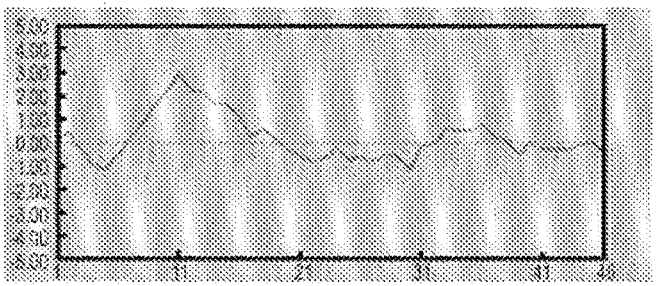

FIGS. 9A-9D are images illustrating the simulated hydropathy profile by the Hopp & Woods scale using a computer program in of Hepcidin I and its variants containing the hydrophilic amino acids in OmpASP$_{1-10}$-( )-Xa:

FIG. 9A, of Hepcidin I (26 aa, Av −0.21);
FIG. 9B, OmpASP$_{1-10}$-Xa-of Hepcidin I (40 aa, Av −0.19);
FIG. 9C, OmpASP$_{1-10}$-LysArg-Xa-of Hepcidin I (42 aa, Av −0.04);
FIG. 9D, OmpASP$_{1-10}$-6×Arg-Xa-of Hepcidin I (46 aa, Av 0.22);
aa: amino acid number; and
Av: hydrophobicity/hydrophilicity average value.

Figure 10A:
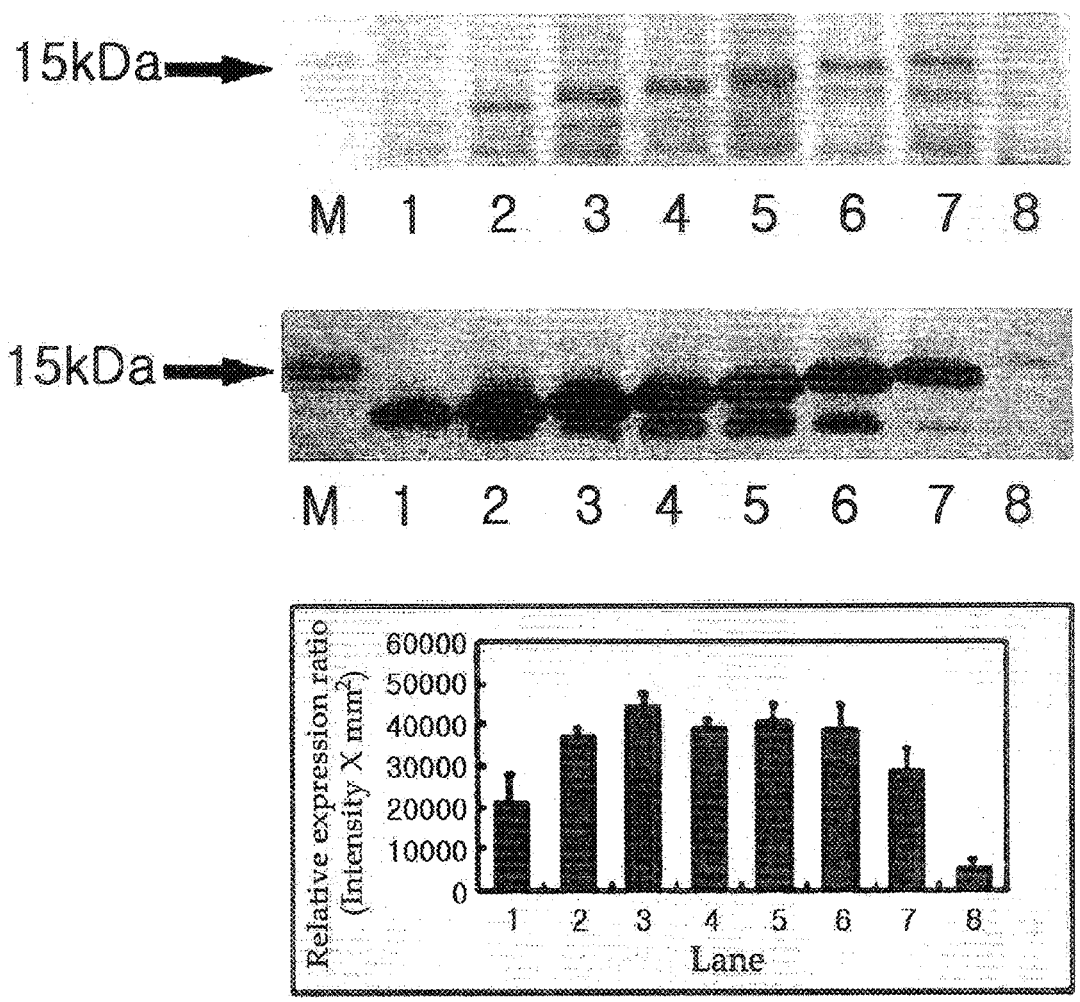

FIGS. 10A and 10B are each a series of panels illustrating the comparative soluble expressions of the adhesive protein Mefp1 (soluble fraction: approximately 20 μg) by the signal sequence OmpASP$_{tr}$ and its variant leader sequences (arrow: recombinant Mefp1). Values obtained from densitometer analysis present the comparative mean values of the expressions of the protein in three different clones:

Top panel, SDS-PAGE;
Middle panel, Western blotting; and,
Bottom panel, densitometer analysis;

FIG. 10A:
M: marker;
lane 1:                                        (SEQ ID NO: 61)
Met-Ala-Lys(pI 9.90);

lane 2:                                        (SEQ ID NO: 62)
Met-Lys-Ala-Lys(pI 10.55);

lane 3:                                        (SEQ ID NO: 63)
Met-Lys-Lys-Ala-Lys(pI 10.82);

lane 4:                                        (SEQ ID NO: 64)
Met-Lys-Lys-Lys-Ala-Lys(pI 10.99);

lane 5:                                        (SEQ ID NO: 65)
Met-Lys-Lys-Lys-Lys-Ala-Lys(pI 11.11);

lane 6:                                        (SEQ ID NO: 66)
Met-Lys-Lys-Lys-Lys-Lys-Ala-Lys(pI 11.21);

lane 7:                                        (SEQ ID NO: 67)
Met-Lys-Lys-Lys-Lys-Lys-Lys-Ala-Lys(pI 11.28);
and, lane 8:                                        (SEQ ID NO: 68)
Met-Lys-Lys-Lys-Lys-Lys-Lys-Lys-Ala-Lys
(pI 11.41).

FIG. 10B:
M: marker;
lane 1:                                        (SEQ ID NO: 61)
Met-Ala-Lys(pI 9.90);

lane 2:                                        (SEQ ID NO: 69)
Met-Arg-Ala-Lys(pI 11.52);

lane 3:                                        (SEQ ID NO: 70)
Met-Arg-Arg-Ala-Lys(pI 12.51);

lane 4:                                        (SEQ ID NO: 71)
Met-Arg-Arg-Arg-Arg-Ala-Lys(pI 12.98);

lane 5:                                        (SEQ ID NO: 72)
Met-Arg-Arg-Arg-Arg-Arg-Ala-Lys(pI 13.20);
and, lane 6:                                        (SEQ ID NO: 73)
Met-Arg-Arg-Arg-Arg-Arg-Arg-Arg-Ala-Lys
(pI 13.35).

Figure 11A:
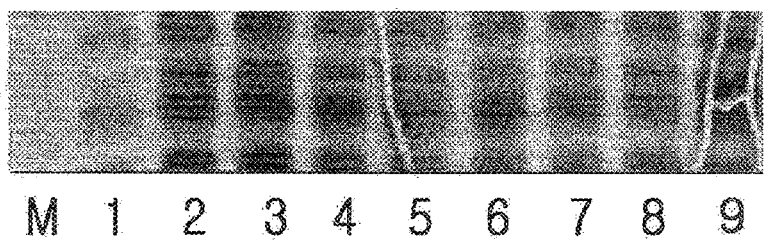
Figure 11B:
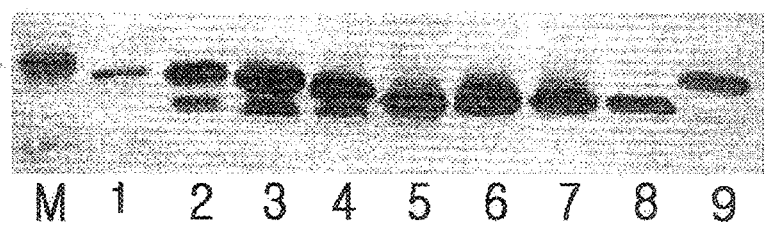
Figure 11C:
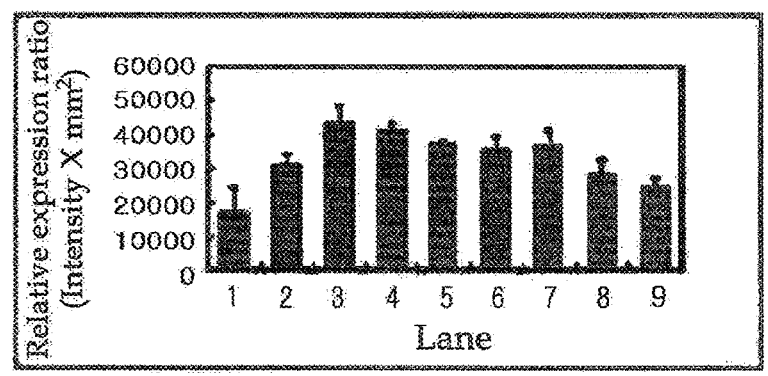

FIGS. 11A-11C are a series of panels illustrating the comparative soluble expressions of the adhesive protein Mefp1 (soluble fraction: approximately 20 μg) by the clones modified in the leader sequence (Met-Ala-Lys, SEQ ID NO: 61) of the recombinant vector pET22b(+)(ompASP$_{1-7}$×mefp1*) (arrow: recombinant Mefp1). Values obtained from densitometer analysis present the comparative mean values of the expressions of the protein in three different clones:

Top panels, SDS-PAGE;
Middle panels, Western blotting; and,
Bottom panels, densitometer analysis;

M: marker;
lane 1:                                        (SEQ ID NO: 81)
Met-Asp-Asp-Asp-Asp-Asp-Ala-Ala(pI 2.73);

lane 2:                                        (SEQ ID NO: 82)
Met-Asp-Asp-Asp-Ala-Ala(pI 2.87);

lane 3:                                        (SEQ ID NO: 83)
Met-Glu-Glu(pI 3.09);

lane 4:                                        (SEQ ID NO: 84)
Met-Ala-Glu(pI 3.25);

lane 5:                                        (SEQ ID NO: 85)
Met-Ala-Ala(pI 5.60);

lane 6:                                        (SEQ ID NO: 86)
Met-Cys-His(pI 7.13);

lane 7:                                        (SEQ ID NO: 87)
Met-Ala-His(pI 7.65);

lane 8:                                        (SEQ ID NO: 61)
Met-Ala-Lys(pI 9.90);
and, lane 9:                                        (SEQ ID NO: 71)
Met-Arg-Arg-Arg-Arg-Ala-Lys(pI 12.98).

Figure 12A:
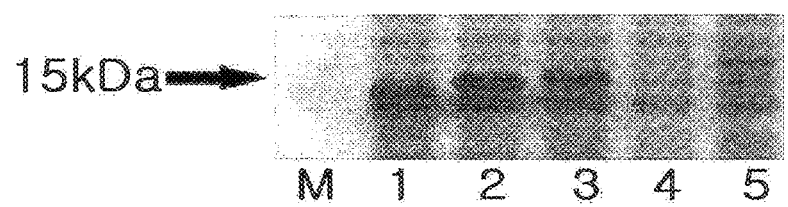
Figure 12B:
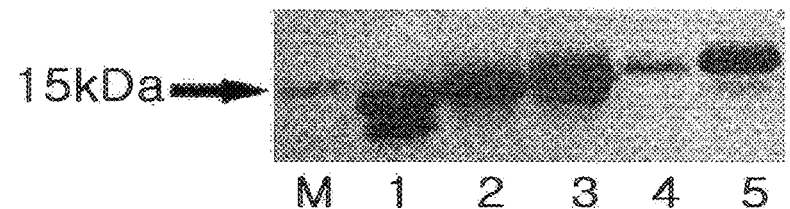

FIGS. 12A and 12B are images illustrating the soluble expression of the recombinant Mefp1 fusion protein (soluble fraction: approximately 20 μg) obtained from the clones having different distances between the leader sequence region Met-Glu-Glu (pI 3.09) and factor Xa recognition site (Xa) (arrow: recombinant Mefp1):

FIG. 12A, SDS-PAGE; and,

FIG. 12B Western blotting;

```
M: marker;
lane 1:                              (SEQ ID NO: 83)
Met-Glu-Glu(pI 3.09);

lane 2:                              (SEQ ID NO: 92)
Met-Glu-Glu-Xa(pI 4.01);

lane 3:                              (SEQ ID NO: 93)
Met-Glu-Glu-Pro-Ser-Xa(pI 4.01);

lane 4:                              (SEQ ID NO: 94)
Met-Glu-Glu-Pro-Ser-Tyr-Pro-Xa(pI 4.01);
and, lane 5:                              (SEQ ID NO: 95)
Met-Glu-Glu-Pro-Ser-Tyr-Pro-Pro-Thr-Xa(pI 4.01).
```

FIGS. 13A and 13B are a series of panels illustrating the soluble expression of the recombinant Mefp1 fusion protein (soluble fraction: approximately 20 µg) obtained from the leader sequence clones designed by modifying the pET-22b (+)[ompASP$_{1-11}$_7×mefp1*](*: Ra-6×His) clone to have different lengths in between Lys-Lys (arrow: recombinant Mefp1):

Top panels, SDS-PAGE; and,

Bottom panels, Western blotting;

FIG. 13A:

```
M: marker;
lane 1:                              (SEQ ID NO: 101)
Met-Lys-Lys-Thr-Ala-Ile-Ala-Ile-Ala-Val-Ala-Ala-
Lys(pI 10.82);

lane 2:                              (SEQ ID NO: 102)
Met-Lys-Lys-Thr-Ala-Ile-Ala-Ile-Ala-Val-Ala-Ala-
Ala(pI 10.55, d₁ = 0 lane 3:                              (SEQ ID NO: 103)
Met-Lys-Ala-Thr-Lys-Ile-Ala-Ile-Ala-Val-Ala-Ala-
Ala(pI 10.55, d₁ = 2);

lane:                                (SEQ ID NO: 104)
Met-Lys-Ala-Thr-Ala-Ile-Lys-Ile-Ala-Val-Ala-Ala-
Ala(pI 10.55, d₁ = 4);

lane 5:                              (SEQ ID NO: 105)
Met-Lys-Ala-Thr-Ala-Ile-Ala-Ile-Lys-Val-Ala-Ala-
Ala(pI 10.55, d₁ = 6);
and, lane 5:                              (SEQ ID NO: 106)
Met-Lys-Ala-Thr-Ala-Ile-Ala-Ile-Ala-Val-Lys-Ala-
Ala(pI 10.55, d₁ = 8.
```

FIG. 13B:

```
M: marker;
lane 1:                              (SEQ ID NO: 63)
Met-Lys-Lys-Ala-Lys(pI 10.82);

lane 2:                              (SEQ ID NO: 144)
Met-Lys-Ala-Thr-Ala-Ile-Lys-Ala-Lys
(pI 10.82, d₁ = 4, d₂ = 1);

lane 3:                              (SEQ ID NO: 145)
Met-Lys-Ala-Thr-Ala-Ile-Lys-Ala-Ala-Lys
(pI 10.82, d₁ = 4, d₂ = 2);

lane 4:                              (SEQ ID NO: 146)
Met-Lys-Ala-Thr-Ala-Ile-Lys-Ala-Ala-Ala-Lys
(pI 10.82, d₁ = 4, d₂ = 3);
and, lane 5:                              (SEQ ID NO: 147)
Met-Lys-Ala-Thr-Ala-Ile-Lys-Ala-Ala-Ala-Ala-Lys
(pI 10.82, d₁ = 4, d₂ = 4).
```

Figure 14A:
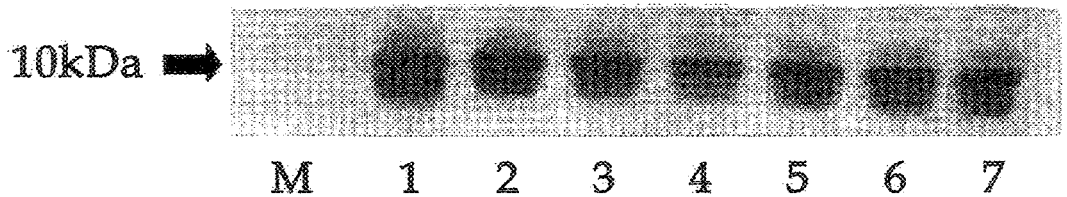
Figure 14B:
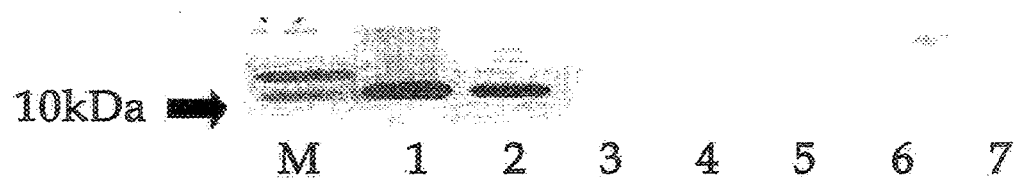

FIGS. 14A and 14B are panels illustrating the effect of the amino acid sequence pI value and hydrophobic value of Met-7×homologous amino acids inserted as a leader sequence to give signaling function and secretion enhancing function on the of Hepcidin I soluble expression (soluble fraction: approximately 20 µg) (arrow: recombinant of Hepcidin I):

FIG. 14A, SDS-PAGE; and,

FIG. 14B Western blotting;

```
M: marker;
lane 1:                              (SEQ ID NO: 114)
MRRRRRRR(pI 13.28, hy +1.97);

lane 2:                              (SEQ ID NO: 115)
MKKKKKKK(pI 11.28, hy +1.97);

lane 3:                              (SEQ ID NO: 116)
MHHHHHHH(pI 8.08, hy -0.35);

lane 4:                              (SEQ ID NO: 117)
MYYYYYYY(pI 5.59, hy -1.55);

lane 5:                              (SEQ ID NO: 118)
MCCCCCCC(pI 4.57, hy -0.69);

lane 6:                              (SEQ ID NO: 119)
MEEEEEEE(pI 2.78, hy +1.97);
and, lane 7:                              (SEQ ID NO: 120)
MDDDDDDD(pI 2.52, hy +1.97).
```

Figure 15A:
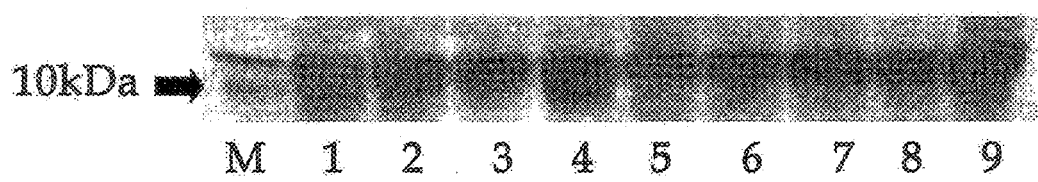
Figure 15B:

FIGS. 15A and 15B are panels illustrating the effects of N-terminal pI value in the leader sequence composed of OmpASP fragment (Met-2 aas)-OmpASP$_{4-10}$-secretional enhancer candidate sequence-Xa with the controlled pI value on the secretional enchancer sequence and the soluble expression (soluble fraction: approximately 20 µg)(arrow: recombinant of Hepcidin I):

FIG. 15A, SDS-PAGE; and,

FIG. 15B, Western blotting

```
M: marker;
lane 1:
MAH(pI 7.65)-OmpASP₄₋₁₀(pI 5.70)-6 × Arg (pI 13.20;
hy +1.75)-Xa(pI 7.05);

lane 2:
MAH-OmpASP₄₋₁₀-6 × Tyr(pI 5.55; hy -1.33)-Xa;

lane 3:
MAH-OmpASP₄₋₁₀-6 × Glu(pI 2.82; hy +1.75)-Xa;

lane 4:
MAA(pI 5.60)-OmpASP₄₋₁₀-6 × Arg-Xa;

lane 5:
MAA-OmpASP₄₋₁₀-6 × Tyr-Xa;

lane 6:
MAA-OmpASP₄₋₁₀-6 × Glu-Xa;

lane 7:
MEE(pI 3.09)-OmpASP₄₋₁₀-6 × Arg-Xa;
``` lane 8:
MEE-OmpASP$_{4-10}$-6 × Tyr-Xa;
and, lane 9:
MEE-OmpASP$_{4-10}$-6 × Glu-Xa.

Figure 16A:
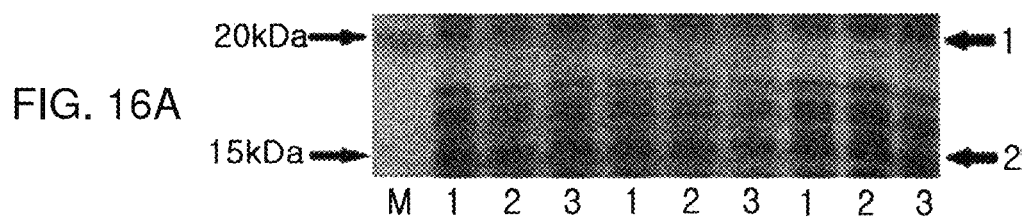
Figure 16B:
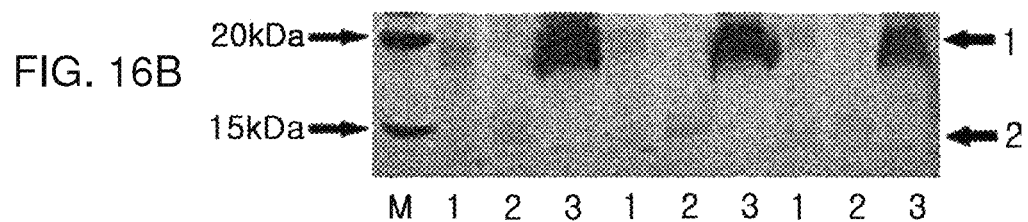
Figure 16C:
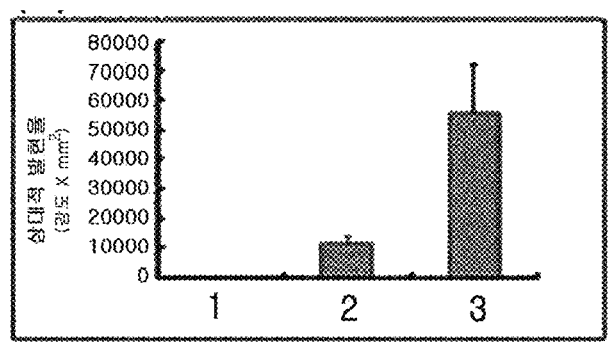
Figure 16D:
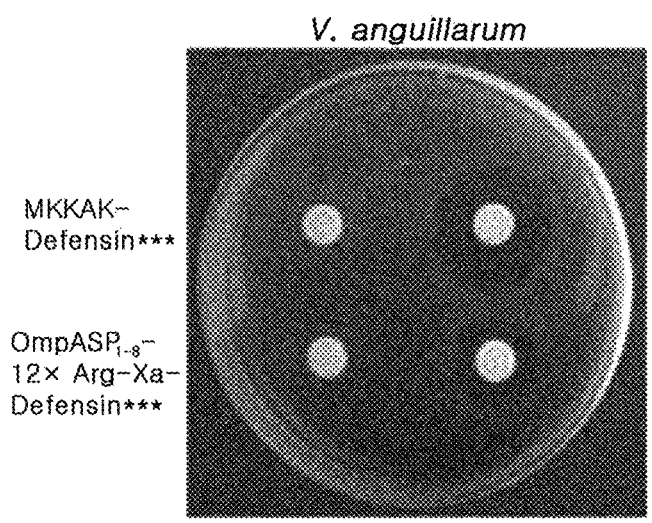

FIGS. 16A-16D are a series of panels showing ofdefensin expression. FIG. 16A is a Coomassie blue staining of cell lysate from transformant transformed with recombinants expression vector containing gene encoding olive flounder defensing like protein under the artificial signal peptide of the present invention; FIG. 16B is a western blot image showing ofdefensin*; FIG. 16C is a densitogram quantifying the result of FIG. 16B; and FIG. 16D is a result of disc diffusion assay for analyzing antimicrobial activity of ofdefensin* produced from the the above transformant (D):

Lane 1: control;
Lane 2: ofdefensin*** produced by PKKAK (SEQ ID NO: 276) as an artificial signal peptide; and
Lane 3: ofdefensin*** produced by OmpASP$_{1-8}$-12×Arg-Xa as an artificial signal peptide.

FIGS. 17A (panels a-e) and 17B are a series of panels showing expression of rMefp1. FIG. 17A is an image of Western blot of rMefp1 solubly expressed by N-terminal leader peptide having various pI value:

(a) M: marker,
1: MAK (SEQ ID NO: 61),
2: MD$_5$AA (SEQ ID NO: 81),
3: MD$_3$AA (SEQ ID NO: 82),
4: MDA (SEQ ID NO: 154),
5: ME$_8$ (SEQ ID NO: 155),
6: ME$_6$ (SEQ ID NO: 156),
7: ME$_4$ (SEQ ID NO: 157),
8: ME$_2$ (SEQ ID NO: 83), and
9: MAE (SEQ ID NO: 84);
(b) M: marker,
1: MAK (SEQ ID NO: 61),
2: MC6 (SEQ ID NO: 158),
3: MC3 (SEQ ID NO: 159),
4: MAC (SEQ ID NO: 160),
5: MAY (SEQ ID NO: 161),
6: MAA (SEQ ID NO: 85),
7: MGG (SEQ ID NO: 162),
8: MAKD (SEQ ID NO: 163), and
9: MAKE (SEQ ID NO: 164);
(c) M: marker,
1: MAK (SEQ ID NO: 61),
2: MCH (SEQ ID NO: 86),
3: MAH (SEQ ID NO: 87),
4: MAH$_3$ (SEQ ID NO: 165),
5: MAH$_5$ (SEQ ID NO: 166),
6: MAKC (SEQ ID NO: 167), and
7: MKY (SEQ ID NO: 168);
(d) M: marker,
1: MAK (SEQ ID NO: 61),
2: MKAK (SEQ ID NO: 62),
3: MK$_2$AK (SEQ ID NO: 63),
4: MK$_3$AK (SEQ ID NO: 64);
5: MK$_4$AK (SEQ ID NO: 65), and
6: MK$_5$AK (SEQ ID NO: 66); and
(e) M: marker,
1: MAK (SEQ ID NO: 61),
2: MRAK (SEQ ID NO: 69),
3: MR$_2$AK (SEQ ID NO: 70),
4: MR$_4$AK (SEQ ID NO: 71),
5: MR$_6$AK (SEQ ID NO: 72), and
6: MR$_8$AK (SEQ ID NO: 73).

FIG. 17B is a graph showing soluble expression curve of rMefp1 at broad pI value range based on the result of Western blot analysis of FIG. 17A.

FIG. 18 is a schematic diagram showing type-II periplasmic secretion pathway at three specific pI ranges, acidic, neutral and basic, predicted from the soluble expression curve of FIG. 17B.

Figure 19A:
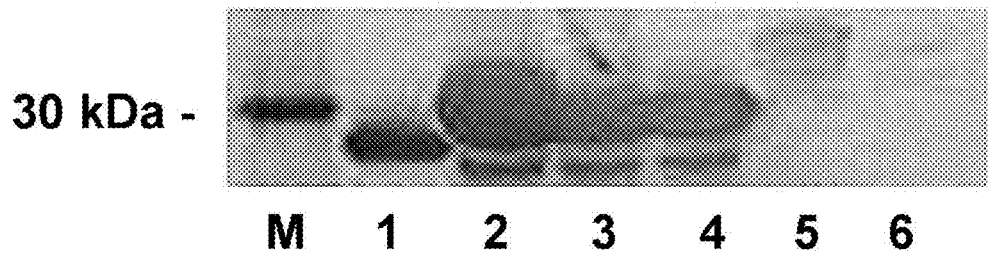
Figure 19B:
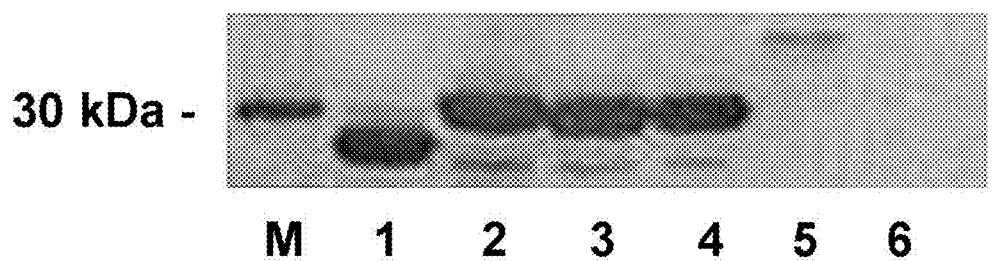
Figure 19C:
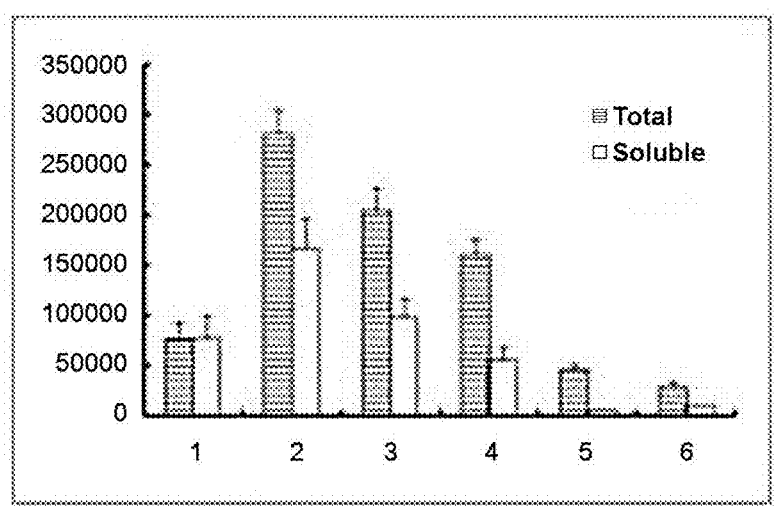

FIGS. 19A-19C is a series of panels of Western blots of whole fraction (FIG. 19A) and soluble fraction (FIG. 19B) of clones transformed with expression vectors having gene constructions sequentially consisting of a polynucleotide encoding various variants of OmpASP$_{1-8}$having modified pI value (Met-(X)(Y)-TAIAI(OmpASP$_{4-8}$)), 8×Arg and a polynucleotide encoding GFP, and a graph (FIG. 19C) showing the result of fluorescent assay of both the fractions:

M: marker,
lane 1:
GFP;

lane 2:                    (SEQ ID NO: 217)
MEE-TAIAI_-8 × Arg-GFP;

lane 3:                    (SEQ ID NO: 218)
MAA-TAIAI-8 × Arg-GFP;

lane 4:                    (SEQ ID NO: 219)
MAH-TAIAI-8 × Arg-GFP;

lane 5:                    (SEQ ID NO: 220)
MKK-TAIAI-8 × Arg-GFP;
and lane 6:                    (SEQ ID NO: 221)
MRR-TAIAI-8 × Arg-GFP.

Figure 20A:
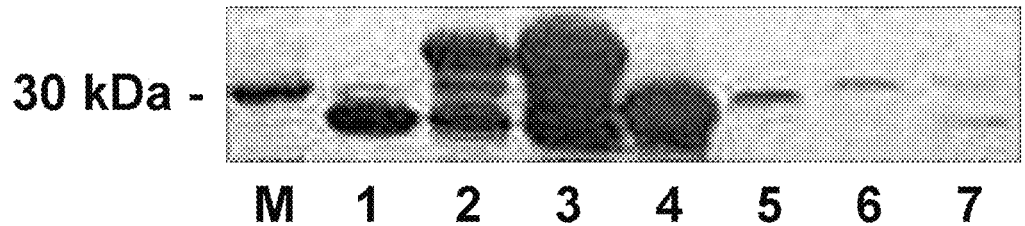
Figure 20B:
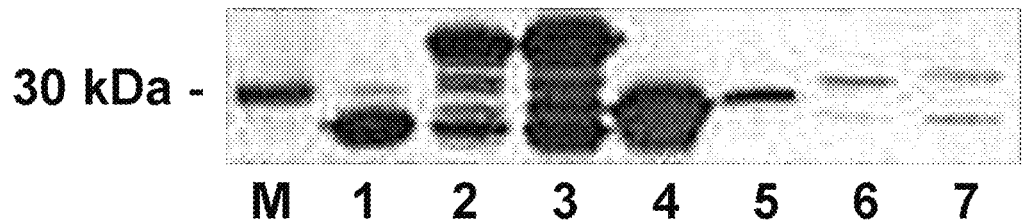
Figure 20C:
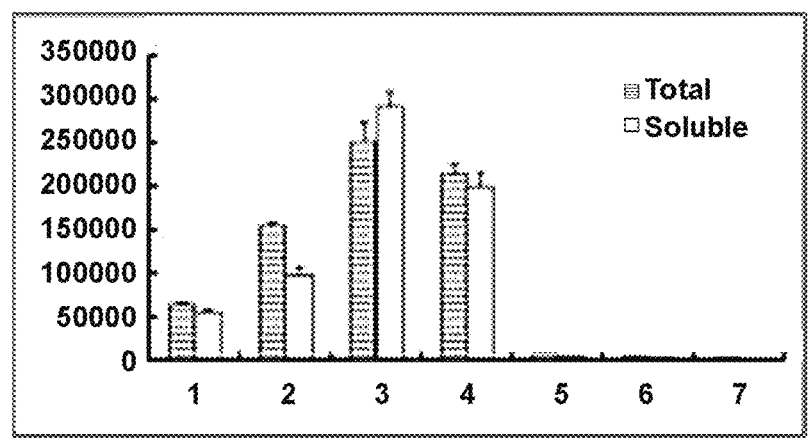

FIGS. 20A-20C are a series of panels of Western blots of whole fraction (FIG. 20A) and soluble fraction (FIG. 20B) of clones transformed with expression vectors having gene constructions sequentially consisting of a polynucleotide encoding various leader peptides and a polynucleotide encoding GFP, wherein the leader peptides consist of homotype acidic or basic hydrophilic amino acids linked to methionine (Met), and a graph (FIG. 20C) showing the result of fluorescent assay of the two fractions:

M: marker;
lane 1:
GFP;

lane 2:                    (SEQ ID NO: 222)
MDDDDDD;

lane 3:                    (SEQ ID NO: 223)
MEEEEEE;

lane 4:                    (SEQ ID NO: 224)
MKKKKKK;

lane 5:                    (SEQ ID NO: 225)
MRRRRRR;

lane 6:                    (SEQ ID NO: 226)
MRRRRRRRRR;
and lane 7:                    (SEQ ID NO: 227)
MRRRRRRRRRRR.

Figure 21A:
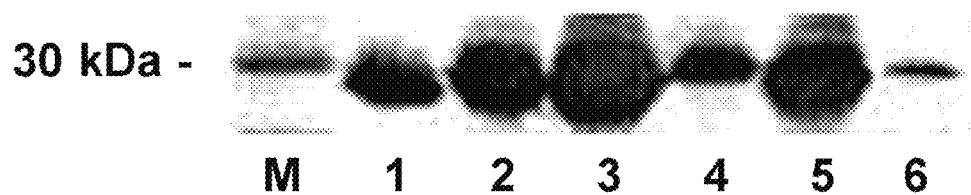
Figure 21B:
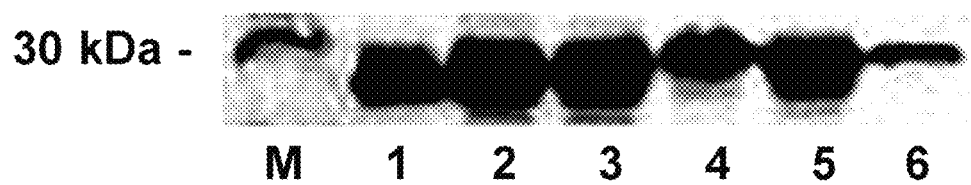
Figure 21C:
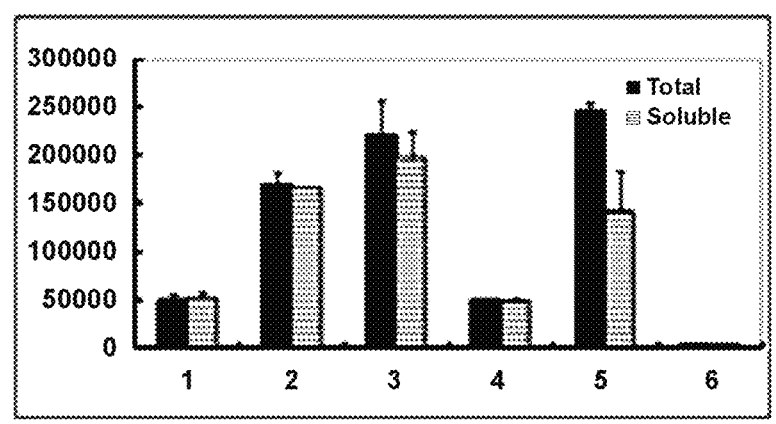

FIGS. 21A-21C are a series of panels of Western blots of whole fraction (FIG. 21A) and soluble fraction (FIG. 21B) of clones transformed with expression vectors having gene constructions sequentially consisting of a polynucleotide encoding various leader peptides and a polynucleotide encoding GFP, wherein the leader peptides consist of homotype and heterotype acidic or basic hydrophilic amino acids linked to methionine and wherein the polynucleotides encoding the leader peptides have various $\Delta G_{RNA}$ value, and a graph (FIG. 21C) showing the result of fluorescent assay of the two fractions:

```
M: marker;
lane 1:
GFP;

lane 2:                                    (SEQ ID NO: 224)
MKKKKKK(Lys^AAA)_6;

lane 3:                                    (SEQ ID NO: 228)
MKKRKKR-I  (Lys^AAA Lys^AAA Arg^CGC)_2;

lane 4:                                    (SEQ ID NO: 229)
MKKRKKR-II (Lys^AAG Lys^AAA Arg^CGC);

lane 5:                                    (SEQ ID NO: 230)
MRRKRRK    (Arg^CGT Arg^CGC Lys^AAA)_2;
and lane 6:                                    (SEQ ID NO: 225)
MRRRRRR    (Arg^CGT Arg^CGC)_3.
```

Figure 22A:
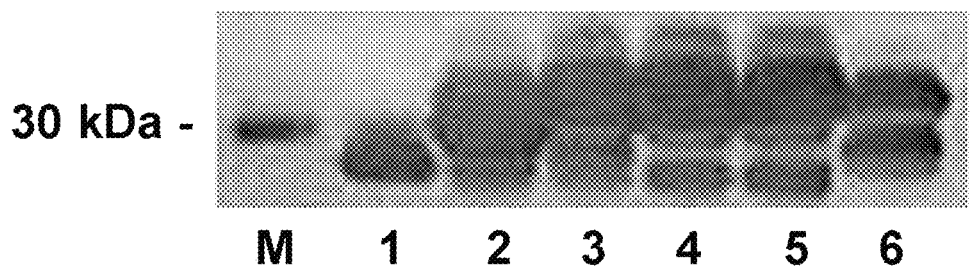
Figure 22B:
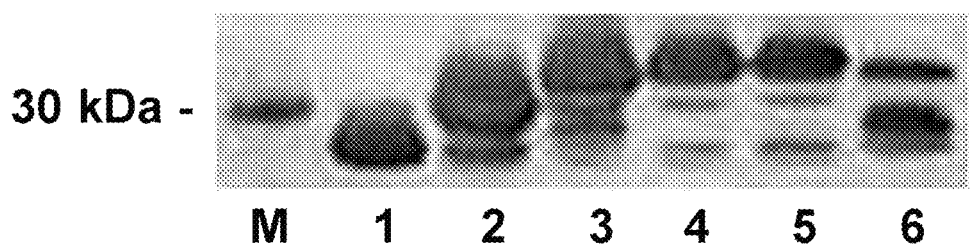
Figure 22C:
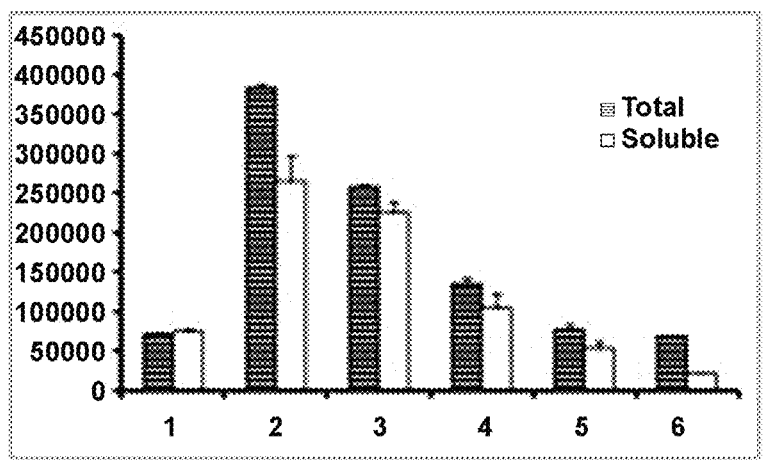

FIGS. 22A-22C are a series of panels of Western blots of whole fraction (FIG. 22A) and soluble fraction (FIG. 22B) of clones transformed with expression vectors having a gene encoding modified GFP, wherein one or more amino acids among the $2^{nd}$ to $5^{th}$ amino acids of the GFP are substituted to glutamate, and a graph (FIG. 22C) showing the result of fluorescent assay of the two fractions:

```
M: marker;
lane 1:                                    (SEQ ID NO: 231)
MVSKGEE (GFP_{1-7}, control);

lane 2:                                    (SEQ ID NO: 232)
MESKGEE (GFP_{1-7}(V2E));

lane 3:                                    (SEQ ID NO: 233)
MEEKGEE (GFP_{1-7}(V2E-S3E));

lane 4:                                    (SEQ ID NO: 234)
MEEEGEE (GFP_{1-7}(V2E-S3E-K4E));

lane 5:                                    (SEQ ID NO: 235)
MEEEEEE (GFP_{1-7}(V2E-S3E-K4E-G5E));
and lane 6:
TorAss-GFP, control.
```

Figure 23A:
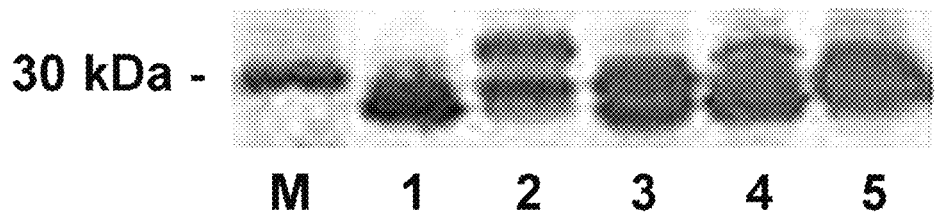
Figure 23B:
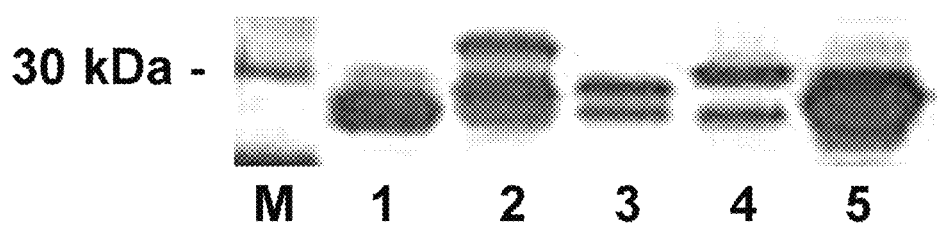
Figure 23C:
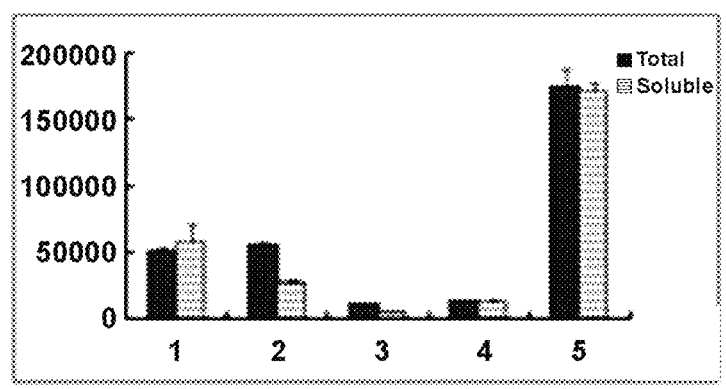

FIGS. 23A-23C are a series of panels of Western blots of whole fraction (FIG. 23A) and soluble fraction (FIG. 23B) of clones transformed with expression vectors having a gene construct sequentially consisting of a polynucleotide encoding a modified OmpA signal sequence whose N-terminal is substituted with a leader peptide, MKKKKKK (SEQ ID NO: 224) which has basic pI and high hydrophilicity, and a graph (FIG. 23C) showing the result of fluorescent assay of the two fractions:

```
M: marker;
lane 1:
                                           (SEQ ID No: 115)
GFP, control;

lane 2:
                                           (SEQ ID No: 120)
TorAss-GFP, control;

lane 3:
                                           (SEQ ID No: 121)
OmpAss_{1-3}-OmpAss_{4-23}-GFP;

lane 4:
                                           (SEQ ID No: 122)
MKKKKKK-OmpAss_{4-23}-GFP;
and lane 5:
                                           (SEQ ID No: 108)
MKKKKKK-GFP.
```

BEST MODE

The present inventors constructed pET-22b(+)(ompASP$_{1-7}$×mefp1*) and pET-22b(+)(ompASP$_{1-2}$-7×mefp1*) clones by the fusion of the coding sequences of OmpASP1 (Met) and OmpASP$_{1-2}$(Met-Lys), which are parts of OmpA signal peptide (OmpASP) that is the signal sequence inducing protein secretion in *E. coli*, to 5' end of 7 ×mefp1 encoding an adhesive protein Mefp1 (see Table 1). *E. coli* BL21 (DE3) was transformed with the constructed clone vectors, followed by expression. As a result, the change of the only one amino acid (Lysine; Lys; K; pI=9.72) made significant difference in soluble expressions of the proteins Met-7×Mefp1* (SEQ. ID. NO: 15) and Met-Lys-7×Mefp1* (SEQ. ID. NO: 16) from the above two clones (see FIG. 1a, line 1 and line 2). So, it was confirmed that Lys that affects the pI value at the N-terminal played an important role in the soluble expression. Then, the sequence ranging from the Met end of OmpASP$_{tr}$ to the second last amino acid Lys (Ala-Lys) of N-terminal was determined as a standard for calculating the pI value of the leader sequence. The pI values from the OmpASP fragment (Met[M] or Met-Lys) to the first two amino acids (Ala-Lys) of the Mefp1proteins were analyzed by using the computer program DNASIS.TM. (Hitachi, Japan). As a result, the pI value of Met-Ala-Lys was 9.90 and the pI value of Met-Lys-Ala-Lys (SEQ ID NO: 62) was 10.55 (see Table 1). To confirm the above results, pET-22b(+)(ompASP$_{1-3}$-7×mefp1*) clone was constructed by the fusion of the coding sequence of the signal sequence fragment OmpASP 1-3 (Met-Lys-Lys) (SEQ. ID. NO: 17) having additional Lys, compared with OmpASP$_{1-2}$, followed by investigation of the soluble expression by the same manner as described above. As a result, the pI value from the OmpASP$_{1-3}$ to the first two amino acids (Ala-Lys) in the leader sequence, which was Met-Lys-Lys-Ala-Lys (SEQ ID NO: 63), was 10.82, which supports the good relation with the increase of the soluble expression (see FIG. 1a, line 3).

To confirm whether or not the control of pI value could affect the soluble protein expression, pET-22b(+)(ompASP$_{1-3}$-Lys$_{n-7}$×mefp1*) clone was constructed by inserting Lys in between the OmpASP$_{1-3}$ fragment and the first amino acid Ala of Mefp1 to increase pI value. And pET-22b(+) (ompASP1-Arg$_{n-7}$×mefp1*) clone was also constructed by inserting Arg in between Met(OmpASP1) and the first amino acid Ala of Mepf1 to increase pI value. The pI values from the N-terminal to the first two amino acids (Ala-Lys) of Mefp1 of the above proteins were analyzed (see Table 5). *E. coli* BL21 (DE3) was transformed with the constructed clone vectors, followed by expression. The expression was compared with the expressions of the proteins Met-7×Mefp1*, Met-Lys-7× Mefp1* and Met-Lys-Lys-7×Mefp1* (SEQ. ID. NO: 17). As a result, the soluble expression of the protein in which the pI value was increased by the additional Lys to 10.99-11.21 was similar to the control with the pI value of 10.55 (see FIG. 10, line 4-line 6), but the reducing expression started from the pI value of 11.28 (see FIG. 1, line 7). Particularly, when the pI value was 11.41 (SEQ. ID. NO: 22), the expression was significantly reduced (see FIG. 1, line 8). The above results indicate that the pI value is specifically involved in membrane permeability when the pI value of the leader sequence is 10.55 or up. When the pI value of the leader sequence is increased by Lys to 10.82-11.41, that is the leader sequence has additional Lys which is OmpASP$_{1-3}$-Lys$_n$Ala-Lys, the sequence is expected to have equal transmembrane channel to OmpASP with the pI value of 10.55.

The soluble expressions of the proteins with the pI values of 11.52-13.35 increased by addition of Arg were reduced as the pI value increased, except that the expression was slightly increased when the pI value of the leader sequence linked to two Args was 12.51. And the expression was significantly reduced when the pI value was 13.35 (see Table 1 and FIG. 1b). In the case of Arg, the reduced molecular weight of the region where two Args were linked (see FIG. 1b, line 3) was presumably resulted from the cleaving of a part of the leader sequence by protease. So, it was presumed that the leader sequences containing additional Arg in their sequence OmpASP$_1$-Arg$_n$-Ala-Lys commonly had Arg specific membrane permeability. However, interrelation between Arg specific membrane permeability mechanism and the signal sequence of TAT (twin-arginine translocation) system (Berks, Mol. Microbiol. 22:393-404, 1966) is not explained herein.

To investigate the effect of the N-terminal of the leader sequence with the low-controlled pI value on the soluble expression of a target protein, pET-22b(+)(ompASP$_{1-7}$× mefp1*) was used as the control and Ala-Lys of the leader sequence Met-Ala-Lys were differently modified to regulate the pI values to 2.73-7.65 (SEQ. ID. NO: 35- NO: 41), resulting in the construction of the leader sequence variants (MDDDDDAA (SEQ ID NO: 81); pI2.73, MDDDAA (SEQ ID NO: 82); pI2.87, MEE (SEQ ID NO: 83); pI3.09, MAE (SEQ ID NO: 84); pI3.25, MAA (SEQ ID NO: 85); pI5.60, MCH (SEQ ID NO: 86); pI7.13, MAH (SEQ ID NO: 87); pI7.65) (see Table 2), followed by investigation of their expressions. As a result, the soluble expression of the adhesive protein Mefp1 was similar or higher than that of the control with the pI value of 9.90, when the pI values were 2.87-7.65. In particular, the expression was the highest when the pI value was 3.09 (SEQ. ID. NO: 37) (see FIG. 2, line 3). The expression pattern was as follows: There were two kinds of expressions (Asp/Glu specific expression at the pI value 2.73-3.25 and moderate increase of the expression at the pI value of 3.25-9.90). So, it was confirmed that there were two different spectrums in the soluble expression of the adhesive protein Mefp1 induced by the pI value of N-terminal in the leader sequence with down-controlled pI. That is, the pI value control of N-terminal affects the soluble protein expression. The leader sequence N-terminal variants, MAA(pI5.60)(SEQ. ID. NO: 85), MCH(pI7.13) (SEQ. ID. NO: 86) and MAH(pI7.65) (SEQ. ID. NO: 87), are the sequences having weak interrelation with electric charge. In that short sequence of the variants, it is unlikely that a secretional enhancer is located which is described in Korean Patent Publication No. 10-2007-0009453. Therefore, the expression is regulated by the pI value of the leader sequence N-terminal variant. As described hereinbefore, the expressions of the adhesive protein Mefp1 having high+charge in the leader sequence expressed from pET-22b (+) (ompASP 1-3-Lys$_{n-7}$×mefp1*) or pET-22b (+) (ompASP1-Arg$_{n-7}$×mefp1*) and the adhesive protein Mefp1 having strong-charge in the leader sequence MDDDDDAA (SEQ. ID. NO: 81) were not related with electric charge.

Based on the above results, the pI-dependent soluble expression patterns were investigated. In the case of the soluble expression of the adhesive protein Mefp1 at high pI, (1) Lys specific membrane permeation mechanism is involved at around the pI value of 10.82 (9.90-11.41), and (2) Arg specific membrane permeation mechanism is involved at around the pI value of 12.51 wherein have the Arg (11.52-13.35). In the wide low range of pI (2.73-9.90), (3) Asp/Glu specific membrane permeation mechanism is involved at the low pI value (2.73-3.25) and (4) comparatively non-specific membrane permeation mechanism is involved at the pI value of 3.25-9.90. Accordingly, it is presumed that the leader sequence with the high pI value has Lys specific OmpASP Sec system (pI 9.90-11.41) and Arg specific membrane permeation mechanism (pI 11.52-13.35), the leader sequence with the wide low range of pI (pI 2.73-9.90) has Asp/Glu specific membrane permeation mechanism (pI 2.73-3.25, optimum pI: 3.09) and has comparatively non-specific membrane permeation, a kind of passive membrane permeation mechanism without the central point pI value in the range of 3.25-9.90. The above four membrane permeation mechanisms had no relationship with the expression and the increase of electric charge. So, the result of the analysis of interrelation between the pI value and the membrane permeability of a protein can be effectively used for the further studies on the expression of a soluble recombinant protein based on the membrane permeation mechanism.

The leader sequences exhibiting low expression rates at the high pI value of 11.41 and 13.35 (SEQ. ID. NO: 22 and SEQ. ID. NO: 27) had comparatively high hydrophilic value of 1.93, and the leader sequence (SEQ. ID. NO: 35) exhibiting low expression rate at the low pI value of 2.73 also had comparatively high hydrophilic value of 1.09. The significantly increased hydrophilicity in the leader sequence might result in the decrease of membrane permeability by inducing the binding of the hydrophilic transmembrane like domain with the lipid bilayer membrane, which is consistent with the hypothesis proposed in the earlier patent application (Korean Patent Publication No. 10-2007-0009453) saying that the hydrophilic transmembrane like domain inhibits the soluble expression of olive flounder Hepcidin I. However, when Lys is added, hydrophilicity of the leader sequence (SEQ. ID. NO: 18-21) can be offset to some degree, even though the leader sequence still has high hydrophilicity. So, It is very interesting that the addition of Lys leads to the increase of membrane permeability.

From the investigation of the expression increased by MEE (pI 3.09) (SEQ. ID. NO: 83), one of the optimum pI for the leader sequence of the adhesive foreign protein Mefp1 was judged to be 3.09. To optimize the distance between the leader sequence variant and a foreign protein linked thereto and to produce a protein having the native amino terminal, factor Xa recognition site (Xa) was inserted into the sequence, resulting in MEE(i=n)-Xa, and the amino acid of OmpASP$_{4-9}$ not affecting the pI value was inserted into the ( )s insert(i)=n(0, 2, 4, 6). As a result, pET-22b(+)(MEE-(i=n)-Xa-7×mefp1*) was constructed (see Table 3). When no amino acids were inserted in between MEE (SEQ ID NO: 83) and Xa, and when two amino acids were inserted therein, the expression of a soluble protein was the highest (see FIG. 3). That is, the distance between the leader sequence and the factor Xa recognition site was the optimum when i=0–2. The soluble protein herein contains a factor Xa recognition site, so that it can be produced as a recombinant protein having the native form of N-terminal by treating factor Xa protease according to the conventional method known to those in the art.

Figure 4A:
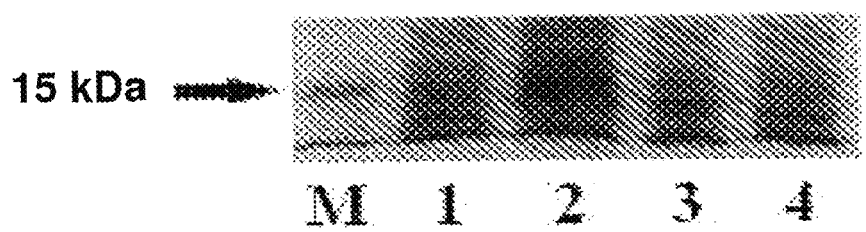
FIGS. 4A and 4B are images illustrating the expression of the soluble recombinant Mefp1 protein produced from the clone pET-22b(+) (ompASP$_{1-8}$-Xa-7×mefp1*) (*: Ra-6× His) and 7×Mefp1* with a native form of amino acid terminus.
Figure 4B:
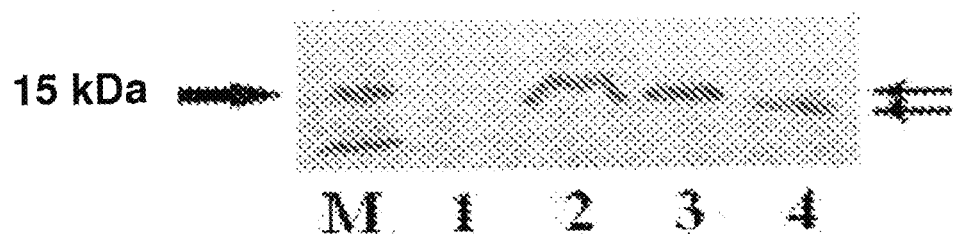

After confirming that the pI value of N-terminal of signal sequence could affect the soluble expression of the adhesive protein Mefp1, the present inventors tried to confirm whether or not the distance of pI affecting amino acids (for example Lys) could be an element affecting the soluble expression of the protein. In N-terminal of a protein, the leader sequences MKAK (SEQ ID NO: 62) and MKK (SEQ ID NO: 265) have same pI values, but when two Lys-Lys are distant because of the insertion of a none pI specific amino acid such as Ala (Alanine; A) in between Lys-Lys, there might be difference in functions. So, based on the amino acid sequence of the signal sequence OmpASP fragment, MK1-(d=n)-K2-(8-n) was constructed and amino acids of OmpASP$_{1-11}$ not affecting the pI value were inserted into ( )as d1=n(0, 2, 4, 6, 8), resulting in the construction of pET.sup.-22b(+)[MK1-(d1=n)-K2-(8-n)-AA-mefp13-10-6.ti-mes.mefp1*] clone (see Table 4). As a result, when d1=4, indicating the distance between two Ks (d1=distance of K1-K2) was 4, the expression of the soluble protein was most significant (see Table 4 and FIG. 4a). That is, the distance of amino acids was optimized when d1=4. Additionally, when d1=4, Ala (underlined part) of the clone was substituted with Lys(K3) and Ala (d2=n(1, 2, 3, 4) was inserted in between K2 and K3, resulting in the construction of pET-22b(+)[MK1-(d1=4)-K2-(d2=n)-AK3-mefp13-10-6×mefp1*] (see Table 4). As a result, the optimum distance between two Ks (d2=distance of K2-K3) was d2=2>1>4>3. These results indicate that the distance is directly related to the soluble expression of an adhesive protein Mefp1. The above results also suggest that the important factor in the expression is not the sequence but the pI value and the distance between Lys-Lys in the leader sequence (see Table 4and FIG. 4b).

As shown in FIG. 1a line 1, the adhesive protein Mefp1 is the protein that is able to be soluble-expressed by attaching only Met of a signal sequence to N-terminal of the protein. The soluble expression of the adhesive protein Mefp1 can be increased by regulating the pI values of the signal sequence and the leader sequence, and the distance between the pI specific amino acids. Olive flounder Hepcidin I protein contains amphipathic domain or transmembrane-like domain. According to Korean Patent Publication No. 10-2007-0009453, this protein could be soluble-expressed only when a secretional enhancer having signal sequence functions and hydrophilicity high enough to offset the internal TM-like domain was added. To soluble-express the olive flounder Hepcidin I protein, the present inventors designed the leader sequence of N-terminal as M-7×homologous amino acids in order to be functioning as a signal sequence and at the same time a secretional enhancer, and then constructed pET-22b(+)(ompASP$_{l-7}$ ×homologous amino acids-ofhep I**) for the expression of the protein having the controlled pI value of 2.52-13.28 and hydrophobicity of -1.55-+1.97 (see Table 5). The homologous amino acid herein was selected from the group consisting of arginine (Arg; R), lysine (Lys, K), histidine (His; H), tyrosine (Tyr; Y), cysteine (Cys; C), glutamic acid (Glu; E) and aspartic acid (Asp; D), which was supposed to have 7 repeats. The hydrophobicity was measured by DNASIS.TM. (Hitachi, Japan) as Hopp & Woods scale (window size: 6, threshold: 0.00). If the hydrophobicity value is +, it means the peptide is hydrophilic, while if the hydrophobicity value is –, the peptide is hydrophobic. At this time, as the absolute value increases, hydrophilicity or hydrophobicity increases. The expressions of those proteins were investigated. As a result, the soluble expression of Hepcidin I was observed only in those clones having MRRRRRRR sequence (pI 13.28, hydrophilicity value +1.97) (SEQ. ID. NO: 114) and MKKKKKKK sequence (pI 11.28, hydrophilicity value +1.97) (SEQ. ID. NO: 115) (see FIG. 5). These leader sequences retain the high pI value as a signal sequence (MRRRRRRR (SEQ ID NO: 114) and MKKKKKKK (SEQ ID NO: 115)) and the high pI value and high hydrophilicity as a secretional enhancer (RRRRRRR (SEQ ID NO: 277) and KKKKKKK (SEQ ID NO: 278)). This result is consistent with the description of Korean Patent Publication No. 10-2007-0009453 saying that the soluble expression of olive flounder Hepcidin I need the high pI value of the signal sequence and higher hydrophilicity value than that of amphipathic domain or transmembrane-like domain included in the sequence. However, in spite of similar sequences to those leader sequences (MRRRRRRR (SEQ ID NO: 114) and MKKKKKKK (SEQ ID NO: 115)), MKK(K)n(n=6)AK (SEQ ID NO: 68) and M(R)n(n=8)AK (SEQ ID NO: 73) sequences could hardly increase the soluble-expression of the adhesive protein Mefp1, compared with MAK, the control. Korean Patent Publication No. 10-2007-0009453 also describes that the soluble secretion of the adhesive protein Mefp1 could be slightly increased by substituting SmaI of pET-22b(+)(ompASP1-8-SmaI-Xa-7×mefp1*) with the nucleotide corresponding to 6×Arg or 6×Lys, but the increase was not as significant as shown in the secretional enhancer sequence of olive flounder Hepcidin I (data not shown). Therefore, it is very difficult to judge whether or not these leader sequences of olive flounder Hepcidin I (MRRRRRRR (SEQ ID NO: 114) and MKKKKKKK (SEQ ID NO: 115)) are functioning as a signal sequence or a secretional enhancer or both (in the case that Met alone is functioning as a leader sequence, pI: 5.70).

To investigate the effect of the low pI value of the modified signal sequence on the soluble expression of olive flounder Hepcidin I, the present inventors prepared the protein in which signal sequence variants (MAH (SEQ ID NO: 87); pI 7.65, MAA (SEQ ID NO: 85); pI5.60 or MEE (SEQ ID NO: 83); pI 3.09), OmpASP$_{4-10}$-6×homologous amino acids and Xa recognition site (Xa) were linked to ofHepI in N-terminal of the protein and then constructed clones for the expression of the protein using the leader sequence having the controlled pI and hydrophobicity/hydrophilicity values (see Table 6). From the results of investigation of the soluble expressions of the clones, it was confirmed that the soluble protein was well expressed in pET-22b(+)[MAH(pI 7.65)-OmpASP$_{4-10}$-6× Arg-Xa-ofHep I] and pET-22b(+)[MAA(pI 5.60)-OmpASP$_{4-10}$-6×Arg-Xa-ofHep I], while the protein expression was weak in pET-22b(+)[MEE(pI 3.09)-OmpASP$_{4-10}$-6×Arg-Xa-ofHep I]However, the soluble expression was moderate in pET-p22b(+)[MEE(pI 3.09) -OmpASP$_{4-10}$-6× Glu-Xa-ofHep I] (see FIG. 6). The above results indicate that the soluble expression of olive flounder Hepcidin I is possibly induced not only in the case that the N-terminal of the protein is designed to have the signal sequence fragment (OmpASP$_{1-10}$) with the high pI value (10.55) and 6×Arg and 6×Lys having the high pI value and high hydrophilicity as a secretion enhancer (Korean Patent Publication No. 10-2007-0009453) but also in the case that the N-terminal of the protein is designed to have the signal sequence fragment with the low pI value and 6×Glu having the low pI value but high hydrophilicity as a secretion enhancer.

By observing the soluble expression of olive flounder Hepcidin I, it was disclosed that the pI value of a signal sequence fragment and the pI value and hydrophilicity of a secretional enhancer sequence are closely related. That is, when the pI value of a signal sequence was 5.60, 7.65 and 10.55, a secretional enhancer comprising amino acids having the high pI value and high hydrophilicity was required, while when the pI value of the signal sequence fragment was as low as 3.09, not only a secretional enhancer comprising amino acids having the high pI value and high hydrophilicity but also another secretional enhancer comprising amino acids having the low pI value but high hydrophilicity could be used. So, it is pretty much likely that the pI value of a signal sequence fragment determines the characteristics of a secretional enhancer such as controlling the pI value and hydrophilicity, and thus the pI value of a signal sequence fragment is closely related to a secretional enhancer.

The above results are limited to the case when a secretional enhancer candidate sequence is directly linked to Met in N-terminal, the soluble expression is induced by Arg and Lys, the amino acids having the high pI value and high hydrophilicity. When the pI value of N-terminal of the signal sequence fragment containing hydrophobic region is controlled, not only the sequence comprising amino acids having the high pI value and high hydrophilicity but also the sequence comprising amino acids having the low pI value but high hydrophilicity, such as Glu, can be used as a secretional enhancer sequence, suggesting that the secretional enhancer sequence has a wide range of usability. So, the range of the hydrophilic secretional enhancer sequence can be expanded by lowering the hydrophilicity of N-terminal by linking a hydrophobic fragment to the N-terminal of the leader sequence with the controlled pI value.

This result also suggests that the pI value of the signal sequence fragment and the pI value of the modified signal sequence fragment have their own spectrum in olive flounder Hepcidin I. The margin of the pI value of the signal sequence fragment affects the functions of a secretional enhancer. So, when the pI value was controlled as low as 3.09 in the signal sequence, the soluble expression of Hepcidin I was induced by 6×Arg functioning as a secretional enhancer having the high pI value and high hydrophilicity and by 6×Glu functioning as another secretional enhancer having the low pI value but high hydrophilicity. At, the other pI values such as 5.60, 7.65, and 10.55, the soluble expression of the protein was induced only by 6×Arg functioning as a secretional enhancer having the high pI value and high hydrophilicity. However, when the pI value of the leader sequence was 3.09, 5.60, and 7.65, as shown in FIG. 2, the pI value was presumed to be involved in membrane permeation process, which was similar to the membrane permeation mechanism induced by the wide pI spectrum of the leader sequence of the adhesive protein Mefp1. However, when the pI value of the leader sequence was 10.55, as shown in FIG. 1, the soluble expression would be controlled by the OmpASP fragment specific pI value.

In conclusion, the pI value of the signal sequence fragment and the pI value of the leader sequence fragment played a critical role in the soluble expression of an adhesive protein Mefp1, but had nothing to do with electrical charge. The present inventors confirmed first the interrelationship between the soluble expression of an adhesive protein Mefp1 and the pI value of the leader sequence. Particularly, the present inventors found out the Lys specific membrane permeation mechanism (pI 9.90-11.41), the Arg specific membrane permeation mechanism (pI 11.52-13.35), the Asp/Glu specific membrane permeation mechanism (pI 2.73-3.25) and the non-specific membrane permeation mechanism (pI 3.25-9.90). However, when the secretional enhancer sequences poly Lys and poly Arg (Korean Patent Publication No. 10-2007-0009453) were linked to the leader sequence of an adhesive protein Mefp1, the expression of the protein was not much increased, suggesting that the binding between the leader sequence and the secretional enhancer does not affect the expression of such proteins which do not contain transmembrane-like domain. The present inventors also confirmed first that the optimum condition for the expression was when the leader sequence is linked to the factor Xa recognition site and when the distance between Lys-Lys in the signal sequence was properly controlled.

In olive flounder Hepcidin I having the transmembrane-like domain, the soluble expression was very weak or impossible only with the pI value of the signal sequence fragment and the pI value of the leader sequence. However, when a secretional enhancer candidate sequence was directly linked to Met, the soluble expression was induced by Arg and Lys having the high pI value and high hydrophilicity, and when the secretional enhancer sequence having the high pI value and hydrophilicity was linked to the signal sequence fragment with the controlled pI so as to have the wide pI spectrum, the soluble expression was induced. When the leader sequence having the low pI value was linked to a secretional enhancer comprising amino acids having the high pI value and hydrophilicity and a secretional enhancer comprising amino acids having the low pI value but high hydrophilicity, the expression was detected as well. This result supports the previous result that the expression of an adhesive protein Mefp1 can be induced in the wide pI spectrums of a signal sequence fragment and the leader sequence. But, secretional enhancer sequences generally need amino acids having the high hydrophilicity regardless of the pI value. Therefore, to induce the soluble expression, hydrophilicity has to be higher than that of the transmembrane-like domain in olive flounder Hepcidin I.

When the pI value of N-terminal of the signal sequence fragment containing a hydrophobic region was changed, the spectrum of the usable secretional enhancer sequence was broadened, compared with when the secretional enhancer candidate sequence was directly linked to Met. This result suggests that the hydrophobic region linked to the signal sequence lowers the hydrophilicity of N-terminal of the leader sequence (the sequence with the controlled pI value in N-terminal of the signal sequence), which makes the leader sequence be functioning freely as an anchor so that range of membrane permeation of the hydrophilic secretional enhancer sequence can be increased. And, it is presumed that there is a certain interaction between the pI value of N-terminal of the leader sequence and the secretional enhancer sequence.

According to an aspect of the present invention, an expression vector for enhancing soluble expression and secretion of bulky folded active heterologous proteins having one or more inherent transmembrane-like domains or intramolecular disulfide bonds, comprising a gene construct consisting of: 1) a promoter; and, 2) a polynucleotide operably linked to the promoter, encoding a leader peptide having N-terminal whose pI value is 2.00 to 9.60 and whose hydrophilicity is 1.00 to 2.00 is provided.

The expression vector may consist of one or more replication origin; one or more selective marker; a gene construct for expression of a heterologous protein consisting sequentially of a promoter, a polynucleotide operably linked to the promoter, encoding a leader peptide having N-terminal whose pI value is 2.00 to 9.60 and whose hydrophilicity is 1.00 to 2.00; and optionally a multicloning site for inserting a polynucleotide encoding the heterologous protein operably. The expression vector may further comprise a transcription terminator operably linked to the gene construct, in order to enhance transcription efficiency. The expression vector may further comprise a polynucleotide corresponding to a protease recognition site operably linked to the gene construct. In addition, the expression vector may further comprise a polynucleotide encoding the heterologous protein operably linked to the polynucleotide encoding the leader peptide or the polynucleotide corresponding to a protease recognition site. Further, the expression vector may contain one or more enhancers if the vector is a eukaryotic vector.

According to an aspect of the present invention, a gene construct consisting of: 1) a promoter; and, 2) a polynucleotide operably linked to the promoter, which encodes a leader peptide having N-terminal whose pI value is 2.00 to 9.60 and whose hydrophilicity is 1.00 to 2.00 is provided.

According to an aspect of the present invention, a method for enhancing soluble expression and secretion of a bulky folded active heterologous protein having one or more inherent transmembrane-like domains or intramolecular disulfide bonds comprising:
  Providing a polynucleotide encoding a leader peptide having N-terminal whose pI value is 2.00 to 9.60 and whose hydrophilicity is 1.00 to 2.00;
  Constructing a gene construct consisting of the polynucleotide and a polynucleotide encoding the bulky folded active heterologous protein having one or more inherent transmembrane-like domains or intramolecular disulfide bonds;
  Constructing a recombinant expression vector by operably inserting the gene construct into an expression vector;
  Producing transformants by transforming host cells with the recombinant expression vector; and,
  Selecting a transformant whose ability for expressing and secreting the bulky folded active heterologous protein is good among the transformants is provided.

According to an aspect of the present invention, a method for producing a bulky folded active heterologous protein having one or more inherent transmembrane-like domains or intramolecular disulfide bonds comprising:
  Providing a polynucleotide encoding a leader peptide having N-terminal whose pI value is 2.00 to 9.60 and whose hydrophilicity is 1.00 to 2.00;
  Constructing a gene construct encoding a fusion protein sequentially consisting of the leader peptide, a protease recognition site and the bulky folded active heterologous protein having one or more inherent transmembrane-like domains or intramolecular disulfide bonds;
  Constructing a recombinant expression vector by operably inserting the gene construct into an expression vector;
  Producing transformants by transforming host cells with the recombinant expression vector; and,
  Culturing the transformants by inoculating culture media with the transformants;
  Isolating the fusion protein; and
  Isolating a native form of the bulky folded active heterologous protein after cleaving the protease recognition site with a protease is provided.

In the expression vector, the gene construct and the method, the promoter may be a viral promoter, a prokaryotic promoter or a eukaryotic promoter. The viral promoter may be cytomegalovirus (CMV) promoter, polioma virus promoter, fowl pox virus promoter, adenovirus promoter, bovine papilloma virus promoter, avian sarcoma virus promoter, retrovirus promoter, hepatitis B virus promoter, herpes simplex virus thymidine kinase promoter, simian virus 40 (SV40) promoter. The prokaryotic promoter may be T7 promoter, SP6 promoter, heat-shock protein (HSP) 70 promoter, β-lactamase promoter, lac operon promoter, alkaline phosphatase promoter, trp operon promoter, or tac promoter. The eukaryotic promoter may be a yeast promoter, a plant promoter, or an animal promoter. The yeast promoter may be 3-phosphoglycerate kinase (PGK-3) promoter, enolase promoter, glyceraldehyde-3-phosphate dehydrogenase promoter, hexokinase promoter, pyruvate decarboxylase promoter, phosphofructokinase promoter, glucose-6-phosphate isomerase promoter, 3-phosphoglycerate mutase promoter, pyruvate kinase promoter, triosephosphate isomerase promoter, phosphoglucose isomerase promoter, glucokinase promoter, alcohol dehydrogenase 2 promoter, isocytochrome C promoter, acidic phosphatase promoter, *Saccharomyces cerevisiae* GAL1 promoter, *Saccharomyces cerevisiae* GAL7 promoter, *Saccharomyces cerevisiae* GAL10 promoter, or *Pichia pastoris* AOX1 promoter. The animal promoter may be heat-shock protein promoter, prolactin promoter or immunoglobulin promoter.

However, any promoters can be used if they normally express heterologous proteins in host cells.

The pI value may be 2.56 to 7.65 or the pI value may be 2.56 to 5.60. Alternatively, the pI value may be 2.73 to 3.25.

The hydrophilicity may be between 1.16 and 1.82. In the meantime, the hydrophilicity may be a value according to Hopp-Woods (Hopp and Woods, *Proc. Natl. Acad. Sci. USA*, 78: 3824-3828, 1981).

The leader peptide may be a variant of a signal peptide fragment, or may have additionally 1 to 30 hydrophilic amino acids linked thereto. The signal peptide fragment may be a peptide in which the $2^{nd}$ and/or the $3^{rd}$ amino acid of N-terminal of the variant is substituted with aspartate (Asp) or glutamate (Glu). The hydrophilic amino acid may be Asp, Glu, glutamine (Gln), asparagine (Asn), threonine (Thr), serine (Ser), arginine (Arg) or lysine (Lys). The variant may be a full-length of the signal peptide or may consist of 2 to 20 amino acids. The variant may consist of 2 to 12 amino acids or 3 to 10 amino acids. The leader peptide may have amino acid sequence of SEQ ID Nos: 101 to 103.

The signal peptide may be a viral signal sequence, a prokaryotic signal sequence or a eukaryotic signal sequence. More particularly, the signal sequence may be OmpA signal sequence, CT-B (cholera toxin subunit B) signal sequence, LTIIb-B (*E. coli* heat-labile enterotoxin B subunit) signal sequence, BAP (bacterial alkaline phosphatase) signal sequence (Izard and Kendall, *Mol. Microbiol.* 13:765-773, 1994), Yeast carboxypeptidase Y signal sequence (Blachly-Dyson and Stevens, *J. Cell. Biol.* 104: 1183-1191, 1987), *Kluyveromyces lactis* killer toxin gamma subunit signal sequence (Stark and Boyd, *EMBO J.* 5(8): 1995-2002, 1986), bovine growth hormone signal sequence (Lewin, B. (Ed), GENES V, p 290. Oxford University Press, 1994), influenza neuraminidase signal-anchor (Lewin B. (Ed), GENES V, p 297. Oxford University Press, 1994), Translocon-associated protein subunit alpha, TRAP-α (Prehn et al., *Eur. J. Biochem.* 188(2): 439-445, 1990) signal sequence, Twin-arginine translocation (Tat) signal sequence (Robinson, *Biol. Chem.* 381 (2): 89-93, 2000).

Alternatively, the leader peptide may be a synthetic peptide having 1 to 30 hydrophilic amino acids linked to the first amino acid, methionine. Alternatively, the synthetic peptide may consist of 3 to 16 amino acids linked to carboxy-terminal of Met, wherein at least 60% of the amino acids are hydrophilic. The hydrophilic amino acids may be homotypic or heterotypic. The hydrophilic amino acids may be selected from a group consisting of Asp, Glu, Gln, Asn, Thr, Ser, Arg, and Lys. In a more particular example, the leader peptide may have an amino acid sequence selected from a group consisting of SEQ ID Nos: 1-22, 106, 107, 116, 117 and 118.

The length of the leader peptide may be 1 to 30 amino acids, 2 to 20 amino acids, 4 to 10 amino acids, or 6 to 8 amino acids.

The protease recognition site may be Xa factor recognition site, enterokinase recognition site, Genenase I recognition site or Furin recognition site or a combination thereof may be used. If a protease to be used is Xa factor, the protease recognition site may be Ile-Glu-Gly-Arg. In addition, between the polynucleotide encoding the leader peptide and the protease recognition site, one to three neutral amino acids such as neutral nonpolar amino acids selected from a group consisting of Gln, Ala, Val, Leu, Ile, Phe, Trp, Met, Cys and Pro or neutral polar amino acids selected from a group consisting of Ser, Thr, Tyr, Asn and Gln may be additionally inserted.

The bulky folded protein may have one or more transmembrane domains, transmembrane-like domains, amphipathic domains or intramolecular disulfide bonds. In an example, the bulky folded protein may be green fluorescent protein (GFP). A heterologous protein having the transmembrane domains, transmembrane-like domains, or amphipathic domains is assumed to be secreted hardly into the periplasm because a region having positive charge may attach to lipid bilayer of membrane and the transmembrane-like domain may play a role as an anchor. In order to secret these unsecretable proteins into the periplasm, the expression vector of the present invention is very effective.

The expression vector is suitable to produce heterologous proteins having transmembrane domain, transmembrane-like domain or amphipathic domain in soluble form. This is assumed that the secretion of expressed heterologous protein is enhanced because the directional force and the effect of high hydrophilicity of a leader peptide is bigger than the force which the domains attach to the lipid bilayer, when the hydrophilicity of the leader peptide of the present invention is bigger than that of the transmembrane domain existing in the heterologous protein.

Further, when the expressed heterologous protein is secreted into the periplasm, the heterologous protein has different secretional pathways according to pI value of N-terminal of the heterologous protein. Particularly, when N-terminal of a heterologous protein has acidic pI value, the heterologous protein is secreted through Tat pathway *E. coli* type-II periplasmic secretion pathway. Although a leader peptide is one which is secreted through other pathways, a bulky folded active heterologous protein linked thereto is secreted through the Tat pathway. Therefore, if a heterologous protein is a bulky protein whose folded form is active, we can enhance secretional efficiency of the heterologous protein by adjusting pI value of the leader peptide to acidic range and selecting Tat pathway thereby (See FIG. 2).

According to an aspect of the present invention, an expression vector for enhancing soluble expression and secretion of bulky folded active heterologous proteins having one or more inherent transmembrane-like domains or intramolecular disulfide bonds, comprising a gene construct consisting of: 1) a promoter; and, 2) a polynucleotide operably linked to the promoter, encoding a leader peptide having N-terminal whose pI value is 9.90 to 13.35 and whose hydrophilicity is 1.00 to 2.50, wherein the polynucleotide has $\Delta G_{RNA}$ value of more than −10.00 is provided. The expression vector may further comprise a transcription terminator operably linked to the gene construct for enhancing transcription efficiency.

The expression vector may consist of one or more replication origin; one or more selective marker; a gene construct for expression of a heterologous protein consisting sequentially of a promoter, a polynucleotide operably linked to the promoter, encoding a leader peptide having N-terminal whose pI value is 9.90 to 13.35 and whose hydrophilicity is 1.00 to 2.50, wherein the polynucleotide has $\Delta G_{RNA}$ value of more than −10.00; and optionally a multicloning site for inserting a polynucleotide encoding the heterologous protein operably. The expression vector may further comprise a polynucleotide corresponding protease recognition site operably linked to the gene construct. In addition, the expression vector may further comprise a polynucleotide encoding the heterologous protein operably linked to the polynucleotide encoding the leader peptide or the polynucleotide corresponding to a protease recognition site. Further, the expression vector may contain one or more enhancers if the vector is a eukaryotic vector.

According to an aspect of the present invention, a gene construct consisting of: 1) a promoter; and, 2) a polynucleotide operably linked to the promoter, encoding a leader peptide having N-terminal whose pI value is 9.90 to 13.35 and whose hydrophilicity is 1.00 to 2.50, wherein the polynucleotide has $\Delta G_{RNA}$ value of more than −10.00 is provided.

According to another aspect of the present invention, a method for enhancing soluble expression and secretion of a bulky folded active heterologous protein having one or more inherent transmembrane-like domains or intramolecular disulfide bonds, the method comprising:

Providing a polynucleotide encoding a leader peptide having N-terminal whose pI value is 9.90 to 13.35 and whose hydrophilicity is 1.00 to 2.50, wherein the polynucleotide has $\Delta G_{RNA}$ value of more than −10.00;

Constructing a gene construct consisting of the polynucleotide and a polynucleotide encoding the bulky folded active heterologous protein having one or more inherent transmembrane-like domains or intramolecular disulfide bonds, wherein the bulky folded active heterologous protein moves into the periplasm as a folded form and has biological activity in the periplasm;

Constructing a recombinant expression vector by operably inserting the gene construct into an expression vector;

Producing transformants by transforming host cells with the recombinant expression vector; and, Selecting a transformant whose ability for expressing and secreting the bulky folded active heterologous protein is good among the transformants is provided.

In the expression vector, the gene construct and the method, the promoter may be a viral promoter, a prokaryotic promoter or a eukaryotic promoter. The viral promoter may be cytomegalovirus (CMV) promoter, polioma virus promoter, fowl pox virus promoter, adenovirus promoter, bovine papilloma virus promoter, avian sarcoma virus promoter, retrovirus promoter, hepatitis B virus promoter, herpes simplex virus thymidine kinase promoter, or simian virus 40 (SV40) promoter. The prokaryotic promoter may be T7 promoter, SP6 promoter, heat-shock protein (HSP) 70 promoter, β-lactamase promoter, lac operon promoter, alkaline phosphatase promoter, trp operon promoter, or tac promoter. The eukaryotic promoter may be a yeast promoter, a plant promoter, or an animal promoter. The yeast promoter may be 3-phosphoglycerate kinase (PGK-3) promoter, enolase promoter, glyceraldehyde-3-phosphate dehydrogenase promoter, hexokinase promoter, pyruvate decarboxylase promoter, phosphofructokinase promoter, glucose-6-phosphate isomerase promoter, 3-phosphoglycerate mutase promoter, pyruvate kinase promoter, triosephosphate isomerase promoter, phosphoglucose isomerase promoter, glucokinase promoter, alcohol dehydrogenase 2 promoter, isocytochrome C promoter, acidic phosphatase promoter, *Saccharomyces cerevisiae* GAL1 promoter, *Saccharomyces cerevisiae* GAL7 promoter, *Saccharomyces cerevisiae* GAL10 promoter, or *Pichia pastoris* AOX1 promoter. The animal promoter may be heat-shock protein promoter, proactin promoter or immunoglobulin promoter.

However, any promoters can be used if they normally express heterologous proteins in host cells.

The pI value may be 10 to 13.2 or 11 to 13.

The hydrophilicity may be adjusted between 1 and 2.5. In the meantime, the hydrophilicity may be a value according to Hopp-Woods (Hopp and Woods, *Proc. Natl. Acad. Sci. USA*, 78: 3824-3828, 1981).

The $\Delta G_{RNA}$ value may be adjusted between −7.6 and 1.6, −5 to 1.0 or −3 to 0.6.

The leader peptide may be a variant of a signal peptide fragment, or may have additionally 1 to 30 hydrophilic amino acids linked thereto. The signal peptide fragment may be a peptide in which the $2^{nd}$ and/or the $3^{rd}$ amino acid of N-terminal of the variant is substituted with aspartate (Asp) or glutamate (Glu). The hydrophilic amino acid may be Asp, Glu, glutamine (Gln), asparagine (Asn), threonine (Thr), serine (Ser), arginine (Arg) or lysine (Lys). The variant may be a full-length of the signal peptide or may consist of 2 to 20 amino acids. The length of the leader peptide may be 1 to 30 amino acids, 2 to 20 amino acids, 4 to 10 amino acids, or 6 to 8 amino acids. In a more particular example, the leader peptide has amino acid sequence of SEQ ID Nos: 104 or 105.

The signal peptide may be a viral signal sequence, a prokaryotic signal sequence or a eukaryotic signal sequence. More particularly, the signal sequence may be OmpA signal sequence, CT-B (cholera toxin subunit B) signal sequence, LTIIb-B (*E. coli* heat-labile enterotoxin B subunit) signal sequence, BAP (bacterial alkaline phosphatase) signal sequence (Izard and Kendall, *Mol. Microbiol.* 13:765-773, 1994), Yeast carboxypeptidase Y signal sequence (Blachly-Dyson and Stevens, *J. Cell. Biol.* 104: 1183-1191, 1987), *Kluyveromyces lactis* killer toxin gamma subunit signal sequence (Stark and Boyd, *EMBO J.* 5(8): 1995-2002, 1986), bovine growth hormone signal sequence (Lewin, B. (Ed), GENES V, p 290. Oxford University Press, 1994), influenza neuraminidase signal-anchor (Lewin B. (Ed), GENES V, p 297. Oxford University Press, 1994), Translocon-associated protein subunit alpha, TRAP-α (Prehn et al., *Eur. J. Biochem.* 188(2): 439-445, 1990) signal sequence, Twin-arginine translocation (Tat) signal sequence (Robinson, *Biol. Chem.* 381 (2): 89-93, 2000).

Alternatively, the leader peptide may be a synthetic peptide having 1 to 30 hydrophilic amino acids linked to the first amino acid, methionine. Alternatively, the synthetic peptide may consist of 3 to 16 amino acids linked to carboxy-terminal of Met, wherein at least 60% of the amino acids are hydrophilic. The hydrophilic amino acids may be homotypic or heterotypic. The hydrophilic amino acids may be selected from a group consisting of Asp, Glu, Gln, Asn, Thr, Ser, Arg, and Lys. In a more particular example, the leader peptide may have amino acid sequence of SEQ ID Nos: 24-33, 108-114.

Further, when the N-terminal of a heterologous protein has basic pI value and moves to the periplasm as unfolded and then is folded in periplasm, the heterologous protein is secreted through Sec pathway *E. coli* type-II periplasmic secretion pathway. Therefore, if a heterologous protein is a protein which moves to the periplasm as unfolded and then is folded in the periplasm, we can enhance secretional efficiency of the heterologous protein by adjusting pI value of the leader peptide to basic range and selecting Sec pathway thereby (See FIG. 2).

Hereinafter, terms and phrases used in the present document are described.

The phrase "heterologous protein" refers to a protein to be produced by genetic recombination technique, more particularly it is a protein expressed in host cells transformed with an expression vector having a polynucleotide encoding the protein.

The phrase "fusion protein" refers to a protein in which another polypeptide is linked or additional amino acid sequence is added to an N- or C-terminal of an original heterologous protein.

The term "folding" refers to a process that a primary polypeptide chain gets unique tertiary structure exhibiting its function via structural deformation.

The phrase "folded active protein" refers to a protein forming tertiary structure in order to possess the inherent activity in the cytosol after the transcription and the translation of mRNA or before the secretion into the periplasm.

The phrases "signal peptide (SP)" and "signal sequence (ss)" which may be used interchangeably other in the art refer to a peptide helping a heterologous protein expressed from viruses, prokaryotes or eukaryotes pass cellular membrane in order to secrete the heterologous protein into the periplasm or outside the cell or into the target organ. Although it seemed that the "signal sequence" does not designate a molecule but sequence information, the "signal sequence" is recognized to designate a polypeptide molecule. Generally the signal sequence consists of positively charge N-region, central characteristic hydrophobic region, and c-region with a cleavage site. The phrase "signal peptide fragment" used herein refers to a whole region or a part of positively charged N-region, central characteristic hydrophobic region, and c-region with cleavage site. In addition, the signal sequence includes Sec signal sequence and Tat signal sequence which have these three parts.

The term "hydrophilicity" refers to extent capable of forming hydrogen bond with water molecules. Unless otherwise defined, the hydrophilicity value is calculated according to Hopp-Woods scale using DNASIS™ (Hitachi, Japan) software (window size: 6 and threshold: 0.00). The term "hy" is an abbreviation of the term "hydrophilicity". When the hydrophilicity value of a peptide is positive the peptide is hydrophilic and the hydrophilicity value is negative the peptide is hydrophobic.

The phrase "leader peptide" or "leader sequence" refers to an additional amino sequence added to N-terminal of a heterologous protein.

The phrase "N-terminal of a leader peptide" refers to 1 to 10 amino acids located in the amino terminal of the leader peptide.

The term "fragment" refers to a peptide or a polynucleotide having minimum length but maintaining the function of full-length peptide or full-length polynucleotide. Unless otherwise defined, the fragment neither includes the full-length peptide nor the full-length polynucleotide. For example, "signal peptide fragment" used in the present document refers to a truncated signal peptide with the deletion of C-terminal cleavage region or central hydrophobic region and the C-terminal cleavage region, which plays a role as a signal sequence and does not include a full-length signal sequence.

The term "polynucleotide" refers to a polymer molecule in which two or more nucleotide molecules are linked one another through phosphodiester bond and DNA and RNA are included therein.

The phrase "N-terminal region of a signal peptide" refers to a conservative region found common signal sequences which 1 to 10 amino acid of amino terminal of a signal peptide.

The phrase "variant of signal peptide fragment" refers to a peptide whose one or more amino acids at any position except the $1^{st}$ methionine are substitute with other amino acids.

The phrase "protease recognition site" means an amino acid sequence which a protease recognizes and cleaves.

The phrase "transmembrane domain" refers to a domain having hydrophilic region and hydrophobic region in turn, and means an internal region of a protein having a similar structure with amphipathic domain. Therefore, it is used as the same meaning as "transmembrane-like domain".

The phrase "transmembrane-like domain" refers to a region predicted to have similar structure as the transmembrane domain of a membrane protein when analyzing amino acid sequence of a polypeptide (Brasseur et al., *Biochim. Biophys. Acta* 1029(2): 267-273, 1990). Usually it can be easily predicted with various computer softwares which predict transmembrane domains. In particular examples of the computer softwares, there are TMpred, HMMTOP, TBBpred, DAS-TMfilter (www.enzim.hu/DAS/DAS.html), etc. The "transmembrane-like domain" includes a "transmembrane domain" which is revealed to pass through membranes indeed.

The phrase "expression vector" refers to a linear or a circular DNA molecule comprising all cis-acting elements for expressing a heterologous protein such as a promoter, a terminator or an enhancer. Conventional expression vectors have a multi cloning site with various restriction sites for cloning a polynucleotide encoding the heterologous protein. However, the expression vector used in the present document includes one including the polynucleotide encoding the heterologous. In addition, the expression vector may further contain one or more replication origins, one or more selective markers, a polyadenylation signal, etc. The expression vector contains elements originated from a plasmid and/or a virus generally.

The phrase "operably linked to" or "operably inserted to" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "$\Delta G_{RNA}$ value" refers to Gibson free energy level which an RNA has in aqueous solution at particular temperature. However when $\Delta G_{RNA}$ value is low, it is expressed that the Gibson free energy is high. Thus lower the value is, more stable the secondary structure is maintained. For example, an RNA whose $\Delta G_{RNA}$ value is −10 has bigger Gibson free energy than one has $\Delta G_{RNA}$ value of −2 and thus the former has more stable secondary structure than the letter.

MODE FOR INVENTION

Hereinafter, the present invention is described below with particular examples.

However, the following examples serve to illustrate the present invention and are not intended to limit its scope in any way.

EXAMPLE 1

Cloning of an Adhesive Protein Gene DNA Multimer Cassette

The present inventors prepared a synthetic mefp1 DNA based on the basic unit of the Mefp1 amino acid sequence represented by SEQ. ID. NO: 1 (Ala Lys Pro Ser Tyr Pro Pro Thr Tyr Lys) by using a forward primer represented by SEQ. ID. NO: 2 (5'-TAC AAA GCT AAG CCG TCT TAT CCG CCA ACC-3') and a reverse primer represented by SEQ. ID. NO: 3 (5'-TTT GTA GGT TGG CGG ATA AGA CGG CTT AGC-3'). For the left adaptor (referred as "LA" hereinafter) synthetic DNA (contains BamHI/EcoRI/SmaI), a forward primer represented by SEQ. ID. NO: 4 (5'-GAT CCG AAT TCC CCG GG-3') and a reverse primer represented by SEQ. ID. NO: 5 (5'-TTT GTA CCC GGG GAA TTC G-3') were used. For the right adaptor (referred as "RA" hereinafter) synthetic DNA (contains Arg/HindIII/SalI/XhoI), a forward primer represented by SEQ. ID. NO: 6 (5'-TAC AAA CGT AAG CTT GTC GAO C-3') and a reverse primer represented by SEQ. ID. NO: 7 (5'-TCG AGG TCG ACA AGC TTA CG-3') were used. Thereafter, mefp1 DNA multimer was constructed by the method described in Korean Patent No. 379,025, which was then cloned into the vector pBluescriptIISK(+) (Stratagene, USA). Screening for transformants yielded a construct containing the left adaptor (LA) sequence, seven mefp1 DNA repeats and the RA sequence was performed and the screened construct was named as pBluescriptIISK(+)La-7×mefp1-RA (FIG. 2).

TABLE 1

Primers, plasmid clones and the expression of the recombinant Mefp1

| SEQ ID. NO: | Primer sequences | Clones constructed in pET22b(+) containing the whole and a part of OmpASP | Mefp1 expression | | |
|---|---|---|---|---|---|
| | | | T | S | P |
| Forward primes containing various length of OmpASP-Mefp1 | | | | | |
| 8 | CAT ATG AAA AAG GCT AAG CCG TCT TAT CCG CCA ACC | pET22b(+)ompASP$_{1-3}$-7 × mefp1* | + | + | + |
| 9 | CAT ATG AAA AAG ACA GCT AAG CCG TCT TAT CCG CCA ACC | pET22b(+)ompASP$_{1-4}$-7 × mefp1* | + | + | + |
| 10 | CAT ATG AAA AAG ACA *GCT* GCT AAG CCG TCT TAT CCG CCA ACC | pET22b(+)ompASP$_{1-5}$-7 × mefp1* | + | + | + |
| 11 | CAT ATG AAA AAG ACA *GCT ATC* GCT AAG CCG TCT TAT CCG CCA ACC | pET22b(+)ompASP$_{1-6}$-7 × mefp1* | + | + | + |
| 12 | CAT ATG AAA AAG ACA *GCT ATC GCG* GCT AAG CCG TCT TAT CCG CCA ACC | pET22b(+)ompASP$_{1-7}$-7 × mefp1* | + | + | + |

TABLE 1-continued

Primers, plasmid clones and the expression of the recombinant Mefp1

| SEQ ID. NO: | Primer sequences | Clones constructed in pET22b(+) containing the whole and a part of OmpASP | Mefp1 expression | | |
|---|---|---|---|---|---|
| | | | T | S | P |
| 13 | <u>CAT</u> *ATG AAA AAG* <u>ACA</u> *GCT ATC GCG ATT* GCT AAG CCG TCT TAT CCG CCA ACC | pET22b(+)ompASP$_{1-8}$-7 × mefp1* | + | + | + |
| 14 | <u>CAT</u> *ATG AAA AAG* <u>ACA</u> *GCT ATC GCG ATT GCA* GCT AAG CCG TCT TAT CCG CCA ACC | pET22b(+)ompASP$_{1-9}$-7 × mefp1* | + | + | + |
| 15 | <u>CAT</u> *ATG AAA AAG* <u>ACA</u> *GCT ATC GCG ATT GCA GTG* GCT AAG CCG TCT TAT CCG CCA ACC | pET22b(+)ompASP$_{1-10}$-7 × mefp1* | + | + | + |
| 16 | <u>CAT</u> *ATG AAA AAG* <u>ACA</u> *GCT ATC GCG ATT GCA GTG GCA* GCT AAG CCG TCT TAT <u>CCG</u> <u>CCA</u> <u>ACC</u> | pET22b(+)ompASP$_{1-11}$-7 × mefp1* | + | + | + |
| 17 | <u>CAT</u> *ATG AAA AAG* <u>ACA</u> *GCT ATC GCG ATT GCA GTG GCA CTG GCT* GCT AAG CCG TCT TAT CCG CCA ACC | pET22b(+)ompASP$_{1-13}$-7 × mefp1* | + | + | + |
| 18 | <u>CAT</u> *ATG AAA AAG* <u>ACA</u> *GCT ATC GCG ATT GCA GTG GCA CTG GCT CGT TTC* GCT AAG CCG TCT TAT CCG CCA ACC | pET22b(+)ompASP$_{1-15}$-7 × mefp1* | + | + | + |
| 19 | <u>CAT</u> *ATG AAA AAG* ACA *GCT ATC GCG ATT GCA GTG GCA CTG GCT GGT TTC GCT ACC GTA GCG CAG GCC* GCT AAG CCG TCT TAT CCG CCA ACC | pET22b(+)ompASP$_{1-21}$-7 × mefp1* | + | + | + |
| 20 | <u>CAT</u> *ATG AAA AAG* ACA *GCT ATC GCG ATT GCA GTG GCA CTG GCT GGT TTC GCT ACC GTA GCG CAG GCC GCT CCG* GCT AAG CCG TCT TAT CCG CCA ACC | pET22b(+)ompASP$_{1-23}$-7 × mefp1* | + | + | + |
| 21 | <u>CAT</u> *ATG AAA AAG* ACA *GCT ATC GCG ATT* ATC <u>GAA</u> <u>GGT</u> <u>CGT</u> GCT AAG CCG TCT TAT CCG CCA ACC | pET22b(+)ompASP$_{1-8}$-Xa-7 × mefp1* | + | + | + |
| 22 | <u>CAT</u> *ATG AAA AAG* ACA *GCT ATC GCG ATT* CCC GGG <u>ATC</u> <u>GAA</u> <u>GGT</u> <u>CGT</u> GCT AAG CCG TCT TAT CCG CCA ACC | pET22b(+)ompASP$_{1-8}$-SmaI-Xa7 × mefp1* | + | + | + |

Reverse primer

| 23 | CTC GAG GTC GAC AAG CTT ACG | No corresponding clone | | | |
|---|---|---|---|---|---|

CAT was extended to preserve an NdeI site.
Thick Italic letters: indicate various sized oligonucleotides of the whole and a part of OmpASP.
Thick letters: oligonucleotides of the SmaI site.
Underlined thick letters: oligonucleotides of the factor Xa recognition site.
General letters: oligonucleotides of Mefp1 region shown in FIG. 2.
Reverse primer: complementary oligonucleotide sequence to RA (right adaptor; Arg/HindIII/SalI/XhoI) shown in FIG. 2.
OmpA signal peptide (OmpASP) is composed of 23 amino acid residues (MKKTAIAIAVALAGFATVAQAAP, SEQ. ID. NO: 46, Movva et al., J. Biol. Chem., 255, 27-29, 1980).
*surplus sequences of RA and His tag (6 × His).
mefp1: Mefp1 gene
Abbreviations: T-total protein; S-soluble fraction; and P-periplasm fraction.
Expression of recombinant Mefp1 protein: '−'; no expression, '+'; expression.

TABLE 2 pI value, hydrophobicity average value and expression of the soluble recombinant Mefp1 protein according to the length of OmpASP

| OmpAsp and its segments of various lengths | pI | Hopp & Woods scale hydrophobicity | Expression of the soluble recombinant Mefp1 |
|---|---|---|---|
| OmpASP$_1$ | 5.70 | — | NT |
| OmpASP$_{1-2}$ | 9.90 | — | NT |
| OmpASP$_{1-3}$ | 10.55 | — | + |
| OmpASP$_{1-4}$ | 10.55 | — | + |
| OmpASP$_{1-5}$ | 10.55 | — | + |
| OmpASP$_{1-6}$ | 10.55 | −.03 | + |
| OmpASP$_{1-7}$ | 10.55 | −0.09 | + |
| OmpASP$_{1-8}$ | 10.55 | −0.31 | + |
| OmpASP$_{1-9}$ | 10.55 | −0.33 | + |
| OmpASP$_{1-10}$ | 10.55 | −0.44 | + |
| OmpASP$_{1-11}$ | 10.55 | −0.56 | + |
| OmpASP$_{1-12}$ | 10.55 | −−0.56 | NT |
| OmpASP$_{1-14}$ | 10.55 | −0.52 | + |
| OmpASP$_{1-15}$ | 10.55 | −0.65 | NT |
| OmpASP$_{1-21}$ | 10.55 | −0.61 | + |
| OmpASP$_{1-23}$ | 10.55 | −0.58 | + |

OmpASP length dependent pI value and hydrophobicity (Hopp & Woods scale with window size: 6 and threshold line: 0.00) were calculated by DNASIS ™. The Hopp and Woods scale hydrophobicity represents that '−' indicates no value, whereas the '−value' indicates hydrophobic. As absolute value increases, hydrophobicity increases. Expression of recombinant Mefp1 protein: 'NT'; not tested, '+'; expression

EXAMPLE 2

Expression of an Adhesive Protein mefp1

In the previous study, Mefp1 expressed an insoluble inclusion body when Met-Mefp1 was used as a leader sequence (Kitamura et al., J. Polym. Sci. Ser. A 37:729-736, 1999). The present inventors introduced the signal sequence OmpASP (OmpA signal peptide) to induce expression of a target protein in soluble form, for which PCR was performed using the mefp1 sequence of FIG. 2 as a template to construct a clone harboring different sizes of ompASP and the mefp1 cassette (Table 1).

Transformants of *E. coli* BL21(DE3) generated by using the expression vector containing the signal sequence shown in Table 1 were cultured in LB medium (tryptone 20 g, yeast extract 5.0 g, NaCl 0.5 g, KCl 1.86 mg/l) in the presence of 50 μg/ml of ampicillin at 30° C. for 16 hours. The culture solution was diluted 200-fold with LB medium. The diluted culture solution was incubated to reach OD$_{600}$ of 0.3 and then IPTG was added to a final concentration of 1 mM. The culture solution was incubated for further 3 hours for expression. Then, 1 ml of the culture solution was centrifuged at 4° C. for 30 minutes with 4,000×g and pellet was resuspended in 100-200 μl of sample buffer (0.05 M Tris-HCl, pH 6.8, 0.1 M DTT, 2% SDS, 1% glycerol, 0.1% bromophenol blue). The resuspension was disrupted by sonication using 100 3-s pulses to release the total proteins and the insoluble fraction was separated by centrifugation at 4° C. with 16,000 rpm for 30 minutes to eliminate cell debris. To prepare periplasmic fractions, induced cells were subjected to osmotic shock (Nossal and Heppel, J. Biol. Chem. 241:3055-3062, 1966). The lysate of total proteins, the soluble fraction, and the periplasmic fraction were separated using 16% SDS-PAGE (Laemmli, Nature 227:680-685, 1970) and visualized using Coomassie brilliant blue stain (Sigma, USA). The gel obtained from SDS-PAGE was transferred to a nitrocellulose membrane (Roche, USA). After blocking with 5% skim milk (Difco, USA), the membrane was incubated in a solution containing 0.4 μg/ml anti-His6 monoclonal antibody (Santa Cruz Biotechnology, USA) for 2 hours at 37° C.

Horseradish peroxidase (HRP) conjugated rabbit anti-mouse IgG (Santa Cruz Biotechnology, USA) was used as the secondary antibody and 3,3'-diaminobenzidine tetrahydrochloride (DAB, Sigma, USA) was used as the staining substrate.

Figure 3A:
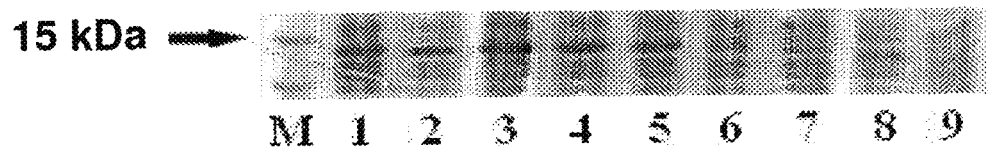
FIGS. 3A and 3B are images illustrating the expression of the recombinant Mefp1 fusion protein, induced from pET-22b(+)[ompASP( )-7×mefp1*] (*: Ra-6×His) clone, in soluble supernatant, and anti-His tag antiserum was used to detect the recombinant Mefp1 produced by pET-22b(+) containing the coding sequence of His tag in the 3'-end.
Figure 3B:

As a result, all of the OmpA signal peptides from the leader sequence OmpASP$_{1-3}$ to OmpASP$_{1-23}$ tested herein successfully directed the expression of soluble periplasmic Mefp1 (Table 1 and FIG. 3). It was also confirmed that what directs the expression of Mefp1 in soluble form is not the full length of OmpASP$_{1-23}$ but the fraction of OmpASP$_{1-3}$, which is only OmpASP$_{1-3}$ is necessary to direct Mefp1 precursor to the periplasm. The expression level was not associated with the length of a leader sequence and no evidence for the presence of a secretional enhancer was found in the central characteristic hydrophobic region (OmpASP$_{7-14}$) and the C-region ending with a cleavage site (OmpASP$_{15-23}$). pI value and the Hopp & Woods scale hydrophobicity of the signal sequence of OmpASP with different length were analyzed. As a result, all the sequences from OmpASP$_{1-3}$ to OmpASP$_{1-23}$ had an equal pI value, which was 10.55, but the Hopp & Woods scale hydrophobicity values were diverse (Table 2). The constant pI value is the most important factor in the functioning of OmpASP fragments as directional signals for soluble protein expression.

EXAMPLE 3

Production of the Native Form of an Adhesive Protein mefp1

To produce Mefp1 with its native N-terminus, the present inventors performed PCR using pBluescriptIISK(+)-La-7×mefp1-Ra (FIG. 2) as a template and a synthetic oligonucleotide encoding the OmpASP$_{1-8}$-Xa-Mefp1 containing factor Xa cleavage site for cleaving the C-terminal end as a forward primer to construct pET-22b(+)(ompASP$_{1-8}$-Xa-7×mefp1*) (*: Ra-6×His, Ra derived from the right adaptor; 6×His derived from His tag) clone, based on the result of soluble expression by the shortened OmpASP (Table 1). The constructed vector was tested for the expression by the transformation and Western blotting as described in Example 2.

As a result, this clone produced soluble protein OmpASP$_{1-8}$-Xa-7×Mefp1*. Further, the 7×Mefp1* protein with a native amino acid terminus was obtained by the removal of the OmpASP$_{1-8}$-Xa sequence with factor Xa protease (FIG. 4).

To modify the signal sequence region of the above clone conveniently, the present inventors introduced a SmaI site into the signal sequence to construct pET-22 Y(+)(ompASP$_{1-8}$-SmaI-Xa-7×mefp1*) clone by PCR (Table 1) in order to maintain the same copy number of target gene cassette against the various copy of mefp1 usually obtained from the repeated mefp1 template by PCR. The resulting OmpASP$_{1-8}$-Sma I-Xa-7×Mefp1* was digested with factor Xa protease to cleave off the OmpASP$_{1-8}$-Sma I-Xa and the obtained protein was confirmed to be 7×Mefp1* with a native amino terminus. By inserting up to six homologous amino acid codons in the SmaI site of pET-22b(+) (ompASP$_{1-8}$-Sma I-Xa-7×mefp1*), it was confirmed that the hydrophilic amino acids Arg and Lys slightly increased the level of expression.

EXAMPLE 4

Investigation on the Function of the Adhesive Protein Mefp1

Mefp1 expressed from the pET-22b(+) (ompASP$_{1-8}$-Xa-7×mefp1*) clone was separated as follows. The induced cells were centrifuged at 4° C. for 30 minutes with 4,000×g. The supernatant was removed and pellet was washed and frozen at −70° C. or suspended in PBS (pH 8.0), followed by sonication using a sonicator. The lysed cells were centrifuged at 4° C. for 30 minutes with 12,000×g. The supernatant was treated with a protease factor Xa (New England Biolabs, USA) to cut off the signal sequence OmpASP$_{1-8}$-Xa, which was then filtered through a 0.45 μm syringe filter. The native Mefp1 protein (7×Mefp1*) was purified by His tag purification kit (Qiagen, USA) according to the manufacturer's instructions. 1 ml of Ni$^{2+}$ chelating resin was equilibrated with 5 ml of distilled water, 3 ml of 50 mM NiSO$_4$, and 5 ml of 1× binding buffer (50 mM NaCl, 20 mM Tris-HCl, 5 mM imidazole, pH 7.9). The supernatant was loaded on the column and washed with 10 ml of 1× binding buffer and 6 ml of washing buffer (60 mM imidazole in PBS). The protein of interest was eluted with 6 ml of elution buffer (1,000 mM imidazole in PBS) and the eluted fractions were analyzed by 12% SDS-PAGE.

The functions of the recombinant Mefp1 with a native amino terminus were investigated.

Protein samples were resolved in 5% acetic acid buffer (Hwang et al., *Appl. Environ. Microbiol.* 70:3352-3359, 2004) and tyrosinase (tyrosinase; Sigma, USA) was used to transform tyrosine into DOPA. Prior to adhesion assay, 1 mg/ml of protein was modified with 10 U of tyrosinase at room temperature for 6 hours with shaking. BSA in 5% acetic acid buffer was used as a non-adhesive protein control.

Figure 5:
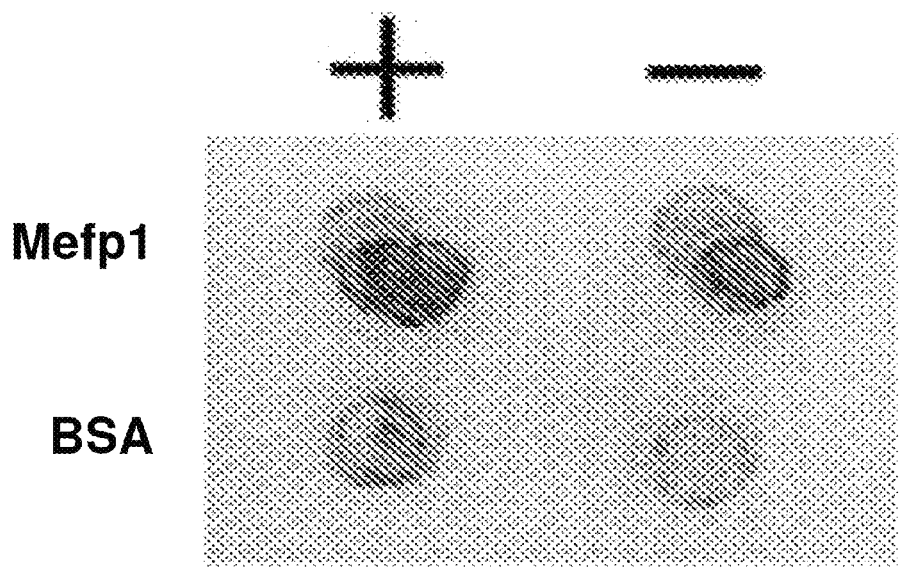
FIG. 5 is a diagram illustrating the coating of the recombinant protein Mefp1 on a glass slide.
  +: treatment of proteins with tyrosinase; and
  −: treatment of proteins without tyrosinase.

As a result, compared with BSA used as a control, the recombinant Mefp1 protein (7×Mefp1*) with a native amino terminus exhibited significant cohesiveness (FIG. 5). Therefore, the soluble recombinant Mefp1 protein produced by the method of the invention was confirmed to have a proper structure and an original protein function.

EXAMPLE 5

Screening of a Secretional Enhancer for the Expression of a Soluble Olive Flounder Hepcidin 1

As the above Example 2, the present inventors expressed olive flounder Hepcidin I (Kim et al., Biosci. Biotechnol. Biochem. 69, 1411-1414, 2005) as a fusion protein with various lengths of OmpASP by the same manner as used for the expression of Mefp1 but the fusion protein was not expressed in soluble form (Table 3). Sequence of olive flounder Hepcidin I is as follows (SEQ. ID. NO: 47):

His Ile Ser His Ile Ser Met Cys Arg Trp Cys Cys Asn Cys Cys Lys Ala Lys Gly Cys Gly Pro Cys Cys Lys Phe.

The present inventors presumed that the presence of four disulfide bonds and one amphipathic domain in olive flounder Hepcidin I was the reason why the fusion protein OmpASP$_{tr}$-olive flounder Hepcidin I could not be expressed in soluble form as effectively as Mefp1 having a plain structure (pI: 10.03; hydrophobicity: −0.05).

Figure 6A:
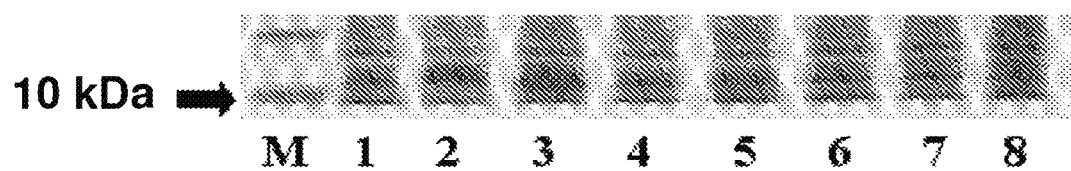
FIGS. 6A and 6B are images illustrating a secretional enhancer of OmpASPtr-( )-Xa for the expression of the recombinant olive flounder (*Paralichthys olivaceus*) Hepcidin I (of Hepcidin I) from pET22b(+)[ompASP$_{1-10}$-( )-Xa-ofhepcidinI**] Glu/HindIII/Sal I/Xho I-6×His) clone. As shown in Table 4, pI value and hydrophobicity/hydrophilicity value are associated with the amino acids inserted in the parenthesis of OmpASP$_{1-10}$-( )-Xa.
Figure 6B:
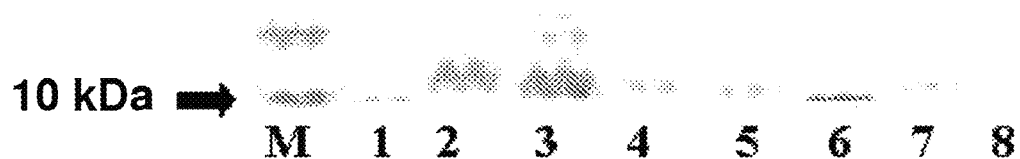

To screen a secretional enhancer for soluble protein expression, the present inventors constructed pET-22b(+)[ompASP$_{1-10}$-( )-Xa-ofhepcidinI**] (Table 3) by modifying the signal sequence as a form of OmpASP$_{1-10}$-( )-Xa, in which the N-terminal region of the signal sequence was set as OmpASP$_{1-10}$ and the 6 homologous sequence of six amino acids such as arginine, lysine, glutamic acid, aspartic acid, tyrosine, phenylalanine and tryptophan affecting pI value and hydrophobicity/hydrophilicity value were added to -( )- to change the C-terminal -( )-Xa region (Table 4), followed by investigation of the expression of soluble olive flounder Hepcidin I. As a result, the hydrophilic amino acids Arg and Lys increased the expression level of soluble Hepcidin I but the clones without these amino acids exhibited weak expression of soluble Hepcidin I (FIG. 6). The above results indicate that these amino acids arginine and lysine attached at the C-terminal of the signal peptide moiety function as a strong secretional enhancer because of their high pI and hydrophilicity, while other amino acids function as a comparatively weak secretional enhancer (FIG. 6 and Table 4). Therefore, the amino acid additioned to the C-terminal of the modified signal sequence increases the secretional efficiency because of the high pI and hydrophilicity of the added amino acids.

TABLE 3

Primers, plasmid clones and the expression of olive flounder Hepcidin I

| SEQ ID. NO: | Primer sequences | Clones constructed in pET22b(+) containing OmpA signal peptide fragment | Expression of olive flounder Hepcidin I | | |
|---|---|---|---|---|---|
| | | | T | S | P |
| Forward primes | | | | | |
| 24 | CAT ATG AAA AAG ACA CAC ATC AGC CAC ATC TCC ATG TGC | pET22b(+)ompASP$_{1-4}$-ofhepI** | − | − | − |
| 25 | CAT ATG AAA AAG ACA GCT ATC CAC ATC AGC CAC ATC TCC ATG TGC | pET22b(+)ompASP$_{1-6}$-ofhepI** | + | − | − |
| 26 | CAT ATG AAA AAG ACA GCT ATC GCG ATT CAC ATC AGC CAC ATC TCC ATG TGC | pET22b(+)ompASP$_{1-8}$-ofhepI** | + | − | − |
| 27 | CAT ATG AAA AAG ACA GCT ATC GCG ATT GCA GTG CAC ATC AGC CAC ATC TCC ATG TGC | pET22b(+)ompASP$_{1-10}$-ofhepI** | + | − | − |
| 28 | CAT ATG AAA AAG ACA GCT ATC GCG ATT GCA 'GTG GCA CTG CAC ATC AGC CAC ATC TCC ATG TGC | pET22b(+)ompASP$_{1-12}$-ofhepI** | + | − | − |

TABLE 3-continued

Primers, plasmid clones and the expression of olive flounder Hepcidin I

| SEQ ID. NO: | Primer sequences | Clones constructed in pET22b(+) containing OmpA signal peptide fragment | Expression of olive flounder Hepcidin I T | S | P |
|---|---|---|---|---|---|
| 29 | CAT ATG AAA AAG ACA GCT ATC GCG ATT GCA GTG *TGG TGG TGG TGG TGG TGG* (ATC GAA GGT CGT) CAC ATC AGC CAC ATC TCC ATG TGC | pET22b(+)ompASP$_{1-10}$-6 × Trp-Xa-ofhepI** | + | +/- | +/- |
| 30 | CAT ATG AAA AAG ACA GCT ATC GCG ATT GCA GTG *CGC CGT CGC CGT CGC CGT* (ATC GAA GGT CGT) CAC ATC AGC CAC ATC TCC ATG TGC | pET22b(+)ompASP$_{1-10}$-6 × Arg-Xa-ofhepI** | + | + | + |
| 31 | CAT ATG AAA AAG ACA GCT ATC GCG ATT GCA GTG *AAA AAG AAA AAG AAA AAG* (ATC GAA GGT CGT) CAC ATC AGC CAC ATC TC TCC ATG TGC | pET22b(+)ompASP$_{1-10}$-6 × Lys-Xa-ofhepI** | + | + | + |
| 32 | CAT ATG AAA AAG ACA GCT ATC GCG ATT GCA GTG *GAA GAG GAA GAG GAA GAG* (ATC GAA GGT CGT) CAC ATC AGC CAC ATC TCC ATG TGC | pET22b(+)ompASP$_{1-10}$-6 × Glu-Xa-ofhepI** | + | +/- | +/- |
| 33 | CAT ATG AAA AAG ACA GCT ATC GCG ATT GCA GTG *GAC GAT GAC GAT CAC GAT* (ATC GAA GGT CGT) CAC ATC AGC CAC ATC TCC ATG TGC | pET22b(+)ompASP$_{1-10}$-6 × Asp-Xa-ofhepI** | + | +/- | +/- |
| 34 | CAT ATG AAA AAG ACA GCT IGCT ATC GCG ATT GCA iGTG *TAC TAT TAC TAT TAC TAT* (ATC GAA GGT CGT) CAC ATC AGC CAC ATC TCC ATG TGC | pET22b(+)ompASP$_{1-10}$-6 × Tyr-Xa-ofhepI** | + | +/- | +/- |
| 35 | CAT ATG AAA AAG ACA GCT ATC GCG ATT GCA GTG *TTC TTT TTC TTT TTC TTT* (ATC GAA GGT CGT) CAC ATC AGC CAC ATC TCC ATG TGC | pET22b(+)ompASP$_{1-10}$-6 × Phe-Xa-ofhepI** | + | +/- | +/- |
| 36 | CAT ATG AAA AAG ACA GCT ATC *CGC CGT CGC CGT CGC CGT* (ATC GAA GGT CGT) CAC ATC AGC CAC ATC TCC ATG TGC | pET22b(+)ompASP$_{1-6}$-6 × Arg-Xa-ofhepI** | + | + | + |
| 37 | CAT ATG AAA AAG ACA GCT ATC GCG ATT *CGC CGT CGC CGT CGC CGT* (ATC GAA GGT CGT) CAC ATC AGC CAC ATC TCC ATG TGC | pET22b(+)ompASP$_{1-8}$-6 × Arg-Xa-ofhepI** | + | + | + |
| 38 | CAT ATG AAA AAG ACA GCT ATC GCG ATT GCA GTG GCA CTG *CGC CGT CGC CGT CGC CGT* (ATC GAA GGT CGT) CAC ATC AGC CAC ATC TCC ATG TGC | pET22b(+)ompASP$_{1-12}$-6 × Phe-Xa-ofhepI** | + | + | + |
| 39 | CAT ATG AAA AAG ACA GCT ATC GCG ATT GCA GTG GCA CTG GCT GGT *CGC CGT CGC CGT ICGC CGT* (ATC GAA GGT CGT) CAC ATC AGC CAC ATC TCC ATG TGC | pET22b(+)ompASP$_{1-14}$-6 × Arg-Xa-ofhepI** | + | + | + |
| 40 | CAT ATG AAA AAG ACA GCT ATC GCG ATT GCA GTG (ATC GAA GGT CGT) CAC ATC AGC CAC ATC TCC ATG TGC | pET22b(+)ompASID$_{1-10}$-Xa-ofhepI** | + | +/- | +/- |
| 41 | CAT ATG AAA AAG ACA GCT ATC GCG ATT GCA GTG *AAA CGC* (ATC GAA GGT CGT) CAC ATC AGC CAC ATC TCC ATG TGC | pET22b(+)ompASP$_{1-10}$-Lys Arg-Xa-ofhepI** | + | +/- | +/- |
| 42 | CAT ATG AAA AAG ACA GCT ATC GCG ATT GCA GTG *CGC CGT CGC CGT* (ATC GAA GGT CGT) CAC ATC AGC CAC ATC TCC ATG TGC | pET22b(+)ompASP$_{1-10}$-4 × Arg-Xa-ofhepI** | + | + | + |

TABLE 3-continued

Primers, plasmid clones and the expression of olive flounder Hepcidin I

| SEQ ID. NO: | Primer sequences | Clones constructed in pET22b(+) containing OmpA signal peptide fragment | Expression of olive flounder Hepcidin I | | |
|---|---|---|---|---|---|
| | | | T | S | P |
| 43 | CAT ATG AAA AAG ACA GeT ATC GCG ATT GCA GTG *CGC CGT CGC CGT CGC CGT CGC CGT* (ATC GAA GGT CGT) CAC ATC AGC CAC ATC TCC ATG TGC | pET22b(+)ompASP₁₋₁₀-8 × Arg-Xa-ofhepI** | + | + | + |
| 44 | CAT ATG AAA AAG ACA GCT ATC GCG ATT GCA GTG *CGC CGT CGC CGT CGC CGT CGC CGT CGC CGT* (ATC GAA GGT CGT) CAC ATC AGC CAC ATC TCC ATG TGC | pET22b(+)ompASP₁₋₁₀-10 × Arg-Xa-ofhepI** | + | + | + |

Reverse primer

| 45 | CTC GAG GTC GAC AAG CTT TTC GAA CTT GCA GCA GGG GCC ACA GCC | No corresponding clone | | | |

CAT was extended to preserve an NdeI site.
Italic letters: indicate various sized oligonucleotides of OmpASP fragment.
Thick Italic letters: oligonucleotides of amino acids involved in pI and hydrophobicity/hydrophilicity average value.
Thick letters: oligonucleotides of hepcidin I.
ofhepI: ofHepcidin I gene.
Reverse primer: complementary oligonucleotide sequences to the sequence containing a C-terminal of ofHepcidin I and Glu/Hind III/Sal I/Xho I region.
Underlined thick letters: oligonucleotides of the factor Xa recognition site.
**Glu/Hind III/Sal I/Xho I-6 × His (Glu/Hind III/Sal I/Xho I derived from the reverse primer design and 6 × His derived from His tag.)
Abbreviations: T-total protein; S-soluble fraction; and P-periplasm fraction.
Expression of recombinant of Hep I**: "−"; no-expression, "+/−"; weak expression, and "+"; expression.

TABLE 4

Hydrophobicity/hydrophilicity value of the signal sequence of OmpASP₁₋₁₀-( )-Xa with the insertion of amino acids having different pI and hydrophobicity/hydrophilicity values in the ( ) region and the expression of soluble olive flounder Hepcidin I in the clone of pET22b(+)ompASP₁₋₁₀-( )-Xa-ofHepI** of FIG. 6 and Table 3

| | Inserted amino acid | pI value of the inserted amino acid | Hopp & Woods scale hydrophobicity/ hydrophilicity of the inserted amino acid | Form of signal peptide | Hopp & Woods scale hydrophobicity/ hydrophilicity of the regulating signal peptide | Expression of of Hepcidin I in FIG. 6 and Table 3 |
|---|---|---|---|---|---|---|
| Crtl | — | — | — | OmpASP₁₋₁₀-( )-Xa | −0.02 | +/− |
| 1 | 6 × Arg | 13.20 | 1.75 | OmpASP₁₋₁₀-(6 × Arg)-Xa | 0.88 | + |
| 2 | 6 × Lys | 11.20 | 1.75 | OmpASP₁₋₁₀-(6 × Lys)-Xa | 0.88 | + |
| 3 | 6 × Glu | 2.82 | 1.75 | OmpASP₁₋₁₀-(6 × Glu)-Xa | 0.88 | +/− |
| 4 | 6 × Asp | 2.56 | −1.33 | OmpASP₁₋₁₀-(6 × Asp)-Xa | 0.88 | +/− |
| 5 | 6 × Tyr | 5.55 | −1.33 | OmpASP₁₋₁₀-(6 × Tyr)-Xa | −0.70 | +/− |
| 6 | 6 × Phe | 5.70 | −1.45 | OmpASP₁₋₁₀-(6 × Phe)-Xa | −0.76 | +/− |
| 7 | 6 × Trp | 5.90 | −1.98 | OmpASP₁₋₁₀-(6 × Trp)-Xa | −1.03 | +/− | pI value and hydrophobicity/hydrophilicity (Hopp & Woods scale with window size: 6 and threshold line: 0.00) were calculated by DNASIS ™.
The '+value' of Hopp and Woods scale hydrophobicity/hydrophilicity index indicates the inserted peptide is hydrophilic, whereas the '−value' indicates hydrophobic.
As absolute value increases, hydrophobicity/hydrophilicity increases. Expression of recombinant of Hep I**: "+/−"; weak expression, and "+"; expression.

EXAMPLE 6

Figure 7A:
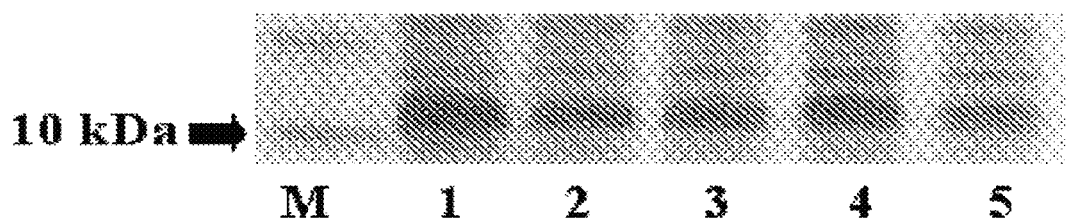
FIGS. 7A and 7B are images illustrating illustrating the effect of the length of OmpASP, as a directional signal, on the expression of Hepcidin I in soluble form. The soluble supernatant fraction was induced with IPTG for 3 hours. Western blotting was performed as described in FIG. 3.
Figure 7B:
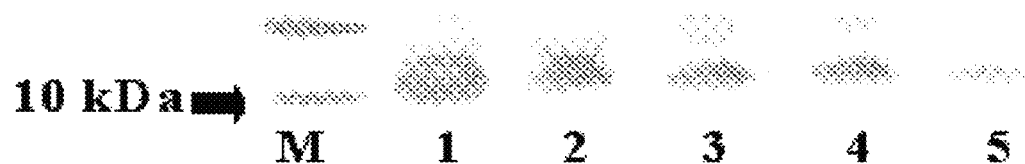

Expression of Olive Flounder Hepcidin I According to the Change of Hydrophobicity/Hydrophilicity of a Signal Sequence To investigate the expression of olive flounder Hepcidin I in relation with the hydrophobicity/hydrophilicity of the modified signal sequence, the present inventors examined the effect of the N-terminal of the OmpASP fragment acting as a directional signal. To do so, various OmpASP.sub.( )-6×Arg (SEQ ID NO: 282)-Xa with different lengths were designed and their corresponding clones were tested for expression. (Table 3 and FIG. 7). The Hopp & Woods hydrophobicity/hydrophilicity values of the modified signal sequences of OmpASP₁₋₆-6×Arg(SEQ ID NO: 282)-Xa, OmpASP₁₋₈-6×Arg(SEQ ID NO: 282)-Xa, OmpASP₁₋₁₀-6×Arg(SEQ ID NO: 282)-Xa, OmpASP₁₋₁₂-6×Arg(SEQ ID NO: 282)-Xa and OmpASP₁₋₁₄-6×Arg(SEQ ID NO: 282)-Xa were 1.37, 1.09, 0.88, 0.69 and 0.62, respectively. The signal sequences having the Hopp and Woods scale hydrophilicity value of at least 0.62 were all expressed in soluble form. The shorter the signal sequence, the higher the hydrophilicity and the more the expression in soluble form were observed. All of the sequences described above (OmpASP$_{1-6}$ through OmpASP$_{1-14}$) with average hydrophilicities of more than 0.62 directed the periplasmic expression of soluble recombinant Hepcidin I. As the length of the signal sequence decreased, the hydrophilicity increased, and the yield of soluble Hepcidin I increased. The shortest signal sequence (OmpASP$_{1-6}$; hydrophobicity -0.03) was linked with the 6×Arg-Xa sequence (hydrophilicity 1.47) to construct the resultant OmpASP$_{1-6}$-6×Arg(SEQ ID NO: 282)-Xa (hydrophilicity 1.37), which showed an extended region of hydrophilicity in the hydropathy profile, lacking a hydrophobic curve at the N-terminus, whereas the other signal sequences (OmpASP$_{1-8}$, OmpASP$_{1-10}$, OmpASP$_{1-12}$, OmpASP$_{1-14}$) (hydrophobicity, see Table 2) were more hydrophobic than OmpASP$_{1-6}$, and the resultant signal sequences had asymmetrical hyperbolic curves of the typical transmembrane-like domain of the hydrophobic-hydrophilic curves in the profile. Therefore, it was suggested that the most preferable size of the signal sequence, in order to have transmembrane-like hydropathy exhibiting hydrophobic-hydrophilic curves, was at least OmpASP$_{1-8}$.

The present inventors also investigated the functions of the secretional enhancer in the C-terminal of the modified signal sequence. The signal sequence OmpASP$_{1-10}$was set as a directional signal and OmpASP$_{1-10}$-( )-Xa was designed to include hydrophilic amino acids with different lengths in the -( )- region and the expression thereof was measured (Table 3 and FIG. 8). The Hopp & Wood scaled hydrophobicity/hydrophilicity values of the modified signal sequences of OmpASP$_{1-10}$-Xa, OmpASP$_{1-10}$-LysArg-Xa, OmpASP$_{1-10}$-4×Arg(SEQ ID NO: 288)-Xa, OmpASP$_{1-10}$-6×Arg(SEQ ID NO: 282)-Xa, OmpASP$_{1-10}$-8-×Arg(SEQ ID NO: 289)-Xa and OmpASP$_{1-10}$-10×Arg(SEQ ID NO: 290)-Xa were -0.02, 0.35, 0.64, 0.88, 1.07 and 1.23, respectively. In conclusion, the signal sequences with Hopp & Woods scale hydrophilicity values ≤0.35 were too weak to direct the expression of soluble form, while the signal sequences with Hopp & Woods scale hydrophilicity values ≥0.64 were able to direct the expression of soluble form (FIG. 8). As the length of the hydrophilic amino acid was extended, the hydrophilicity and soluble expression were increased. The Hopp & Wood scale hydropathy profile of every signal sequence inducing soluble expression was further investigated. As a result, every signal sequence above had transmembrane-like hydropathy profile exhibited a hydrophobic curve in the N-terminal and a hydrophilic curve in the C-terminal.

It is judged from the above results that the hydrophobicity/hydrophilicity value of a signal sequence region determined by the Hopp & Woods scale can be a standard for a secretional enhancer for the soluble expression of olive flounder Hepcidin I and thereby the hydropathy profile according to the Hopp & Wood scale can be a secondary standard for a secretional enhancer.

EXAMPLE 7

The Relation Between the Hydropathy Profile According to the Hopp & Woods Scale of a Signal Sequence and the Expression of Olive Flounder Hepcidin I It was proved in Example 6 that the Hopp & Woods scale hydrophobicity/hydrophilicity value was a reliable standard for the expression of olive flounder Hepcidin I in soluble form. Thus, the usability of the Hopp & Woods scale hydropathy profile as a standard for a secretional enhancer was investigated. The present inventors simulated the hydropathy profiles of the fusion protein of olive flounder Hepcidin I using of Hepcidin I as a control by computer program. of Hepcidin I, OmpASP$_{1-10}$-Xa- of Hepcidin I, OmpASP$_{1-10}$-LysArg-Xa-of Hepcidin I, and OmpASP$_{1-10}$-6×Arg-Xa-of Hepcidin I were investigated (FIG. 9). As a result, the simulated olive flounder Hepcidin I had an internal amphipathic domain, while the simulated OmpASP$_{1-10}$-Xa-of Hepcidin I and OmpASP$_{1-10}$-LysArg-of Hepcidin I had two transmembrane-like domains in similar sizes; one of which was originated from a signal sequence and the other was originated from the amphipathic domain of olive flounder Hepcidin I. The recombinant OmpASP$_{1-10}$-Xa-of Hepcidin I and OmpASP$_{1-10}$-LysArg-of Hepcidin I which were corresponding to the simulated OmpASP$_{1-10}$-Xa-of Hepcidin I and OmpASP$_{1-10}$-LysArg-of Hepcidin I fusion proteins were expressed in soluble form at a very low level (Table 3 and FIG. 8). However, the Hopp & Woods scale hydropathy profile of the simulated OmpASP$_{1-10}$-6×Arg-Xa-of Hepcidin I revealed that it had two transmembrane-like domains, one in the signal sequence and the other in the olive flounder Hepcidin I. The transmembrane-like domain in the signal sequence region was larger than the amphipathic domain in the olive flounder Hepcidin I. The corresponding clone produced a form of OmpASP$_{1-10}$-6×Arg-Xa-of Hepcidin I** with enhanced solubility (FIG. 8) and the expression level was consistent with the size of transmembrane-like hydropathy profile.

Therefore, it is concluded that the expression of soluble target proteins in this system requires the leader sequence to have a hydropathy profile that corresponds to a transmembrane like domain that is larger than the amphipathic domain of the target protein.

The present inventors initially postulated that because olive flounder Hepcidin I had four disulfide bonds and an amphipathic domain, it would not be expressed as effectively as Mefp1 when fused with the OmpASP fragment. However, the above experiments suggested that a transmembrane-like domain would be the biggest barrier. The disulfide bonds are formed when the nascent polypeptide chains are secreted to the periplasm, on oxidizing environment where disulfide isomerases such as DsbA are present (Bardwell et al., Cell 67, 581-589, 1991; Kamitani et al., EMBO J. 11, 57-62, 1992). Co-expression of DsbA as a potential folding aid does not influence the yield of an active target protein (Beck and Burtscher, Protein Expr. Purif. 5, 192-197, 1994). Therefore, the inventors postulate that the nascent Hepcidin I polypeptide is secreted to the periplasm without forming any disulfide bonds or at least it does not encounter any structural obstacle caused by disulfide bonds.

EXAMPLE 8

Expression of an Adhesive Protein in the N-Terminal Variant Clone

The present inventors performed PCR using pBluescriptI-ISK(+)LA-7×mefp1-RA as a template to introduce the OmpA signal peptide (OmpASP) fragment for the soluble expression according to the controlled pI value of the N-terminal of Mefp1. As a result, expression vectors having N-terminal were constructed by linking pET-22b(+) vector with the OmpASP fragment or its variants having the different pI values, the leader sequence of Mefp1 and the mefp1 cassette prepared in Example 1 (Tables 5-8).

*E. coli* BL21 (DE3) was transformed with the expression vectors containing N-terminal constructed as shown in Table 1-Table 4 according to the conventional method, followed by culture in LB medium (tryptone 10 g, yeast extract 5 g, NaCl 10 g/l) supplemented with 50 µg/ml of ampicillin at 30° C. for 16 hours. The culture solution was diluted 200 times with the LB medium. 1 mM of IPTG was added to the diluted culture solution, followed by culture until OD.sub.600 reached 0.3. Culture continued for three more hours. 1 ml of the culture solution proceeded to centrifugation at 4° C., 4,000×g for 30 minutes and the pellet was resuspended in 100-200 µl of PBS. The suspension was homogenized to separate a protein by using a sonicator at 15×2-s cycle pulses (at 30% power output). Centrifugation was performed at 4° C., 16,000 rpm for 30 minutes to eliminate cell debris, resulting in the separation of an insoluble fraction. The protein of a soluble fraction was quantified by Bradford method (Bradford, Anal Biochem 72:248-254, 1976), followed by SDS-PAGE by using 15% SDS-PAGE gel according to the method of Laemmli et al (Laemmli, Nature 227:680-685, 1970). Coomassie Brilliant Blue (Sigma, USA) staining was performed. The SDS-PAGE gel was transferred onto a nitrocellulose membrane (Roche, USA). After dipping in 5% skim milk (skimmed milk; Difco, USA), the membrane was soaked in 0.4 µg/ml of anti-His6 monoclonal antibody solution (Santa Cruz Biotechnology, USA) at 37° C. for 2 hours. DAB (3,3'-diaminobenzidine tetrahydrochloride, Sigma, USA) staining was performed using horseradish peroxidase conjugated rabbit anti-mouse IgG (Santa Cruz Biotechnology, USA) as a secondary antibody. The concentration of the adhesive protein Mefp1 band obtained thereby was measured by densitometer analysis using Quantity One program (Bio Rad, USA).

EXAMPLE 9

Effect of a Short Signal Sequence Fragment Having the Increased pI Value and its Variants on the Expression of an Adhesive Protein 5'-end of the nucleotide sequence 7×mefp1 encoding the adhesive foreign protein Mefp1 was fused with coding sequences of OmpASP$_1$(Met), OmpASP$_{1-2}$(Met-Lys) and OmpASP$_{1-3}$(Met-Lys-Lys), the fragments of OmpA signal peptide (OmpASP, Korean Patent Publication No. 10-2007-0009453, SEQ. ID. NO: 46 or Movva et al., *J. Biol. Chem.*, 255, 27-29, 1980) inducing the protein secretion, resulting in the construction of the clones pET-22b(+)(OmpASP$_{1-7}$× mefp1*), pET-22b(+)(OmpASP$_{1-2}$-7×mefp1*) and pET-22b(+)(OmpASP$_{1-3}$-7×mefp1*) (Table 5).

TABLE 5

Primers, leader sequences and the expression of Mefp1 from the pI value increased OmpASPtr and its variant clones of recombinant vector pET22b(+) (ompASP$_{1-7}$ × mefp1*)

| SEQ. ID. NO: | Forward primer sequence | SEQ. ID. NO: | Leader sequence in which OmpASP$_n$ and its variants are linked to N-terminal (Ala-Lys) of an adhesive protein (pI value) | Soluble expression |
|---|---|---|---|---|
| 48 | CAT ATG GCT AAG CCG TCT TAT CCG CCA ACC TAC | 61 | OmpASP$_1$(Met)-Ala-Lys (pI 9.90) | ++ |
| 49 | CAT ATG AAA GCT AAG CCG TCT TAT CCG CCA ACC TAC | 62 | OmpASP$_{1-2}$(Met-Lys)-Ala-Lys (pI 10.55) | +++ |
| 50 | CAT ATG AAA AAG GCT AAG CCG TCT TAT CCG CCA ACC | 63 | OmpASP$_{1-3}$(Met-Lys-Lys)-Ala-Lys (pI 10.82) | +++ |
| 51 | CAT ATG AAA AAA AAA GcT AAG CCG TCT TAT CCG CCA ACC | 64 | Met-Lys-Lys-Lys-Ala-Lys (pI 10.99) | +++ |
| 52 | CAT ATG AAA AAA AAA AAA GCT AAG CCG TCT TAT CCG CCA ACC | 65 | Met-Lys-Lys-Lys-Lys-Ala-Lys (pI 11.11) | +++ |
| 53 | CAT ATG AAA AAA AAA AAA AAA GCT AAG CCG TCT TAT CCG CCA ACC | 66 | Met-Lys-Lys-Lys-Lys-Lys-Ala-Lys (pI 11.21) | +++ |
| 54 | CAT ATG AAA AAA AAA AAA AAA AAA GCT AAG CCG TCT TAT CCG CCA ACC | 67 | Met-Lys-Lys-Lys-Lys-Lys-Lys-Ala-Lys (pI 11.28) | ++ |
| 55 | CAT ATG AAA AAA AAA AAA AAA AAA AAA GCT AAG CCG TCT TAT CCG CCA ACC | 68 | Met-Lys-Lys-Lys-Lys-Lys-Lys-Lys-Ala-Lys (pI 11.41) | +/− |
| 56 | CAT ATG CGT GCT AAG CCG TCT TAT CCG CCA ACC TAC | 69 | Met-Arg-Ala-Lys (pI 11.52) | ++ |
| 57 | CAT ATG CGT GGC GCT AAG CCG TCT TAT CCG CCA ACC | 70 | Met-Arg-Arg-Ala-Lys (pI 12.51) | ++ |
| 58 | CAT ATG CGT GGC CGT GCG GCT AAG CCG TCT TAT CCG CCA ACC | 71 | Met-Arg-Arg-Arg-Arg-Ala-Lys (pI 12.98) | ++ |

TABLE 5-continued

Primers, leader sequences and the expression of Mefp1 from the pI value increased
OmpASPtr and its variant clones of recombinant vector pET22b(+) (ompASP$_{1-7}$ × mefp1*)

| SEQ ID. NO: | Forward primer sequence | SEQ. ID. NO: | Leader sequence in which OmpASP$_n$ and its variants are linked to N-terminal (Ala-<u>Lys</u>) of an adhesive protein (pI value) | Soluble expression |
|---|---|---|---|---|
| 59 | <u>CAT</u> *ATG CGT CGC CGT CGC CGT CGC GCT AAG* TAT CCG CCA CCG TCT ACC | 72 | Met-Arg-Arg-Arg-Arg-Arg-<u>Ala-Lys</u> (pI 13.20) | ++ |
| 60 | <u>CAT</u> *ATG CGT CGC CGT CGC CGT CGC CGT CGC GCT AAG* CCG TCT TAT CCG CCA ACC | 73 | Met-Arg-Arg-Arg-Arg-Arg-Arg-Arg-<u>Ala-Lys</u> (pI 13.35) | + |

Reverse primer

| 23 | CTC GAG GTC GAC AAG CTT ACG | | | - |

*Surplus sequence of RA and His tag (6 × His) shown in FIG. 2 of Korean Patent Publication No. 10-2007-0009453.
CAT: extended for the preservation of NdeI site.
Italic bold letters: oligonucleotides in different sizes encoding the signal sequence fragment-adhesive protein (to the second amino acid of Mefp1: Ala-Lys) and its variants.
General letters: oligonucleotides encoding from the third amino acid of Mefp1 except the first two amino acids Ala-Lys.
( ): The pI value of the leader sequence wherein the signal sequence fragment and its variants are fused to N-terminal (Ala-Lys) of the adhesive protein.
OmpASP.sub.tr: OmpASP fragment described in Korean Patent Publication No. 10-2007-0009453.
Reverse primer: Oligonucleotide sequence complementary to RA (right adapter; Arg/HindIII/SalI/XhoI) shown in FIG. 2 of Korean Patent Publication No. 10-2007-0009453.
As for the expression of the recombinant Mefp1 protein, "-" indicates no expression, "+/-" indicates weak expression and the number of "+" indicates the level of expression.

*E. coli* BL21 (DE3) was transformed with the clone vectors constructed above by the same manner as described in Example 2, and the protein expression was quantified. As a result, the change of one amino acid (Lysine; Lys; K; pI=9.72) made a significant difference in the soluble expression of Met-7×Mefp1* (SEQ. ID. NO: 61) and Met-Lys-7×mefp1* (SEQ. ID. NO: 62) from the above two clones (FIG. 10A, lane 1 and lane 2, Table 5). The above result indicates that the amino acid Lys affects significantly the expression of the adhesive protein Mefp1 at the N-terminal of the fusion protein, and thereby it is also expected that the second Lys of N-terminal can affect the soluble expression of the adhesive protein Mefp1. A leader sequence was determined as from OmpASP fragment (Met[M] and Met-Lys) to the first two amino acids (Ala-Lys) of Mefp1 and the pI value of the leader sequence was analyzed by the computer program DNASIS.TM. (Hitachi, Japan). As a result, the pI value of Met-Ala-Lys (SEQ. ID. NO: 61) peptide was 9.90, and the pI value of Met-Lys-Ala-Lys (SEQ. ID. NO: 62) was 10.55. To confirm the above result, more clones were constructed by using the coding sequence of a signal sequence fragment OmpASP$_{1-3}$(Met-Lys-Lys) (SEQ ID NO: 265) having one more Lys than OmpASP$_{1-2}$ by the same manner as described above, followed by quantification of the soluble expression of the adhesive protein Mefp1 (FIG. 10A, lane 3). As a result, the soluble expression was related to the controlled pI value of the leader sequence OmpASP$_{1-3}$(Met-Lys-Lys)-Ala-Lys (SEQ ID NO: 63), which was 10.82 (FIG. 10A, lane 3 and Table 1). Therefore, the above result proved that the controlled pI value by Lys in the leader sequence to 9.90-10.82 was related to the soluble expression.

EXAMPLE 10

Effect of the Increased pI Value of a Leader Sequence on the Expression of an Adhesive Protein The present inventors confirmed in Example 9 that the control of the pI value of a leader sequence by using Lys was related to the soluble expression of a protein. And the inventors further wanted to confirm whether or not the control of the pI value could affect the general expression of a soluble protein as well. To do so, Lys was additionally inserted in between OmpASP$_{1-3}$ fragment and Mefp1, resulting in the construction of pET-22b(+)[ompASP$_{1-3}$-(Lys)$_n$-7×mefp1*] (n=1, 2, 3, 4, 6) (SEQ. ID. NOs: 49-54 and SEQ. ID. NOs: 62-67), and the amino acid Arg increasing the pI value was also additionally inserted in between Met(OmpASP$_1$) and Mefp1, resulting in the construction of pET-22b(+)[ompASP$_1$-(Arg).sub.n-7×mefp1] (n=1, 2, 4, 6, 8) (SEQ. ID. NOs: 56-60 and SEQ. ID. NOs: 69-73) (Table 5). The pI value of the leader sequence ranging from the OmpASP fragment to the first two amino acids of Mefp1 (Ala-Lys) of each clone was investigated.

*E. coli* BL21 (DE3) was transformed with the clone vectors constructed above by the same manner as described in Example 2, and the protein expression induced therein was quantified. As a result, the soluble expression of the adhesive protein Mefp1 fused with the leader sequence having the increased pI value of 10.99-11.21 by the addition of Lys (FIG. 10A, lanes 4-6 and Table 5, SEQ. ID. NOs: 69-73) was similar to the level of the control having the pI value of 10.55 (FIG. 10A, lane 2 and Table 5, SEQ. ID. NO: 62) or slightly increased. In the meantime, the soluble expression of the adhesive protein Mefp1 fused with the leader sequence having the pI value of 11.28 (FIG. 10A, lane 7 and Table 5, SEQ. ID. NO: 67) was reduced, compared with the control having the pI value 10.55. And the soluble expression of the adhesive protein Mefp1 fused with the leader sequence having the pI value of 11.41 (FIG. 10A, lane 8 and Table 5, SEQ. ID. NO: 68) was hardly observed. In spite of the increase of the pI value, the leader sequence (SEQ. ID. NO: 68) which having the pI value of 11.41 and exhibiting the reduced expression had comparatively high hydrophilicity (1.93). So, it was presumed that significant increase of hydrophilicity in the leader sequence rather reduced membrane permeability by increasing the binding force to lipid bilayer (Korean Patent Publication No. 10-2007-0009453). However, in spite of high hydrophilicity in the leader sequence (1.14, 1.32, 1.53, and 1.69) having the pI value of 10.99, 11.11, 11.21, and 11.28 respectively, when Lys was additionally inserted, the hydrophilicity was offset to some degree, suggesting that membrane permeation was possible. However, the expression of the adhesive protein Mefp1 had nothing to do with the increase of electric charge.

In addition, of the pI value increased leader sequences (pI 11.52-13.35: SEQ. ID. NOs: 69-73), the soluble expression of the adhesive protein Mefp1 fused with the leader sequence having the increased pI value of 11.52-12.51 by the addition of Arg (SEQ. ID. NOs: 69 and 70) was similar to that of the control having the pI value of 9.90 (SEQ. ID. NO: 61) or slightly increased (leader sequence having the pI value of 12.51 by the addition of 2 Args, SEQ. ID. NO: 70), though the increase was not significant. The soluble expression of the adhesive protein Mefp1 fused with the leader sequences having the pI value of 12.98, 13.20 and 13.35 (SEQ. ID. NOs: 71-73) was reduced with the increase of the pI value (Table 5 and FIG. 10B). The leader sequence having the pI value of 13.35 that exhibited the lowest expression (SEQ. ID. NO: 73) had comparatively high hydrophilicity (1.93). So, it was presumed that significant increase of hydrophilicity in the leader sequence rather reduced membrane permeability by increasing the binding force to lipid bilayer (Korean Patent Publication No. 10-2007-0009453). At this time, the expression had nothing to do with the increase of electric charge.

The expression of the adhesive protein Mefp1 fused with the leader sequence having the pI value of 12.51 by the addition of two Args (MRRAK, SEQ. ID. NO: 70) was slightly increased. The soluble adhesive protein Mefp1 having the leader sequence had reduced molecular weight with 3/3 frequencies, suggesting that N-terminal was cut off (FIG. 10B, lane 3). This phenomenon was consistently observed in periplasm fractions (data not shown). However, other leader sequences with additional Arg had no deletion. So, the deletion seemed to be attributed to a protease and those leader sequences with additional Arg were expected to have Arg specific membrane permeation mechanism.

EXAMPLE 11

Effect of the Low pI Value of a Leader Sequence on the Soluble Expression of an Adhesive Protein The present inventors investigated the effect of the down-controlled pI value of N-terminal of a leader sequence on the soluble expression of Mefp1.

Particularly, OmpASP$_{1-7}$×mefp1* was used as the control and the amino acid sequence of the leader sequence Met (OmpASP$_1$)+Ala-Lys (N-terminal of Mefp1) was differently modified to produce variants of the leader sequence represented by SEQ. ID. NOs: 81-87 [MDDDDDAA (SEQ. ID. NO: 81; pI=2.73), MDDDAA (SEQ. ID. NO: 82; pI=2.87), MEE (SEQ. ID. NO: 83; pI=3.09), MAE (SEQ. ID. NO: 84; pI=3.25), MAA (SEQ. ID. NO: 85; pI=5.60), MCH (SEQ. ID. NO: 86; pI=7.13), MAH (SEQ. ID. NO: 87; pI=7.65)] having the pI value of 2.73-7.65 (Table 6). The pI values of those variants were investigated. MAK (SEQ. ID. NO: 61; pI=9.90) and MRRRRAK (SEQ. ID. NO: 71; pI=12.98) were used as the controls and the expressions were investigated.

E. coli BL21 (DE3) was transformed with the clone vectors constructed above by the same manner as described in Example 2, and the protein expression therein was quantified. As a result, the soluble adhesive protein Mefp1 expression was observed in every clone containing the leader sequences represented by SEQ. ID. NOs: 81-87. Particularly, the clones containing the leader sequences having the pI values of 3.09-7.65 (SEQ. ID. NOs: 83-87) exhibited significantly higher expression than those in the clones containing the leader sequences having the pI values of 9.90 (SEQ. ID. NO: 61) and 12.98 (SEQ. ID. NO: 71), and especially higher expression was observed when the pI value was controlled to 3.09 (SEQ. ID. NO: 83) (FIG. 11 and Table 6). Even the leader sequence exhibiting the lowest expression (SEQ. ID. NO: 81; pI=2.73) had comparatively high hydrophilicity of 1.09. So, it was presumed that significant increase of hydrophilicity in the leader sequence rather reduced membrane permeability by increasing the binding force to lipid bilayer (Korean Patent Publication No. 10-2007-0009453). At this time, the expression had nothing to do with the increase of electric charge.

TABLE 6

Expressions of variant clones of the leader sequence (Met-Ala-Lys) of recombinant vector pET22b(+) ompASP$_{1-7}$ × mefp1*

| SEQ ID. NO: | Forward primer sequence | SEQ ID. NO: | Leader sequence with modified OmpASP$_1$(Met)-Ala-Lys (pI value) | Soluble expression |
|---|---|---|---|---|
| 74 | CAT ATG GAC GAT GAC GAT GAC GCT GCA CCG TCT TAT CCG CCA ACC TAC | 81 | Met-Asp-Asp-Asp-Asp-Ala-Ala (pI 2.73) | + |
| 75 | CAT ATG GAC GAT GAC GCT GCA CCG TCT TAT CCG CCA ACC TAC | 82 | Met-Asp-Asp-Asp-Ala-Ala (pI 2.87) | ++ |
| 76 | CAT ATG GAA GAG CCG TCT TAT CCG CCA ACC TAC | 83 | Met-Glu-Glu (pI 3.09) | +++ |
| 77 | CAT ATG GCT GAA CCG TCT TAT CCG CCA ACC TAC | 84 | Met-Ala-Glu (pI 3.25) | +++ |
| 78 | CAT ATG GCT GCA CCG TCT TAT CCG CCA ACC TAC | 85 | Met-Ala-Ala (pI 5.60) | +++ |
| 79 | CAT ATG TGC CAC CCG TCT TAT CCG CCA ACC TAC | 86 | Met-Cys-His (pI 7.13) | +++ |

TABLE 6-continued

Expressions of variant clones of the leader sequence (Met-Ala-Lys) of recombinant vector pET22b(+) ompASP$_{1-7}$ x mefp1*

| SEQ ID. NO: | Forward primer sequence | SEQ ID. NO: | Leader sequence with modified OmpASP$_1$(Met)-Ala-Lys (pI value) | Soluble expression |
|---|---|---|---|---|
| 80 | <u>CAT</u> *ATG GCT CAC* CCG TCT TAT CCG CCA ACC TAC | 87 | Met-Ala-His (pI 7.65) | +++ |
|  | Reverse primer |  |  |  |
| 23 | CTC GAG GTC GAC AAG CTT ACG |  | - |  |

*Surplus sequence of RA and His tag (6 x His) shown in FIG. 2 of Korean Patent Publication No. 10-2007-0009453.
CAT: extended for the preservation of NdeI site.
Italic bold letters: oligonucleotides in different sizes encoding the leader sequence (Met-Ala-Lys) and its variants.
General letters: oligonucleotides encoding from the third amino acid of Mefp1 except the first two amino acids Ala-Lys.
( ): The pI value of the leader sequence (Met-Ala-Lys) variant.
Oligonucleotide sequence complementary to RA (right adaptor; Arg/HindIII/SalI/XhoI) shown 10 in FIG. 2 of Korean Patent Publication No. 10-2007-0009453.
As for the expression of the recombinant Mefp1 protein, "-" indicates no expression, "+/-" indicates weak expression and the number of "+" indicates the level of expression.

EXAMPLE 12

Optimization of the Distance Between a Leader Sequence and a Factor Xa Recognition Site (Xa) for the Production of an Adhesive Protein in Native Form In Example 11, from the investigation of the expression patterns of Mefp1 protein, which resulted in the increase of the expression by the controlled pI value of the leader sequence, it was confirmed that one of the optimum pI value of the leader sequence of the adhesive foreign protein Mefp1 was 3.09 (MEE; SEQ. ID. NO: 83). Then, the distance between the leader sequence having the pI value of 3.09 (MEE) and the Xa factor recognition site (Xa) was optimized by controlling the distance between the leader sequence and Mefp1 sequence linked thereto, followed by production of a fusion protein facilitating the recovery of a soluble protein having the native amino terminal according to the method described in Korean Patent Publication No. 10-2007-0009453. The structural change resulted from the extension of the leader sequence was minimized by using some parts (Mefp1$_3$-8) of amino acids of Mefp1 linked to the leader sequence (MEE) as an insert (i).

Particularly, the factor Xa recognition site (Xa) was included, resulting in MEE-(i=n)-Xa, and amino acids of a part of Mefp1 linked to the leader sequence MEE, which is presented as n, were inserted (n=0, 2, 4, and 6) to construct the clone pET-22b(+)(MEE-(i=n)-Xa-7xmefp1*) for the optimum protein expression (Table 7).

*E. coli* BL21 (DE3) was transformed with the clone vector constructed above by the same manner as described in Example 2, and the protein expression was quantified. As a result, the expression was most significantly reduced when the distance between MEE and Xa was 4, precisely in the order of i=0>2>6>4 (FIG. 12). The soluble protein included the factor Xa recognition site (Xa), so that the recombinant protein having native N-terminal (7xMefp1*) with the elimination of MEE-(i=n)-Xa could be produced by the conventional method after treating the recombinant protein with factor Xa protease.

TABLE 7

Expression of the recombinant vector pET-22b(+)(MEE-(1 = n)-Xa-7 x mefp1*)

| SEQ ID. NO: | Forward primer sequence | SEQ ID. NO: | Leader sequence with modified OmpASP1(Met)-Ala-Lys (pI value) | Soluble expression |
|---|---|---|---|---|
| 88 | CAT *ATG GAA GAG ATC GAA GCT CGT GCT AAG* CCG TCT TAT CCG CCA ACC TAC | 92 | Met-Glu-Glu-Xa(i = 0) | +++ |
| 89 | CAT ATG GAA GAG CCG TCT ATC GAA GGT CGT GCT AAG CCG TCT TAT CCG CCA ACC TAC | 93 | Met-Glu-Glu-Pro-Ser-Xa (i = 2) | +++ |
| 90 | CAT ATG GAA GAG CCG TCT TAT CCG ATC GAA GGT CGT GCT AAG CCG TCT TAT CCG CCA ACC TAC | 94 | Met-Glu-Glu-Pro-Ser-Tyr-Pro-Xa (i = 4) | + |

TABLE 7-continued

Expression of the recombinant vector pET-22b(+)(MEE-(1 = n)-Xa-7 x mefp1*)

| SEQ ID. NO: | Forward primer sequence | SEQ ID. NO: | Leader sequence with modified OmpASP1(Met)-Ala-Lys (pI value) | Soluble expression |
|---|---|---|---|---|
| 91 | CAT ATG GAA GAG CCG TCT TAT CCG CCA ACC ATC GAA GGT CGT GCT AAG CCG TCT TAT CCG CCA ACC TAC | 95 | Met-Glu-Glu-Pro-Ser-Ty-Pro-Pro-Thr-Xa (i = 6) | ++ |

Reverse primer

| 23 | CTC GAG GTC GAC AAG CTT ACG | | - | |

*Surplus sequence of Ra and His tag (6 x His) shown in FIG. 2 of Korean Patent Publication No. 10-2007-0009453.
CAT: extended for the preservation of NdeI site.
Bold letters: oligonucleotide of the leader sequence (MEE).
Italic bold letters: oligonucleotide of a part of Mefp1 (Mefp13-8) linked to the leader sequence (MEE) of Table 6.
ATC GAA GGT CGT (SEQ ID NO: 279): oligonucleotide of the Xa factor recognition site.
General letters: oligonucleotide encoding the basic amino acid sequence of Mefp1 represented by SEQ. ID. NO: 1 described in Korean Patent Publication No. 10-2007-0009453. .
Oligonucleotide sequence complementary to RA (right adaptor; Arg/HindIII/SalI/XhoI) shown in FIG. 2 of Korean Patent Publication No. 10-2007-0009453.
As for the expression of the recombinant Mefp1 protein, "-" indicates no expression, "+/-" indicates weak expression and the number of "+" indicates the level of expression.
(i): amino acid number inserted in between the leader sequence (MEE) and Xa.

EXAMPLE 13

Soluble Expression of an Adhesive Protein by the Control of the Distance Between Lys-Lys in OmpASP$_{1-11}$ The present inventors confirmed that the pI value of N-terminal containing a signal sequence could affect the soluble expression of an adhesive foreign protein Mefp1. Then, the inventors further investigated if the distance between amino acids (for example between Lys-Lys) affecting the pI value in OmpA signal sequence fragment (OmpASP.sub.tr) could affect the soluble expression of Mefp1. Particularly, the leader sequences MKK (SEQ ID NO: 265) and MKAK (SEQ. ID. NO: 62) had the equal pI value of 10.55 in N-terminal, but if the distance (d) between Lys-Lys was farther because of the insertion of the amino acid less affecting the pI value (for example, Ala [Alanine; A]), there might be changes in functions.

Based on the amino acid sequence of the signal sequence fragment OmpASP$_{1}$-11, pET-22b(+)[MK$_1$-(d$_1$=n)-K$_2$-(8-n)-AA-mefp1$_{3-10}$-6×mefp1*] was constructed by inserting OmpASP$_{1}$-11 composing amino acids d$_1$=n(0, 2, 4, 6, 8) not affecting the pI value into the ( ) which was designed as MK$_1$-(d=n)-K$_2$-(8-n) analogue (Table 4). The leader sequence of the above clone had the equal pI value of 10.55 from OmpASP$_{1-2}$ fragment (Met-Lys) to the underlined second Ala (Ala-Ala) taking the place of the second Lys of Mefp1 affecting the pI value. E. coli BL21 (DE3) was transformed with the clone constructed above as shown in Table 8 by the same manner as described in Example 2 and the protein expression therein was quantified.

As a result, the expression was reduced in the order of d$_1$=4>2>6>0>8 (d$_1$=distance of K$_1$-K$_2$). That is, when d$_1$=4, the soluble expression was most significant so that d$_1$=4 was determined as the optimum distance between amino acids. Additionally, d$_1$ was regulated as 4 and the underlined Ala of the clone was substituted with Lys (K$_3$) and Ala was inserted with d$_2$=n(1, 2, 3, 4), resulting in the construction of the clone pET-22b(+)[MK$_1$-(d$_1$=4)-K$_2$-(d$_2$=n)-AK$_3$-mefp1$_3$-10-6× mefp1*] (Table 8), followed by quantification of the protein expression by the same manner as described above.

The optimum distance between two amino acids (K$_2$-K$_3$) was d$_2$=2 and d$_2$=2>1>4>3 followed in that order. This result indicates that the optimum distance is also an important factor affecting the soluble expression of the adhesive protein Mefp1.

It was also suggested that the important factor is the distance between Lys-Lys and the pI value of the leader sequence not the sequence itself (Table 8 and FIG. 13).

In conclusion, the pI value of the leader sequence played an important role in the soluble expression of the adhesive protein Mefp1 and there was the optimum pI value in its spectrum for the best expression. However, the soluble expression of the adhesive protein Mefp1 had nothing to do with electric charge. The distance between Lys and Lys affecting the pI value was also an important factor for the expression.

TABLE 8

Primers, leader sequence and the expression of Mefp1 from OmpASP clones of pET22b(+) ompASP-7 x mefp1*

| SEQ ID. NO: | Forward primer sequence | SEQ. ID. NO: | Amino acid sequence show the leader sequence in which OmpASP$_{1-11}$'s variants are linked to N-terminal (Ala-Ala) of an adhesive protein (pI 10.55 and 10.82) and the distance (d) between Lys | Soluble expression |
|---|---|---|---|---|
| 16 | CAT ATG AAA AAG ACA GCT ATC GCG ATT GCA GTG GCA GCT AAG CCG TCT TAT CCG CCA ACC | 101 | Met-Lys-Lys-Thr-Ala-Ile-Ala-Ile-Ala-Val-Ala-Ala-Lys (pI 10.82) | positive control +++ |

TABLE 8-continued

Primers, leader sequence and the expression of Mefp1 from OmpASP clones of pET22b(+) ompASP-7 x mefp1*

| SEQ ID. NO: | Forward primer sequence | SEQ. ID. NO: | Amino acid sequence show the leader sequence in which OmpASP$_{1-11}$'s variants are linked to N-terminal (Ala-Ala) of an adhesive protein (pI 10.55 and 10.82) and the distance (d) between Lys | Soluble expression |
|---|---|---|---|---|
| 96 | CAT ATG AAA AAG ACA GCT ATC GCG ATT GCA GTG GCA GCT GCA CCG TCT TAT CCG CCA ACC TAC | 102 | Met-Lys-Lys-Thr-Ala-Ile-Ala-Ile-Ala-Val-Ala-Ala-<u>Ala</u> (pI 10.55, D$_1$ = 0) | Ala mutant control, ++ |
| 97 | CAT ATG AAA GCT ACA AAG ATC GCG ATT GCA GTG GCA GCT GCA CCG TCT TAT CCG CCA ACC TAC | 103 | Met-Lys-Ala-Thr-Lys-Ile-Ala-Ile-Ala-Val-Ala-Ala-<u>Ala</u> (pI 10.55, D$_1$ = 2) | +++ |
| 98 | CAT ATG AAA GCT ACA GCT ATC AAG ATT GCA GTG GCA GCT GCA CCG TCT TAT CCG CCA ACC TAC | 104 | Met-Lys-Ala-Thr-Ala-Ile-Lys-Ile-Ala-Val-Ala-Ala-<u>Ala</u> (pI 10.55, D$_1$ = 4) | +++ |
| 99 | CAT ATG AAA GCT ACA GCT ATC GCG ATT AAG GTG GCA GCT GCA CCG TCT TAT CCG CCA ACC TAC | 105 | Met-Lys-Ala-Thr-Ala-Ile-Ala-Ile-Lys-Val-Ala-Ala-<u>Ala</u> (pI 10.55, D$_1$ = 6) | ++ |
| 100 | CAT ATG AAA GCT ACA GCT ATC GCG ATT GCA GTG AAG GCT GCA CCG TCT TAT CCG CCA ACC TAC | 106 | Met-Lys-Ala-Thr-Ala-Ile-Ala-Ile-Ala-Val-Lys-Ala-<u>Ala</u> (pI 10.55, D$_1$ = 8) | + |
| 140 | CAT ATG AAA GCT ACA GCT ATC AAG ATT AAG GTG GCA GCT GCA CCG TCT TAT CCG CCA ACC TAC | 144 | Met-Lys-Ala-Thr-Ala-lle-Lys-Ala-Lys (pI 10.82, D$_1$ = 4, D$_2$ = 1) | +++ |
| 141 | CAT ATG AAA GCT ACA GCT ATC AAG ATT GCA AAG GCA GCT GCA CCG TCT TAT CCG CCA ACC TAC | 145 | Met-Lys-Ala-Thr-Ala-lle-Lys-Ala-Ala-Lys (pI 10.82, D$_1$ = 4, D$_2$ = 2) | ++++ |
| 142 | CAT ATG AAA GCT ACA GCT ATC AAG GCT GCA GCT AAG GCT GCA CCG TCT TAT CCG CCA ACC TAC | 146 | Met-Lys-Ala-Thr-Ala-lle-Lys-Ala-Ala-Ala-Lys (pI 10.82, D$_1$ = 4, D$_2$ = 3) | ++ |
| 143 | CAT ATG AAA GCT ACA GCT ATC AAG ATT GCA GTG GCA AAG GCA CCG TCT TAT CCG CCA ACC TAC | 147 | Met-Lys-Ala-Thr-Ala-lle-Lys-Ala-Ala-Ala-Ala-Lys (pI 10.82, D$_1$ = 4, D$_2$ = 4) | +++ |
| Reverse primer | | | | |
| 23 | CTC GAG GTC GAC AAG CTT ACG | | - | |

*Surplus sequence of RA and His tag (6xHis) shown in FIG. 2 of Korean Patent Publication No. 10-2007-0009453.
CAT: extended for the preservation of NdeI site.
Italic letters: oligonucleotide encoding the leader sequence of the signal sequence fragment OmpASP$_{1-11}$ or its variants linked to N-terminal (Ala-Ala) of an adhesive protein.
Italic bold letters: oligonucleotide encoding the amino acid lys in the leader sequence fragment.
Ala: Lys of Ala-Lys of N-terminal of an adhesive protein was substituted with Ala.
General letters: oligonucleotide encoding from the third amino acid of Mefp1 except the first two amino acids Ala-Lys. .
Reverse primer: Oligonucleotide sequence complementary to RA (right adaptor; Arg/HindIII/SalI/XhoI) shown in FIG. 2 of Korean Patent Publication No. 10-2007-0009453.
As for the expression of the recombinant Mefp1 protein, "-" indicates no expression, and the number of "+" indicates the level of expression.
(d): distance between Lys-Lys.

EXAMPLE 14

Soluble Expression of Olive Flounder Hepcidin I by N-Terminal Variants

Based on the earlier experiment results reported in Korean Patent Publication No. 10-2007-009453 saying that the soluble expression of Hepcidin I (Kim et al., Biosci Biotechnol Biochem 69:1411-1414, 2005) requires a signal sequence and a secretional enhancer, the present inventors constructed a recombinant vector for the soluble expression of Hepcidin I with controlling the pI value of N-terminal of the leader sequence of Hepcidin I. Particularly, a leader sequence functioning as a signal sequence and at the same time as a secretional enhancer or a signal sequence OmpASP fragment variant, a secretional enhancer candidate sequence or/and Xa recognition site were operably linked to of Hep1, which was introduced into pET-22b(+) (Tables 9 and 10).

E. coli BL21 (DE3) was transformed with the expression vector containing N-terminal constructed as shown in Tables 9 and 10, followed by culture in LB medium (tryptone 10 g, yeast extract 5 g, NaCl 10 g/l) supplemented with 50 µg/ml of ampicillin at 30° C. for 16 hours. The culture solution was diluted 200 times with the LB medium. 1 mM of IPTG was added to the diluted culture solution, followed by culture until $OD_{600}$ reached 0.3. The culture continued for 3 hours to induce the expression. 1 ml of the culture solution proceeded to centrifugation at 4° C., 4,000×g for 30 minutes and the pellet was resuspended in 100-200 µl of PBS. The suspension was homogenized to separate a protein by using a sonicator at 15×2-s cycle pulses (at 30% power output). Centrifugation was performed at 4° C., 16,000 rpm for 30 minutes to eliminate cell debris, resulting in the separation of an insoluble fraction. The protein of a soluble fraction was quantified by Bradford method (Bradford, Anal Biochem 72:248-254, 1976), followed by SDS-PAGE by using 15% SDS-PAGE gel according to the method of Laemmli et al (Laemmli, Nature 227:680-685, 1970). Coomassie Brilliant Blue (Sigma, USA) staining was performed. The SDS-PAGE gel was transferred onto a nitrocellulose membrane (Roche, USA). After dipping in 5% skim milk (skimmed milk; Difco, USA), the membrane was soaked in 0.4 µg/ml of anti-His6 monoclonal antibody solution (Santa Cruz Biotechnology, USA) at 37° C. for 2 hours. DAB (3,3'-diaminobenzidine tetrahydrochloride, Sigma, USA) staining was performed using horseradish peroxidase conjugated rabbit anti-mouse IgG (Santa Cruz Biotechnology, USA) as a secondary antibody.

TABLE 9

Expression of the recombinant vector pET-22b(+)(Met-7 x homologous ass-ofhepI**)

| SEQ ID. NO: | Forward primer sequence | SEQ. ID. NO: | Amino acid sequence (pI value, hydrophobicity value hy) | Soluble expression |
|---|---|---|---|---|
| 107 | <u>CAT</u> ATG CGT CGC CGT CGC CGT CGC CGT CAC ATC AGC CAC ATC TCC ATG TGC | 114 | MRRRRRRR (pI 13.28, hy + 1.97) | ++ |
| 108 | <u>CAT</u> ATG AAA AAA AAA AAA AAA AAA AAA CAC ATC AGC CAC ATC TCC ATG TGC | 115 | MKKKKKKK (pI 11.28, hy + 1.97) | ++ |
| 109 | <u>CAT</u> ATG CAC CAC CAC CAC CAC CAC CAC CAC ATC AGC CAC ATC TCC ATG TGC | 116 | MHHHHHHH (pI 8.08, hy − 0.35) | − |
| 110 | <u>CAT</u> ATG TAC TAC TAC TAC TAC TAC TAC CAC ATC AGC CAC ATC TCC ATG TGC | 117 | MYYYYYYY (pI 5.59, hy − 1.55) | − |
| 111 | <u>CAT</u> ATG TGC TCT TGC TGT TGC TGT TGC CAC ATC AGC CAC ATC TCC ATG TGC | 118 | MCCCCCCC (pI 4.57, hy − 1.97) | − |
| 112 | <u>CAT</u> ATG GAA GAA GAA GAA GAA GAA GAA CAC ATC AGC CAC ATC TCC ATG TGC | 119 | MEEEEEEE (pI 2.78, hy + 1.97) | − |
| 113 | <u>CAT</u> ATG GAC GAT GAC GAT GAC GAT GAC CAC ATC AGC CAC ATC TCC ATG TGC | 120 | MDDDDDDD (pI 2.52, hy + 1.97) | − |
| Reverse primer | | | | |
| 45 | CTC GAG GTC GAC AAG CTT TTC GAA CTT GCA GCA GGG GCC ACA GCC | | | − |

CAT: extended for the preservation of NdeI site.
Bold letters: oligonucleotides having different sizes of the leader sequences affecting the pI value and the hydrophobicity.
ofhepI: olive flounder Hepcidin I (ofHepcidinI: ofHepI) gene (Korean Patent Publication No. 10-2007-0009453; Kim et al., Biosci. Biotechnol. Biochem. 69, 1411-1414, 2005).
**Glu/HindIII/SalI/XhoI − 6 x His described in Korean Patent Publication No. 10-2007-0009453 (Glu/HindIII/SalI/XhoI is originated from the reverse primer design).
General letters: oligonucleotide of Hepcidin I region.
Reverse primer: Oligonucleotide sequence containing C-terminal and Glu/HindIII/SalI/XhoI site of ofHepcidinI of Korean Patent Publication No. 10-2007-0009453.
As for the expression of the recombinant ofHep I**, "−" indicates no expression, and the number of "+" indicates the level of expression.
Hydrophobicity: calculated by DNASISTM(Hitachi, Japan) as Hopp & Woods scale (window size: 6, threshold: 0.00). If the hydrophobicity value is +, the peptide is hydrophilic, while if the hydrophobicity value is −, the peptide is hydrophobic. And, as the absolute value increases, hydrophilicity or hydrophobicity increases.

TABLE 10

Expression of the recombinant vector pET-22b(+)(ompASP₁₋₂ ass-ompASP4-10-6 x homologous ass-Xa-ofhepI**)

| SEQ ID. NO: | Forward primer sequence | SEQ. ID. NO: | Signal sequence with the low pI value + secretional enhancer candidate sequence (pI value and hydrophobicity value) | Soluble expression |
|---|---|---|---|---|
| 121 | CAT ATG GCT CAC ACA GCT ATC GCG ATT GCA GTG *CGC CGT CGC CGT CGC CGT* (ATC GAA GGT CGT) CAC ATC AGC CAC ATC TCC ATG TGC | 130 | MAH (pI 7.65)-TAI AIA V(OmpASP$_{4-10}$, pI5.70)-6 × Arg(pI 13.20; hy 1.75)--Xa (pI 7.05) | +++ |
| 122 | CAT ATG GCT CAC ACA GCT ATC GCG ATT GCA GTG *TAC TAT TAC TAT TAC TAT* (ATC GAA GGT CGT) CAC ATC AGC CAC ATC TCC ATG TGC | 131 | MAH-OmpASP$_{4-10}$-6 × Tyr (pI 5.55; hy -1.33)-Xa | - |
| 123 | CAT ATG GCT CAC ACA GCT ATC GCG ATT GCA GTG *GAA GAG GAA GAG GAA GAG* (ATC GAA GGT CGT) CAC ATC AGC CAC ATC TCC ATG TGC | 132 | MAH-OmpASP$_{4-10}$-6 × Glu (pI 2.82; hy 1.75)Xa | +/- |
| 124 | CAT ATG GCT GCA ACA GCT ATC GCG ATT GCA GTG *CGC CGT CGC CGT CGC CGT* (ATC GAA GGT CGT) CAC ATC AGC CAC ATC TCC ATG TGC | 133 | MAA (pI 5.60)-OmpASP$_{4-10}$-6 × Arg-Xa | +++ |
| 125 | CAT ATG GCT GCA ACA GCT ATC GCG ATT GCA GTG *TAC TAT TAC TAT TAC* (ATC GAA GGT CGT) CAC ATC AGC CAC ATC TCC ATG TGC | 134 | MAA (pI 5.60)-OmpASP$_{4-10}$-6 × Tyr-Xa | + |
| 126 | CAT ATG GCT GCA ACA GCT ATC GCG ATT GCA GTG *GAA GAG GAA GAG GAA GAG* (ATC GAA GGT CGT) CAC ATC AGC CAC ATC TCC ATG TGC | 135 | MAA (pI 5.60)-OmpASP$_{4-10}$-6 × Glu-Xa | |
| 127 | CAT ATG GCT GCA ACA GCT ATC GCG ATT GCA GTG *CGC CGT CGC CGT CGC CGT* (ATC GAA GGT CGT) CAC ATC AGC CAC ATC TCC ATG TGC | 136 | MEE (pI 3.09)-OmpASP$_{4-10}$-6 × Arg-Xa | + |
| 128 | CAT ATG GCT GAA GAG ACA GCT ATC GCG ATT GCA GTG *TAC TAT TAC TAT TAC TAT* (ATC GAA GGT CGT) CAC ATC AGC CAC ATC TCC ATG TGC | 137 | MEE-OmpASP$_{4-10}$-6 × Tyr-Xa | - |
| 129 | CAT ATG GCT GAA GAG ACA GCT ATC GCG ATT GCA GTG *GAA GAA GAA GAG GAA* (ATC GAA GGT CGT) CAC ATC AGC CAC ATC TCC ATG TGC | 138 | MEE-OmpASP$_{4-10}$-6 × Glu-Xa | ++ |

TABLE 10-continued

Expression of the recombinant vector pET-22b(+)(ompASP$_{1-2}$
ass-ompASP4-10-6 × homologous ass-Xa-ofhepI**)

| SEQ ID. NO: | Forward primer sequence | SEQ. ID. NO: | Signal sequence with the low pI value + secretional enhancer candidate sequence (pI value and hydrophobicity value) | Soluble expression |
|---|---|---|---|---|
| | Reverse primer | | | |
| 45 | CTC GAG GTC GAC AAG CTT TTC GAA CTT GCA GCA GGG GCC ACA GCC | | - | | ofhepI: olive flounder Hepcidin I (of HepcidinI) gene (Kim et al., Biosci Biotechnol Biochem 69: 1411-1414, 2005).
**:Glu/HindIII/SalI/XhoI-6 × His described in Korean Patent Publication No. 10-2007-0009453 (Glu/HindIII/SalI/XhoI is originated from the reverse primer design).
CAT: extended for the preservation of NdeI site.
Bold letters: oligonucleotides of the signal sequence variants affecting the pI value.
General letters: oligonucleotides of the OmpASP$_{4-10}$.
Italic bold letters: oligonucleotides of amino acids related with the different pI values and the hydrophobicity values, which is the secretional enhancer candidate sequences. Underlined plain the letters: oligonucleotides of the factor Xa recognition site.
Italic letters: oligonucleotide of Hepcidin I region (Korean Patent Publication No. 10-2007-0009453; Kim et al., Biosci Biotechnol Biochem 69: 1411-1414, 2005).
Reverse primer: oligonucleotide sequence containing C-terminal and Glu/HindIII/SalI/XhoI site of HepcidinI of Korean Patent Publication No. 10-2007-0009453.
As for the expression of the recombinant of HepI**, "-" indicates no expression, "+/-" indicates weak expression and the number of "+" indicates the level of expression.
Hydrophobicity: calculated by DNASIS .TM.(Hitachi, Japan) as Hopp & Woods scale (window size: 6, threshold line: 0.00). If the hydrophobicity value is +, the peptide is hydrophilic, while if the hydrophobicity value is -, the peptide is hydrophobic. And, as the absolute value increases, hydrophilicity or hydrophobicity increases.

EXAMPLE 15

Soluble Expression of Olive Flounder Hepcidin I by Controlling the pI Value of a Leader Sequence The present inventors investigated the effect of pI control in a leader sequence on the soluble expression of olive flounder Hepcidin I by the similar manner as described in Examples 10 and 11.

For the soluble expression of olive flounder Hepcidin I, similarly to the screening method of a secretional enhancer described in Korean Patent Publication No. 10-2007-0009453, pET-22b(+)(Met-7× homologous amino acids-of-hepI**) clone was constructed for the expression of the protein having the controlled pI value of 2.52-13.28 and the hydrophobicity/hydrophilicity of −1.55-+1.97 which was designed to connect N-terminal of the protein to Met-7× homologous amino acids to contain Met and a secretional enhancer candidate sequence (Table 9). The homologous amino acid herein was selected from the group consisting of arginine (Arg; R), lysine (Lys, K), histidine (His; H), tyrosine (Tyr; Y), cysteine (Cys; C), glutamic acid (Glu; E) and aspartic acid (Asp; D), which was supposed to have repeats. The hydrophobicity was measured by DNASIS™ (Hitachi, Japan) as Hopp & Woods scale (window size: 6, threshold: 0.00). If the hydrophobicity value is +, the peptide is hydrophilic, while if the hydrophobicity value is −, the peptide is hydrophobic. And, as the value increases, hydrophilicity or hydrophobicity increases.

E. coli BL21 (DE3) was transformed with the clone vector constructed above by the same manner as described in Example 8, followed by quantification of the protein expression. As a result, the soluble expression of Hepcidin I was observed only in the clones having MRRRRRRR (SEQ ID NO: 114) (pI: 13.28, hydrophobicity: +1.97 [hydrophilic]) and MKKKKKKK (SEQ ID NO: 115) (pI: 11.28, hydrophobicity: +1.97 [hydrophilic]) (FIG. 14).

EXAMPLE 16

Soluble Expression of Olive Flounder Defensin Using Artificial Signal Peptides and Antibial Activity Thereof The present inventors prepared pET-22b(+)[ofdefensin*](*: XhoI-His-tag) expression vector by amplifying an ORF encoding olive flounder beta-defensin like protein (SEQ ID NO:148) using a forward primer (SEQ ID NO: 149) containing NdeI recognition sequence (CAT) and a reverse primer (SEQ ID NO: 150) and inserting the PCR product into pET-22b(+) NdeI-λ7101 site. The resulting recombinant expression vector was transformed with E. coli BL2(DE3) and soluble expression of ofdefensin was investigated.

However, no soluble expression of ofdensin was observed (FIGS. 16B and 16C, lane 1).

Thus the present inventors investigated whether the artificial signal peptides designed in above-described Examples can be used for expressing ofdefensin in soluble form.

Particularly, the present inventors introduced MKKAK (SEQ ID NO: 63) and OmpASP$_{1-8}$-12×Arg-Xa signal peptides as the artificial signal peptide. The signal peptides were proven to be effective to express 7×Mefp1 and olive flounder hepcidin I in soluble form, respectively.

In order to introduce the artificial signal peptides, forward primers containing NdeI recognition site (SEQ ID NO: 151 for MKKAK (SEQ ID NO: 63) and SEQ ID NO: 152 for OmpASP$_{1-8}$-12×Arg-Xa) and a reverse primer (SEQ ID NO: 153) were used for the PCR reaction and the PCR products were cloned to pET-22(+) expression vector via NdeI λ7101 site. The resulting recombinant expression vectors were designated as pET-22b(+)pET-22b(+)[MKKAK (SEQ ID NO: 63)-ofdefensin*] and pET-22b(+)[ompASP1-12×Arg-Xa-ofdefensin*], respectively and transformed with *E. coli* BL21(DE3). The trasnformants expressed ofdefensin as soluble form (FIGS. 16B and 18C, lanes 2 and 3).

Then, the present inventors investigated whether the expressed defensins had functional activity. Particularly, the cultured transformants were harvested and then lysed using a sonicator and supernatant containing defensing was collected and purified using His-tag purification kit (Qiagen, USA) as instructed by the provider. The purified fractions were diluted with PBS (pH 8.0) and quantified with Bradford method (Bradford, *Anal. Biochem.* 72:248-254, 1976). The antimicrobial activity against V. anquillarum of the quantified fractions was analyzed using paper discs (diameter 8 mm, Difco, USA).

As a result, the recombinant MKKAK (SEQ ID NO: 63)-ofdefensin* and OmpASP1-8-12×Arg-Xa-ofdefensin* showed strong cell lysis at 5 ug/ml (FIG. 16D). However, OmpASP$_{1-8}$-12×Arg-Xa-ofdefensin*** does not show antimicrobial activity at 1 μg/ml suggesting that longer signal peptides are somewhat inefficient for expressing ofdefensin.

EXAMPLE 17

Analysis of Soluble Expression of a Protein According to pI Value of N-Terminal of a Leader Peptide 17-1: Construction of Expression Vectors Having Gene Constructs Comprising Polynucleotides Encoding Recombinant 7×Mefp1 Having Broad Range of pI Value The present inventors constructed pET-22b(+)(ompASP$_1$)(Met)-7×mefp1*) which is a N-terminal fused plasmid by introducing OmpASP$_1$(Met) and 7×mefp1 into pET-22b(+) vector using the method described in Korean Patent Gazette No: 2009-0055457 and then constructed 33pET-22b(+) clones which have polynucleotides encoding a fusion protein consisting of various leader peptide (SEQ ID Nos: 61-73, 81-87, and 154-168) with broad range of pI value (2.73 to 13.35) and 7×Mefp1 whereby performing PCR reactions using forward primers having nucleotide sequence of SEQ ID Nos: 34-66), a reverse primer having nucleotide sequence of SEQ ID No: 67 and pET -22b(+)(ompASP$_1$(Met)-7× mefp1 *) as a template (Table 11).

TABLE 11

Relative soluble expression level of rMefpI according to various pI value of N-terminal of leader peptides

| SEQ ID Nos | a.a sequence of N-terminal of leader peptide | pI value | SEQ ID Nos | Forward primers used for designing leader sequences | Relative soluble expression |
|---|---|---|---|---|---|
| 81 | MDDDDDAA | 2.73 | 74 | CAT ATG GAC GAT GAC GAT GAC GCT GCA CCG TCT TAT CCG CCA ACC TAC | 0.50 |
| 82 | MDDDAA | 2.87 | 75 | CAT ATG GAC GAT GAC GCT GCA CCG TCT TAT CCG CCA ACC TAC | 0.91 |
| 154 | MDA | 3.00 | 169 | CAT ATG GAC GCT CCG TCT TAT CCG CCA ACC TAC | 1.40 |
| 155 | MEEEEEEE | 2.75 | 170 | CAT ATG GAA GAG GAA GAG GAA GAG GAA GAG CCG TCT TAT CCG CCA ACC TAC | 0.49 |
| 156 | MEEEEEE | 2.82 | 171 | CAT ATG GAA GAG GAA GAG GAA GAG CCG TCT TAT CCG CCA ACC TAC | 0.65 |
| 157 | MEEEE | 2.92 | 172 | CAT ATG GAA GAG GAA GAG CCG TCT TAT CCG CCA ACC TAC | 0.79 |
| 83 | MEE | 3.09 | 76 | CAT ATG GAA GAG CCG TCT TAT CCG CCA ACC TAC | 1.42 |
| 84 | MAE | 3.25 | 77 | CAT ATG GCT GAA CCG TCT TAT CCG CCA ACC TAC | 1.72 |
| 158 | MCCCCCC | 4.61 | 173 | CAT ATG TGC TGT TGC TGT TGC TGT CCG TCT TAT CCG CCA ACC TAC | 1.65 |
| 159 | MCCC | 4.75 | 174 | CAT ATG TGC TGT TGC CCG TCT TAT CCG CCA ACC TAC | 1.93 |
| 160 | MAC | 4.83 | 175 | CAT ATG GCT TGC CCG TCT TAT CCG CCA ACC TAC | 1.96 |
| 161 | MAY | 5.16 | 176 | CAT ATG GCT TAC CCG TCT TAT CCG CCA ACC TAC | 1.74 |
| 85 | MAA | 5.60 | 78 | CAT ATG GCT GCA CCG TCT TAT CCG CCA ACC TAC | 2.25 |
| 162 | MGG | 5.85 | 177 | CAT ATG GGT GGT CCG TCT TAT CCG CCA ACC TAC | 1.93 |
| 163 | MAKD | 6.59 | 178 | CAT ATG GCT AAA GAC CCG TCT TAT CCG CCA ACC TAC | 2.30 |

TABLE 11-continued

Relative soluble expression level of rMefpI according to various pI value of N-terminal of leader peptides

| SEQ a.a sequence ID of N-terminal of leader peptide Nos | pI value | SEQ ID Nos | Forward primers used for designing leader sequences | Relative soluble expression |
|---|---|---|---|---|
| 164 MAKE | 6.79 | 179 | CAT ATG GCT AAA GAA CCG TCT TAT CCG CCA ACC TAC | 2.05 |
| 86 MCH | 7.13 | 79 | CAT ATG TGC CAC CCG TCT TAT CCG CCA ACC TAC | 1.83 |
| 87 MAH | 7.65 | 80 | CAT ATG GCT CAC CCG TCT TAT CCG CCA ACC TAC | 1.81 |
| 165 MAHHH | 7.89 | 180 | CAT ATG GCT CAC CAT CAC CCG TCT TAT CCG CCA ACC TAC | 1.54 |
| 166 MAHHHHH | 8.01 | 181 | CAT ATG GCT CAC CAT CAC CAT CAC CCG TCT TAT CCG CCA ACC TAC | 1.37 |
| 167 MAKC | 8.78 | 182 | CAT ATG GCT AAA TGC CCG TCT TAT CCG CCA ACC TAC | 1.73 |
| 168 MKY | 9.58 | 183 | CAT ATG AAA TAC CCG TCT TAT CCG CCA ACC TAC | 1.51 |
| 61 MAK (control) | 9.90 | 48 | CAT ATG GCT AAG CCG TCT TAT CCG CCA ACC TAC | 1.00 |
| 62 MKAK | 10.55 | 49 | CAT ATG AAA GCT AAG CCG TCT TAT CCG CCA ACC TAC TAC | 1.57 |
| 63 MKKAK | 10.82 | 50 | CAT ATG AAA AAA GCT AAG CCG TCT TAT CCG CCA ACC TAC | 1.69 |
| 64 MKKKAK | 10.99 | 51 | CAT ATG AAA AAA AAA GCT AAG CCG TCT TAT CCG CCA ACC TAC | 1.80 |
| 65 MKKKKAK | 11.11 | 52 | CAT ATG AAA AAA AAA AAA GCT AAG CCG TCT TAT CCG CCA ACC TAC | 1.72 |
| 66 MKKKKKAK | 11.21 | 53 | CAT ATG AAA AAA AAA AAA AAA GCT AAG CCG TCT TAT CCG CCA ACC TAC | 1.93 |
| 69 MRAK | 11.52 | 56 | CAT ATG AGA GCT AAG CCG TCT TAT CCG CCA ACC TAC | 1.69 |
| 70 MRRAK | 12.51 | 57 | CAT ATG CGT CGC GCT AAG CCG TCT TAT CCG CCA ACC | 1.26 |
| 71 MRRRAK | 12.98 | 58 | CAT ATG CGT CGC CGT CGC GCT AAG CCG TCT TAT CCG CCA ACC | 1.07 |
| 72 MRRRRRAK | 13.20 | 59 | CAT ATG CGT CGC CGT CGC CGT CGC GCT AAG CCG TCT TAT CCG CCA ACC | 0.93 |
| 73 MRRRRRRRAK | 13.35 | 60 | CAT ATG CGT CGC CGT CGC CGT CGC CGT CGC GCT AAG CCG TCT TAT CCG CCA ACC | 0.55 |
| Reverse primer | | 23 | CTC GAG GTC GAC AAG CTT ACG | |

CAT: Extended for preserving Nde I site.
Bold characters refer to polynucleotides encoding signal peptide variant effecting pI value.
Normal characters refer to polynucleotide encoding the 3$^{rd}$ to the 8$^{th}$ amino acid of Mefp1.
*Amino acid sequences of N-terminals of leader peptides and nucleotide sequence of forward primers corresponding to the amino acid sequences which are reported in Korean Patent Gazette No: 2009-0055457.

17-2: Analysis of the Extent of Soluble Expression of Recombinant Proteins Using 7×Mefp1 Clones E. coli BL21(DE3) was transformed with the expression vectors constructed above using a conventional method and the transformants were cultured in LB media (tryptone 20 g/L, yeast extract 5 g/L, NaCl 0.5 g/L, KCl 1.86 mg/L) with 100 µg/L ampicillin overnight at 30° C. and then the culture was diluted 100 times with LB media and cultured until $OD_{600}$ is 0.6. And then, 1 mM IPTG was added for induction and was further cultured for 3 hr. One ml of the culture was centrifuged at 4,000×g for 30 min at 4° C. and pellet was suspended with 100 to 200 µl of PBS. The suspension was sonicated with 15×2-s cycle pulses (at 30% power output) in order to isolate proteins and then the sonicated solution was centrifuged at 16,000 rpm for 30 min at 4° C. Supernatant was taken as a soluble protein fraction. The protein fractions were quantified using Bradford method (Bradford, *Anal. Biochem.*, 72: 248-254, 1976). And then, 20 µg of proteins per well were loaded on 15% SDS-PAGE gel and SDS-PAGE analyses were performed according to Laemmli (*Nature*, 227: 680-685, 1970). The gels were stained with Coomassie Brilliant Blue stain (Sigma, USA). In the meantime the gels after SDS-PAGE analyses were transferred to Hybond-P™ membrane; GE, USA. Since the expression vectors produce rMefp1 as a fusion protein linked to His tag, the extent of expression of the recombinant protein was quantified using anti-His tag antibody as a primary antibody and alkaline phosphatase-conjugated anti-mouse antibody was used as a secondary antibody. Finally the rMefp1 was detected with a chromogenic Western blotting kit (Invitrogen, USA) according to manufacturer's instruction (FIG. 17A). The band density of the recombinant proteins obtained by the above method was quantified with densitometer analyzing method using image analysis software (Quantity One 1-D image analysis software, Bio-Rad, USA). Soluble expression level was averaged with the result of the above Western blot analysis (FIG. 17A), and the extent of soluble expression of rMefp1 fusion protein having a leader peptide MAK (pI 9.90, SEQ ID No: 61) was used a control and designated as 1.00.

As a result, the present inventors acknowledged that there are three different soluble expression curves showing different features in acidic (pI 2.73-3.25), neutral (pI 4.61-9.58) and basic (pI 9.90-13.35) pI range, respectively (FIG. 17B). The acidic, neutral and basic pI ranges in soluble expression curve of rMefp1 of FIG. 17B were illustrated in red, yellow and blue lines, respectively.

Therefore, the present inventors hypothesized that recombinant proteins are secreted through 3 different inner membrane channels according to pI value of a leader peptide.

In addition, after analyzing soluble expression of rMefp1, in pI value of 3.00, 3.09 and 3.25 among acidic pI values higher expression level than control was observed, in all neutral pI value much higher expression level than control was observed, and in pI value of 10.55, 10.82, 10.99, 11.11, 11.21 and 11.52 among basic pI values much higher expression level than control was observed. Thus, it is acknowledged that using a leader peptide having basic pI value is beneficial for inducing soluble expression of a heterologous protein without transmembrane-like domain.

Further, after analyzing the characteristic of soluble expression of rMefp1, decrease of soluble expression level when using $MD_5AA$ (SEQ ID NO: 81) and $ME_8$ leader peptide whose pI value is acidic and having increased hydrophilic amino acids and $MR_8AK$ whose pI value is basic was observed. From the result, we can hypothesize that soluble expression of a heterologous protein without transmembrane-like domain is related to pI value rather than increment of hydrophilicity, unlike soluble expression of Olive flounder hepcidin I was increased by using leader peptides including poly Lys and Arg (Korean Patent No: 981356) or poly Lys and Arg and poly Glu (Korean Patent Gazette No: 2009-0055457).

Soluble expression level was averaged with the result of the above Western blot analysis (FIG. 17A), and the extent of soluble expression of rMefp1 fusion protein having a leader peptide MAK (pI 9.90, SEQ ID No: 61) was used a control and designated as 1.00.

EXAMPLE 18

Prediction of Protein Secretion According to pI Value and Hydrophilicity of N-Terminals of Leader Peptides Although *E. coli* type-II periplasmic secretion pathway (Mergulhão et al., Biotechnol. Adv. 23: 177-202, 2005) is classified roughly as Sec pathway, SRP pathway and Tat pathway; the present inventors think that the classification is not perfect because the *E. coli* type-II periplasmic secretion pathway which is known as a pathway related to soluble expression of proteins is very complex. Thus, the present inventors analyzed the *E. coli* type-II periplasmic secretion pathway in a new classification, the pI value of N-terminal of a signal sequence as shown in Tables 12 and 13, based on our previous reports (Korean Patent Gazette No: 2009-0055457 and Lee et al., *Mol. Cells* 26: 34-40, 2008) which disclose that N-terminal fragment of a signal peptide with specific pI value can substitute for whole length of the signal sequence. The pI values of signal sequences were analyzed using computer software DNASIS™ (Hitachi, Japan).

TABLE 12

Amino acid sequences, pI value of N-terminal and predicted pI curve of representative Sec signal sequences

| SEQ ID Nos | Signal sequences | Amino acid sequences | pI value | Predicted pI curve |
| --- | --- | --- | --- | --- |
| 184 | PhoA | MKQSTIALALLPLLFTPVTKA | 9.90 | Basic |
| 185 | OmpA | MKKTAIAIAVALAGFATVAQA | 10.55 | Basic |
| 186 | StII | MKKNIAFLLASMFVFSIATNAYA | 10.55 | Basic |
| 187 | PhoE | MKKSTLALVVMGIVASASVQA | 10.55 | Basic |
| 188 | MalE | MKIKTGARILALSALTTMMFSASALA | 10.55 | Basic |
| 189 | OmpC | MKVKVLSLLVPALLVAGAANA | 10.55 | Basic |
| 190 | Lpp | MKATKLVLGAVILGSTLLAG | 10.55 | Basic |
| 191 | LTB | MNKVKCYVLFTALLSSLYAHG | 10.55 | Basic |
| 192 | OmpF | MMKRNILAVIVPALLVAGTANA | 11.52 | Basic |
| 193 | LamB | MMITLRKLPLAVAVAAGVMSAQAMA | 11.52 | Basic |
| 194 | OmpT | MRAKLLGIVLTTPIAISSFA | 11.52 | Basic |

Signal sequences and N-domains thereof were adopted as referenced (Choi and Lee, Appl. Microbiol. Biotechnol. 64: 625-635, 2004).
Amino acid sequences used to calculate pI value of N-terminal are shown in Bold

TABLE 13

Amino acid sequences, pI value of N-terminal and predicted pI curve of representative Tat signal sequences

| SEQ ID Nos | Signal sequences | Amino acid sequence | Length of N-terminal (≤10 a.a.) and pI values thereof | Predicted pI curve |
|---|---|---|---|---|
| 195 | FdnG | MDVSRRQFFKICAGGMAGTTVAALGFAPKQALA | 1-4: 3.05<br>1-6: 10.75 | Acidic or basic |
| 196 | FdoG | MQVSRRQFFKICAGGMAGTTAAALGFAPSVALA | 1-4: 5.75<br>1-6: 12.50 | Neutral or basic |
| 197 | NapG | MSRSAKPQNG<u>RRR</u>FLRDVVRTAGGLAAVGVALGLQQQTARA | 1-3: 10.90<br>1-6: 11.52 | Basic |
| 198 | HyaA | MNNEETFYQAM<u>RR</u>QGVTRRSFLKYCSLAATSLGLGAGMAPKIAWA | 1-3: 5.70<br>1-5: 3.09 | Neutral or acidic |
| 199 | YnfE | MSKNERMVGIS<u>RR</u>TLVKSTAIGSLALAAGGFSLPFTLRNAAA | 1-3: 9.90<br>1-6: 9.90 | Basic |
| 200 | WcaM | MPFKKLSRRTFLTASSALAFLHTPFARA | 1-3: 5.75<br>1-5: 10.55<br>1-9: 12.52 | Neutral or basic |
| 201 | TorA | MNNNDLFQAS<u>RRR</u>FLAQLGGLTVAGMLGPSLLTPRRATAAQA | 1-4: 5.70<br>1-5: 3.00 | Neutral or acidic |
| 202 | NapA | MKLSRRSFMKANAVAAAAAAAGLSVPGVARA | 1-2: 9.90<br>1-6: 12.51 | Basic |
| 203 | YcbK | MDKFDAN<u>RRK</u>LLALGGVALGAAILPTPAFA | 1-3: 6.59<br>1-5: 3.91<br>1-10: 10.53 | Neutral, acidic or basic |
| 204 | DmsA | MKTKIPDAVLAAEVS<u>RR</u>GLVKTTAIGGLAMASSALTLPFSRIAHA | 1-4: 10.55<br>1-7: 9.71 | Basic |
| 205 | YahJ | MKESNS<u>RRE</u>FLSQSGKMVTAAALFGTSVPLAHA | 1-3: 6.79<br>1-9: 9.89 | Neutral or basic |
| 206 | YedY | MKKNQFLKESDVTAESVFFMK<u>RR</u>QVLKALGISATALSLPHAAHA | 1-3: 10.55<br>1-9: 10.26 | Basic |
| 207 | SufI | MSLSRRQFIQASGIALCAGAVPLKASA | 1-4: 5.75<br>1-6: 12.50 | Neutral or basic |
| 208 | YcdB | MQYKDENGVNEPS<u>RRR</u>LLKVIGALALAGSCPVAHA | 1-3: 5.16<br>1-6: 4.11 | Neutral or acidic |
| 209 | TorZ | MIREEVMTLT<u>RRE</u>FIKHSGIAAGALVVTSAAPLPAWA | 1-5: 4.31 | Neutral or acidic |
| 210 | HybA | MN<u>RR</u>NFIKAASCGALLTGALPSVSHAAA | 1-4: 12.50 | Basic |
| 211 | YnfF | MMKIHTTEALMKAEIS<u>RR</u>SLMKTSALGSLALASSAFTLPFSQMVRAAEA | 1-3: 9.90<br>1-8: 7.64 | Basic or neutral |
| 212 | HybO | MTGDNTLIHSHGIN<u>RR</u>DFMKLCAALAATMGLSSKAAA | 1-3: 5.85<br>1-4: 3.00 | Neutral or acidic |
| 213 | AmiA | MSTFKPLKTLTS<u>RR</u>QVLKAGLAALTLSGMSQAIA | 1-4: 5.75<br>1-5: 9.90<br>1-8: 10.55 | Neutral or basic |
| 214 | MdoD | MD<u>RRR</u>FIKGSMAMAAVCGTSGIASLFSQAAFA | 1-5: 12.20 | Basic |
| 215 | FhuD | MSGLPLIS<u>RR</u>RLLTAMALSPLLWQMNTAHA | 1-8: 5.75<br>1-10: 12.50 | Neutral or basic |
| 216 | YcdO | MTINF<u>RR</u>NALQLSVAALFSSAFMANA | 1-5: 5.75<br>1-7: 12.50 | Neutral or basic |

The above amino acids sequences of Tat signal sequences known in *E. coli* includes cleavage site were adopted as referenced (Tullman-Ercek et al. *J. Biol. Chem.*, 282: 8309-8316, 2007).
Amino acid sequences used to calculate pI value of N-terminal are shown in Bold characters and twin Args are underlined.

As a result, it is confirmed that well known Sec signal sequence such as PhoA, OmpA, StII, PhoE, MalE, OmpC, Lpp, LTB, OmpF, LamB and OmpT has basic pI value between 9.90 and 11.52 and they have common feature with the soluble expression curve at basic pI range of FIG. 17B.

In addition, since Pf3 is known as showing a strict hyperbolic shape within neutral pI range when binding to YidC (Gerken et al., *Biochemistry*, 47: 6052-6058, 2008) and it means that there is neutral pI range specific binding pathway, it is confirmed that this factor shares common feature with the soluble expression curve at neutral pI range of FIG. 17B. The present inventors designated this new secretion pathway as Yid pathway, since the YidC is coisolated with SecDFyajC (Nouwen and Driessen, *Mol. Microbiol.*, 44: 1397-1405, 2002). After analyzing the N-terminal of the Pf3 which is predicted to be related to Yid pathway, we confirmed that its N-terminal has neutral pI value of 5.70 at the $1^{st}$ to the $6^{th}$ amino acids (MQSVIT, SEQ ID No: 263) and has acidic pI value of 3.30 at the $1^{st}$ to the $7^{th}$ amino acid (MQSVITD, SEQ ID No: 264). However, it is predicted that since the Yid pathway follows threading mechanism (DeLisa et al., *J. Biol. Chem.* 277: 29825-29831, 2002) which secrets proteins as unfolded like Sec pathway, pI value of leader peptide is important (Pf3 consists of 44 amino acids whose pI value is 6.74). In addition, after analyzing N-terminal of M13 coat protein which consists of 73 amino acids, although MKK (pI 10.55, SEQ ID No: 265) and MKKSLVLK (pI 10.82, SEQ ID No: 266) have basic pI value and thus it is the rule that the protein pass through Sec translocon like other Sec signal sequences. However, it was reported that there is no effect for the secretion in a secY mutant (Wolfe et al., *J. Biol. Chem.* 260: 1836-1841, 1985). With this result, we can assume that there are problems in Sec translocon by secY mutation, proteins can be secreted through Yid pathway which has near pI range. Therefore, the above Yid pathway is restricted to the secretion of relative small protein and may be an alternative pathway to Sec pathway according to intracellular situation.

Further, after analyzing pI values of N-terminals of signal sequences related to Tat pathway based on our previous reports (Korean Patent No: 981356 and Lee et al., *Mol. Cells* 26: 34-40, 2008) which disclose that N-terminal fragment of a signal sequence with specific pI value can substitute for whole length of the signal sequence, the present inventors confirmed that combinational length of N-terminal peptide within 10 amino acids have various range of pI, acidic to basic (Table 13). Although when the N-terminal has only one pI range, we can define the N-terminal definitely as one among acidic, neutral and basic, it is difficult to define pI range of the N-terminal when pI value of the N-terminal includes two or more ranges illustrated in FIG. 17B according to its length. However, we can acknowledge that Tat signal sequences use leader peptides with various pI values in order to secret folded proteins into the periplasm.

Even though Tat signal sequences have various acidic, neutral or basic pI ranges with a single range or with complicated ranges, considering that N-terminal with neutral pI and one with basic pI are secreted through Yid and Sec pathway, respectively, it is assumed that Tat signal sequences are secreted through Tat translocon with acidic pI value originally.

From the above result, the present inventors hypothesized that folded proteins whose signal sequences have acidic pI value are secreted through Tat pathway, ones whose signal peptides have neutral pI value are secreted through Yid pathway and ones whose signal peptides have basic pI value are secreted through Sec pathway, but exceptionally through Tat pathway. Because the diameter of Tat translocon is 70 Å (Sargent et al., *Arch. Microbiol.* 178: 77-84, 2002), whereas translocon related to Yid pathway participates in secreting very small proteins as describe above and thus supposed to have the smallest diameter, and SecYEG translocon has 12 Å of diameter and participates in unfolded polypeptides as chains (van den Berg et al., *Nature*, 427: 36-44, 2004), we can assume that the above exceptional case resulted from increment of volume of heterologous proteins fused to Sec signal peptide with basic pI value due to folding thereof. This have something to do with recent studies reporting that soluble expression of ribose binding protein having Sec signal peptide (pI of N-terminal (the $1^{st}$ to the $5^{th}$ amino acids) is 10.55) is enhanced with tatABC operon (Pradel et al., *BBRC*, 306: 786-791, 2003) and reporting that soluble expression of L2 β-lactamase (pI of N-terminal (the $1^{st}$ to the $6^{th}$ amino acids) is 12.80) is related to tatC (Pradel et al., *Antimicrob. Agents Chemother.*, 53: 242-248, 2009).

Therefore the present inventors acknowledged that unfolded proteins are secreted through Tat pathway when signal sequences have N-terminals with acidic pI value, through Yid pathway when the signal sequences have N-terminals with neutral pI value, and through Sec pathway when the signal sequences have N-terminals with basic pI value. In addition, the present inventors acknowledged that folded bulky proteins are secreted through Tat pathway because they get larger volume regardless of pI value of N-terminal of their signal sequence. Thus, present inventors suggest a schematic diagram regarding secretional pathways classifying the *E. coli* type-II periplasmic secretion pathway into three categories, Sec, Yid and Tat (FIG. 18).

EXAMPLE 19

Analysis of Effect of pI Value and Hydrophilicity of Leader Peptides on Soluble Expression of GFP The present inventors predicted that GFP, a bulky folded active protein will be secreted through Tat pathway and it will possible to enhance the secretion of GFP by a leader peptide whose pI value is acidic and whose hydrophilicity is high to that of N-terminal of the GFP, based on the result of Example 18 in that a protein whose N-terminal has acidic pI value is secreted through Tat pathway and even though a signal peptide is one using the other secretional pathway such as Sec pathway and Yid pathway, when a secreted protein is a bulky folded active protein the protein is secreted through Tat pathway.

19-1: Construction of GFP Expression Vectors and Analyses of Soluble Expression

In order to construct GFP expression vectors, a PCR reaction was performed with forward primers having nucleotide sequences of SEQ ID Nos: 239 to 258 and 260 to 231 comprising Nde I recognition site (CAT ATG) at 5'-end and a reverse primer having nucleotide sequence of SEQ ID No: 262 which deletes the stop codon TAA and comprising Xho I recognition site (CTC GAG) using GFP ORF as a template and then the PCR product was cloned to Nde I-Xho I site of pET-22b(+) resulting in the construction of pET-22b(+) (N-terminal-gfp-XhoI-His tag) expression vector. pET-22b (+) (gfp-XhoI-His tag) expression vector was used as a control. In addition, in order to construct TorAss-GFP clone having TorA signal sequence (Méjean et al., *Mol. Microbiol.* 11: 1169-1179, 1994), one of Tat signal sequences as a control, a first PCR reaction was performed with a forward primer having nucleotide sequences of SEQ ID No: 258(TorAss$_{20-39}$-agaa-GFP$_{1-7}$) and a reverse primer having nucleotide sequence of SEQ ID No: 262 using pEGFP-N2 vector, a GFP expression vector as a template. And then the first PCR product was used as a template for a second PCR reaction. The second PCR reaction was performed with a forward primer having nucleotide sequences of SEQ ID No: 259 (TorAss$_{1-27}$) and a reverse primer having nucleotide sequence of SEQ ID No: 262 and the second PCR product was cloned into pET-22b(+) vector. The GFP protein used in the present example was confirmed as one having several transmembrane-like domains by analyzing hydrophilicity according to Hopp-Woods scale.

E. coli BL21(DE3) was transformed with the expression vectors constructed above using a conventional method and the transformants were cultured in LB media (Tryptone 20 g/L, yeast extract 5 g/L, NaCl 0.5 g/L, KCl 1.86 mg/L) with 100 μg/L ampicillin overnight at 30° C. and then the culture was diluted 100 times with LB media and cultured until OD$_{600}$ is 0.3. And then, 1 mM IPTG was added for induction and was further cultured for 3 hr. One ml of the culture was centrifuged at 4,000×g for 30 min at 4° C. and wet weight of pellet was measured for fluorescent assay before resuspending the pellet with 100 to 200 μL of 50 mM Tris buffer (pH 8.0). The suspension was sonicated with 15×2-s cycle pulses (at 30% power output) in order to isolate total protein fraction and then the sonicated solution was centrifuged at 16,000 rpm for 30 min at 4° C. and supernatant was isolated as soluble fraction. Fluorescence of a fixed quantity of total protein fraction and corresponding soluble fraction was detected using a fluorescent analyzer (Perkin Elmer Victor3, USA) at an excitation wavelength of 485 nm and an emission wavelength of 535 nm, respectively (FIGS. 22C and 23C). 50 μg of proteins per well were loaded on 15% SDS-PAGE gel and SDS-PAGE analyses were performed according to Laemmli (Nature, 227: 680-685, 1970). The gels were stained with Coomassie Brilliant Blue stain (Sigma, USA). In the meantime the gels after SDS-PAGE analyses were transferred to Hybond-P membrane; GE, The extent of expression of the recombinant GFP was quantified using anti-His tag antibody as a primary antibody and alkaline phosphatase-conjugated anti-mouse antibody was used as a secondary antibody. Finally the recombinant GFP was detected with a chromogenic Western blotting kit (Invitrogen, USA) according to manufacturer's instruction (FIGS. 22A and 22B).

19-2: Analysis of Effect of pI Value of N-Terminal of a Signal Peptide Variant on Soluble Expression of GFP In order to analyze effect of pI value of N-terminal of signal peptide on soluble expression of GFP, the present inventors investigated the extent of soluble expression of GFP linked to leader peptides consisting of variant of OmpA signal peptide whose N-terminal pI value is adjusted and hydrophilic Arg polymer rather than using twin Arg motif which is a conservative region in Tat pathway signal sequence. For this purpose, the present inventors used GFP expressed from pET-22b(+)(gfp-XhoI-His tag) constructed by cloning of gfp region of pEGFP-N2 vector into Nde 1-Xho I site of pET-22b (+) as described in Example 19-1. That is, the leader peptides consisting of variants of OmpASP$_{1-8}$ (M(X)(Y) in which pI value of N-terminal of OmpASP$_{1-8}$ is empirically adjusted except the first amino acid Met) and a hydrophilic Arg polymer were designed as M(X)(Y)-TAIAI(OmpASP$_{4-8}$)-8×Arg and then pI value of M(X)(Y) and the hydrophilicity of M(X)(Y)-TAIAI(OmpASP$_{4-8}$)-8×Arg were measured (Table 14).

The present inventors investigated GFP expression level by transforming E. coli BL21(DE3) with the constructed GFP expression vector using the method described in Example 19-1. As a result, when the leader peptide has N-terminal of MEE (pI 3.09, SEQ ID No: 83) which belongs to acidic pI range, higher expression level than control was observed; when the leader peptide has N-terminal of MAA (pI 5.60, SEQ ID No: 85) and MAH (pI 7.65, SEQ ID No: 87), which belong to neutral pI range, higher or lower expression level than control was observed; and when the leader peptide has N-terminal of MKK (pI 10.55, SEQ ID No: 265) and MRR (pI 12.50, SEQ ID No: 267) which belong to basic pI range, little expression level was observed (FIG. 3). However even though the N-terminal of the leader peptide is MKK or MRR somewhat fluorescent was detected in total protein fraction thus it was confirmed that some amount of GFP exists in cytosol whereas little fluorescent was detected in soluble fraction. Thus it is assumed that GFP whose N-terminal is MKK or MRR has difficulty to pass through Sec translocon which is relative narrow. This result is interpreted that GFP binds to proteins associated to transmembrane proteins thus was not detected in Western blot analysis, as shown that GFP bands of total protein fraction and soluble fraction were seen as smear appearance upper position than that of control (FIG. 19).

Therefore, the present inventors acknowledged that bulky folded heterologous proteins may be secreted through Tat pathway when a leader peptide consisting of an OmpA signal peptide fragment variant whose N-terminal pI value is adjusted to acidic and neutral range and hydrophilic Arg polymer is fused thereto.

In addition, the present inventors confirmed that pI value of N-terminal of a leader peptide has strong effect on the selection of transmembrane channel and Sec pathway which is different from Tat pathway from the result that when a leader peptide consisting of an OmpA signal peptide fragment variant whose N-terminal pI value is adjusted to basic range and hydrophilic Arg polymer is fused thereto, it is difficult to secrete GFP because the GFP, a bulky folded protein has channel selectivity on Sec transmembrane channel and thus it should path through the Sec channel relative narrow to Tat channel.

Further, it is assumed that a leader peptide with neutral pI value can induce the secretion of a heterologous protein linked thereto through Tat pathway without attenuation as seen in Sec pathway, since the leader peptide may have weak channel selectivity on Yid pathway corresponding thereto or the heterologous protein may not pass through the Yid pathway because Yid translocon may have narrower diameter than Sec translocon, from the result that GFP having a leader peptide with neutral pI value was somewhat well secreted although the extent of soluble expression was lower than that of GFP having a leader peptide with acidic pI value and no inhibition of soluble expression through Yid pathway was not observed. It is assumed that when a protein having larger molecular weight is folded, it will be secreted through Tat translocon without blocking through Yid pathway due to the large volume of the folded protein than the diameter of the Yid translocon since the blocking phenomenon shown in Sec pathway may be due to GFP consisting of relative small number of amino acids (239 amino acids), whose size is slightly bigger to cause blocking, but not much bigger to prevent blocking than the diameter of the Sec translocon. In addition, the above result is coincident with the result that leader peptides and secretional enhances of MEE (pI 3.09, SEQ ID No: 83), MAA (pI 5.60, SEQ ID No: 85), MAH(pI 7.65)-OmpASP$_{4-10}$-6×Arg (SEQ ID No: 268) or MEE(pI 3.09)-OmpASP$_{4-10}$-6×Glu (SEQ ID No: 269) induced soluble expression of Olive flounder hepcidin I (Korean Patent Gazette No: 2009-0055457).

From the above result that when a leader peptide of GFP, a bulky folded active protein, has N-terminal with acidic or neutral pI value, the GFP was secreted through Tat pathway, when the leader peptide has N-terminal with basic pI value, the GFP blocked Sec translocon passing therethrough, the present inventors confirmed that the suggestion that soluble secretional pathway is determined according to pI value of N-terminal of a protein and all the bulky folded proteins are secreted through Tat pathway is reasonable (FIG. 18).

19-3: Analysis of Effect of Met-Hydrophilic Amino Acid Sequence and $\Delta G_{RNA}$ Value on Soluble Expression of GFP 19-3-1: Analysis of Effect of Met-Hydrophilic Amino Acid Sequence on Soluble Expression of GFP In order to investigate effect of hydrophilic amino acids linked to methionine (Met) as a leader peptide on soluble expression of GFP, the present inventors designed leader peptides which sequentially consisting of Met and 6 homotype hydrophilic amino acids linked thereto and constructed expression vectors expressing the leader peptides and GFP fused thereto. *E. coli* BL21(DE3) was transformed with the expression vectors using the method described in Example 19-1 and expression level of GFP was determined (FIG. 20). The homotype hydrophilic amino acids were selected from a group consisting of Asp, Glu, Lys and Arg, and pI value and hydrophilicity corresponding thereto were analyzed (Table 4).

As a result, GFPs having MDDDDDD (pI 2.56, hy 1.82, SEQ ID No: 222) and MEEEEEE (pI 2.82, hy 1.82, SEQ ID No: 156) with acidic pI value and high hydrophilicity as leader peptides showed high level of soluble expression, MEEEEEE (SEQ ID NO: 156) among them showed the highest soluble expression level. From these results, it is assumed that soluble expression of bulky folded GFP may be mediated by Tat pathway when MDDDDDD (SEQ ID NO: 222) or MEEEEEE (SEQ ID NO: 156) which are hydrophilic leader peptide having N-terminal with acidic pI are linked to the GFP.

However in the case of leader peptides having N-terminal with basic pI value, a leader peptide MRRRRRR (pI 13.20, hy 1.82, SEQ ID No: 225) did not induce soluble expression of GFP whereas a leader peptide MKKKKKK (pI 11.21, hy 1.82, SEQ ID No: 224) showed high level of expression of active GFP.

The case of MKKKKKK (SEQ ID NO: 224), high level of expression and fluorescence in total protein fraction continued to those in soluble fraction, and thus it seems that the folded bulky GFP was secreted through Tat translocon rather than Sec pathway. Therefore, it is coincident with the suggestion of the present inventors that a leader peptide having N-terminal with basic pI value should pass through Tat pathway if a folded protein has larger volume (FIG. 20).

Although the result that MRRRRRR (SEQ ID NO: 225) which is predicted to have similar result to MKKKKKK (SEQ ID NO: 224) indeed inhibited soluble expression of GFP is not coincident with our prediction, all clones constructed to express GFP fusion protein having leader peptides MRRRRRR (SEQ ID NO: 225) (pI 13.20, hy +1.82), MRRRRRRRRR (pI 13.40, hy +2.17, SEQ ID No: 226) and MRRRRRRRRRRR (pI 13.54, hy +2.36, SEQ ID No: 227) have very little expression level of GFP after Western blot analysis on whole protein fraction. Thus, from the result of MKKKKKK (SEQ ID NO: 224) whose high level of soluble expression and fluorescence in whole protein fraction continued to those in soluble fraction, the extent of soluble expression of a heterologous protein having N-terminal with basic pI and high hydrophilicity is dependent on expression level of the heterologous protein among whole proteins.

Consequently, it was confirmed that a bulky folded heterologous protein linked to a leader peptide having an N-terminal with acidic or basic pI value and comprising high hydrophilicity was secreted through Tat pathway in a folded form. Particularly, when the leader peptide has both basic pI value in its N-terminal and highly hydrophilic amino acids, the selectivity on Sec channel is weaken, and there is critical difference in the selection of secretional channel from a leader peptide having an anchor function space, TAIAI (OmpASP$_{4-8}$) consisting of amino acids not effecting pI value of the leader peptide between the N-terminal and the hydrophilic amino acids as shown in EXAMPLE 19-2.

In addition, from the result, the secretion of bulky folded GFP linked to a leader peptide consisting of a basic N-terminal, an anchor function space and hydrophilic amino acids such as MKK(OmpASP$_{1-3}$, pI 10.55)-TAIAI(OmpASP$_{4-8}$)-8×Arg (SEQ ID No: 220) and MRR(pI 12.50)-TAIAI(OmpASP$_{4-8}$)-8×Arg (SEQ ID No: 221) through Sec translocon was inhibited because the N-terminal of the leader peptide maintained a function as an anchor to the Sec translocon (FIG. 19), it was confirmed that the leader peptides are Sec translocon-specific leader peptides and the difference in channel selection was due to characteristic of the leader peptide, folding state, size of a heterologous protein linked thereto.

19-3-2: Analysis effect of total expression level in leader peptides having N-terminals with basic pI value and high hydrophilicity on soluble expression of GFP From the result of Example 19-3-1, the present inventors confirmed that there are other key factors for soluble expression besides pI value and hydrophilicity. Thus the present inventors analyzed $\Delta G_{RNA}$ value of polynucleotides consisting of translation initiation region of pET-22b(+) vector and MKKKKKK (SEQ ID NO: 224)-GFP$_{1-5}$ or MRRRRRR (SED ID NO: 225)-GFP$_{1-5}$ encoding regions (SEQ ID No: 270, 5'-AAG AAG GAG ATA TAC AT-ATG AAA AAA AAA AAA AAA AAA-ATG GTG AGC AAG GGC-3'; or SEQ ID No: 271, 5'-AAG AAG GAG ATA TAC AT-ATG CGT CGC CGT CGC CGT CGC -ATG GTG AGC AAG GGC-3', respectively), in order to investigate whether the difference of soluble expression between MKKKKKK (SEQ ID NO: 224) and MRRRRRR (SEQ ID NO: 225) which are leader peptides having similar pI value and hydrophilicity is due to translation efficiency. MFOLD 3software (Zuker, *Nucleic Acids Res.* 31: 3406-3415, 2003) was used for calculating $\Delta G_{RNA}$ value. If there are several $\Delta G_{RNA}$ values for a RNA molecule, it means that there may be several secondary structures. However, the lower $\Delta G_{RNA}$ values the RNA molecule has the more stable secondary structure it has.

As a result, the present inventors confirmed that $\Delta G_{RNA}$ values at the position described above of MKKKKKK (SEQ ID NO: 224) is 0.60 and 1.60 and that of MRRRRRR (SEQ ID NO: 225) is -13.80, thus two clones are very different from each other and it is acknowledged that an RNA encoding MRRRRRR (SEQ ID NO: 225) has more stable secondary structure than one encoding MKKKKKK (SEQ ID NO: 224) because the former has less $\Delta G_{RNA}$ value than the latter.

In addition, the present inventors constructed GFP fusion clones using polypeptides encoding leader peptides of MKKRKKR-I(Lys$^{AAA}$Lys$^{AAA}$Arg$^{CGC}$)$_2$ ($\Delta G_{RNA}$ -1.00, -0.50, -0.30, SEQ ID No: 228), MKKRKKR-II(Lys$^{AAG}$Lys$^{AAA}$Arg$^{CGC}$)$_2$ ($\Delta G_{RNA}$ -1.00, -0.50, -0.30, SEQ ID No: 229) and MRRKRRK(Arg$^{CGT}$Arg$^{CGC}$Lys$^{AAA}$)$_2$ ($\Delta G_{RNA}$ -7.60, SEQ ID No: 230), which are variants of MKKKKKK(Lys$^{AAA}$)$_6$($\Delta G_{RNA}$ 0.60, 1.60, SEQ ID No: 224) and MRRRRRR(Arg$^{CGT}$Arg$^{CGC}$)$_3$ ($\Delta G_{RNA}$ -13.80, SEQ ID No: 225), having same hydrophilicity therewith (Table 14) and then analyzed the extent of soluble expression of the GFP fusion clones (FIG. 21). The MKKKKKK(Lys$^{AAA}$)$_6$ (SEQ ID NO: 224) and MRRRRRR(Arg$^{CGT}$Arg$^{CGC}$)$_3$(SEQ ID NO: 225) clones were used as controls.

As a result, there is no difference between MKKKKKK (SEQ ID NO: 224) and MKKRKKR-I (SEQ ID NO: 228) in soluble expression. However MKKRKKR-I (SEQ ID NO: 228) and -II (SEQ ID NO: 229) having same $\Delta G_{RNA}$ value showed noticeable difference in the extent of soluble expression, and MRRKRRK(Arg$^{CGT}$Arg$^{CGC}$Lys$^{AAA}$)$_2$ (SEQ ID NO: 230) which has relative low $\Delta G_{RNA}$ value showed somewhat high level fluorescence. Clones showing the correlation between the expression level of GFP and $\Delta G_{RNA}$ value, and clones not showing the correlation coexist and MKKRKKR-I (SEQ ID NO: 228) and -II (SEQ ID NO: 229) showed remarkable difference even though they have same $\Delta G_{RNA}$ value. However it seems that this remarkable difference is due to codon wobble phenomenon (Lee et al., Mol. Cells, 30: 127-135, 2010) against anticodon UUU for Lys between Lys$^{AAA}$ and Lys$^{AAG}$. Thus, excluding exceptional cases due to wobble phenomenon, the $\Delta G_{RNA}$ value may be a criterion for expression level of a heterologous protein.

In addition, since GFP expression level in total protein fraction was correlated to the extent of soluble expression of GFP and hydrophilicity was related to the secretion of GFP consistently, it is acknowledged that total translational level of a heterologous protein having N-terminal with basic pI value and comprising a plurality of hydrophilic amino acids is correlated to soluble expression of the heterologous protein.

Further, the above phenomenon may be applied to a leader peptide having N-terminal with acidic and basic pI value and comprising a plurality of hydrophilic amino acids, and total translational level of a heterologous protein fused to the leader peptide may be connected to soluble expression. That is, the secretion of a heterologous protein through Tat pathway may be dependent on channel selectivity and total translational efficiency of the heterologous protein. Thus, it is important to design a leader peptide having N-terminal with acidic or neutral pI in order to enhance soluble expression of the heterologous protein when the heterologous protein is a bulky folded active protein. In addition, if one chooses a leader peptide having N-terminal with basic pI, it is important to design a polynucleotide encoding the leader peptide and N-terminal of a heterologous protein with high $\Delta G_{RNA}$ value as well as to design the leader sequence in order to obviate Sec pathway, which tends to be blocked with basic N-terminal of the leader peptide.

Although the leader peptide MRRRRRR (SEQ ID No: 225) did not induce moderately soluble expression of GFP, an interaction between a leader peptide and a characteristic of a heterologous protein linked thereto seems to be correlated to soluble expression of the heterologous protein, from the result of Korean Patent Gazette No: 2009-0055457 which discloses that leader peptides MKKKKKKK (SEQ ID No: 115) and MRRRRRRR (SEQ ID No: 114) induced soluble expression of Olive flounder hepcidin I successfully.

19-4: Analysis of Effect of Modification of N-Terminal of GFP on Soluble Expression of GFP From the previous result, the inventors recognized that a leader peptide MEEEEEE (SEQ ID No: 223) induced the highest level of soluble expression of GFP (FIG. 22, lane 3). The present inventors constructed GFP expression vectors comprising polynucleotides encoding modified GFP whose one or more amino acids among the 2$^{nd}$ to the 5$^{th}$ position was substituted with a hydrophilic amino acid, Glu, transformed E. coli BL21(DE3) with the expression vectors using a method described Example 19-1, and determined GFP expression level in total protein fraction and soluble fraction in order to investigate whether the modification of N-terminal of a heterologous protein effects on soluble expression of GFP (FIG. 6). The above GFP expression vectors were designated as GFP$_{1-7}$(V2E) (SEQ ID No: 232), GFP$_{1-7}$(V2E-S3E) (SEQ ID No: 233), GFP$_{1-7}$(V2E-S3E-K4E) (SEQ ID No: 234) and GFP$_{1-7}$(V2E-S3E-K4E-G5E) (SEQ ID No: 235), respectively, and pI values and hydrophilicities thereof were analyzed (Table 14 and FIG. 22).

Consequently, clones having GFP$_{1-7}$(V2E), GFP$_{1-7}$(V2E-S3E) or GFP$_{1-7}$(V2E-S3E-K4E) showed higher level of soluble expression than control. Particularly, V2E made by substitution of the 2$^{nd}$ valine followed by the 1$^{st}$ Met with glutamate, which showed the highest level of soluble expression and GFP$_{1-7}$(V2E-S3E-K4E-G5E) whose hydrophilicity is highest showed little lower level of soluble expression than control (FIG. 22, lane 5). From the above result, it is acknowledged that pI value according to the position where a hydrophilic amino acid is inserted at the N-terminal correlates to soluble expression of GFP rather than just only hydrophilicity if the hydrophilicity is over certain degree, although the more hydrophilic amino acids such as glutamate are added, the higher the level of soluble expression of GFP gets generally.

TABLE 4

Soluble expression level of GFP according to amino acid sequences, pI values and hydrophilicities

| SEQ ID Nos | Amino acid sequences of N-terminal of leader peptides | pI value | Hy* | SEQ ID Nos | Forward primers used for designing leader peptides | Relative soluble expression |
|---|---|---|---|---|---|---|
| 217 | MEE-TAIAI-8 × Arg | 3.09 | 1.34 | 239 | CAT ATG GAA GAG ACA GCT ATC GCG ATT CGC CGT CGC CGT CGC CGT CGC CGT ATG GTG AGC AAG GGC GAG GAG | ++ |
| 218 | MAA-TAIAI-8 × Arg | 5.60 | 1.16 | 240 | CAT ATG GCT GCA ACA GCT ATC GCG ATT CGC CGT CGC CGT CGC CGT CGC CGT ATG GTG AGC AAG GGC GAG GAG | + |
| 219 | MAH-TAIAI-8 × Arg | 7.65 | 1.16 | 241 | CAT ATG GCT CAC ACA GCT ATC GCG ATT CGC CGT CGC CGT CGC CGT CGC CGT ATG GTG AGC AAG GGC GAG GAG | + |
| 220 | MKK-TAIAI-8 × Arg | 10.55 | 1.34 | 242 | CAT ATG AAA AAA ACA GCT ATC GCG ATT CGC CGT CGC CGT CGC CGT CGC CGT ATG GTG AGC AAG GGC GAG GAG | − |

TABLE 4-continued

Soluble expression level of GFP according to amino acid sequences, pI values and hydrophilicities

| SEQ ID Nos | Amino acid sequences of N-terminal of leader peptides | pI value | Hy* | SEQ ID Nos | Forward primers used for designing leader peptides | Relative soluble expression |
|---|---|---|---|---|---|---|
| 221 | MRR-TAIAI-8 × Arg | 12.50 | 1.34 | 243 | CAT ATG CGT CGC ACA GCT ATC GCG ATT CGC CGT CGC CGT CGC CGT CGC CGT ATG GTG AGC AAG GGC GAG GAG | − |
| 222 | M-D6 | 2.56 | 1.82 | 244 | CAT ATG GAC GAT GAC GAT GAC GAT ATG GTG AGC AAG GGC GAG GAG | ++ |
| 223 | M-E6 | 2.82 | 1.82 | 245 | CAT ATG GAA GAA GAA GAA GAA GAA ATG GTG AGC AAG GGC GAG GAG | +++++ |
| 224 | M-K6 | 11.21 | 1.82 | 246 | CAT ATG GAA GAA GAA GAA GAA GAA ATG GTG AGC AAG GGC GAG GAG | ++++ |
| 225 | M-R6 | 13.20 | 1.82 | 247 | CAT ATG CGT CGC CGT CGC CGT CGC ATG GTG AGC AAG GGC GAG GAG | − |
| 226 | M-R9 | 13.40 | 2.17 | 248 | CAT ATG CGT CGC CGT CGC CGT CGC CGT CGC CGT ATG GTG AGC AAG GGC GAG GAG | − |
| 227 | M-R12 | 13.54 | 2.36 | 249 | CAT ATG CGT CGC CGT CGC CGT CGC CGT CGC CGT CGC CGT CGC ATG GTG AGC AAG GGC GAG GAG | − |
| 228 | MKKRKKR-I | 12.53 | 1.82 | 250 | CAT ATG AAA AAA CGC AAA AAA CGC ATG GTG AGC AAG GGC GAG GAG | ++++ |
| 229 | MKKRKKR-II | 12.53 | 1.82 | 251 | CAT ATG AAG AAA CGC AAG AAA CGC ATG GTG AGC AAG GGC GAG GAG | + |
| 230 | MRRKRRK | 12.98 | 1.82 | 252 | CAT ATG CGT CGC AAA CGT CGC AAA ATG GTG AGC AAG GGC GAG GAG | +++ |
| 231 | GFP$_{1-7}$(control) | 4.31 | 1.06 | 253 | CAT ATG GTG AGC AAG GGC GAG GAG | + |
| 232 | GFP$_{1-7}$(V2E) | 4.01 | 1.27 | 254 | CAT ATG GAA AGC AAG GGC GAG GAG CTG TTC ACC GGG GTG | ++++ |
| 233 | GFP$_{1-7}$(V2E-S3E) | 3.84 | 1.46 | 255 | CAT ATG GAA GAA AAG GGC GAG GAG CTG TTC ACC GGG GTG | +++ |
| 234 | GFP$_{1-7}$(V2E-S3E-K4E) | 2.87 | 1.46 | 256 | CAT ATG GAA GAA GAA GGC GAG GAG CTG TTC ACC GGG GTG | ++ |
| 235 | GFP$_{1-7}$(V2E-S3E-K4E-G5E) | 2.82 | 1.82 | 257 | CAT ATG GAA GAA GAA GAA GAG GAG CTG TTC ACC GGG GTG | + |
| 236 | TorAss-GFP$_{1-7}$ (control) | N.T | N.T | 258 | TTA ACC GTC GCC GGG ATG CTG GGG CCG TCA TTG TTA ACG CCG CGA CGT GCG ACT GCG GCG CAA GCG GCG ATG GTG AGC AAG GGC GAG GAG (TorAss$_{20-39}$-aqaa-GFP$_{1-7}$) (primary primer) | N.T |
| | | | | 259 | CAT ATG AAC AAT AAC GAT CTC TTT CAG GCA TCA CGT CGG CGT TTT CGT GCA CAA CTC GGC GGC TTA ACC GTC GCC GGG ATG CTG (TorAss$_{1-27}$) (secondary primer) | + |
| 237 | OmpASP$_{1-3}$-OmpAss$_{4-23}$ (control) | 10.55 | N.T | 260 | CAT ATG AAA AAG ACA GCT ATC GCG ATT GCA GTG GCA CTG GCT GGT TTC GCT ACC GTA GCG CAG GCC GCT CCG ATG GTG AGC AAG GGC GAG GAG | +/− |
| 238 | MKKKKKK(pI 11.21, hy 1.82)-OmpAss$_{4-23}$ | 11.21 | 1.82 | 261 | CAT ATG AAA AAA AAA AAA AAA AAA ACA GCT ATC GCG ATT GCA GTG GCA CTG GCT GGT TTC GCT ACC GTA GCG CAG GCC GCT CCG ATG GTG AGC AAG GGC GAG GAG | +/− |

TABLE 4-continued

Soluble expression level of GFP according to amino acid sequences, pI values and hydrophilicities

| SEQ ID Nos | Amino acid sequences of N-terminal of leader peptides | pI value | Hy* | SEQ ID Nos | Forward primers used for designing leader peptides | Relative soluble expression |
|---|---|---|---|---|---|---|
| Reverse primer | | | | 262 | CTC GAG CTT GTA CAG CTC GTC CAT GCC | N.T |

Hy is an abbreviation for hydrophilicity and was calculated by DNASIS™ software according to Hoop-Woods scale (window size: 6 and threshold line: 0.00). If the hydrophobicity value is +, the peptide is hydrophilic, while if the hydrophobicity is −, the peptide is hydrophobic.
Bold characters in amino acid sequences refer to regions used for the calculation of pI value.
TAIAI refers to OmpASP$_{4-8}$ (Korean Patent No: 981356).
OmpAss refers to a full-length OmpA signal sequence (OmpASP$_{1-21}$ + OmPA$_{1-2}$, Korean Patent No: 981356).
Hydrophilicities were calculated with amino acid sequence of N-terminal of leader peptide listed in the second column.
CAT refers to an extended nucleotides for conserving Nde I site.
Bold characters in nucleotide sequences refer to polynucleotides effecting pI values of signal peptide variants.
Bold italic characters refer to polynucleotides corresponding to amino acids related to various pI values and hydrophilicities.
Bold underlined characters refer to polynucleotides corresponding to substituted amino acids.
Normal characters refer to polynucleotides corresponding GFP encoding region (pEGFP-N2 vector, Clontech).
Italic characters refer to polynucleotides corresponding OmpA and TorA signal sequence.
Reverse primer refers to a complementary nucleotide sequence to a polynucleotide comprising region corresponding to C-terminal of GFP, Xho I site and a region corresponding In this case, pI value of GFP$_{1-7}$(V2E) was 3.25 when calculated for ME and 4.01 when calculated for MESKGEE (SEQ ID No: 257) whereas pI value for GFP$_{1-7}$(V2E-S3E-K4E-G5E) (MEEEEEE, SEQ ID No: 156) was calculated as 2.82 which is pI value of whole sequence MEEEEEE (SEQ ID NO: 156) because all glutamate are connected to one another thus it is difficult to isolate amino acids effecting pI value. Regarding these soluble expression levels according to pI value of N-terminal, it is confirmed that expression patterns at N-terminal pI value of 3.25 and 4.01 is correlated to relative high soluble expression pattern of rMefp1 having leader peptides with N-terminal pI value of 3.25 to 4.61 shown in FIG. 17B, Table 1 and FIG. 11, and expression patterns at N-terminal pI value of 2.82 is correlated to relative low soluble expression pattern of rMefp1 having a leader peptide with N-terminal pI value of 2.82 shown in FIG. 17B, Table 1 and FIG. 11.

In addition, although GFP$_{1-7}$(V2E-S3E) and GFP$_{1-7}$(V2E-S3E-K4E) has same hydrophilicities before GFP$_{5-7}$, they have different pI values (MEEK (SEQ ID NO: 280), pI 4.31 and MEEE (SEQ ID NO: 281), pI 2.99) and showed remarkable difference in the extent of soluble expression of GFP. Thus, regarding the difference in the extent of soluble expression of GFP, it is recognized that the expression pattern at N-terminal pI value of 4.31 is correlated to relative high soluble expression pattern of rMefp1 having leader peptides with N-terminal pI value of 3.25 to 4.61 shown in FIG. 17B, Table 11 and FIG. 20, and expression patterns at N-terminal pI value of 2.99 is correlated to relative low soluble expression pattern of rMefp1 having a leader peptide with N-terminal pI value of 2.92 to 3.09 shown in FIG. 17B, Table 11 and FIG. 20.

Further, although MEEEEEE (SEQ ID No: 156) and GFP$_{1-7}$(V2E-S3E-K4E-G5E) (SEQ ID No: 235) have the same pI value and hydrophilicity, GFP$_{1-7}$(V2E-S3E-K4E-G5E) in which GFP$_{8-14}$ (LFTGVVP, pI 5.85, hy -0.58, SEQ ID No: 272) is linked to MEEEEEE (SEQ ID NO: 156) showed lower soluble expression level than control whereas MEEEEEE (SEQ ID NO: 156) in which GFP$_{1-7}$(MVSKGEE, pI 4.31, hy +1.06, SEQ ID No: 231) is linked thereto showed higher soluble expression than control. From the result, although a leader peptide has the same N-terminal pI and hydrophilicity, it is acknowledged that the hydrophilicity of successive amino acids strongly affects on the soluble expression of a heterologous protein.

Therefore, one can recognize that it is possible to enhance the expression and the secretion of a bulky folded heterologous protein through Tat pathway by substituting several amino acids with acidic or neutral but hydrophilic amino acids in N-terminal of the bulky folded heterologous protein thereby adjusting pI value and hydrophilicity thereof and optimizing the expression condition and that the closer the substituted amino acids are to the N-terminal, the stronger effect the substitution has. It is suggested that other homotype or heterotype amino acids may be applied to induce high level of soluble expression by adjusting pI value and hydrophilicity of a leader peptide of a bulky folded active protein from the present example.

19-5: Analysis of Effect of High Hydrophilicity of N-Terminal in a Signal Peptide/Sequence on Soluble Expression of GFP The present inventors constructed an expression vector, MKKKKKK (SEQ ID NO: 224)-OmpAss$_{4-23}$(SEQ ID No: 238)-GFP (N-terminal: MKKKKKK (SEQ ID NO: 224), pI 11.21) and a control, OmpAss$_{1-23}$(SEQ ID No: 46)-GFP (N-terminal: MKK (SEQ ID NO: 265), pI 10.55) using a relatively short length fragment of OmpA signal peptide (Korean Patent No: 981356) and determined soluble expression level by the method described in Example 19-1 (Table 14 and FIG. 23), in order to investigate whether high hydrophilicity of signal peptide N-terminal affects on soluble expression of GFP from the result of Examples 19-3 and 19-4 which disclose that a leader peptide having N-terminal with acidic or basic pI value and high hydrophilicity enhanced soluble expression of GFP.

As a result, expression of GFP in total protein fractions of both the clones with Western blot analysis were good but the fluorescent levels thereof quite lower than that of TorAss-GFP used as another control. Expressions of GFP in soluble fractions of both the clones were lower than that of control TorAss-GFP and the fluorescent levels thereof were very low too. The Fluorescent level of MKKKKKK (SEQ ID NO: 224)-OmpAss$_{4-23}$-GFP was little higher than that of the control OmpAss$_{1-23}$-GFP, but it is lower than that of another control, TorAss-GFP. Thus, it is recognized that high hydrophilicity of signal peptide N-terminal is not effective for soluble expression of GFP from the result that the MKKKKKK (SEQ ID NO: 224)-OmpAss$_{4-23}$-GFP showed lower soluble expression level than a clone having only MKKKKKK (SEQ ID No: 224) as a leader peptide (FIG. 23, lane 5), although hydrophilicity of signal peptide N-terminal was increased.

It is thought that the above consequences resulted from the inhibition of the secretion into the periplasm of a heterologous protein by binding of SecA protein which binds to central hydrophobic region (Wang et al., *J. Biol. Chem.* 275: 10154-10159, 2000) and signal peptidase which binds to C-terminal cleavage site of a signal peptide thereto, although elevating hydrophilicity of the N-terminal of the heterologous protein when a Sec signal peptide is used. Thus, it is assumed that N-terminal having basic pI value and high hydrophilicity within a Sec signal sequence will be less effective to induce soluble expression than an independent leader peptide having basic pI value and high hydrophilicity without common regions of the Sec signal sequences.

In addition, it assumed that a folding process of a bulky folded heterologous protein using Tat signal peptides in the cytosol will be inhibited by binding of proteins which bind to hydrophobic and cleavage region of the signal peptides (FIG. 23, see low molecular weight band of lane 2) because the Tat signal peptides have N-terminal region, a central hydrophobic region and a C-terminal cleavage region. Further, considering the characteristic of Tat translocon that there is no folding process in the periplasm (see below), the activity of the heterologous protein will decline although it would be secreted into the periplasm. Therefore, it is assumed that N-terminal having acidic pI value and high hydrophilicity within a Tat signal sequence will be less effective to induce soluble expression than an independent leader peptide having acidic pI value and high hydrophilicity without common regions of the Tat signal sequences.

In the case of TorA signal sequence, control TorAss-GFP showed both primitive GFP (upper band) form and mature GFP form (lower band) in soluble fraction (FIG. 23B, lane 2 and FIG. 22B, lane 6) but the soluble fraction has only ⅓ to ½ of fluorescent compared to control GFP (FIG. 22C and FIG. 23C) although the band areas of the soluble GFP are similar to that of control GFP (FIG. 22B, lane 6 and FIG. 23B, lane 2). It is acknowledged that mature GFP (lower band) in which a signal peptide is deleted by a signal peptidase does not emit sufficient fluorescence although primitive TorAss-GFP emits fluorescence from the result. It is assumed that TorAss-GFP which is a primitive form of a heterologous protein having Tat signal peptide such as TorA signal sequence passes through in folded form and emits fluorescence, but mature GFP whose TorA signal peptide is deleted by a signal peptidase is secreted but folding process is inhibited by binding of the signal peptidase in cleavage processing and the secreted protein which is partially folded or not folded any more in the periplasm thus emits weak fluorescence.

However, GFP having OmpA signal sequence (FIG. 23, lane 3), one of Sec signal sequences as a leader peptide and GFP having MKKKKKK (SEQ ID NO: 224)-OmpAss$_{4-23}$ as a leader peptide (FIG. 23, lane 4) emitted weak fluorescence although they showed high level of expression in total protein fraction. Thus, it assumed that a signal peptidase inhibited folding process. In addition, since the both proteins showed relatively low expression level in soluble fraction, it seems that both the GFPs emit weak fluorescence because they are secreted into the periplasm as unfolded forms through Sec translocon with diameter of about 12 Å and folded in the periplasm regardless their forms, primitive or mature.

Therefore, it is assumed that a heterologous protein selecting through the Sec pathway cannot pass through the Sec pathway when the secretion process is relative slow and the original protein is folded thereby, while the secretion via Sec translocon is induced by the formation of a mature protein which is unfolded by binding of a signal peptidase to the immature protein and then the unfolded mature protein secreted into the periplasm and folded in the periplasm.

However, it is assumed that GFP having a Tat signal peptide emits fluorescent by passing Tat translocon in a primitive folded form and a mature GFP whose signal peptide is cleaved and secreted into the periplasm through the Tat translocon is unfolded whereby the folding process is partially performed or not performed any more in the periplasm and thus it emits weak fluorescence. Thus, the unfolded GFP passing through Tat pathway does not folded in the periplasm or the folding process in the periplasm is not effective contrary to the case that unfolded GFP passing through Sec pathway is folded in the periplasm.

Since unfolded GFP by a leader peptide with basic pI value passes through Sec pathway and folded in the periplasm and then emits fluorescence, heterologous proteins passing through Sec pathway and Tat pathway, respectively, are complementary each other regarding whether they have folding mechanisms in the cytosol and in the periplasm, respectively.

Therefore, in order to express a bulky folded active protein in soluble form, when one constitutes a leader peptide with several acidic or basic hydrophilic amino acids linked to Met, 1) proper pI value for the selection of Tat channel, 2) hydrophilicity determining secretion rate, and 3) expression level of the protein (excluding exceptional case of wobble phenomenon) are key factors for soluble expression of the bulky folded active protein thus it is possible to induce soluble expression of the heterologous protein by optimizing the factors properly according to their secretional pathway.

From the examples, the present inventors accomplished the present invention by confirming that soluble expression and secretion of a heterologous protein, particularly a bulky folded active protein which has one or more intrinsic disulfide bonds or transmembrane-like domain is induced by linking a leader peptide with acidic pI and high hydrophilicity thereto; by substituting one or more amino acids within N-terminal of the heterologous protein with ones having acidic or neutral pI and high hydrophilicity; or elevating $\Delta G_{RNA}$ value of a polynucleotide encoding the leader peptide having basic pI value and high hydrophilicity.

INDUSTRIAL APPLICABILITY

The expression vector and the method according to an example of the present invention may be used for the production of recombinant proteins as well as the transduction of therapeutic proteins because it can prevent formation of insoluble inclusion body of an insoluble heterologous protein efficiency thereof.

While the present invention has been described in connection with certain exemplary examples, it is to be understood that the invention is not limited to the disclosed examples, but, on the contrary, is intended to cover various modifications and equivalent arrangements included within the spirit and scope of the appended claims, and equivalents thereof.

The invention claimed is:

1. An artificial signal peptide consisting of an amino acid sequence of $M(X)_{5-8}$, wherein X is arginine, glutamic acid, or aspartic acid.

2. The artificial signal peptide according to claim 1, wherein the artificial signal peptide is selected from the group consisting of:
MRRRRRRR (SEQ ID NO: 114);
MEEEEEE (SEQ ID NO: 223); and
MDDDDDD (SEQ ID NO: 222).

3. A recombinant fusion protein comprising the artificial signal peptide of claim 1 linked to a heterologous protein, wherein there is no intervening amino acid between the artificial signal peptide and the heterologous protein.

4. A method for expressing an insoluble heterologous protein in a soluble form comprising:
providing a recombinant gene construct consisting of a promoter and a nucleotide encoding the artificial signal peptide of claim 1 and a heterologous protein fused thereto and there is no intervening amino acid sequence between the artificial signal sequence and the heterologous protein,
transforming a host cell with the recombinant gene construct, and
culturing the transformed host cell.

5. The method according to claim 4, wherein the artificial signal peptide is selected from the group consisting of:
MRRRRRRR (SEQ ID NO: 114);
MEEEEEE (SEQ ID NO: 223); and
MDDDDDD (SEQ ID NO: 222).

6. The method according to claim 4, wherein the host cell is gram-negative bacteria.

* * * * *

SEQUENCE LISTING

<160> NUMBER OF SEQ ID NOS: 290

<210> SEQ ID NO 1
<211> LENGTH: 10
<212> TYPE: PRT
<213> ORGANISM: Artificial Sequence
<220> FEATURE:
<223> OTHER INFORMATION: Mefp1

<400> SEQUENCE: 1

Ala Lys Pro Ser Tyr Pro Pro Thr Tyr Lys
1               5                   10

<210> SEQ ID NO 2
<211> LENGTH: 30
<212> TYPE: DNA
<213> ORGANISM: Artificial Sequence
<220> FEATURE:
<223> OTHER INFORMATION: sense primer for Mefp1

<400> SEQUENCE: 2
tacaaagcta agccgtctta tccgccaacc                                      30

<210> SEQ ID NO 3
<211> LENGTH: 30
<212> TYPE: DNA
<213> ORGANISM: Artificial Sequence
<220> FEATURE:
<223> OTHER INFORMATION: antisense primer for Mefp1

<400> SEQUENCE: 3
tttgtaggtt ggcggataag acggcttagc                                      30

<210> SEQ ID NO 4
<211> LENGTH: 17
<212> TYPE: DNA
<213> ORGANISM: Artificial Sequence
<220> FEATURE:
<223> OTHER INFORMATION: sense primer

<400> SEQUENCE: 4
gatccgaatt ccccggg                                                    17

<210> SEQ ID NO 5
<211> LENGTH: 19
<212> TYPE: DNA
<213> ORGANISM: Artificial Sequence
<220> FEATURE:
<223> OTHER INFORMATION: antisense primer

<400> SEQUENCE: 5
tttgtacccg gggaattcg                                                  19

<210> SEQ ID NO 6
<211> LENGTH: 22
<212> TYPE: DNA
<213> ORGANISM: Artificial Sequence
<220> FEATURE:
<223> OTHER INFORMATION: sense primer

<400> SEQUENCE: 6
tacaaacgta agcttgtcga cc                                              22

<210> SEQ ID NO 7
<211> LENGTH: 20
<212> TYPE: DNA

```
<213> ORGANISM: Artificial Sequence
<220> FEATURE:
<223> OTHER INFORMATION: antisense primer

<400> SEQUENCE: 7
tcgaggtcga caagcttacg                                                    20

<210> SEQ ID NO 8
<211> LENGTH: 36
<212> TYPE: DNA
<213> ORGANISM: Artificial Sequence
<220> FEATURE:
<223> OTHER INFORMATION: pET-22b(+)OmpASP1-3-7xMefp1* sense primer

<400> SEQUENCE: 8
catatgaaaa aggctaagcc gtcttatccg ccaacc                                  36

<210> SEQ ID NO 9
<211> LENGTH: 39
<212> TYPE: DNA
<213> ORGANISM: Artificial Sequence
<220> FEATURE:
<223> OTHER INFORMATION: pET22b(+)OmpASP1-4-7xMefp1* sense primer

<400> SEQUENCE: 9
catatgaaaa agacagctaa gccgtcttat ccgccaacc                               39

<210> SEQ ID NO 10
<211> LENGTH: 42
<212> TYPE: DNA
<213> ORGANISM: Artificial Sequence
<220> FEATURE:
<223> OTHER INFORMATION: pET22b(+)OmpASP1-5-7xMefp1* sense primer

<400> SEQUENCE: 10
catatgaaaa agacagctgc taagccgtct tatccgccaa cc                           42

<210> SEQ ID NO 11
<211> LENGTH: 45
<212> TYPE: DNA
<213> ORGANISM: Artificial Sequence
<220> FEATURE:
<223> OTHER INFORMATION: pET22b(+)OmpASP1-6-7xMefp1* sense primer

<400> SEQUENCE: 11
catatgaaaa agacagctat cgctaagccg tcttatccgc caacc                        45

<210> SEQ ID NO 12
<211> LENGTH: 48
<212> TYPE: DNA
<213> ORGANISM: Artificial Sequence
<220> FEATURE:
<223> OTHER INFORMATION: pET22b(+)OmpASP1-7-7xMefp1* sense primer

<400> SEQUENCE: 12
catatgaaaa agacagctat cgcggctaag ccgtcttatc cgccaacc                     48

<210> SEQ ID NO 13
<211> LENGTH: 51
<212> TYPE: DNA
<213> ORGANISM: Artificial Sequence
<220> FEATURE:
<223> OTHER INFORMATION: pET22b(+)-OmpASP1-8-7xMefp1* sense primer

<400> SEQUENCE: 13
catatgaaaa agacagctat cgcgattgct aagccgtctt atccgccaac c                 51
```

<210> SEQ ID NO 14
<211> LENGTH: 54
<212> TYPE: DNA
<213> ORGANISM: Artificial Sequence
<220> FEATURE:
<223> OTHER INFORMATION: pET22b(+)OmpASPI-9-7xMefp1* sense primer

<400> SEQUENCE: 14
catatgaaaa agacagctat cgcgattgca gctaagccgt cttatccgcc aacc    54

<210> SEQ ID NO 15
<211> LENGTH: 57
<212> TYPE: DNA
<213> ORGANISM: Artificial Sequence
<220> FEATURE:
<223> OTHER INFORMATION: pET22b(+)OmpASPI-I0-7xMefp1* sense primer

<400> SEQUENCE: 15
catatgaaaa agacagctat cgcgattgca gtggctaagc cgtcttatcc gccaacc    57

<210> SEQ ID NO 16
<211> LENGTH: 60
<212> TYPE: DNA
<213> ORGANISM: Artificial Sequence
<220> FEATURE:
<223> OTHER INFORMATION: pET22b(+)OmpASPI-II-7xMefp1* sense primer

<400> SEQUENCE: 16
catatgaaaa agacagctat cgcgattgca gtggcagcta agccgtctta tccgccaacc    60

<210> SEQ ID NO 17
<211> LENGTH: 66
<212> TYPE: DNA
<213> ORGANISM: Artificial Sequence
<220> FEATURE:
<223> OTHER INFORMATION: pET22b(+)OmpASPI-13-7xMefp1* sense primer

<400> SEQUENCE: 17
catatgaaaa agacagctat cgcgattgca gtggcactgg ctgctaagcc gtcttatccg    60
ccaacc    66

<210> SEQ ID NO 18
<211> LENGTH: 72
<212> TYPE: DNA
<213> ORGANISM: Artificial Sequence
<220> FEATURE:
<223> OTHER INFORMATION: pET22b(+)OmpASPI-15-7xMefp1* sense primer

<400> SEQUENCE: 18
catatgaaaa agacagctat cgcgattgca gtggcactgg ctggtttcgc taagccgtct    60
tatccgccaa cc    72

<210> SEQ ID NO 19
<211> LENGTH: 90
<212> TYPE: DNA
<213> ORGANISM: Artificial Sequence
<220> FEATURE:
<223> OTHER INFORMATION: pET22b(+)OmpASP1-21-7xMefp1* sense primer

<400> SEQUENCE: 19
catatgaaaa agacagctat cgcgattgca gtggcactgg ctggtttcgc taccgtagcg    60
caggccgcta agccgtctta tccgccaacc    90

<210> SEQ ID NO 20
<211> LENGTH: 96
<212> TYPE: DNA
<213> ORGANISM: Artificial Sequence
<220> FEATURE:
<223> OTHER INFORMATION: pET22b(+)OmpASP1-23-7xMefp1* sense primer

<400> SEQUENCE: 20

```
catatgaaaa agacagctat cgcgattgca gtggcactgg ctggtttcgc taccgtagcg    60
caggccgctc cggctaagcc gtcttatccg ccaacc                              96
```

<210> SEQ ID NO 21
<211> LENGTH: 63
<212> TYPE: DNA
<213> ORGANISM: Artificial Sequence
<220> FEATURE:
<223> OTHER INFORMATION: pET22b(+)OmpASP1-8-xa-7xMefp1* sense primer

<400> SEQUENCE: 21

```
catatgaaaa agacagctat cgcgattatc gaaggtcgtg ctaagccgtc ttatccgcca    60
acc                                                                  63
```

<210> SEQ ID NO 22
<211> LENGTH: 69
<212> TYPE: DNA
<213> ORGANISM: Artificial Sequence
<220> FEATURE:
<223> OTHER INFORMATION: pET22b(+)OmpASP1-8-SmaI-xa-7xMefp1* sense
      primer

<400> SEQUENCE: 22

```
catatgaaaa agacagctat cgcgattccc gggatcgaag gtcgtgctaa gccgtcttat    60
ccgccaacc                                                            69
```

<210> SEQ ID NO 23
<211> LENGTH: 21
<212> TYPE: DNA
<213> ORGANISM: Artificial Sequence
<220> FEATURE:
<223> OTHER INFORMATION: reverse primer

<400> SEQUENCE: 23

```
ctcgaggtcg acaagcttac g                                              21
```

<210> SEQ ID NO 24
<211> LENGTH: 39
<212> TYPE: DNA
<213> ORGANISM: Artificial Sequence
<220> FEATURE:
<223> OTHER INFORMATION: pET22b(+)OmpASP1-4 ofHepI** sense primer

<400> SEQUENCE: 24

```
catatgaaaa agacacacat cagccacatc tccatgtgc                           39
```

<210> SEQ ID NO 25
<211> LENGTH: 45
<212> TYPE: DNA
<213> ORGANISM: Artificial Sequence
<220> FEATURE:
<223> OTHER INFORMATION: pET22b(+)OmpASP1-6 ofHepI** sense primer

<400> SEQUENCE: 25

```
catatgaaaa agacagctat ccacatcagc cacatctcca tgtgc                    45
```

<210> SEQ ID NO 26
<211> LENGTH: 51
<212> TYPE: DNA
<213> ORGANISM: Artificial Sequence
<220> FEATURE:
<223> OTHER INFORMATION: pET22b(+)OmpASP1-8 ofHepI** snse primer

<400> SEQUENCE: 26
catatgaaaa agacagctat cgcgattcac atcagccaca tctccatgtg c        51

<210> SEQ ID NO 27
<211> LENGTH: 57
<212> TYPE: DNA
<213> ORGANISM: Artificial Sequence
<220> FEATURE:
<223> OTHER INFORMATION: pET22b(+)OmpASP1-10 ofHepI** primer

<400> SEQUENCE: 27
catatgaaaa agacagctat cgcgattgca gtgcacatca gccacatctc catgtgc    57

<210> SEQ ID NO 28
<211> LENGTH: 63
<212> TYPE: DNA
<213> ORGANISM: Artificial Sequence
<220> FEATURE:
<223> OTHER INFORMATION: pET22b(+)OmpASP1-12 ofHepI** sense primer

<400> SEQUENCE: 28
catatgaaaa agacagctat cgcgattgca gtggcactgc acatcagcca catctccatg    60
tgc    63

<210> SEQ ID NO 29
<211> LENGTH: 87
<212> TYPE: DNA
<213> ORGANISM: Artificial Sequence
<220> FEATURE:
<223> OTHER INFORMATION: pET22b(+)OmpASP1-10-6xTrp-xa-ofHepI** sense
      primer

<400> SEQUENCE: 29
catatgaaaa agacagctat cgcgattgca gtgtggtggt ggtggtggtg gatcgaaggt    60
cgtcacatca gccacatctc catgtgc    87

<210> SEQ ID NO 30
<211> LENGTH: 87
<212> TYPE: DNA
<213> ORGANISM: Artificial Sequence
<220> FEATURE:
<223> OTHER INFORMATION: pET22b(+)OmpASP1-10-6xArg-xa-ofHepI** sense
      primer

<400> SEQUENCE: 30
catatgaaaa agacagctat cgcgattgca gtgcgccgtc gccgtcgccg tatcgaaggt    60
cgtcacatca gccacatctc catgtgc    87

<210> SEQ ID NO 31
<211> LENGTH: 87
<212> TYPE: DNA
<213> ORGANISM: Artificial Sequence
<220> FEATURE:
<223> OTHER INFORMATION: pET22b(+)OmpASP1-10-6xLys-xa-ofHepI** sense
      primer

<400> SEQUENCE: 31

```
catatgaaaa agacagctat cgcgattgca gtgaaaaaga aaagaaaaa gatcgaaggt    60 cgtcacatca gccacatctc catgtgc                                      87
```

<210> SEQ ID NO 32
<211> LENGTH: 87
<212> TYPE: DNA
<213> ORGANISM: Artificial Sequence
<220> FEATURE:
<223> OTHER INFORMATION: pET22b(+)OmpASP1-10-6xGlu-xa-ofHepI** sense
      primer

<400> SEQUENCE: 32

```
catatgaaaa agacagctat cgcgattgca gtggaagagg aagaggaaga gatcgaaggt    60
cgtcacatca gccacatctc catgtgc                                        87
```

<210> SEQ ID NO 33
<211> LENGTH: 87
<212> TYPE: DNA
<213> ORGANISM: Artificial Sequence
<220> FEATURE:
<223> OTHER INFORMATION: pET22b(+)OmpASP1-10-6xAsp-xa-ofHepI** sense
      primer

<400> SEQUENCE: 33

```
catatgaaaa agacagctat cgcgattgca gtggacgatg acgatgacga tatcgaaggt    60
cgtcacatca gccacatctc catgtgc                                        87
```

<210> SEQ ID NO 34
<211> LENGTH: 87
<212> TYPE: DNA
<213> ORGANISM: Artificial Sequence
<220> FEATURE:
<223> OTHER INFORMATION: pET22b(+)OmpASP1-10-6xTyr-xa-ofHepI** sense
      primer

<400> SEQUENCE: 34

```
catatgaaaa agacagctat cgcgattgca gtgtactatt actattacta tatcgaaggt    60
cgtcacatca gccacatctc catgtgc                                        87
```

<210> SEQ ID NO 35
<211> LENGTH: 87
<212> TYPE: DNA
<213> ORGANISM: Artificial Sequence
<220> FEATURE:
<223> OTHER INFORMATION: pET22b(+)OmpASP1-10-6xphe-xa-ofHepI** sense
      primer

<400> SEQUENCE: 35

```
catatgaaaa agacagctat cgcgattgca gtgttctttt cttttttctt tatcgaaggt    60
cgtcacatca gccacatctc catgtgc                                        87
```

<210> SEQ ID NO 36
<211> LENGTH: 75
<212> TYPE: DNA
<213> ORGANISM: Artificial Sequence
<220> FEATURE:
<223> OTHER INFORMATION: pET22b(+)OmpASP1-6-6xArg-xa-ofHepI** sense
      primer

<400> SEQUENCE: 36

```
catatgaaaa agacagctat ccgccgtcgc cgtcgccgta tcgaaggtcg tcacatcagc    60
cacatctcca tgtgc                                                     75
```

```
<210> SEQ ID NO 37
<211> LENGTH: 81
<212> TYPE: DNA
<213> ORGANISM: Artificial Sequence
<220> FEATURE:
<223> OTHER INFORMATION: pET22b(+)OmpASP1-8-6xArg-xa-ofHepI** sense
      primer

<400> SEQUENCE: 37
catatgaaaa agacagctat cgcgattcgc cgtcgccgtc gccgtatcga aggtcgtcac        60
atcagccaca tctccatgtg c                                                 81

<210> SEQ ID NO 38
<211> LENGTH: 93
<212> TYPE: DNA
<213> ORGANISM: Artificial Sequence
<220> FEATURE:
<223> OTHER INFORMATION: pET22b(+)OmpASP1-12-6xArg-xa-ofHepI** sense
      primer

<400> SEQUENCE: 38
catatgaaaa agacagctat cgcgattgca gtggcactgc gccgtcgccg tcgccgtatc        60
gaaggtcgtc acatcagcca catctccatg tgc                                    93

<210> SEQ ID NO 39
<211> LENGTH: 99
<212> TYPE: DNA
<213> ORGANISM: Artificial Sequence
<220> FEATURE:
<223> OTHER INFORMATION: pET22b(+)OmpASP1-14-6xArg-xa-ofHepI* sense
      primer

<400> SEQUENCE: 39
catatgaaaa agacagctat cgcgattgca gtggcactgg ctggtcgccg tcgccgtcgc        60
cgtatcgaag gtcgtcacat cagccacatc tccatgtgc                              99

<210> SEQ ID NO 40
<211> LENGTH: 69
<212> TYPE: DNA
<213> ORGANISM: Artificial Sequence
<220> FEATURE:
<223> OTHER INFORMATION: pET22b(+)OmpASP1-10-xa-ofHepI** sense primer

<400> SEQUENCE: 40
catatgaaaa agacagctat cgcgattgca gtgatcgaag gtcgtcacat cagccacatc        60
tccatgtgc                                                               69

<210> SEQ ID NO 41
<211> LENGTH: 75
<212> TYPE: DNA
<213> ORGANISM: Artificial Sequence
<220> FEATURE:
<223> OTHER INFORMATION: pET22b(+)OmpASP1-10-LysArg-xa-ofHepI** sense
      primer

<400> SEQUENCE: 41
catatgaaaa agacagctat cgcgattgca gtgaaacgca tcgaaggtcg tcacatcagc        60
cacatctcca tgtgc                                                        75

<210> SEQ ID NO 42
<211> LENGTH: 81
<212> TYPE: DNA
<213> ORGANISM: Artificial Sequence
```

```
<220> FEATURE:
<223> OTHER INFORMATION: pET22b(+)OmpASPI-I0-4xArg-xa-ofHepI** sense
      primer

<400> SEQUENCE: 42
catatgaaaa agacagctat cgcgattgca gtgcgccgtc gccgtatcga aggtcgtcac    60
atcagccaca tctccatgtg c                                             81

<210> SEQ ID NO 43
<211> LENGTH: 93
<212> TYPE: DNA
<213> ORGANISM: Artificial Sequence
<220> FEATURE:
<223> OTHER INFORMATION: pET22b(+)OmpASPI-I0-8xArg-xa-ofHepI** sense
      primer

<400> SEQUENCE: 43
catatgaaaa agacagctat cgcgattgca gtgcgccgtc gccgtcgccg tcgccgtatc    60
gaaggtcgtc acatcagcca catctccatg tgc                                93

<210> SEQ ID NO 44
<211> LENGTH: 99
<212> TYPE: DNA
<213> ORGANISM: Artificial Sequence
<220> FEATURE:
<223> OTHER INFORMATION: pET22b(+)OmpASPI-I0-I0xArg-xa-ofHepI** sense
      primer

<400> SEQUENCE: 44
catatgaaaa agacagctat cgcgattgca gtgcgccgtc gccgtcgccg tcgccgtcgc    60
cgtatcgaag gtcgtcacat cagccacatc tccatgtgc                          99

<210> SEQ ID NO 45
<211> LENGTH: 45
<212> TYPE: DNA
<213> ORGANISM: Artificial Sequence
<220> FEATURE:
<223> OTHER INFORMATION: reverse primer

<400> SEQUENCE: 45
ctcgaggtcg acaagctttt cgaacttgca gcaggggcca cagcc                   45

<210> SEQ ID NO 46
<211> LENGTH: 23
<212> TYPE: PRT
<213> ORGANISM: Artificial Sequence
<220> FEATURE:
<223> OTHER INFORMATION: OmpA signal peptide

<400> SEQUENCE: 46

Met Lys Lys Thr Ala Ile Ala Ile Ala Val Ala Leu Ala Gly Phe Ala
1               5                   10                  15

Thr Ala Gln Ala Ala Pro
            20

<210> SEQ ID NO 47
<211> LENGTH: 26
<212> TYPE: PRT
<213> ORGANISM: Paralichthys olivaceus

<400> SEQUENCE: 47

His Ile Ser His Ile Ser Met Cys Arg Trp Cys Cys Asn Cys Cys Lys
1               5                   10                  15
```

```
Ala Lys Gly Cys Gly Pro Cys Cys Lys Phe
         20                  25
```

<210> SEQ ID NO 48
<211> LENGTH: 33
<212> TYPE: DNA
<213> ORGANISM: Artificial Sequence
<220> FEATURE:
<223> OTHER INFORMATION: forward primer for OmpASP1(Met)-Ala-Lys

<400> SEQUENCE: 48
catatggcta agccgtctta tccgccaacc tac                              33

<210> SEQ ID NO 49
<211> LENGTH: 36
<212> TYPE: DNA
<213> ORGANISM: Artificial Sequence
<220> FEATURE:
<223> OTHER INFORMATION: forward primer for OmpASP1(Met-Lys)-Ala-Lys

<400> SEQUENCE: 49
catatgaaag ctaagccgtc ttatccgcca acctac                           36

<210> SEQ ID NO 50
<211> LENGTH: 36
<212> TYPE: DNA
<213> ORGANISM: Artificial Sequence
<220> FEATURE:
<223> OTHER INFORMATION: forward primer for OmpASP1(Met-Lys-Lys)-Ala-Lys

<400> SEQUENCE: 50
catatgaaaa aggctaagcc gtcttatccg ccaacc                           36

<210> SEQ ID NO 51
<211> LENGTH: 39
<212> TYPE: DNA
<213> ORGANISM: Artificial Sequence
<220> FEATURE:
<223> OTHER INFORMATION: forward primer for MKKKAK

<400> SEQUENCE: 51
catatgaaaa aaaagctaa gccgtcttat ccgccaacc                         39

<210> SEQ ID NO 52
<211> LENGTH: 42
<212> TYPE: DNA
<213> ORGANISM: Artificial Sequence
<220> FEATURE:
<223> OTHER INFORMATION: forward primer for MKKKKAK

<400> SEQUENCE: 52
catatgaaaa aaaaaaagc taagccgtct tatccgccaa cc                     42

<210> SEQ ID NO 53
<211> LENGTH: 45
<212> TYPE: DNA
<213> ORGANISM: Artificial Sequence
<220> FEATURE:
<223> OTHER INFORMATION: forward primer for MKKKKKAK

<400> SEQUENCE: 53
catatgaaaa aaaaaaaaaa agctaagccg tcttatccgc caacc                 45

<210> SEQ ID NO 54
<211> LENGTH: 48
<212> TYPE: DNA

```
<213> ORGANISM: Artificial Sequence
<220> FEATURE:
<223> OTHER INFORMATION: forward primer for MKKKKKKAK

<400> SEQUENCE: 54
catatgaaaa aaaaaaaaa aaaagctaag ccgtcttatc cgccaacc          48

<210> SEQ ID NO 55
<211> LENGTH: 54
<212> TYPE: DNA
<213> ORGANISM: Artificial Sequence
<220> FEATURE:
<223> OTHER INFORMATION: forward primer for MKKKKKKKKAK

<400> SEQUENCE: 55
catatgaaaa aaaaaaaaa aaaaaaaaa gctaagccgt cttatccgcc aacc    54

<210> SEQ ID NO 56
<211> LENGTH: 36
<212> TYPE: DNA
<213> ORGANISM: Artificial Sequence
<220> FEATURE:
<223> OTHER INFORMATION: forward primer for MRAK

<400> SEQUENCE: 56
catatgcgtg ctaagccgtc ttatccgcca acctac                     36

<210> SEQ ID NO 57
<211> LENGTH: 36
<212> TYPE: DNA
<213> ORGANISM: Artificial Sequence
<220> FEATURE:
<223> OTHER INFORMATION: forward primer for MRRAK

<400> SEQUENCE: 57
catatgcgtc gcgctaagcc gtcttatccg ccaacc                     36

<210> SEQ ID NO 58
<211> LENGTH: 42
<212> TYPE: DNA
<213> ORGANISM: Artificial Sequence
<220> FEATURE:
<223> OTHER INFORMATION: forward primer for MRRRRAK

<400> SEQUENCE: 58
catatgcgtc gccgtcgcgc taagccgtct tatccgccaa cc              42

<210> SEQ ID NO 59
<211> LENGTH: 48
<212> TYPE: DNA
<213> ORGANISM: Artificial Sequence
<220> FEATURE:
<223> OTHER INFORMATION: forward primer for MRRRRRRAK

<400> SEQUENCE: 59
catatgcgtc gccgtcgccg tcgcgctaag ccgtcttatc cgccaacc        48

<210> SEQ ID NO 60
<211> LENGTH: 54
<212> TYPE: DNA
<213> ORGANISM: Artificial Sequence
<220> FEATURE:
<223> OTHER INFORMATION: forward primer for MRRRRRRRRAK

<400> SEQUENCE: 60
catatgcgtc gccgtcgccg tcgccgtcgc gctaagccgt cttatccgcc aacc  54
```

```
<210> SEQ ID NO 61
<211> LENGTH: 3
<212> TYPE: PRT
<213> ORGANISM: Artificial Sequence
<220> FEATURE:
<223> OTHER INFORMATION: OmpASP1(Met)-Ala-Lys

<400> SEQUENCE: 61

Met Ala Lys
1

<210> SEQ ID NO 62
<211> LENGTH: 4
<212> TYPE: PRT
<213> ORGANISM: Artificial Sequence
<220> FEATURE:
<223> OTHER INFORMATION: OmpASP1(Met-Lys)-Ala-Lys

<400> SEQUENCE: 62

Met Lys Ala Lys
1

<210> SEQ ID NO 63
<211> LENGTH: 5
<212> TYPE: PRT
<213> ORGANISM: Artificial Sequence
<220> FEATURE:
<223> OTHER INFORMATION: OmpASP1(Met-Lys-Lys)-Ala-Lys

<400> SEQUENCE: 63

Met Lys Lys Ala Lys
1               5

<210> SEQ ID NO 64
<211> LENGTH: 6
<212> TYPE: PRT
<213> ORGANISM: Artificial Sequence
<220> FEATURE:
<223> OTHER INFORMATION: 18

<400> SEQUENCE: 64

Met Lys Lys Lys Ala Lys
1               5

<210> SEQ ID NO 65
<211> LENGTH: 7
<212> TYPE: PRT
<213> ORGANISM: Artificial Sequence
<220> FEATURE:
<223> OTHER INFORMATION: artificial signal peptide MKKKKAK

<400> SEQUENCE: 65

Met Lys Lys Lys Lys Ala Lys
1               5

<210> SEQ ID NO 66
<211> LENGTH: 8
<212> TYPE: PRT
<213> ORGANISM: Artificial Sequence
<220> FEATURE:
<223> OTHER INFORMATION: artificial signal peptide MKKKKKAK

<400> SEQUENCE: 66

Met Lys Lys Lys Lys Lys Ala Lys
1               5
```

```
<210> SEQ ID NO 67
<211> LENGTH: 9
<212> TYPE: PRT
<213> ORGANISM: Artificial Sequence
<220> FEATURE:
<223> OTHER INFORMATION: artificial signal peptide MKKKKKAK

<400> SEQUENCE: 67

Met Lys Lys Lys Lys Lys Lys Ala Lys
1               5

<210> SEQ ID NO 68
<211> LENGTH: 11
<212> TYPE: PRT
<213> ORGANISM: Artificial Sequence
<220> FEATURE:
<223> OTHER INFORMATION: artificial signal peptide MKKKKKKKKAK

<400> SEQUENCE: 68

Met Lys Lys Lys Lys Lys Lys Lys Lys Ala Lys
1               5                   10

<210> SEQ ID NO 69
<211> LENGTH: 4
<212> TYPE: PRT
<213> ORGANISM: Artificial Sequence
<220> FEATURE:
<223> OTHER INFORMATION: artificial signal peptide MRAK

<400> SEQUENCE: 69

Met Arg Ala Lys
1

<210> SEQ ID NO 70
<211> LENGTH: 5
<212> TYPE: PRT
<213> ORGANISM: Artificial Sequence
<220> FEATURE:
<223> OTHER INFORMATION: artificial signal peptide MRRAK

<400> SEQUENCE: 70

Met Arg Arg Ala Lys
1               5

<210> SEQ ID NO 71
<211> LENGTH: 7
<212> TYPE: PRT
<213> ORGANISM: Artificial Sequence
<220> FEATURE:
<223> OTHER INFORMATION: artificial signal peptide MRRRRAK

<400> SEQUENCE: 71

Met Arg Arg Arg Arg Ala Lys
1               5

<210> SEQ ID NO 72
<211> LENGTH: 9
<212> TYPE: PRT
<213> ORGANISM: Artificial Sequence
<220> FEATURE:
<223> OTHER INFORMATION: artificial signal peptide MRRRRRRAK

<400> SEQUENCE: 72

Met Arg Arg Arg Arg Arg Arg Ala Lys
1               5
```

```
<210> SEQ ID NO 73
<211> LENGTH: 11
<212> TYPE: PRT
<213> ORGANISM: Artificial Sequence
<220> FEATURE:
<223> OTHER INFORMATION: artificial signal peptide MRRRRRRRRAK

<400> SEQUENCE: 73

Met Arg Arg Arg Arg Arg Arg Arg Arg Ala Lys
1               5                   10

<210> SEQ ID NO 74
<211> LENGTH: 45
<212> TYPE: DNA
<213> ORGANISM: Artificial Sequence
<220> FEATURE:
<223> OTHER INFORMATION: forward primer for MDDDDDAA

<400> SEQUENCE: 74
catatggacg atgacgatgc tgcaccgtct tatccgccaa cctac            45

<210> SEQ ID NO 75
<211> LENGTH: 42
<212> TYPE: DNA
<213> ORGANISM: Artificial Sequence
<220> FEATURE:
<223> OTHER INFORMATION: forward primer for MDDDDAA

<400> SEQUENCE: 75
catatggacg atgacgctgc accgtcttat ccgccaacct ac               42

<210> SEQ ID NO 76
<211> LENGTH: 33
<212> TYPE: DNA
<213> ORGANISM: Artificial Sequence
<220> FEATURE:
<223> OTHER INFORMATION: forward primer for MEE

<400> SEQUENCE: 76
catatggaag agccgtctta tccgccaacc tac                         33

<210> SEQ ID NO 77
<211> LENGTH: 33
<212> TYPE: DNA
<213> ORGANISM: Artificial Sequence
<220> FEATURE:
<223> OTHER INFORMATION: forward primer for MAE

<400> SEQUENCE: 77
catatggctg aaccgtctta tccgccaacc tac                         33

<210> SEQ ID NO 78
<211> LENGTH: 33
<212> TYPE: DNA
<213> ORGANISM: Artificial Sequence
<220> FEATURE:
<223> OTHER INFORMATION: forward primer for MAA

<400> SEQUENCE: 78
catatggctg caccgtctta tccgccaacc tac                         33

<210> SEQ ID NO 79
<211> LENGTH: 33
<212> TYPE: DNA
<213> ORGANISM: Artificial Sequence
<220> FEATURE:
<223> OTHER INFORMATION: forward primer for MCH
```

<400> SEQUENCE: 79
catatgtgcc acccgtctta tccgccaacc tac                                    33

<210> SEQ ID NO 80
<211> LENGTH: 33
<212> TYPE: DNA
<213> ORGANISM: Artificial Sequence
<220> FEATURE:
<223> OTHER INFORMATION: forward primer for MAH

<400> SEQUENCE: 80
catatggctc acccgtctta tccgccaacc tac                                    33

<210> SEQ ID NO 81
<211> LENGTH: 8
<212> TYPE: PRT
<213> ORGANISM: Artificial Sequence
<220> FEATURE:
<223> OTHER INFORMATION: artificial signal peptide MDDDDAA

<400> SEQUENCE: 81

Met Asp Asp Asp Asp Ala Ala
1               5

<210> SEQ ID NO 82
<211> LENGTH: 6
<212> TYPE: PRT
<213> ORGANISM: Artificial Sequence
<220> FEATURE:
<223> OTHER INFORMATION: artificial signal peptide MDDDAA

<400> SEQUENCE: 82

Met Asp Asp Asp Ala Ala
1               5

<210> SEQ ID NO 83
<211> LENGTH: 3
<212> TYPE: PRT
<213> ORGANISM: Artificial Sequence
<220> FEATURE:
<223> OTHER INFORMATION: artificial signal peptide MEE

<400> SEQUENCE: 83

Met Glu Glu
1

<210> SEQ ID NO 84
<211> LENGTH: 3
<212> TYPE: PRT
<213> ORGANISM: Artificial Sequence
<220> FEATURE:
<223> OTHER INFORMATION: artificial signal peptide MAE

<400> SEQUENCE: 84

Met Ala Glu
1

<210> SEQ ID NO 85
<211> LENGTH: 3
<212> TYPE: PRT
<213> ORGANISM: Artificial Sequence
<220> FEATURE:
<223> OTHER INFORMATION: artificial signal peptide MAA

<400> SEQUENCE: 85

Met Ala Ala
1

<210> SEQ ID NO 86
<211> LENGTH: 3
<212> TYPE: PRT
<213> ORGANISM: Artificial Sequence
<220> FEATURE:
<223> OTHER INFORMATION: artificial signal peptide MCH

<400> SEQUENCE: 86

Met Cys His
1

<210> SEQ ID NO 87
<211> LENGTH: 3
<212> TYPE: PRT
<213> ORGANISM: Artificial Sequence
<220> FEATURE:
<223> OTHER INFORMATION: artificial signal peptide MAH

<400> SEQUENCE: 87

Met Ala His
1

<210> SEQ ID NO 88
<211> LENGTH: 51
<212> TYPE: DNA
<213> ORGANISM: Artificial Sequence
<220> FEATURE:
<223> OTHER INFORMATION: forward primer for MEE-Xa

<400> SEQUENCE: 88
catatggaag agatcgaagg tcgtgctaag ccgtcttatc cgccaaccta c          51

<210> SEQ ID NO 89
<211> LENGTH: 57
<212> TYPE: DNA
<213> ORGANISM: Artificial Sequence
<220> FEATURE:
<223> OTHER INFORMATION: forward primer for MEEPS-Xa

<400> SEQUENCE: 89
catatggaag agccgtctat cgaaggtcgt gctaagccgt cttatccgcc aacctac    57

<210> SEQ ID NO 90
<211> LENGTH: 63
<212> TYPE: DNA
<213> ORGANISM: Artificial Sequence
<220> FEATURE:
<223> OTHER INFORMATION: forward primer for MEEPSYP-Xa

<400> SEQUENCE: 90
catatggaag agccgtctta tccgatcgaa ggtcgtgcta agccgtctta tccgccaacc    60
tac                                                                63

<210> SEQ ID NO 91
<211> LENGTH: 69
<212> TYPE: DNA
<213> ORGANISM: Artificial Sequence
<220> FEATURE:
<223> OTHER INFORMATION: forward primer for MEEPSYPPT-Xa

<400> SEQUENCE: 91
catatggaag agccgtctta tccgccaacc atcgaaggtc gtgctaagcc gtcttatccg    60
ccaacctac                                                                    69

<210> SEQ ID NO 92
<211> LENGTH: 7
<212> TYPE: PRT
<213> ORGANISM: Artificial Sequence
<220> FEATURE:
<223> OTHER INFORMATION: artificial signal peptide MEE-Xa

<400> SEQUENCE: 92

Met Glu Glu Ile Glu Gly Arg
1               5

<210> SEQ ID NO 93
<211> LENGTH: 9
<212> TYPE: PRT
<213> ORGANISM: Artificial Sequence
<220> FEATURE:
<223> OTHER INFORMATION: artificial signal peptide MEEPS-Xa

<400> SEQUENCE: 93

Met Glu Glu Pro Ser Ile Glu Gly Arg
1               5

<210> SEQ ID NO 94
<211> LENGTH: 11
<212> TYPE: PRT
<213> ORGANISM: Artificial Sequence
<220> FEATURE:
<223> OTHER INFORMATION: artificial signal peptide MEEPSYP-Xa

<400> SEQUENCE: 94

Met Glu Glu Pro Ser Tyr Pro Ile Glu Gly Arg
1               5                   10

<210> SEQ ID NO 95
<211> LENGTH: 13
<212> TYPE: PRT
<213> ORGANISM: Artificial Sequence
<220> FEATURE:
<223> OTHER INFORMATION: artificial signal peptide MEEPSYPPT-Xa

<400> SEQUENCE: 95

Met Glu Glu Pro Ser Tyr Pro Pro Thr Ile Glu Gly Arg
1               5                   10

<210> SEQ ID NO 96
<211> LENGTH: 63
<212> TYPE: DNA
<213> ORGANISM: Artificial Sequence
<220> FEATURE:
<223> OTHER INFORMATION: forward primer for MKKTKIAlAVAAA

<400> SEQUENCE: 96
catatgaaaa agacagctat cgcgattgca gtggcagctg caccgtctta tccgccaacc    60
tac                                                                  63

<210> SEQ ID NO 97
<211> LENGTH: 63
<212> TYPE: DNA
<213> ORGANISM: Artificial Sequence
<220> FEATURE:
<223> OTHER INFORMATION: forward primer for MKATKIAlAVAAA

<400> SEQUENCE: 97
catatgaaag ctacaaagat cgcgattgca gtggcagctg caccgtctta tccgccaacc    60

-continued

```
tac                                                          63

<210> SEQ ID NO 98
<211> LENGTH: 63
<212> TYPE: DNA
<213> ORGANISM: Artificial Sequence
<220> FEATURE:
<223> OTHER INFORMATION: forward primer for MKATAIKIAVAAA

<400> SEQUENCE: 98
catatgaaag ctacagctat caagattgca gtggcagctg caccgtctta tccgccaacc    60
tac                                                          63

<210> SEQ ID NO 99
<211> LENGTH: 63
<212> TYPE: DNA
<213> ORGANISM: Artificial Sequence
<220> FEATURE:
<223> OTHER INFORMATION: forward primer for MKATAlAIKVAAA

<400> SEQUENCE: 99
catatgaaag ctacagctat cgcgattaag gtggcagctg caccgtctta tccgccaacc    60
tac                                                          63

<210> SEQ ID NO 100
<211> LENGTH: 63
<212> TYPE: DNA
<213> ORGANISM: Artificial Sequence
<220> FEATURE:
<223> OTHER INFORMATION: forward primer for MKATAlAlAVKAA

<400> SEQUENCE: 100
catatgaaag ctacagctat cgcgattgca gtgaaggctg caccgtctta tccgccaacc    60
tac                                                          63

<210> SEQ ID NO 101
<211> LENGTH: 13
<212> TYPE: PRT
<213> ORGANISM: Artificial Sequence
<220> FEATURE:
<223> OTHER INFORMATION: artificial signal peptide MKKTAlAlAVAAK

<400> SEQUENCE: 101

Met Lys Lys Thr Ala Ile Ala Ile Ala Val Ala Ala Lys
1               5                   10

<210> SEQ ID NO 102
<211> LENGTH: 13
<212> TYPE: PRT
<213> ORGANISM: Artificial Sequence
<220> FEATURE:
<223> OTHER INFORMATION: artificial signal peptide MKKTAlAlAVAAA

<400> SEQUENCE: 102

Met Lys Lys Thr Ala Ile Ala Ile Ala Val Ala Ala Ala
1               5                   10

<210> SEQ ID NO 103
<211> LENGTH: 13
<212> TYPE: PRT
<213> ORGANISM: Artificial Sequence
<220> FEATURE:
<223> OTHER INFORMATION: artificial signal peptide MKATKIAlAVAAA
```

<400> SEQUENCE: 103

Met Lys Ala Thr Lys Ile Ala Ile Ala Val Ala Ala Ala
1               5                   10

<210> SEQ ID NO 104
<211> LENGTH: 13
<212> TYPE: PRT
<213> ORGANISM: Artificial Sequence
<220> FEATURE:
<223> OTHER INFORMATION: artificial signal peptide MKATAIKIAVAAA

<400> SEQUENCE: 104

Met Lys Ala Thr Ala Ile Lys Ile Ala Val Ala Ala Ala
1               5                   10

<210> SEQ ID NO 105
<211> LENGTH: 13
<212> TYPE: PRT
<213> ORGANISM: Artificial Sequence
<220> FEATURE:
<223> OTHER INFORMATION: artificial signal peptide MKATAlAIKVAAA

<400> SEQUENCE: 105

Met Lys Ala Thr Ala Ile Ala Ile Lys Val Ala Ala Ala
1               5                   10

<210> SEQ ID NO 106
<211> LENGTH: 13
<212> TYPE: PRT
<213> ORGANISM: Artificial Sequence
<220> FEATURE:
<223> OTHER INFORMATION: artificial signal peptide MKATAlAlAVKAA

<400> SEQUENCE: 106

Met Lys Ala Thr Ala Ile Ala Ile Ala Val Lys Ala Ala
1               5                   10

<210> SEQ ID NO 107
<211> LENGTH: 51
<212> TYPE: DNA
<213> ORGANISM: Artificial Sequence
<220> FEATURE:
<223> OTHER INFORMATION: forward primer for MRRRRRRR

<400> SEQUENCE: 107
catatgcgtc gccgtcgccg tcgccgtcac atcagccaca tctccatgtg c          51

<210> SEQ ID NO 108
<211> LENGTH: 51
<212> TYPE: DNA
<213> ORGANISM: Artificial Sequence
<220> FEATURE:
<223> OTHER INFORMATION: forward primer for MKKKKKKK

<400> SEQUENCE: 108
catatgaaaa aaaaaaaaa aaaaaaacac atcagccaca tctccatgtg c          51

<210> SEQ ID NO 109
<211> LENGTH: 51
<212> TYPE: DNA
<213> ORGANISM: Artificial Sequence
<220> FEATURE:
<223> OTHER INFORMATION: forward primer for MHHHHHHH

<400> SEQUENCE: 109
catatgcacc atcaccatca ccatcaccac atcagccaca tctccatgtg c          51

<210> SEQ ID NO 110
<211> LENGTH: 51
<212> TYPE: DNA
<213> ORGANISM: Artificial Sequence
<220> FEATURE:
<223> OTHER INFORMATION: forward primer for MYYYYYYY

<400> SEQUENCE: 110
catatgtact attactatta ctattaccac atcagccaca tctccatgtg c        51

<210> SEQ ID NO 111
<211> LENGTH: 51
<212> TYPE: DNA
<213> ORGANISM: Artificial Sequence
<220> FEATURE:
<223> OTHER INFORMATION: forward primer for MCCCCCCC

<400> SEQUENCE: 111
catatgtgct gttgctgttg ctgttgccac atcagccaca tctccatgtg c        51

<210> SEQ ID NO 112
<211> LENGTH: 51
<212> TYPE: DNA
<213> ORGANISM: Artificial Sequence
<220> FEATURE:
<223> OTHER INFORMATION: forward primer for MEEEEEEE

<400> SEQUENCE: 112
catatggaag aggaagagga agaggaacac atcagccaca tctccatgtg c        51

<210> SEQ ID NO 113
<211> LENGTH: 51
<212> TYPE: DNA
<213> ORGANISM: Artificial Sequence
<220> FEATURE:
<223> OTHER INFORMATION: forward primer for MDDDDDDD

<400> SEQUENCE: 113
catatggacg atgacgatga cgatgaccac atcagccaca tctccatgtg c        51

<210> SEQ ID NO 114
<211> LENGTH: 8
<212> TYPE: PRT
<213> ORGANISM: Artificial Sequence
<220> FEATURE:
<223> OTHER INFORMATION: artificial signal peptide MRRRRRRR

<400> SEQUENCE: 114

Met Arg Arg Arg Arg Arg Arg Arg
1               5

<210> SEQ ID NO 115
<211> LENGTH: 8
<212> TYPE: PRT
<213> ORGANISM: Artificial Sequence
<220> FEATURE:
<223> OTHER INFORMATION: artificial signal peptide MKKKKKKK

<400> SEQUENCE: 115

Met Lys Lys Lys Lys Lys Lys Lys
1               5

<210> SEQ ID NO 116
<211> LENGTH: 8
<212> TYPE: PRT

<210> SEQ ID NO 117
<211> LENGTH: 8
<212> TYPE: PRT
<213> ORGANISM: Artificial Sequence
<220> FEATURE:
<223> OTHER INFORMATION: artificial signal peptide MHHHHHHH

<400> SEQUENCE: 116

Met His His His His His His His
1               5

<210> SEQ ID NO 117
<211> LENGTH: 8
<212> TYPE: PRT
<213> ORGANISM: Artificial Sequence
<220> FEATURE:
<223> OTHER INFORMATION: artificial signal peptide MYYYYYYY

<400> SEQUENCE: 117

Met Tyr Tyr Tyr Tyr Tyr Tyr Tyr
1               5

<210> SEQ ID NO 118
<211> LENGTH: 8
<212> TYPE: PRT
<213> ORGANISM: Artificial Sequence
<220> FEATURE:
<223> OTHER INFORMATION: artificial signal peptide MCCCCCCC

<400> SEQUENCE: 118

Met Cys Cys Cys Cys Cys Cys Cys
1               5

<210> SEQ ID NO 119
<211> LENGTH: 8
<212> TYPE: PRT
<213> ORGANISM: Artificial Sequence
<220> FEATURE:
<223> OTHER INFORMATION: artificial signal peptide MEEEEEEE

<400> SEQUENCE: 119

Met Glu Glu Glu Glu Glu Glu Glu
1               5

<210> SEQ ID NO 120
<211> LENGTH: 8
<212> TYPE: PRT
<213> ORGANISM: Artificial Sequence
<220> FEATURE:
<223> OTHER INFORMATION: artificial signal peptide MDDDDDDD

<400> SEQUENCE: 120

Met Asp Asp Asp Asp Asp Asp Asp
1               5

<210> SEQ ID NO 121
<211> LENGTH: 87
<212> TYPE: DNA
<213> ORGANISM: Artificial Sequence
<220> FEATURE:
<223> OTHER INFORMATION: forward primer for MAH-TAlAlaV-6xArg(pI
      13.20; hy 1.75-Xa(pI7.05)

<400> SEQUENCE: 121
catatggctc acacagctat cgcgattgca gtgcgccgtc gccgtcgccg tatcgaaggt        60
cgtcacatca gccacatctc catgtgc                                            87

<210> SEQ ID NO 122
<211> LENGTH: 87

<212> TYPE: DNA
<213> ORGANISM: Artificial Sequence
<220> FEATURE:
<223> OTHER INFORMATION: forward primer for MAH-OmpASP4-10-6xTyr(pI
      5.55; hy -1.33)-Xa

<400> SEQUENCE: 122
catatggctc acacagctat cgcgattgca gtgtactatt actattacta tatcgaaggt    60
cgtcacatca gccacatctc catgtgc                                        87

<210> SEQ ID NO 123
<211> LENGTH: 87
<212> TYPE: DNA
<213> ORGANISM: Artificial Sequence
<220> FEATURE:
<223> OTHER INFORMATION: forward priemr for MAH-OmpASP4-10-6xGlu(pI
      2.82; hy 1.75)-Xa

<400> SEQUENCE: 123
catatggctc acacagctat cgcgattgca gtggaagagg aagaggaaga gatcgaaggt    60
cgtcacatca gccacatctc catgtgc                                        87

<210> SEQ ID NO 124
<211> LENGTH: 87
<212> TYPE: DNA
<213> ORGANISM: Artificial Sequence
<220> FEATURE:
<223> OTHER INFORMATION: forward primer for MAA(pI
      5.60)-OmpASP4-10-6xArg-Xa

<400> SEQUENCE: 124
catatggctg aacagctat cgcgattgca gtgcgccgtc gccgtcgccg tatcgaaggt     60
cgtcacatca gccacatctc catgtgc                                        87

<210> SEQ ID NO 125
<211> LENGTH: 87
<212> TYPE: DNA
<213> ORGANISM: Artificial Sequence
<220> FEATURE:
<223> OTHER INFORMATION: forward priemr for MAA(pI
      5.60)-OmpASP4-10-6xTyr-Xa

<400> SEQUENCE: 125
catatggctg aacagctat cgcgattgca gtgtactatt actattacta tatcgaaggt    60
cgtcacatca gccacatctc catgtgc                                        87

<210> SEQ ID NO 126
<211> LENGTH: 87
<212> TYPE: DNA
<213> ORGANISM: Artificial Sequence
<220> FEATURE:
<223> OTHER INFORMATION: forward primer for MAA(pI
      5.60)-OmpASP4-10-6xGlu-Xa

<400> SEQUENCE: 126
catatggctg aacagctat cgcgattgca gtggaagagg aagaggaaga gatcgaaggt    60
cgtcacatca gccacatctc catgtgc                                        87

<210> SEQ ID NO 127
<211> LENGTH: 87
<212> TYPE: DNA
<213> ORGANISM: Artificial Sequence
<220> FEATURE:
<223> OTHER INFORMATION: forward primer for MEE(pI 3.09)-OmpASP4-10-6xArg-Xa

<400> SEQUENCE: 127
catatggaag agacagctat cgcgattgca gtgcgccgtc gccgtcgccg tatcgaaggt    60
cgtcacatca gccacatctc catgtgc    87

<210> SEQ ID NO 128
<211> LENGTH: 87
<212> TYPE: DNA
<213> ORGANISM: Artificial Sequence
<220> FEATURE:
<223> OTHER INFORMATION: forward primer for MEE-OmpASP4-10-6xTyr-Xa

<400> SEQUENCE: 128
catatggaag agacagctat cgcgattgca gtgtactatt actattacta tatcgaaggt    60
cgtcacatca gccacatctc catgtgc    87

<210> SEQ ID NO 129
<211> LENGTH: 87
<212> TYPE: DNA
<213> ORGANISM: Artificial Sequence
<220> FEATURE:
<223> OTHER INFORMATION: forward priemr for MEE-OmpASP4-10-6xGlu-Xa

<400> SEQUENCE: 129
catatggaag agacagctat cgcgattgca gtggaagagg aagaggaaga gatcgaaggt    60
cgtcacatca gccacatctc catgtgc    87

<210> SEQ ID NO 130
<211> LENGTH: 20
<212> TYPE: PRT
<213> ORGANISM: Artificial Sequence
<220> FEATURE:
<223> OTHER INFORMATION: artificial signal peptide MAH-TAlAlaV-6xArg-Xa

<400> SEQUENCE: 130

Met Ala His Thr Ala Ile Ala Ile Ala Val Arg Arg Arg Arg Arg Arg
1               5                   10                  15

Ile Glu Gly Arg
            20

<210> SEQ ID NO 131
<211> LENGTH: 20
<212> TYPE: PRT
<213> ORGANISM: Artificial Sequence
<220> FEATURE:
<223> OTHER INFORMATION: artificial signal peptide MAH-Omp4-10-6xTyr-Xa

<400> SEQUENCE: 131

Met Ala His Thr Ala Ile Ala Ile Ala Val Tyr Tyr Tyr Tyr Tyr Tyr
1               5                   10                  15

Ile Glu Gly Arg
            20

<210> SEQ ID NO 132
<211> LENGTH: 20
<212> TYPE: PRT
<213> ORGANISM: Artificial Sequence
<220> FEATURE:
<223> OTHER INFORMATION: artificial signal peptide MAH-Omp4-10-6xGlu-Xa

<400> SEQUENCE: 132

Met Ala His Thr Ala Ile Ala Ile Ala Val Glu Glu Glu Glu Glu Glu

```
1               5                   10                  15

Ile Glu Gly Arg
            20

<210> SEQ ID NO 133
<211> LENGTH: 20
<212> TYPE: PRT
<213> ORGANISM: Artificial Sequence
<220> FEATURE:
<223> OTHER INFORMATION: artificial signal peptide MAA-Omp4-10-6xArg-Xa

<400> SEQUENCE: 133

Met Ala Ala Thr Ala Ile Ala Ile Ala Val Arg Arg Arg Arg Arg Arg
1               5                   10                  15

Ile Glu Gly Arg
            20

<210> SEQ ID NO 134
<211> LENGTH: 20
<212> TYPE: PRT
<213> ORGANISM: Artificial Sequence
<220> FEATURE:
<223> OTHER INFORMATION: artificial signal peptide MAA-Omp4-10-6xTyr-Xa

<400> SEQUENCE: 134

Met Ala Ala Thr Ala Ile Ala Ile Ala Val Tyr Tyr Tyr Tyr Tyr Tyr
1               5                   10                  15

Ile Glu Gly Arg
            20

<210> SEQ ID NO 135
<211> LENGTH: 20
<212> TYPE: PRT
<213> ORGANISM: Artificial Sequence
<220> FEATURE:
<223> OTHER INFORMATION: artificial signal peptide MAA-Omp4-10-6xGlu-Xa

<400> SEQUENCE: 135

Met Ala Ala Thr Ala Ile Ala Ile Ala Val Glu Glu Glu Glu Glu Glu
1               5                   10                  15

Ile Glu Gly Arg
            20

<210> SEQ ID NO 136
<211> LENGTH: 20
<212> TYPE: PRT
<213> ORGANISM: Artificial Sequence
<220> FEATURE:
<223> OTHER INFORMATION: artificial signal peptide MEE-Omp4-10-6xArg-Xa

<400> SEQUENCE: 136

Met Glu Glu Thr Ala Ile Ala Ile Ala Val Arg Arg Arg Arg Arg Arg
1               5                   10                  15

Ile Glu Gly Arg
            20

<210> SEQ ID NO 137
<211> LENGTH: 20
<212> TYPE: PRT
<213> ORGANISM: Artificial Sequence
<220> FEATURE:
<223> OTHER INFORMATION: artificial signal peptide MEE-Omp4-10-6xTyr-Xa

<400> SEQUENCE: 137
```

Met Glu Glu Thr Ala Ile Ala Ile Ala Val Tyr Tyr Tyr Tyr Tyr
1               5                   10                  15

Ile Glu Gly Arg
            20

<210> SEQ ID NO 138
<211> LENGTH: 20
<212> TYPE: PRT
<213> ORGANISM: Artificial Sequence
<220> FEATURE:
<223> OTHER INFORMATION: artificial signal peptide MEE-Omp4-10-6xGlu-Xa

<400> SEQUENCE: 138

Met Glu Glu Thr Ala Ile Ala Ile Ala Val Glu Glu Glu Glu Glu Glu
1               5                   10                  15

Ile Glu Gly Arg
            20

<210> SEQ ID NO 139
<211> LENGTH: 30
<212> TYPE: DNA
<213> ORGANISM: Artificial Sequence
<220> FEATURE:
<223> OTHER INFORMATION: foward primer for Mefp1

<400> SEQUENCE: 139
tacaaagcta agccgtctta tccgccaacc                                    30

<210> SEQ ID NO 140
<211> LENGTH: 51
<212> TYPE: DNA
<213> ORGANISM: Artificial Sequence
<220> FEATURE:
<223> OTHER INFORMATION: forward primer for MKATAIKAK

<400> SEQUENCE: 140
catatgaaag ctacagctat caaggctaag ccgtcttatc cgccaaccta c             51

<210> SEQ ID NO 141
<211> LENGTH: 54
<212> TYPE: DNA
<213> ORGANISM: Artificial Sequence
<220> FEATURE:
<223> OTHER INFORMATION: forward primer for MKATAIKAAK

<400> SEQUENCE: 141
catatgaaag ctacagctat caaggcagct aagccgtctt atccgccaac ctac          54

<210> SEQ ID NO 142
<211> LENGTH: 57
<212> TYPE: DNA
<213> ORGANISM: Artificial Sequence
<220> FEATURE:
<223> OTHER INFORMATION: forward primer for MKATAIKAAAK

<400> SEQUENCE: 142
catatgaaag ctacagctat caaggctgca gctaagccgt cttatccgcc aacctac       57

<210> SEQ ID NO 143
<211> LENGTH: 60
<212> TYPE: DNA
<213> ORGANISM: Artificial Sequence
<220> FEATURE:
<223> OTHER INFORMATION: forward primer for MKATAIKAAAAK

<400> SEQUENCE: 143
catatgaaag ctacagctat caaggcagct gcagctaagc cgtcttatcc gccaacctac    60

<210> SEQ ID NO 144
<211> LENGTH: 9
<212> TYPE: PRT
<213> ORGANISM: Artificial Sequence
<220> FEATURE:
<223> OTHER INFORMATION: artificial signal peptide MKATAIKAK

<400> SEQUENCE: 144

Met Lys Ala Thr Ala Ile Lys Ala Lys
1               5

<210> SEQ ID NO 145
<211> LENGTH: 10
<212> TYPE: PRT
<213> ORGANISM: Artificial Sequence
<220> FEATURE:
<223> OTHER INFORMATION: artificial signal peptide MKATAIKAAK

<400> SEQUENCE: 145

Met Lys Ala Thr Ala Ile Lys Ala Ala Lys
1               5                   10

<210> SEQ ID NO 146
<211> LENGTH: 11
<212> TYPE: PRT
<213> ORGANISM: Artificial Sequence
<220> FEATURE:
<223> OTHER INFORMATION: artificial signal peptide MKATAIKAAAK

<400> SEQUENCE: 146

Met Lys Ala Thr Ala Ile Lys Ala Ala Ala Lys
1               5                   10

<210> SEQ ID NO 147
<211> LENGTH: 12
<212> TYPE: PRT
<213> ORGANISM: Artificial Sequence
<220> FEATURE:
<223> OTHER INFORMATION: artificial signal peptide MKATAIKAAAAK

<400> SEQUENCE: 147

Met Lys Ala Thr Ala Ile Lys Ala Ala Ala Ala Lys
1               5                   10

<210> SEQ ID NO 148
<211> LENGTH: 67
<212> TYPE: PRT
<213> ORGANISM: Artificial Sequence
<220> FEATURE:
<223> OTHER INFORMATION: olive flounder beta-defensin like protein

<400> SEQUENCE: 148

Met Ser Arg Tyr Arg Val Ala Val Leu Ala Leu Val Val Val Leu Leu
1               5                   10                  15

Val Phe Val Ala Glu Asn Glu Ala Asp Gln Pro Lys Leu Asp Cys Ser
            20                  25                  30

Thr Ile Gln Gly Val Cys Lys Asp Ser Cys Leu Ser Thr Glu Phe Ser
        35                  40                  45

Ile Gly Ala Leu Gly Cys Ser Ala Glu Ser Ser Thr Val Cys Cys Ile
    50                  55                  60

Thr Lys Pro
65

```
<210> SEQ ID NO 149
<211> LENGTH: 27
<212> TYPE: DNA
<213> ORGANISM: Artificial Sequence
<220> FEATURE:
<223> OTHER INFORMATION: forward primer for ofdefensin

<400> SEQUENCE: 149
catatgtctt gttatcgtgt ggctgtt                                       27

<210> SEQ ID NO 150
<211> LENGTH: 27
<212> TYPE: DNA
<213> ORGANISM: Artificial Sequence
<220> FEATURE:
<223> OTHER INFORMATION: reverse primer for ofdefensin

<400> SEQUENCE: 150
ctcgagtggt ttggttacgc aacatac                                       27

<210> SEQ ID NO 151
<211> LENGTH: 45
<212> TYPE: DNA
<213> ORGANISM: Artificial Sequence
<220> FEATURE:
<223> OTHER INFORMATION: forward primer contating NdeI recognition
      site

<400> SEQUENCE: 151
catatgaaaa aggctaagat gtcttgttat cgtgtggctg ttttg                   45

<210> SEQ ID NO 152
<211> LENGTH: 102
<212> TYPE: DNA
<213> ORGANISM: Artificial Sequence
<220> FEATURE:
<223> OTHER INFORMATION: forward primer containing NdeI recognition site

<400> SEQUENCE: 152
catatgaaaa agacagctat cgcgattcgc cgtcgccgtc gccgtcgccg tcgccgtcgc   60
cgtatcgaag gtcgtatgtc ttgttatcgt gtggctgttt tg                     102

<210> SEQ ID NO 153
<211> LENGTH: 27
<212> TYPE: DNA
<213> ORGANISM: Artificial Sequence
<220> FEATURE:
<223> OTHER INFORMATION: reverse primer containing NdeI recognition site

<400> SEQUENCE: 153
ctcgagtggt ttggttacgc aacatac                                       27

<210> SEQ ID NO 154
<211> LENGTH: 3
<212> TYPE: PRT
<213> ORGANISM: Artificial Sequence
<220> FEATURE:
<223> OTHER INFORMATION: Amino acid sequence of leader polypeptide 3

<400> SEQUENCE: 154

Met Asp Ala
1

<210> SEQ ID NO 155
```

```
<211> LENGTH: 9
<212> TYPE: PRT
<213> ORGANISM: Artificial Sequence
<220> FEATURE:
<223> OTHER INFORMATION: Amino acid sequence of leader polypeptide 4

<400> SEQUENCE: 155

Met Glu Glu Glu Glu Glu Glu Glu Glu
1               5

<210> SEQ ID NO 156
<211> LENGTH: 7
<212> TYPE: PRT
<213> ORGANISM: Artificial Sequence
<220> FEATURE:
<223> OTHER INFORMATION: Amino acid sequence of leader polypeptide 5

<400> SEQUENCE: 156

Met Glu Glu Glu Glu Glu Glu
1               5

<210> SEQ ID NO 157
<211> LENGTH: 5
<212> TYPE: PRT
<213> ORGANISM: Artificial Sequence
<220> FEATURE:
<223> OTHER INFORMATION: Amino acid sequence of leader polypeptide 6

<400> SEQUENCE: 157

Met Glu Glu Glu Glu
1               5

<210> SEQ ID NO 158
<211> LENGTH: 7
<212> TYPE: PRT
<213> ORGANISM: Artificial Sequence
<220> FEATURE:
<223> OTHER INFORMATION: Amino acid sequence of leader polypeptide 9

<400> SEQUENCE: 158

Met Cys Cys Cys Cys Cys Cys
1               5

<210> SEQ ID NO 159
<211> LENGTH: 4
<212> TYPE: PRT
<213> ORGANISM: Artificial Sequence
<220> FEATURE:
<223> OTHER INFORMATION: Amino acid sequence of leader polypeptide 10

<400> SEQUENCE: 159

Met Cys Cys Cys
1

<210> SEQ ID NO 160
<211> LENGTH: 3
<212> TYPE: PRT
<213> ORGANISM: Artificial Sequence
<220> FEATURE:
<223> OTHER INFORMATION: Amino acid sequence of leader polypeptide 11

<400> SEQUENCE: 160

Met Ala Cys
1

<210> SEQ ID NO 161
<211> LENGTH: 3
```

```
<212> TYPE: PRT
<213> ORGANISM: Artificial Sequence
<220> FEATURE:
<223> OTHER INFORMATION: Amino acid sequence of leader polypeptide 12

<400> SEQUENCE: 161

Met Ala Tyr
1

<210> SEQ ID NO 162
<211> LENGTH: 3
<212> TYPE: PRT
<213> ORGANISM: Artificial Sequence
<220> FEATURE:
<223> OTHER INFORMATION: Amino acid sequence of leader polypeptide 14

<400> SEQUENCE: 162

Met Gly Gly
1

<210> SEQ ID NO 163
<211> LENGTH: 4
<212> TYPE: PRT
<213> ORGANISM: Artificial Sequence
<220> FEATURE:
<223> OTHER INFORMATION: Amino acid sequence of leader polypeptide 15

<400> SEQUENCE: 163

Met Ala Lys Asp
1

<210> SEQ ID NO 164
<211> LENGTH: 4
<212> TYPE: PRT
<213> ORGANISM: Artificial Sequence
<220> FEATURE:
<223> OTHER INFORMATION: Amino acid sequence of leader polypeptide 16

<400> SEQUENCE: 164

Met Ala Lys Glu
1

<210> SEQ ID NO 165
<211> LENGTH: 5
<212> TYPE: PRT
<213> ORGANISM: Artificial Sequence
<220> FEATURE:
<223> OTHER INFORMATION: Amino acid sequence of leader polypeptide 19

<400> SEQUENCE: 165

Met Ala His His His
1               5

<210> SEQ ID NO 166
<211> LENGTH: 7
<212> TYPE: PRT
<213> ORGANISM: Artificial Sequence
<220> FEATURE:
<223> OTHER INFORMATION: Amino acid sequence of leader polypeptide 20

<400> SEQUENCE: 166

Met Ala His His His His His
1               5

<210> SEQ ID NO 167
<211> LENGTH: 4
<212> TYPE: PRT
```

```
<213> ORGANISM: Artificial Sequence
<220> FEATURE:
<223> OTHER INFORMATION: Amino acid sequence of leader polypeptide 21

<400> SEQUENCE: 167

Met Ala Lys Cys
1

<210> SEQ ID NO 168
<211> LENGTH: 3
<212> TYPE: PRT
<213> ORGANISM: Artificial Sequence
<220> FEATURE:
<223> OTHER INFORMATION: Amino acid sequence of leader polypeptide 22

<400> SEQUENCE: 168

Met Lys Tyr
1

<210> SEQ ID NO 169
<211> LENGTH: 33
<212> TYPE: DNA
<213> ORGANISM: Artificial Sequence
<220> FEATURE:
<223> OTHER INFORMATION: Forward primer for leader polypeptide 3

<400> SEQUENCE: 169
catatggacg ctccgtctta tccgccaacc tac                                    33

<210> SEQ ID NO 170
<211> LENGTH: 51
<212> TYPE: DNA
<213> ORGANISM: Artificial Sequence
<220> FEATURE:
<223> OTHER INFORMATION: Forward primer for leader polypeptide 4

<400> SEQUENCE: 170
catatggaag aggaagagga agaggaagag ccgtcttatc cgccaaccta c                51

<210> SEQ ID NO 171
<211> LENGTH: 45
<212> TYPE: DNA
<213> ORGANISM: Artificial Sequence
<220> FEATURE:
<223> OTHER INFORMATION: Forward primer for leader polypeptide 5

<400> SEQUENCE: 171
catatggaag aggaagagga agagccgtct tatccgccaa cctac                       45

<210> SEQ ID NO 172
<211> LENGTH: 39
<212> TYPE: DNA
<213> ORGANISM: Artificial Sequence
<220> FEATURE:
<223> OTHER INFORMATION: Forward primer for leader polypeptide 6

<400> SEQUENCE: 172
catatggaag aggaagagcc gtcttatccg ccaacctac                              39

<210> SEQ ID NO 173
<211> LENGTH: 45
<212> TYPE: DNA
<213> ORGANISM: Artificial Sequence
<220> FEATURE:
<223> OTHER INFORMATION: Forward primer for leader polypeptide 9

<400> SEQUENCE: 173
```
catatgtgct gttgctgttg ctgtccgtct tatccgccaa cctac         45

<210> SEQ ID NO 174
<211> LENGTH: 36
<212> TYPE: DNA
<213> ORGANISM: Artificial Sequence
<220> FEATURE:
<223> OTHER INFORMATION: Forward primer for leader polypeptide 10

<400> SEQUENCE: 174
catatgtgct gttgcccgtc ttatccgcca acctac                   36

<210> SEQ ID NO 175
<211> LENGTH: 33
<212> TYPE: DNA
<213> ORGANISM: Artificial Sequence
<220> FEATURE:
<223> OTHER INFORMATION: Forward primer for leader polypeptide 11

<400> SEQUENCE: 175
catatggctt gcccgtctta tccgccaacc tac                      33

<210> SEQ ID NO 176
<211> LENGTH: 33
<212> TYPE: DNA
<213> ORGANISM: Artificial Sequence
<220> FEATURE:
<223> OTHER INFORMATION: Forward primer for leader polypeptide 12

<400> SEQUENCE: 176
catatggctt acccgtctta tccgccaacc tac                      33

<210> SEQ ID NO 177
<211> LENGTH: 33
<212> TYPE: DNA
<213> ORGANISM: Artificial Sequence
<220> FEATURE:
<223> OTHER INFORMATION: Forward primer for leader polypeptide 14

<400> SEQUENCE: 177
catatgggtg gtccgtctta tccgccaacc tac                      33

<210> SEQ ID NO 178
<211> LENGTH: 36
<212> TYPE: DNA
<213> ORGANISM: Artificial Sequence
<220> FEATURE:
<223> OTHER INFORMATION: Forward primer for leader polypeptide 15

<400> SEQUENCE: 178
catatggcta agacccgtc ttatccgcca acctac                    36

<210> SEQ ID NO 179
<211> LENGTH: 36
<212> TYPE: DNA
<213> ORGANISM: Artificial Sequence
<220> FEATURE:
<223> OTHER INFORMATION: Forward primer for leader polypeptide 16

<400> SEQUENCE: 179
catatggcta aagaaccgtc ttatccgcca acctac                   36

<210> SEQ ID NO 180
<211> LENGTH: 39
<212> TYPE: DNA

```
<213> ORGANISM: Artificial Sequence
<220> FEATURE:
<223> OTHER INFORMATION: Forward primer for leader polypeptide 19

<400> SEQUENCE: 180
catatggctc accatcaccc gtcttatccg ccaacctac                              39

<210> SEQ ID NO 181
<211> LENGTH: 45
<212> TYPE: DNA
<213> ORGANISM: Artificial Sequence
<220> FEATURE:
<223> OTHER INFORMATION: Forward primer for leader polypeptide 20

<400> SEQUENCE: 181
catatggctc accatcacca tcacccgtct tatccgccaa cctac                       45

<210> SEQ ID NO 182
<211> LENGTH: 36
<212> TYPE: DNA
<213> ORGANISM: Artificial Sequence
<220> FEATURE:
<223> OTHER INFORMATION: Forward primer for leader polypeptide 21

<400> SEQUENCE: 182
catatggcta aatgcccgtc ttatccgcca acctac                                 36

<210> SEQ ID NO 183
<211> LENGTH: 33
<212> TYPE: DNA
<213> ORGANISM: Artificial Sequence
<220> FEATURE:
<223> OTHER INFORMATION: Forward primer for leader polypeptide 22

<400> SEQUENCE: 183
catatgaaat acccgtctta tccgccaacc tac                                    33

<210> SEQ ID NO 184
<211> LENGTH: 21
<212> TYPE: PRT
<213> ORGANISM: Artificial Sequence
<220> FEATURE:
<223> OTHER INFORMATION: Anticipated amino acid sequence of PhoA

<400> SEQUENCE: 184

Met Lys Gln Ser Thr Ile Ala Leu Ala Leu Leu Pro Leu Leu Phe Thr
1               5                   10                  15

Pro Val Thr Lys Ala
            20

<210> SEQ ID NO 185
<211> LENGTH: 21
<212> TYPE: PRT
<213> ORGANISM: Artificial Sequence
<220> FEATURE:
<223> OTHER INFORMATION: Anticipated amino acid sequence of OmpA

<400> SEQUENCE: 185

Met Lys Lys Thr Ala Ile Ala Ile Ala Val Ala Leu Ala Gly Phe Ala
1               5                   10                  15

Thr Val Ala Gln Ala
            20

<210> SEQ ID NO 186
<211> LENGTH: 23
```

```
<212> TYPE: PRT
<213> ORGANISM: Artificial Sequence
<220> FEATURE:
<223> OTHER INFORMATION: Anticipated amino acid sequence of StII

<400> SEQUENCE: 186

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 187
<211> LENGTH: 21
<212> TYPE: PRT
<213> ORGANISM: Artificial Sequence
<220> FEATURE:
<223> OTHER INFORMATION: Anticipated amino acid sequence of PhoE

<400> SEQUENCE: 187

Met Lys Lys Ser Thr Leu Ala Leu Val Val Met Gly Ile Val Ala Ser
1               5                   10                  15

Ala Ser Val Gln Ala
            20

<210> SEQ ID NO 188
<211> LENGTH: 26
<212> TYPE: PRT
<213> ORGANISM: Artificial Sequence
<220> FEATURE:
<223> OTHER INFORMATION: Anticipated amino acid sequence of MalE

<400> SEQUENCE: 188

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 189
<211> LENGTH: 21
<212> TYPE: PRT
<213> ORGANISM: Artificial Sequence
<220> FEATURE:
<223> OTHER INFORMATION: Anticipated amino acid sequence of OmpC

<400> SEQUENCE: 189

Met Lys Val Lys Val Leu Ser Leu Leu Val Pro Ala Leu Leu Val Ala
1               5                   10                  15

Gly Ala Ala Asn Ala
            20

<210> SEQ ID NO 190
<211> LENGTH: 20
<212> TYPE: PRT
<213> ORGANISM: Artificial Sequence
<220> FEATURE:
<223> OTHER INFORMATION: Anticipated amino acid sequence of Lpp

<400> SEQUENCE: 190

Met Lys Ala Thr Lys Leu Val Leu Gly Ala Val Ile Leu Gly Ser Thr
1               5                   10                  15

Leu Leu Ala Gly
            20

<210> SEQ ID NO 191
```

<211> LENGTH: 21
<212> TYPE: PRT
<213> ORGANISM: Artificial Sequence
<220> FEATURE:
<223> OTHER INFORMATION: Anticipated amino acid sequence of LTB

<400> SEQUENCE: 191

Met Asn Lys Val Lys Cys Tyr Val Leu Phe Thr Ala Leu Leu Ser Ser
1               5                   10                  15

Leu Tyr Ala His Gly
            20

<210> SEQ ID NO 192
<211> LENGTH: 22
<212> TYPE: PRT
<213> ORGANISM: Artificial Sequence
<220> FEATURE:
<223> OTHER INFORMATION: Anticipated amino acid sequence of OmpF

<400> SEQUENCE: 192

Met Met Lys Arg Asn Ile Leu Ala Val Ile Val Pro Ala Leu Leu Val
1               5                   10                  15

Ala Gly Thr Ala Asn Ala
            20

<210> SEQ ID NO 193
<211> LENGTH: 25
<212> TYPE: PRT
<213> ORGANISM: Artificial Sequence
<220> FEATURE:
<223> OTHER INFORMATION: Anticipated amino acid sequence of LamB

<400> SEQUENCE: 193

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 194
<211> LENGTH: 20
<212> TYPE: PRT
<213> ORGANISM: Artificial Sequence
<220> FEATURE:
<223> OTHER INFORMATION: Anticipated amino acid sequence of OmpT

<400> SEQUENCE: 194

Met Arg Ala Lys Leu Leu Gly Ile Val Leu Thr Thr Pro Ile Ala Ile
1               5                   10                  15

Ser Ser Phe Ala
            20

<210> SEQ ID NO 195
<211> LENGTH: 33
<212> TYPE: PRT
<213> ORGANISM: Artificial Sequence
<220> FEATURE:
<223> OTHER INFORMATION: Anticipated amino acid sequence of FdnG

<400> SEQUENCE: 195

Met Asp Val Ser Arg Arg Gln Phe Phe Lys Ile Cys Ala Gly Gly Met
1               5                   10                  15

Ala Gly Thr Thr Val Ala Ala Leu Gly Phe Ala Pro Lys Gln Ala Leu
            20                  25                  30

Ala

```
<210> SEQ ID NO 196
<211> LENGTH: 33
<212> TYPE: PRT
<213> ORGANISM: Artificial Sequence
<220> FEATURE:
<223> OTHER INFORMATION: Anticipated amino acid sequence of FdoG

<400> SEQUENCE: 196
```

Met Gln Val Ser Arg Arg Gln Phe Phe Lys Ile Cys Ala Gly Gly Met
1               5                   10                  15

Ala Gly Thr Thr Ala Ala Ala Leu Gly Phe Ala Pro Ser Val Ala Leu
            20                  25                  30

Ala

```
<210> SEQ ID NO 197
<211> LENGTH: 41
<212> TYPE: PRT
<213> ORGANISM: Artificial Sequence
<220> FEATURE:
<223> OTHER INFORMATION: Anticipated amino acid sequence of NapG

<400> SEQUENCE: 197
```

Met Ser Arg Ser Ala Lys Pro Gln Asn Gly Arg Arg Phe Leu Arg
1               5                   10                  15

Asp Val Val Arg Thr Ala Gly Gly Leu Ala Ala Val Gly Val Ala Leu
            20                  25                  30

Gly Leu Gln Gln Gln Thr Ala Arg Ala
        35                  40

```
<210> SEQ ID NO 198
<211> LENGTH: 45
<212> TYPE: PRT
<213> ORGANISM: Artificial Sequence
<220> FEATURE:
<223> OTHER INFORMATION: Anticipated amino acid sequence of HyaA

<400> SEQUENCE: 198
```

Met Asn Asn Glu Glu Thr Phe Tyr Gln Ala Met Arg Arg Gln Gly Val
1               5                   10                  15

Thr Arg Arg Ser Phe Leu Lys Tyr Cys Ser Leu Ala Ala Thr Ser Leu
            20                  25                  30

Gly Leu Gly Ala Gly Met Ala Pro Lys Ile Ala Trp Ala
        35                  40                  45

```
<210> SEQ ID NO 199
<211> LENGTH: 42
<212> TYPE: PRT
<213> ORGANISM: Artificial Sequence
<220> FEATURE:
<223> OTHER INFORMATION: Anticipated amino acid sequence of YnfE

<400> SEQUENCE: 199
```

Met Ser Lys Asn Glu Arg Met Val Gly Ile Ser Arg Arg Thr Leu Val
1               5                   10                  15

Lys Ser Thr Ala Ile Gly Ser Leu Ala Leu Ala Ala Gly Gly Phe Ser
            20                  25                  30

Leu Pro Phe Thr Leu Arg Asn Ala Ala Ala
        35                  40

```
<210> SEQ ID NO 200
<211> LENGTH: 28
```

-continued

```
<212> TYPE: PRT
<213> ORGANISM: Artificial Sequence
<220> FEATURE:
<223> OTHER INFORMATION: Anticipated amino acid sequence of WcaM

<400> SEQUENCE: 200

Met Pro Phe Lys Lys Leu Ser Arg Arg Thr Phe Leu Thr Ala Ser Ser
1               5                   10                  15

Ala Leu Ala Phe Leu His Thr Pro Phe Ala Arg Ala
            20                  25

<210> SEQ ID NO 201
<211> LENGTH: 42
<212> TYPE: PRT
<213> ORGANISM: Artificial Sequence
<220> FEATURE:
<223> OTHER INFORMATION: Anticipated amino acid sequence of TorA

<400> SEQUENCE: 201

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala
        35                  40

<210> SEQ ID NO 202
<211> LENGTH: 31
<212> TYPE: PRT
<213> ORGANISM: Artificial Sequence
<220> FEATURE:
<223> OTHER INFORMATION: Anticipated amino acid sequence of NapA

<400> SEQUENCE: 202

Met Lys Leu Ser Arg Arg Ser Phe Met Lys Ala Asn Ala Val Ala Ala
1               5                   10                  15

Ala Ala Ala Ala Ala Gly Leu Ser Val Pro Gly Val Ala Arg Ala
            20                  25                  30

<210> SEQ ID NO 203
<211> LENGTH: 30
<212> TYPE: PRT
<213> ORGANISM: Artificial Sequence
<220> FEATURE:
<223> OTHER INFORMATION: Anticipated amino acid sequence of YcbK

<400> SEQUENCE: 203

Met Asp Lys Phe Asp Ala Asn Arg Arg Lys Leu Leu Ala Leu Gly Gly
1               5                   10                  15

Val Ala Leu Gly Ala Ala Ile Leu Pro Thr Pro Ala Phe Ala
            20                  25                  30

<210> SEQ ID NO 204
<211> LENGTH: 45
<212> TYPE: PRT
<213> ORGANISM: Artificial Sequence
<220> FEATURE:
<223> OTHER INFORMATION: Anticipated amino acid sequence of DmsA

<400> SEQUENCE: 204

Met Lys Thr Lys Ile Pro Asp Ala Val Leu Ala Ala Glu Val Ser Arg
1               5                   10                  15

Arg Gly Leu Val Lys Thr Thr Ala Ile Gly Gly Leu Ala Met Ala Ser
            20                  25                  30
```

Ser Ala Leu Thr Leu Pro Phe Ser Arg Ile Ala His Ala
            35                  40                  45

<210> SEQ ID NO 205
<211> LENGTH: 33
<212> TYPE: PRT
<213> ORGANISM: Artificial Sequence
<220> FEATURE:
<223> OTHER INFORMATION: Anticipated amino acid sequence of YahJ

<400> SEQUENCE: 205

Met Lys Glu Ser Asn Ser Arg Arg Glu Phe Leu Ser Gln Ser Gly Lys
1               5                   10                  15

Met Val Thr Ala Ala Ala Leu Phe Gly Thr Ser Val Pro Leu Ala His
            20                  25                  30

Ala

<210> SEQ ID NO 206
<211> LENGTH: 44
<212> TYPE: PRT
<213> ORGANISM: Artificial Sequence
<220> FEATURE:
<223> OTHER INFORMATION: Anticipated amino acid sequence of YedY

<400> SEQUENCE: 206

Met Lys Lys Asn Gln Phe Leu Lys Glu Ser Asp Val Thr Ala Glu Ser
1               5                   10                  15

Val Phe Phe Met Lys Arg Arg Gln Val Leu Lys Ala Leu Gly Ile Ser
            20                  25                  30

Ala Thr Ala Leu Ser Leu Pro His Ala Ala His Ala
            35                  40

<210> SEQ ID NO 207
<211> LENGTH: 27
<212> TYPE: PRT
<213> ORGANISM: Artificial Sequence
<220> FEATURE:
<223> OTHER INFORMATION: Anticipated amino acid sequence of SufI

<400> SEQUENCE: 207

Met Ser Leu Ser Arg Arg Gln Phe Ile Gln Ala Ser Gly Ile Ala Leu
1               5                   10                  15

Cys Ala Gly Ala Val Pro Leu Lys Ala Ser Ala
            20                  25

<210> SEQ ID NO 208
<211> LENGTH: 35
<212> TYPE: PRT
<213> ORGANISM: Artificial Sequence
<220> FEATURE:
<223> OTHER INFORMATION: Anticipated amino acid sequence of YcdB

<400> SEQUENCE: 208

Met Gln Tyr Lys Asp Glu Asn Gly Val Asn Glu Pro Ser Arg Arg Arg
1               5                   10                  15

Leu Leu Lys Val Ile Gly Ala Leu Ala Leu Ala Gly Ser Cys Pro Val
            20                  25                  30

Ala His Ala
        35

<210> SEQ ID NO 209
<211> LENGTH: 37

```
<212> TYPE: PRT
<213> ORGANISM: Artificial Sequence
<220> FEATURE:
<223> OTHER INFORMATION: Anticipated amino acid sequence of TorZ

<400> SEQUENCE: 209

Met Ile Arg Glu Glu Val Met Thr Leu Thr Arg Arg Glu Phe Ile Lys
1               5                   10                  15

His Ser Gly Ile Ala Ala Gly Ala Leu Val Val Thr Ser Ala Ala Pro
            20                  25                  30

Leu Pro Ala Trp Ala
        35

<210> SEQ ID NO 210
<211> LENGTH: 28
<212> TYPE: PRT
<213> ORGANISM: Artificial Sequence
<220> FEATURE:
<223> OTHER INFORMATION: Anticipated amino acid sequence of HybA

<400> SEQUENCE: 210

Met Asn Arg Arg Asn Phe Ile Lys Ala Ala Ser Cys Gly Ala Leu Leu
1               5                   10                  15

Thr Gly Ala Leu Pro Ser Val Ser His Ala Ala Ala
            20                  25

<210> SEQ ID NO 211
<211> LENGTH: 49
<212> TYPE: PRT
<213> ORGANISM: Artificial Sequence
<220> FEATURE:
<223> OTHER INFORMATION: Anticipated amino acid sequence of YnfF

<400> SEQUENCE: 211

Met Met Lys Ile His Thr Thr Glu Ala Leu Met Lys Ala Glu Ile Ser
1               5                   10                  15

Arg Arg Ser Leu Met Lys Thr Ser Ala Leu Gly Ser Leu Ala Leu Ala
            20                  25                  30

Ser Ser Ala Phe Thr Leu Pro Phe Ser Gln Met Val Arg Ala Ala Glu
        35                  40                  45

Ala

<210> SEQ ID NO 212
<211> LENGTH: 37
<212> TYPE: PRT
<213> ORGANISM: Artificial Sequence
<220> FEATURE:
<223> OTHER INFORMATION: Anticipated amino acid sequence of HybO

<400> SEQUENCE: 212

Met Thr Gly Asp Asn Thr Leu Ile His Ser His Gly Ile Asn Arg Arg
1               5                   10                  15

Asp Phe Met Lys Leu Cys Ala Ala Leu Ala Ala Thr Met Gly Leu Ser
            20                  25                  30

Ser Lys Ala Ala Ala
        35

<210> SEQ ID NO 213
<211> LENGTH: 34
<212> TYPE: PRT
<213> ORGANISM: Artificial Sequence
<220> FEATURE:
<223> OTHER INFORMATION: Anticipated amino acid sequence of AmiA
```

<400> SEQUENCE: 213

Met Ser Thr Phe Lys Pro Leu Lys Thr Leu Thr Ser Arg Arg Gln Val
1               5                   10                  15

Leu Lys Ala Gly Leu Ala Ala Leu Thr Leu Ser Gly Met Ser Gln Ala
            20                  25                  30

Ile Ala

<210> SEQ ID NO 214
<211> LENGTH: 32
<212> TYPE: PRT
<213> ORGANISM: Artificial Sequence
<220> FEATURE:
<223> OTHER INFORMATION: Anticipated amino acid sequence of MdoD

<400> SEQUENCE: 214

Met Asp Arg Arg Arg Phe Ile Lys Gly Ser Met Ala Met Ala Ala Val
1               5                   10                  15

Cys Gly Thr Ser Gly Ile Ala Ser Leu Phe Ser Gln Ala Ala Phe Ala
            20                  25                  30

<210> SEQ ID NO 215
<211> LENGTH: 30
<212> TYPE: PRT
<213> ORGANISM: Artificial Sequence
<220> FEATURE:
<223> OTHER INFORMATION: Anticipated amino acid sequence of FhuD

<400> SEQUENCE: 215

Met Ser Gly Leu Pro Leu Ile Ser Arg Arg Arg Leu Leu Thr Ala Met
1               5                   10                  15

Ala Leu Ser Pro Leu Leu Trp Gln Met Asn Thr Ala His Ala
            20                  25                  30

<210> SEQ ID NO 216
<211> LENGTH: 26
<212> TYPE: PRT
<213> ORGANISM: Artificial Sequence
<220> FEATURE:
<223> OTHER INFORMATION: Anticipated amino acid sequence of YcdO

<400> SEQUENCE: 216

Met Thr Ile Asn Phe Arg Arg Asn Ala Leu Gln Leu Ser Val Ala Ala
1               5                   10                  15

Leu Phe Ser Ser Ala Phe Met Ala Asn Ala
            20                  25

<210> SEQ ID NO 217
<211> LENGTH: 16
<212> TYPE: PRT
<213> ORGANISM: Artificial Sequence
<220> FEATURE:
<223> OTHER INFORMATION: Amino acid sequence of leader polypeptide 101

<400> SEQUENCE: 217

Met Glu Glu Thr Ala Ile Ala Ile Arg Arg Arg Arg Arg Arg Arg Arg
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Amino acid sequence of leader polypeptide 102

```
<400> SEQUENCE: 218

Met Ala Ala Thr Ala Ile Ala Ile Arg Arg Arg Arg Arg Arg Arg Arg
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: Amino acid sequence of leader polypeptide 103

<400> SEQUENCE: 219

Met Ala His Thr Ala Ile Ala Ile Arg Arg Arg Arg Arg Arg Arg Arg
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Amino acid sequence of leader polypeptide 104

<400> SEQUENCE: 220

Met Lys Lys Thr Ala Ile Ala Ile Arg Arg Arg Arg Arg Arg Arg Arg
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Amino acid sequence of leader polypeptide 105

<400> SEQUENCE: 221

Met Arg Arg Thr Ala Ile Ala Ile Arg Arg Arg Arg Arg Arg Arg Arg
1               5                   10                  15

<210> SEQ ID NO 222
<211> LENGTH: 7
<212> TYPE: PRT
<213> ORGANISM: Artificial Sequence
<220> FEATURE:
<223> OTHER INFORMATION: Amino acid sequence of leader polypeptide 106

<400> SEQUENCE: 222

Met Asp Asp Asp Asp Asp Asp
1               5

<210> SEQ ID NO 223
<211> LENGTH: 7
<212> TYPE: PRT
<213> ORGANISM: Artificial Sequence
<220> FEATURE:
<223> OTHER INFORMATION: Amino acid sequence of leader polypeptide 107

<400> SEQUENCE: 223

Met Glu Glu Glu Glu Glu Glu
1               5

<210> SEQ ID NO 224
<211> LENGTH: 7
<212> TYPE: PRT
<213> ORGANISM: Artificial Sequence
<220> FEATURE:
<223> OTHER INFORMATION: Amino acid sequence of leader polypeptide 108
```

```
<400> SEQUENCE: 224

Met Lys Lys Lys Lys Lys Lys
1               5

<210> SEQ ID NO 225
<211> LENGTH: 7
<212> TYPE: PRT
<213> ORGANISM: Artificial Sequence
<220> FEATURE:
<223> OTHER INFORMATION: Amino acid sequence of leader polypeptide 109

<400> SEQUENCE: 225

Met Arg Arg Arg Arg Arg Arg
1               5

<210> SEQ ID NO 226
<211> LENGTH: 10
<212> TYPE: PRT
<213> ORGANISM: Artificial Sequence
<220> FEATURE:
<223> OTHER INFORMATION: Amino acid sequence of leader polypeptide 110

<400> SEQUENCE: 226

Met Arg Arg Arg Arg Arg Arg Arg Arg Arg
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Amino acid sequence of leader polypeptide 111

<400> SEQUENCE: 227

Met Arg Arg Arg Arg Arg Arg Arg Arg Arg Arg Arg Arg
1               5                   10

<210> SEQ ID NO 228
<211> LENGTH: 7
<212> TYPE: PRT
<213> ORGANISM: Artificial Sequence
<220> FEATURE:
<223> OTHER INFORMATION: Amino acid sequence of leader polypeptide 112

<400> SEQUENCE: 228

Met Lys Lys Arg Lys Lys Arg
1               5

<210> SEQ ID NO 229
<211> LENGTH: 7
<212> TYPE: PRT
<213> ORGANISM: Artificial Sequence
<220> FEATURE:
<223> OTHER INFORMATION: Amino acid sequence of leader polypeptide 113

<400> SEQUENCE: 229

Met Lys Lys Arg Lys Lys Arg
1               5

<210> SEQ ID NO 230
<211> LENGTH: 7
<212> TYPE: PRT
<213> ORGANISM: Artificial Sequence
<220> FEATURE:
<223> OTHER INFORMATION: Amino acid sequence of leader polypeptide 114

<400> SEQUENCE: 230
```

```
Met Arg Arg Lys Arg Arg Lys
1               5

<210> SEQ ID NO 231
<211> LENGTH: 7
<212> TYPE: PRT
<213> ORGANISM: Artificial Sequence
<220> FEATURE:
<223> OTHER INFORMATION: N-terminal(1-7) of GFP

<400> SEQUENCE: 231

Met Val Ser Lys Gly Glu Glu
1               5

<210> SEQ ID NO 232
<211> LENGTH: 7
<212> TYPE: PRT
<213> ORGANISM: Artificial Sequence
<220> FEATURE:
<223> OTHER INFORMATION: N-terminal(1-7) of GFP variant(V2E)

<400> SEQUENCE: 232

Met Glu Ser Lys Gly Glu Glu
1               5

<210> SEQ ID NO 233
<211> LENGTH: 7
<212> TYPE: PRT
<213> ORGANISM: Artificial Sequence
<220> FEATURE:
<223> OTHER INFORMATION: N-terminal(1-7) of GFP variant(V2E-S3E)

<400> SEQUENCE: 233

Met Glu Glu Lys Gly Glu Glu
1               5

<210> SEQ ID NO 234
<211> LENGTH: 7
<212> TYPE: PRT
<213> ORGANISM: Artificial Sequence
<220> FEATURE:
<223> OTHER INFORMATION: N-terminal(1-7) of GFP variant(V2E-S3E-K4E)

<400> SEQUENCE: 234

Met Glu Glu Glu Gly Glu Glu
1               5

<210> SEQ ID NO 235
<211> LENGTH: 7
<212> TYPE: PRT
<213> ORGANISM: Artificial Sequence
<220> FEATURE:
<223> OTHER INFORMATION: N-terminal(1-7) of GFP variant(V2E-S3E-K4E-G5E)

<400> SEQUENCE: 235

Met Glu Glu Glu Glu Glu Glu
1               5

<210> SEQ ID NO 236
<211> LENGTH: 25
<212> TYPE: PRT
<213> ORGANISM: Artificial Sequence
<220> FEATURE:
<223> OTHER INFORMATION: TorAss-GFP(1-7)

<400> SEQUENCE: 236
```

```
Met Leu Gly Pro Ser Leu Leu Thr Pro Arg Arg Ala Thr Ala Ala Gln
1               5                   10                  15

Ala Ala Met Val Ser Lys Gly Glu Glu
            20                  25

<210> SEQ ID NO 237
<211> LENGTH: 23
<212> TYPE: PRT
<213> ORGANISM: Artificial Sequence
<220> FEATURE:
<223> OTHER INFORMATION: MKK-OmpAss(4-23)

<400> SEQUENCE: 237

Met Lys Lys Thr Ala Ile Ala Ile Ala Val Ala Leu Ala Gly Phe Ala
1               5                   10                  15

Thr Val Ala Gln Ala Ala Pro
            20

<210> SEQ ID NO 238
<211> LENGTH: 27
<212> TYPE: PRT
<213> ORGANISM: Artificial Sequence
<220> FEATURE:
<223> OTHER INFORMATION: MKKKKKK-OmpAss(4-23)

<400> SEQUENCE: 238

Met Lys Lys Lys Lys Lys Lys Thr Ala Ile Ala Ile Ala Val Ala Leu
1               5                   10                  15

Ala Gly Phe Ala Thr Val Ala Gln Ala Ala Pro
            20                  25

<210> SEQ ID NO 239
<211> LENGTH: 72
<212> TYPE: DNA
<213> ORGANISM: Artificial Sequence
<220> FEATURE:
<223> OTHER INFORMATION: Forward primer for Seq ID No. 101

<400> SEQUENCE: 239
catatggaag agacagctat cgcgattcgc cgtcgccgtc gccgtcgccg tatggtgagc      60
aagggcgagg ag                                                         72

<210> SEQ ID NO 240
<211> LENGTH: 72
<212> TYPE: DNA
<213> ORGANISM: Artificial Sequence
<220> FEATURE:
<223> OTHER INFORMATION: Forward primer for Seq ID No. 102

<400> SEQUENCE: 240
catatggctg caacagctat cgcgattcgc cgtcgccgtc gccgtcgccg tatggtgagc      60
aagggcgagg ag                                                         72

<210> SEQ ID NO 241
<211> LENGTH: 72
<212> TYPE: DNA
<213> ORGANISM: Artificial Sequence
<220> FEATURE:
<223> OTHER INFORMATION: Forward primer for Seq ID No. 103

<400> SEQUENCE: 241
catatggctc acacagctat cgcgattcgc cgtcgccgtc gccgtcgccg tatggtgagc      60
aagggcgagg ag                                                         72
```

-continued

```
<210> SEQ ID NO 242
<211> LENGTH: 72
<212> TYPE: DNA
<213> ORGANISM: Artificial Sequence
<220> FEATURE:
<223> OTHER INFORMATION: Forward primer for Seq ID No. 104

<400> SEQUENCE: 242
catatgaaaa aaacagctat cgcgattcgc cgtcgccgtc gccgtcgccg tatggtgagc      60
aagggcgagg ag                                                         72

<210> SEQ ID NO 243
<211> LENGTH: 72
<212> TYPE: DNA
<213> ORGANISM: Artificial Sequence
<220> FEATURE:
<223> OTHER INFORMATION: Forward primer for Seq ID No. 105

<400> SEQUENCE: 243
catatgcgtc gcacagctat cgcgattcgc cgtcgccgtc gccgtcgccg tatggtgagc      60
aagggcgagg ag                                                         72

<210> SEQ ID NO 244
<211> LENGTH: 45
<212> TYPE: DNA
<213> ORGANISM: Artificial Sequence
<220> FEATURE:
<223> OTHER INFORMATION: Forward primer for Seq ID No. 106

<400> SEQUENCE: 244
catatggacg atgacgatga cgatatggtg agcaagggcg aggag                     45

<210> SEQ ID NO 245
<211> LENGTH: 45
<212> TYPE: DNA
<213> ORGANISM: Artificial Sequence
<220> FEATURE:
<223> OTHER INFORMATION: Forward primer for Seq ID No. 107

<400> SEQUENCE: 245
catatggaag aagaagaaga agaaatggtg agcaagggcg aggag                     45

<210> SEQ ID NO 246
<211> LENGTH: 45
<212> TYPE: DNA
<213> ORGANISM: Artificial Sequence
<220> FEATURE:
<223> OTHER INFORMATION: Forward primer for Seq ID No. 108

<400> SEQUENCE: 246
catatgaaaa aaaaaaaaaa aaaaatggtg agcaagggcg aggag                     45

<210> SEQ ID NO 247
<211> LENGTH: 45
<212> TYPE: DNA
<213> ORGANISM: Artificial Sequence
<220> FEATURE:
<223> OTHER INFORMATION: Forward primer for Seq ID No. 109

<400> SEQUENCE: 247
catatgcgtc gccgtcgccg tcgcatggtg agcaagggcg aggag                     45

<210> SEQ ID NO 248
```

-continued

```
<211> LENGTH: 54
<212> TYPE: DNA
<213> ORGANISM: Artificial Sequence
<220> FEATURE:
<223> OTHER INFORMATION: Forward primer for Seq ID No. 110

<400> SEQUENCE: 248
catatgcgtc gccgtcgccg tcgccgtcgc cgtatggtga gcaagggcga ggag          54

<210> SEQ ID NO 249
<211> LENGTH: 63
<212> TYPE: DNA
<213> ORGANISM: Artificial Sequence
<220> FEATURE:
<223> OTHER INFORMATION: Forward primer for Seq ID No. 111

<400> SEQUENCE: 249
catatgcgtc gccgtcgccg tcgccgtcgc cgtcgccgtc gcatggtgag caagggcgag    60
gag                                                                  63

<210> SEQ ID NO 250
<211> LENGTH: 45
<212> TYPE: DNA
<213> ORGANISM: Artificial Sequence
<220> FEATURE:
<223> OTHER INFORMATION: Forward primer for Seq ID No. 112

<400> SEQUENCE: 250
catatgaaaa aacgcaaaaa acgcatggtg agcaagggcg aggag                    45

<210> SEQ ID NO 251
<211> LENGTH: 45
<212> TYPE: DNA
<213> ORGANISM: Artificial Sequence
<220> FEATURE:
<223> OTHER INFORMATION: Forward primer for Seq ID No. 113

<400> SEQUENCE: 251
catatgaaga aacgcaagaa acgcatggtg agcaagggcg aggag                    45

<210> SEQ ID NO 252
<211> LENGTH: 45
<212> TYPE: DNA
<213> ORGANISM: Artificial Sequence
<220> FEATURE:
<223> OTHER INFORMATION: Forward primer for Seq ID No. 114

<400> SEQUENCE: 252
catatgcgtc gcaaacgtcg caaaatggtg agcaagggcg aggag                    45

<210> SEQ ID NO 253
<211> LENGTH: 24
<212> TYPE: DNA
<213> ORGANISM: Artificial Sequence
<220> FEATURE:
<223> OTHER INFORMATION: Forward primer for GFP

<400> SEQUENCE: 253
catatggtga gcaagggcga ggag                                           24

<210> SEQ ID NO 254
<211> LENGTH: 39
<212> TYPE: DNA
<213> ORGANISM: Artificial Sequence
<220> FEATURE:
<223> OTHER INFORMATION: Forward primer for GFP variant(V2E)
```

<400> SEQUENCE: 254
catatggaaa gcaagggcga ggagctgttc accggggtg        39

<210> SEQ ID NO 255
<211> LENGTH: 39
<212> TYPE: DNA
<213> ORGANISM: Artificial Sequence
<220> FEATURE:
<223> OTHER INFORMATION: Forward primer for GFP variant(V2E-S3E)

<400> SEQUENCE: 255
catatggaag aaaagggcga ggagctgttc accggggtg        39

<210> SEQ ID NO 256
<211> LENGTH: 39
<212> TYPE: DNA
<213> ORGANISM: Artificial Sequence
<220> FEATURE:
<223> OTHER INFORMATION: Forward primer for GFP variant(V2E-S3E-K4E)

<400> SEQUENCE: 256
catatggaag aagaaggcga ggagctgttc accggggtg        39

<210> SEQ ID NO 257
<211> LENGTH: 39
<212> TYPE: DNA
<213> ORGANISM: Artificial Sequence
<220> FEATURE:
<223> OTHER INFORMATION: Forward primer for GFP variant(V2E-S3E-K4E-G5E)

<400> SEQUENCE: 257
catatggaag aagaagaaga ggagctgttc accggggtg        39

<210> SEQ ID NO 258
<211> LENGTH: 90
<212> TYPE: DNA
<213> ORGANISM: Artificial Sequence
<220> FEATURE:
<223> OTHER INFORMATION: Primary forward primer for TorAss-GFP(1-7)

<400> SEQUENCE: 258
ttaaccgtcg ccgggatgct ggggccgtca ttgttaacgc cgcgacgtgc gactgcggcg        60
caagcggcga tggtgagcaa gggcgaggag        90

<210> SEQ ID NO 259
<211> LENGTH: 84
<212> TYPE: DNA
<213> ORGANISM: Artificial Sequence
<220> FEATURE:
<223> OTHER INFORMATION: Secondary forward primer for TorAss-GFP(1-7)

<400> SEQUENCE: 259
catatgaaca ataacgatct cttttcaggca tcacgtcggc gttttcgtgc acaactcggc        60
ggcttaaccg tcgccgggat gctg        84

<210> SEQ ID NO 260
<211> LENGTH: 93
<212> TYPE: DNA
<213> ORGANISM: Artificial Sequence
<220> FEATURE:
<223> OTHER INFORMATION: Forward primer for MKK-OmpAss(4-23)

<400> SEQUENCE: 260

```
catatgaaaa agacagctat cgcgattgca gtggcactgg ctggtttcgc taccgtagcg      60
caggccgctc cgatggtgag caagggcgag gag                                   93
```

<210> SEQ ID NO 261
<211> LENGTH: 105
<212> TYPE: DNA
<213> ORGANISM: Artificial Sequence
<220> FEATURE:
<223> OTHER INFORMATION: Forward primer for MKKKKKK-OmpAss(4-23)

<400> SEQUENCE: 261

```
catatgaaaa aaaaaaaaaa aaaaacagct atcgcgattg cagtggcact ggctggtttc      60
gctaccgtag cgcaggccgc tccgatggtg agcaagggcg aggag                     105
```

<210> SEQ ID NO 262
<211> LENGTH: 27
<212> TYPE: DNA
<213> ORGANISM: Artificial Sequence
<220> FEATURE:
<223> OTHER INFORMATION: Reverse primer for GFP with leader polypeptides
      and variants thereof

<400> SEQUENCE: 262

```
ctcgagcttg tacagctcgt ccatgcc                                          27
```

<210> SEQ ID NO 263
<211> LENGTH: 6
<212> TYPE: PRT
<213> ORGANISM: Artificial Sequence
<220> FEATURE:
<223> OTHER INFORMATION: 1st-6th amino acids of N-terminal of Pf3

<400> SEQUENCE: 263

```
Met Gln Ser Val Ile Thr
1               5
```

<210> SEQ ID NO 264
<211> LENGTH: 7
<212> TYPE: PRT
<213> ORGANISM: Artificial Sequence
<220> FEATURE:
<223> OTHER INFORMATION: 1st-7th amino acids of N-terminal of Pf3

<400> SEQUENCE: 264

```
Met Gln Ser Val Ile Thr Asp
1               5
```

<210> SEQ ID NO 265
<211> LENGTH: 3
<212> TYPE: PRT
<213> ORGANISM: Artificial Sequence
<220> FEATURE:
<223> OTHER INFORMATION: 1st-3rd amino acids of N-terminal of M13 coat
      protein

<400> SEQUENCE: 265

```
Met Lys Lys
1
```

<210> SEQ ID NO 266
<211> LENGTH: 8
<212> TYPE: PRT
<213> ORGANISM: Artificial Sequence
<220> FEATURE:
<223> OTHER INFORMATION: 1st-8th amino acids of N-terminal of M13 coat
      protein

<400> SEQUENCE: 266

Met Lys Lys Ser Leu Val Leu Lys
1               5

<210> SEQ ID NO 267
<211> LENGTH: 3
<212> TYPE: PRT
<213> ORGANISM: Artificial Sequence
<220> FEATURE:
<223> OTHER INFORMATION: Synthetic signal peptide MRR

<400> SEQUENCE: 267

Met Arg Arg
1

<210> SEQ ID NO 268
<211> LENGTH: 16
<212> TYPE: PRT
<213> ORGANISM: Artificial Sequence
<220> FEATURE:
<223> OTHER INFORMATION: MAH-OmpSP4-10-6XArg

<400> SEQUENCE: 268

Met Ala His Thr Ala Ile Ala Ile Ala Val Arg Arg Arg Arg Arg Arg
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: MEE-OmpSP4-10-6XGlu

<400> SEQUENCE: 269

Met Glu Glu Thr Ala Ile Ala Ile Ala Val Glu Glu Glu Glu Glu Glu
1               5                   10                  15

<210> SEQ ID NO 270
<211> LENGTH: 53
<212> TYPE: DNA
<213> ORGANISM: Artificial Sequence
<220> FEATURE:
<223> OTHER INFORMATION: pET-22(+) and MKKKKKK-GFP1-5 encoding region

<400> SEQUENCE: 270
aagaaggaga tatacatatg aaaaaaaaaa aaaaaaaat ggtgagcaag ggc         53

<210> SEQ ID NO 271
<211> LENGTH: 53
<212> TYPE: DNA
<213> ORGANISM: Artificial Sequence
<220> FEATURE:
<223> OTHER INFORMATION: pET-22(+) and MRRRRRR-GFP1-5 encoding region

<400> SEQUENCE: 271
aagaaggaga tatacatatg cgtcgccgtc gccgtcgcat ggtgagcaag ggc         53

<210> SEQ ID NO 272
<211> LENGTH: 7
<212> TYPE: PRT
<213> ORGANISM: Artificial Sequence
<220> FEATURE:
<223> OTHER INFORMATION: GFP8-14

<400> SEQUENCE: 272

```
Leu Phe Thr Gly Val Val Pro
1               5

<210> SEQ ID NO 273
<211> LENGTH: 4
<212> TYPE: PRT
<213> ORGANISM: Artificial Sequence
<220> FEATURE:
<223> OTHER INFORMATION: faxtor Xa recognition sequence

<400> SEQUENCE: 273

Ile Glu Gly Arg
1

<210> SEQ ID NO 274
<211> LENGTH: 5
<212> TYPE: PRT
<213> ORGANISM: Artificial Sequence
<220> FEATURE:
<223> OTHER INFORMATION: enterokinase recognition sequence

<400> SEQUENCE: 274

Asp Asp Asp Asp Lys
1               5

<210> SEQ ID NO 275
<211> LENGTH: 4
<212> TYPE: PRT
<213> ORGANISM: Artificial Sequence
<220> FEATURE:
<223> OTHER INFORMATION: furin recognition sequence
<220> FEATURE:
<221> NAME/KEY: VARIANT
<222> LOCATION: (2)..(3)
<223> OTHER INFORMATION: Xaa may be any amino acid.

<400> SEQUENCE: 275

Arg Xaa Xaa Arg
1

<210> SEQ ID NO 276
<211> LENGTH: 5
<212> TYPE: PRT
<213> ORGANISM: Artificial Sequence
<220> FEATURE:
<223> OTHER INFORMATION: artificial signal peptide

<400> SEQUENCE: 276

Pro Lys Lys Ala Lys
1               5

<210> SEQ ID NO 277
<211> LENGTH: 7
<212> TYPE: PRT
<213> ORGANISM: Artificial Sequence
<220> FEATURE:
<223> OTHER INFORMATION: secretional enhancer

<400> SEQUENCE: 277

Arg Arg Arg Arg Arg Arg Arg
1               5

<210> SEQ ID NO 278
<211> LENGTH: 7
<212> TYPE: PRT
<213> ORGANISM: Artificial Sequence
<220> FEATURE:
<223> OTHER INFORMATION: secretional enhancer
```

```
<400> SEQUENCE: 278

Lys Lys Lys Lys Lys Lys Lys
1               5

<210> SEQ ID NO 279
<211> LENGTH: 12
<212> TYPE: DNA
<213> ORGANISM: Artificial Sequence
<220> FEATURE:
<223> OTHER INFORMATION: nucleotide sequence encoding Xa factor
      recognition site

<400> SEQUENCE: 279
atcgaaggtc gt                                                           12

<210> SEQ ID NO 280
<211> LENGTH: 4
<212> TYPE: PRT
<213> ORGANISM: Artificial Sequence
<220> FEATURE:
<223> OTHER INFORMATION: artificial signal peptide

<400> SEQUENCE: 280

Met Glu Glu Lys
1

<210> SEQ ID NO 281
<211> LENGTH: 4
<212> TYPE: PRT
<213> ORGANISM: Artificial Sequence
<220> FEATURE:
<223> OTHER INFORMATION: artificial signal peptide

<400> SEQUENCE: 281

Met Glu Glu Glu
1

<210> SEQ ID NO 282
<211> LENGTH: 6
<212> TYPE: PRT
<213> ORGANISM: Artificial Sequence
<220> FEATURE:
<223> OTHER INFORMATION: Synthetic peptide

<400> SEQUENCE: 282

Arg Arg Arg Arg Arg Arg
1               5

<210> SEQ ID NO 283
<211> LENGTH: 6
<212> TYPE: PRT
<213> ORGANISM: Artificial Sequence
<220> FEATURE:
<223> OTHER INFORMATION: Synthetic peptide

<400> SEQUENCE: 283

Lys Lys Lys Lys Lys Lys
1               5

<210> SEQ ID NO 284
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 284

Glu Glu Glu Glu Glu Glu
1               5

<210> SEQ ID NO 285
<211> LENGTH: 6
<212> TYPE: PRT
<213> ORGANISM: Artificial Sequence
<220> FEATURE:
<223> OTHER INFORMATION: Synthetic peptide

<400> SEQUENCE: 285

Asp Asp Asp Asp Asp Asp
1               5

<210> SEQ ID NO 286
<211> LENGTH: 6
<212> TYPE: PRT
<213> ORGANISM: Artificial Sequence
<220> FEATURE:
<223> OTHER INFORMATION: Synthetic peptide

<400> SEQUENCE: 286

Tyr Tyr Tyr Tyr Tyr Tyr
1               5

<210> SEQ ID NO 287
<211> LENGTH: 6
<212> TYPE: PRT
<213> ORGANISM: Artificial Sequence
<220> FEATURE:
<223> OTHER INFORMATION: Synthetic peptide

<400> SEQUENCE: 287

Trp Trp Trp Trp Trp Trp
1               5

<210> SEQ ID NO 288
<211> LENGTH: 4
<212> TYPE: PRT
<213> ORGANISM: Artificial Sequence
<220> FEATURE:
<223> OTHER INFORMATION: Synthetic peptide

<400> SEQUENCE: 288

Arg Arg Arg Arg
1

<210> SEQ ID NO 289
<211> LENGTH: 8
<212> TYPE: PRT
<213> ORGANISM: Artificial Sequence
<220> FEATURE:
<223> OTHER INFORMATION: Synthetic peptide

<400> SEQUENCE: 289

Arg Arg Arg Arg Arg Arg Arg Arg
1               5

<210> SEQ ID NO 290
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 290

Arg Arg Arg Arg Arg Arg Arg Arg Arg Arg
1               5                   10
```